US012709753B2

(12) United States Patent
Li et al.

(10) Patent No.: US 12,709,753 B2
(45) **Date of Patent: *Aug. 18, 2026**

(54) HIV IMMUNOTHERAPY WITH NO PRE-IMMUNIZATION STEP

(71) Applicant: American Gene Technologies International Inc., Rockville, MD (US)

(72) Inventors: Haishan Li, Rockville, MD (US); Tyler Lahusen, Rockville, MD (US); Lingzhi Xiao, Rockville, MD (US); Charles David Pauza, Rockville, MD (US)

(73) Assignee: American Gene Technologies International Inc., Rockville, MD (US)

( * ) Notice: Subject to any disclaimer, the term of this patent is extended or adjusted under 35 U.S.C. 154(b) by 1180 days.

This patent is subject to a terminal disclaimer.

(21) Appl. No.: 16/476,529

(22) PCT Filed: Jan. 9, 2018

(86) PCT No.: PCT/US2018/012998
§ 371 (c)(1),
(2) Date: Jul. 8, 2019

(87) PCT Pub. No.: WO2018/129540
PCT Pub. Date: Jul. 12, 2018

(65) Prior Publication Data

US 2020/0384021 A1 Dec. 10, 2020

Related U.S. Application Data

(60) Provisional application No. 62/444,147, filed on Jan. 9, 2017.

(51) Int. Cl.

| | |
|---|---|
| ***C12N 15/86*** | (2006.01) |
| ***A61K 40/11*** | (2025.01) |
| ***A61K 40/46*** | (2025.01) |
| ***A61P 31/18*** | (2006.01) |
| ***C12N 5/078*** | (2010.01) |
| ***C12N 5/0783*** | (2010.01) |
| ***C12N 15/113*** | (2010.01) |

(52) U.S. Cl.
CPC .......... *C12N 15/1138* (2013.01); *A61K 40/11* (2025.01); *A61K 40/46* (2025.01); *A61P 31/18* (2018.01); *C12N 5/0634* (2013.01); *C12N 5/0636* (2013.01); *C12N 5/0637* (2013.01); *C12N 15/1132* (2013.01); *C12N 15/86* (2013.01); *A61K 2239/38* (2023.05); *C12N 2310/141* (2013.01); *C12N 2740/15043* (2013.01); *C12N 2740/16034* (2013.01)

(58) Field of Classification Search
CPC ................................................ C12N 2310/141
See application file for complete search history.

(56) References Cited

U.S. PATENT DOCUMENTS

| | | | | |
|---|---|---|---|---|
| 5,654,195 | A | 8/1997 | Sodroski et al. | |
| 5,668,255 | A | 9/1997 | Murphy | |
| 5,674,703 | A | 10/1997 | Woo et al. | |
| 6,156,514 | A | 12/2000 | Acevedo et al. | |
| 6,399,383 | B1 | 6/2002 | Apt et al. | |
| 6,635,472 | B1 | 10/2003 | Lauermann | |
| 6,800,281 | B2 | 10/2004 | Aebischer et al. | |
| 7,371,542 | B2 | 5/2008 | Ivanova et al. | |
| 8,124,752 | B2 | 2/2012 | Bumcrot et al. | |
| 8,287,857 | B2 | 10/2012 | Dudley et al. | |
| 8,288,094 | B2 | 10/2012 | Wain-Hobson et al. | |
| 8,481,315 | B2 | 7/2013 | Fong et al. | |
| 8,546,555 | B2 | 10/2013 | Gould-Fogerite et al. | |
| 8,993,532 | B2 | 3/2015 | Hannon et al. | |
| 9,522,176 | B2 | 12/2016 | DeRosa et al. | |
| 9,527,904 | B2 | 12/2016 | Balazs | |
| 9,834,790 | B1 | 12/2017 | Pauza et al. | |
| 9,834,791 | B2 | 12/2017 | Zhang | |
| 9,914,938 | B2 | 3/2018 | Pauza et al. | |
| 10,023,880 | B2 | 7/2018 | Pauza et al. | |
| 10,036,038 | B2 * | 7/2018 | Pauza | A61K 45/06 |
| 10,036,040 | B2 | 7/2018 | Pauza et al. | |
| 10,137,144 | B2 | 11/2018 | Pauza et al. | |
| 10,208,295 | B2 | 2/2019 | DeRosa et al. | |
| 10,233,464 | B2 * | 3/2019 | Pauza | C12N 15/86 |
| 10,420,789 | B2 | 9/2019 | Pauza et al. | |
| 10,428,350 | B2 | 10/2019 | Pauza et al. | |
| 10,472,649 | B2 | 11/2019 | Pauza et al. | |
| 10,494,647 | B2 * | 12/2019 | Pauza | A61K 35/14 |

(Continued)

FOREIGN PATENT DOCUMENTS

| | | |
|---|---|---|
| BR | 2515 | 3/2019 |
| BR | 112018075399 A2 | 3/2019 |

(Continued)

OTHER PUBLICATIONS

Franchini, G., and M. L. Bosch, 1989, Genetic relatedness of the human immunodeficiency viruses type 1 and 2 (HIV-1, HIV-2) and the simian immunodeficiency virus, Annal NY Acad. Sci. 554(1):81-87.*
Hill, C. G., et al., Dec. 2014, Functional and Evolutionary Significance of Human MicroRNA Seed Region Mutations, PLoS ONE 9(12):e115241, pp. 1-13.*
Bergvall et al. "The E1 proteins", Virology 445; p. 35-56, (Year:2013).
McBride, A., "The Papillomavirus E2 proteins", Virology 445: p. 57-79, (Year: 2013).
Chiang C-m et al., "Viral E1 and E2 proteins support replication of homologous and heterologous papillomaviral origins." PNAS 89: p. 5799-5803, (Year: 1992).
Krajinovic et al., "Sequencing data on the long control region of human papillomavirus type 16." Journal of General Viology 72:2573-2576, (Year: 1991).

(Continued)

*Primary Examiner* — Jeffrey S Parkin
(74) *Attorney, Agent, or Firm* — COOLEY LLP

(57) ABSTRACT

The present invention relates generally to immunotherapy for the treatment or prevention of HIV. In particular, the disclosure provides lentiviral vectors and associated methods that are optimized to treat HIV without a pre-immunization step.

26 Claims, 48 Drawing Sheets

Specification includes a Sequence Listing.

(56) References Cited

U.S. PATENT DOCUMENTS

| | | | |
|---|---|---|---|
| 10,548,914 | B2 | 2/2020 | Lai et al. |
| 10,767,183 | B2 | 9/2020 | Lahusen et al. |
| 10,772,905 | B2 | 9/2020 | Pauza et al. |
| 10,888,613 | B2 * | 1/2021 | Pauza .................... C12N 15/86 |
| 10,975,374 | B2 | 4/2021 | Lahusen et al. |
| 11,007,209 | B2 | 5/2021 | Lai et al. |
| 11,090,379 | B2 * | 8/2021 | Pauza ................ C07K 14/7158 |
| 11,242,527 | B1 | 2/2022 | Lahusen et al. |
| 11,352,646 | B2 | 6/2022 | Lahusen et al. |
| 11,519,006 | B2 | 12/2022 | Pauza et al. |
| 11,534,450 | B2 | 12/2022 | Pauza et al. |
| 11,583,562 | B2 | 2/2023 | Lahusen et al. |
| 11,612,649 | B2 | 3/2023 | Pauza et al. |
| 11,617,760 | B2 | 4/2023 | Lai et al. |
| 11,820,999 | B2 | 11/2023 | Lahusen et al. |
| 11,911,458 | B2 | 2/2024 | Pauza et al. |
| 11,976,292 | B2 | 5/2024 | Pauza et al. |
| 11,980,663 | B2 | 5/2024 | Pauza |
| 12,090,200 | B2 | 9/2024 | Pauza et al. |
| 2002/0086356 | A1 | 7/2002 | Tuschl et al. |
| 2002/0168345 | A1 | 11/2002 | Dong et al. |
| 2003/0013196 | A1 | 1/2003 | Engleman et al. |
| 2003/0096787 | A1 | 5/2003 | Perridcaudet et al. |
| 2003/0119770 | A1 | 6/2003 | Lai |
| 2003/0138444 | A1 | 7/2003 | Zavitz et al. |
| 2003/0138954 | A1 | 7/2003 | Trono et al. |
| 2003/0170642 | A1 | 9/2003 | Caldwell et al. |
| 2003/0198620 | A1 | 10/2003 | Ozawa et al. |
| 2004/0142416 | A1 | 7/2004 | Laipis et al. |
| 2004/0161412 | A1 | 8/2004 | Penn et al. |
| 2004/0180847 | A1 | 9/2004 | Dobie et al. |
| 2004/0192629 | A1 | 9/2004 | Xu et al. |
| 2004/0214158 | A1 | 10/2004 | Sethi et al. |
| 2004/0229266 | A1 | 11/2004 | Tuschl et al. |
| 2004/0248296 | A1 | 12/2004 | Beresford et al. |
| 2004/0265306 | A1 | 12/2004 | Arthos et al. |
| 2005/0019927 | A1 | 1/2005 | Markus et al. |
| 2005/0138677 | A1 | 6/2005 | Pfister et al. |
| 2006/0057553 | A1 | 3/2006 | Aguilar-Cordova |
| 2006/0073576 | A1 | 4/2006 | Barnett et al. |
| 2006/0183230 | A1 | 8/2006 | Silla et al. |
| 2006/0239966 | A1 | 10/2006 | Tornøe et al. |
| 2006/0246520 | A1 | 11/2006 | Champagne et al. |
| 2006/0269518 | A1 | 11/2006 | Chang et al. |
| 2007/0026521 | A1 | 2/2007 | Colosi |
| 2007/0036740 | A1 | 2/2007 | Reed |
| 2007/0059820 | A1 | 3/2007 | Fang et al. |
| 2007/0122385 | A1 | 5/2007 | Carette et al. |
| 2007/0141679 | A1 | 6/2007 | Sodroski |
| 2007/0203333 | A1 | 8/2007 | McSwiggen et al. |
| 2007/0254850 | A1 | 11/2007 | Lieberman et al. |
| 2008/0003225 | A1 | 1/2008 | Vie et al. |
| 2008/0003682 | A1 | 1/2008 | Lois-Caballe et al. |
| 2008/0039413 | A1 | 2/2008 | Morris et al. |
| 2008/0131940 | A1 | 6/2008 | Chiu |
| 2008/0153737 | A1 | 6/2008 | Lieberman et al. |
| 2008/0199961 | A1 | 8/2008 | Rasko et al. |
| 2008/0227736 | A1 | 9/2008 | Chen et al. |
| 2008/0293142 | A1 | 11/2008 | Liu et al. |
| 2009/0017543 | A1 | 1/2009 | Wilkes et al. |
| 2009/0148936 | A1 | 6/2009 | Stout et al. |
| 2009/0304688 | A1 | 12/2009 | Fournie et al. |
| 2010/0017911 | A1 | 1/2010 | Dawson et al. |
| 2010/0069372 | A1 | 3/2010 | Kazantsev |
| 2010/0119511 | A1 | 5/2010 | Wang et al. |
| 2010/0120155 | A1 | 5/2010 | Brennan et al. |
| 2010/0183558 | A1 | 7/2010 | Lai et al. |
| 2010/0286166 | A1 | 11/2010 | Rodriguez et al. |
| 2010/0316676 | A1 | 12/2010 | Sanders |
| 2011/0008417 | A1 | 1/2011 | Peut et al. |
| 2011/0008803 | A1 | 1/2011 | Stockwell et al. |
| 2011/0177155 | A1 | 7/2011 | Peer et al. |
| 2011/0207226 | A1 | 8/2011 | Ni et al. |
| 2012/0027725 | A1 | 2/2012 | Galvin |
| 2012/0034197 | A1 | 2/2012 | Young et al. |
| 2012/0053223 | A1 | 3/2012 | Benkirane et al. |
| 2012/0076763 | A1 | 3/2012 | Anderson et al. |
| 2012/0114607 | A1 | 5/2012 | Lai et al. |
| 2012/0201794 | A1 | 8/2012 | Chen et al. |
| 2013/0078276 | A1 | 3/2013 | Robinson et al. |
| 2013/0090371 | A1 | 4/2013 | Lu et al. |
| 2013/0122380 | A1 | 5/2013 | Visco et al. |
| 2013/0142766 | A1 | 6/2013 | Dodo et al. |
| 2013/0211380 | A1 | 8/2013 | Aquino et al. |
| 2014/0105965 | A1 | 4/2014 | Bancel et al. |
| 2014/0155468 | A1 | 6/2014 | Gregory et al. |
| 2014/0162894 | A1 | 6/2014 | Hatchwell et al. |
| 2014/0178340 | A1 | 6/2014 | Robbins et al. |
| 2014/0234958 | A1 | 8/2014 | Kasahara et al. |
| 2014/0248277 | A1 | 9/2014 | Hoffman et al. |
| 2014/0336245 | A1 | 11/2014 | Mingozzi et al. |
| 2014/0348794 | A1 | 11/2014 | Chiorini et al. |
| 2015/0010578 | A1 | 1/2015 | Balazs et al. |
| 2015/0018539 | A1 | 1/2015 | Fellmann |
| 2015/0110858 | A1 | 4/2015 | DeRosa et al. |
| 2015/0126580 | A1 | 5/2015 | DePinho et al. |
| 2015/0132255 | A1 | 5/2015 | Sorensen et al. |
| 2015/0176006 | A1 | 6/2015 | Krause et al. |
| 2016/0060707 | A1 | 3/2016 | Goldenberg et al. |
| 2016/0243169 | A1 | 8/2016 | Chen et al. |
| 2016/0287635 | A1 | 10/2016 | Hariri et al. |
| 2016/0289681 | A1 | 10/2016 | Rossi |
| 2017/0015976 | A1 | 1/2017 | Nelson |
| 2017/0028036 | A1 | 2/2017 | Mingozzi et al. |
| 2017/0029777 | A1 | 2/2017 | Pillai |
| 2017/0037369 | A1 | 2/2017 | Ramsborg et al. |
| 2017/0240899 | A1 | 8/2017 | Wu |
| 2017/0314041 | A1 | 11/2017 | Derosa et al. |
| 2017/0335344 | A1 | 11/2017 | Pauza et al. |
| 2018/0010147 | A1 | 1/2018 | Pauza |
| 2018/0142257 | A1 | 5/2018 | Pauza |
| 2018/0142258 | A1 | 5/2018 | Pauza |
| 2018/0161455 | A1 | 6/2018 | Pauza |
| 2018/0177866 | A1 | 6/2018 | Pauza |
| 2018/0195046 | A1 | 7/2018 | Deng |
| 2018/0195050 | A1 | 7/2018 | Szalay |
| 2018/0256624 | A1 | 9/2018 | Pauza |
| 2018/0291399 | A1 | 10/2018 | Pauza et al. |
| 2018/0305716 | A1 | 10/2018 | Pauza |
| 2018/0355032 | A1 | 12/2018 | Roberts |
| 2019/0046633 | A1 | 2/2019 | Pauza et al. |
| 2019/0062786 | A1 | 2/2019 | Pauza et al. |
| 2019/0078096 | A1 | 3/2019 | Lahusen et al. |
| 2019/0083523 | A1 | 3/2019 | Pauza |
| 2019/0201523 | A1 | 7/2019 | Pauza et al. |
| 2019/0218573 | A1 | 7/2019 | Pauza et al. |
| 2019/0255190 | A1 | 8/2019 | Pauza et al. |
| 2019/0264226 | A1 | 8/2019 | Pauza et al. |
| 2019/0282639 | A1 | 9/2019 | Lahusen et al. |
| 2019/0388456 | A1 | 12/2019 | Pauza et al. |
| 2020/0017570 | A1 | 1/2020 | Walcheck et al. |
| 2020/0063161 | A1 | 2/2020 | Pauza |
| 2020/0087682 | A1 | 3/2020 | Lahusen et al. |
| 2020/0109417 | A1 | 4/2020 | Pauza et al. |
| 2020/0155590 | A1 | 5/2020 | Zhennan |
| 2020/0181645 | A1 | 6/2020 | Pauza |
| 2020/0318081 | A1 | 10/2020 | Lahusen et al. |
| 2020/0354679 | A1 | 11/2020 | Niazi |
| 2021/0008093 | A1 | 1/2021 | Pauza et al. |
| 2021/0015868 | A1 | 1/2021 | Li et al. |
| 2021/0047644 | A1 | 2/2021 | Lahusen |
| 2021/0121561 | A1 | 4/2021 | Pauza |
| 2021/0330783 | A1 | 10/2021 | Pauza et al. |
| 2021/0401868 | A1 | 12/2021 | Lai et al. |
| 2021/0403949 | A1 | 12/2021 | Lahusen et al. |
| 2022/0062293 | A1 | 3/2022 | Geleziunas et al. |
| 2022/0162643 | A1 | 5/2022 | Lahusen et al. |
| 2022/0251563 | A1 | 8/2022 | Lahusen et al. |
| 2022/0372513 | A1 | 11/2022 | Lahusen et al. |
| 2023/0241200 | A1 | 8/2023 | Pauza |
| 2023/0277579 | A1 | 9/2023 | Pauza et al. |
| 2023/0285480 | A1 | 9/2023 | Lahusen et al. |
| 2023/0340531 | A1 | 10/2023 | Pauza et al. |
| 2024/0000822 | A1 | 1/2024 | Lai et al. |

(56) References Cited

U.S. PATENT DOCUMENTS

| | | | |
|---|---|---|---|
| 2024/0075140 | A1 | 3/2024 | Li et al. |
| 2024/0091339 | A1 | 3/2024 | Pauza et al. |
| 2024/0091340 | A1 | 3/2024 | Pauza |
| 2024/0108714 | A1 | 4/2024 | Pauza et al. |
| 2024/0115604 | A1 | 4/2024 | Li et al. |
| 2024/0141374 | A1 | 5/2024 | Li et al. |
| 2024/0141381 | A1 | 5/2024 | Lahusen et al. |
| 2024/0238406 | A1 | 7/2024 | Pauza et al. |
| 2024/0252615 | A1 | 8/2024 | Pauza |
| 2024/0279678 | A1 | 8/2024 | Li et al. |
| 2025/0042975 | A1 | 2/2025 | Pauza et al. |
| 2025/0121050 | A1 | 4/2025 | Pauza et al. |
| 2025/0121051 | A1 | 4/2025 | Pauza et al. |

FOREIGN PATENT DOCUMENTS

| | | | |
|---|---|---|---|
| CN | 101160055 | | 4/2008 |
| CN | 101516365 | | 8/2009 |
| CN | 101679466 | | 3/2010 |
| CN | 101805750 | | 8/2010 |
| CN | 103184224 | | 7/2013 |
| CN | 104428009 | A | 3/2015 |
| CN | 105112370 | | 12/2015 |
| CN | 106459932 | A | 2/2017 |
| CN | 108093639 | A | 5/2018 |
| CN | 108883100 | | 11/2018 |
| EP | 1647595 | | 4/2006 |
| EP | 3402483 | | 11/2018 |
| EP | 3413926 | | 12/2018 |
| EP | 3426777 | | 1/2019 |
| EP | 3468617 | | 4/2019 |
| EP | 3468618 | | 4/2019 |
| EP | 3481418 | | 5/2019 |
| EP | 3481435 | | 5/2019 |
| IN | 201947000153 | | 2/2019 |
| JP | 2001510053 | A | 7/2001 |
| JP | 2002506652 | | 3/2002 |
| JP | 2003511082 | A | 3/2003 |
| JP | 2003517839 | A | 6/2003 |
| JP | 2004535190 | A | 11/2004 |
| JP | 2007-527240 | | 9/2007 |
| JP | 2008518591 | | 6/2008 |
| JP | 2008-538174 | | 10/2008 |
| JP | 2010-520757 | | 6/2010 |
| JP | 2011036263 | A | 2/2011 |
| JP | 2011-517409 | | 6/2011 |
| JP | 2012508591 | | 4/2012 |
| JP | 2012523243 | A | 10/2012 |
| JP | 2012533299 | | 12/2012 |
| JP | 2013-507107 | | 3/2013 |
| JP | 2013-5300152 | | 7/2013 |
| JP | 2013544600 | A | 12/2013 |
| JP | 2014511704 | A | 5/2014 |
| JP | 2015501301 | A | 1/2015 |
| JP | 2015-518838 | | 7/2015 |
| JP | 2016-502404 | | 1/2016 |
| JP | 2016534739 | A | 11/2016 |
| JP | 2018518196 | A | 7/2018 |
| JP | 2019509029 | A | 4/2019 |
| KR | 20000049251 | A | 7/2000 |
| KR | 20040054699 | A | 6/2004 |
| KR | 20060012567 | A | 2/2006 |
| KR | 20160093325 | A | 8/2016 |
| WO | WO-9527512 | A2 | 10/1995 |
| WO | WO-9817815 | A1 | 4/1998 |
| WO | WO-9904026 | A2 | 1/1999 |
| WO | WO-9921979 | A1 | 5/1999 |
| WO | 199947691 | | 9/1999 |
| WO | WO-0136620 | A2 | 5/2001 |
| WO | WO-0146408 | A2 | 6/2001 |
| WO | 2002020554 | | 3/2002 |
| WO | WO-02099101 | A1 | 12/2002 |
| WO | WO-03029412 | A2 | 4/2003 |
| WO | WO-03087383 | A1 | 10/2003 |
| WO | 2003093436 | | 11/2003 |
| WO | 2004053137 | | 6/2004 |
| WO | WO-2004065549 | A2 | 8/2004 |
| WO | WO-2004104185 | A1 | 12/2004 |
| WO | 2005028634 | | 3/2005 |
| WO | 2005033282 | | 4/2005 |
| WO | WO-2005051927 | A1 | 6/2005 |
| WO | WO-2005085443 | A2 | 9/2005 |
| WO | WO-2006026667 | A2 | 3/2006 |
| WO | 2006039721 | | 4/2006 |
| WO | 2006048215 | | 5/2006 |
| WO | WO-2006089001 | A2 | 8/2006 |
| WO | 2007000668 | | 1/2007 |
| WO | 2007015122 | | 2/2007 |
| WO | WO-2007087113 | A2 | 8/2007 |
| WO | WO-2007109131 | A2 | 9/2007 |
| WO | 2007132292 | | 11/2007 |
| WO | 2007133674 | | 11/2007 |
| WO | WO-2008014311 | A2 | 1/2008 |
| WO | WO2008/025025 | | 2/2008 |
| WO | WO-2008069942 | A2 | 6/2008 |
| WO | 2008090185 | | 7/2008 |
| WO | WO 2008/109837 | | 9/2008 |
| WO | WO-2008128056 | A1 | 10/2008 |
| WO | WO-2009001224 | A2 | 12/2008 |
| WO | 2009100928 | | 8/2009 |
| WO | WO2009100955 | | 8/2009 |
| WO | WO-2009120947 | A1 | 10/2009 |
| WO | 2009147445 | | 12/2009 |
| WO | WO-2010048352 | A2 | 4/2010 |
| WO | 2010051521 | | 5/2010 |
| WO | WO-2010111522 | A2 | 9/2010 |
| WO | 2010117974 | | 10/2010 |
| WO | WO-2010119039 | A1 | 10/2010 |
| WO | 2010127166 | | 11/2010 |
| WO | 2011008348 | | 1/2011 |
| WO | WO-2011029914 | A1 | 3/2011 |
| WO | WO-2011042180 | A1 | 4/2011 |
| WO | 2011071476 | | 6/2011 |
| WO | 2011119942 | | 9/2011 |
| WO | WO-2011148194 | A1 | 12/2011 |
| WO | 2012048303 | | 4/2012 |
| WO | 2012061075 | | 5/2012 |
| WO | WO-2012071559 | A2 | 5/2012 |
| WO | WO-2012140127 | A2 | 10/2012 |
| WO | WO2012145624 | | 10/2012 |
| WO | WO-2012159120 | A2 | 11/2012 |
| WO | WO-2013056148 | A2 | 4/2013 |
| WO | 2013096455 | | 6/2013 |
| WO | WO-2013119880 | A1 | 8/2013 |
| WO | WO-2013174509 | A1 | 11/2013 |
| WO | 2014016817 | | 1/2014 |
| WO | WO-2014076137 | A1 | 5/2014 |
| WO | 2014117050 | | 7/2014 |
| WO | 2014187881 | | 11/2014 |
| WO | WO-2014195159 | A1 | 12/2014 |
| WO | WO2015012924 | | 1/2015 |
| WO | 2015017755 | | 2/2015 |
| WO | 2015042308 | | 3/2015 |
| WO | WO-2015038625 | A1 | 3/2015 |
| WO | 2015061491 | | 4/2015 |
| WO | WO-2015042720 | A1 | 4/2015 |
| WO | WO-2015044292 | A1 | 4/2015 |
| WO | WO-2015073818 | A1 | 5/2015 |
| WO | 2015078999 | | 6/2015 |
| WO | 2015086854 | | 8/2015 |
| WO | WO-2015162302 | A2 | 10/2015 |
| WO | WO2015164759 | | 10/2015 |
| WO | 2016046234 | | 3/2016 |
| WO | 2016054654 | | 4/2016 |
| WO | 2016061232 | | 4/2016 |
| WO | 2016069518 | | 5/2016 |
| WO | 2016069716 | | 5/2016 |
| WO | WO-2016081927 | A2 | 5/2016 |
| WO | 2016200997 | | 7/2016 |
| WO | WO-2016122058 | A1 | 8/2016 |
| WO | WO-2016168728 | A2 | 10/2016 |
| WO | WO 2016/186708 | A1 | 11/2016 |
| WO | 2016189159 | | 12/2016 |
| WO | 2017007994 | | 1/2017 |

(56) References Cited

FOREIGN PATENT DOCUMENTS

| | | | |
|---|---|---|---|
| WO | WO-2017025061 | A1 | 2/2017 |
| WO | WO2017053556 | | 3/2017 |
| WO | 20170068077 | | 4/2017 |
| WO | WO-2017074526 | A1 | 5/2017 |
| WO | 2017100551 | | 6/2017 |
| WO | 2017123918 | | 7/2017 |
| WO | 2017139065 | | 8/2017 |
| WO | 2017156311 | | 9/2017 |
| WO | WO-2017165641 | A1 | 9/2017 |
| WO | 20170173453 | | 10/2017 |
| WO | 2017213697 | | 12/2017 |
| WO | 2017214327 | | 12/2017 |
| WO | 2018009246 | | 1/2018 |
| WO | 2018009847 | | 1/2018 |
| WO | 2018017882 | | 1/2018 |
| WO | 2018126112 | | 7/2018 |
| WO | 2018129540 | | 7/2018 |
| WO | 20180148443 | | 8/2018 |
| WO | WO 2018/025923 | | 8/2018 |
| WO | 2018187231 | | 10/2018 |
| WO | WO-2018204694 | A1 | 11/2018 |
| WO | 2018232359 | | 12/2018 |
| WO | WO2019070674 | | 4/2019 |
| WO | WO-2019070888 | A1 | 4/2019 |
| WO | WO-2019148656 | A1 | 8/2019 |
| WO | WO-2019191314 | A1 | 10/2019 |
| WO | WO-2019217513 | A2 | 11/2019 |
| WO | WO-2020011247 | A1 | 1/2020 |
| WO | 2020097049 | | 5/2020 |
| WO | 2020243717 | | 12/2020 |
| WO | WO-2021178571 | A1 | 9/2021 |
| WO | WO-2025050047 | A1 | 3/2025 |
| WO | WO-2025064901 | A2 | 3/2025 |

OTHER PUBLICATIONS

Seedorg et al., "Human Papillomavirus type 16 DNA sequence." Virology 145: p. 181-185, (Year: 1985).
Jaalouk, et al. "A Self-inactivating retrovector incorporating the IL-2 promoter for activation-induced transgene expression engineered t-cells," Virology Journal: p. 1-12, (Year: 2006).
USPTO; Non-Final Office Action dated Sep. 22, 2020 in the U.S. Appl. No. 16/308,373.
IL Notice of Allowance in Israeli Application No. 284348, dated Oct. 23, 2022, 3 pages.
IN Office Action in Indian Application No. 201947000153, dated Oct. 28, 2022, 8 pages.
US Final Office Action in U.S. Appl. No. 17/089,468, dated Nov. 1, 2022, 19 pages.
US Notice of Allowance in U.S. Appl. No. 17/175,278, dated Nov. 9, 2022, 16 pages.
PCT; International Search Report and Written Opinion in the PCT Application No. PCT/US2019/059828 dated Feb. 14, 2020.
USPTO; Restriction Requirement dated Jan. 29, 2020 in the U.S. Appl. No. 16/312,056.
EPO; Supplementary European Search Report dated Dec. 19, 2019 in the Application No. 16904834.5.
EPO; Supplementary European Search Report dated Dec. 19, 2019 in the Application No. 17810976.5.
Quan Jun-Jie et al., "Parp3 interacts with FoxM1 to confer glioblastoma cell radio resistance", Tumor Biology, Karger, Basel, CH, vol. 36, No. 11, Jun. 4, 2015 (Jun. 4, 2015), pp. 8617-8624, XP036217799, ISSN: 1010-4283, DOI: 10.1007/S13277-015-3554-4 [retrieved on Jun. 4, 2015].
Jakobsson J. and Lundberg C.: "Lentiviral 1, 2, 4-10 vectors for use in the central nervous system", Molecular Therapy: The Journal of the American Society of Gene Therapy, Cell Press, US, vol. 13, No. 3, Mar. 1, 2006 (Mar. 1, 2006), pp. 484-493, XP005326761, ISSN: 1525-0016, DOI: 10.1016/ J. Ymthe.2005.11.012 *the whole document*.
YunJong Lee et al., "Poly (ADP-ribose) in 1-15 the pathogenesis of Parkinson's disease", BMB Reports, vol. 47, No. 8, Aug. 31, 2014 (Aug. 31, 2014), pp. 424-432, XP55671927, KR, ISSN: 1976-6696, DOI: 10.5483/BMBRep.2014.47.8.119 *the whole document*.
Lang Yoo et al., "Parp-1 regulates the expression of caspase-11", Biochemical and Biophysical Research Communications, vol. 408, No. 3, Apr. 22, 2011 (Apr. 22, 2011), pp. 489-493, XP028209824, ISSN: 0006-291X, DOI: 10.1016/ J. BBRC.2011.04.070 [retrieved on Apr. 22, 2011] *whole document*.
Tae-In Kam et al., "Poly (ADP-ribose) derived pathologic [alpha]—synuclein neurodegeneration in Parkinson's disease", Science, vol. 362, No. 6414, Nov. 1, 2018 (Nov. 1, 2018), p. eaat8407, XP55672116, US, ISSN: 00368075, DOI: 10.1126/science. aat8407 *whole document*.
Olsen A.L. and Feany M.B., "Parp Inhibitors and Parkinson's Disease", Jan. 1, 2019 (Jan. 1, 2019), XP55672111, retrieved from the Internet: URL: https://mfprac.com/web2019/07literature/literature/Neurology/ParkinsonPARPI_Olsen.pdf [retrieved on Feb. 27, 2020] *the whole document*.
Richard Lu et al., "Siman Virus 40-Based Replication of Catalytically Inactive Human Immunodeficiency Virus Type 1 Integrase Mutants in Nonpermissive T Cells and Monocyte-Derived Macrophages", Journal of Virology, Jan. 2004, p. 658-668. DOI: 10.1128/JVI.78.2658-668.2004.
FM Sverdrup et al., "Development of human papillomavirus plasmids capable of episomal replication in human cell lines", Gene Therapy, Mar. 26, 1999, p. 1317-1321, Retrieved from the Internet: URL: http://www.stockton-pressco.uk/gt.
Kathleen Van Craenenbroeck et al., "Episomal vectors for gene expression in mammalian cells", Eur J. Biochem, vol. 267, p. 5665-5678, Jul. 14, 2000.
USPTO; Non-Final Office Action dated Mar. 16, 2020 in the U.S. Appl. No. 16/083,384.
EPO; Extended European Supplemental Search Report dated Mar. 11, 2020 in the Application No. 17831904.2.
JP; Japanese Office Action in the Application No. 2017-564550 dated Mar. 18, 2020.
EP Search Report in European Application No. 19777212.2, dated Nov. 2, 2021, 8 pages.
JP Notice of Allowance in Japanese Application No. 2019-500475, dated Sep. 15, 2021, 6 pages (with English translation).
JP Office Action in Japanese Application No. 2019-536901, dated Nov. 19, 2021, 16 pages (with English translation).
Kaur et al., "Antigen stimulation induces HIV envelope gp120-specific CD4+ T cells to secret CCR5 ligands and suppress HIV infection", Virology, Dec. 2007, 369(1): 214-225.
US Non-Final Office Action in U.S. Appl. No. 16/312,056, dated Nov. 17, 2021, 26 pages.
Venturini et al., "Characterization of Human Immunodeficiency Virus Type 1 (HIV-1) Gag- and Gag Peptide-Specific CD4+ T-Cell Clones from an HIX-a-Seronegative Donor following In Vitro Immunization", Journal of Virology, Jul. 2002, 76(14): 6987-6999.
JP Office Action in Application No. 2021-84813, dated Jun. 23, 2022, 6 pages.
Wolstein et al., "Preclinical Safety and Efficacy of an Anti-HIV-1 Lentiviral Vector Containing a Short Hairpin RNA to CCR5 and the C46 Fusion Inhibitor," Molecular Therapy—Methods & Clinical Development (2014).
Anderson et al., "HIV-1 Resistance Conferred by siRNA Cosuppression of CXCR4 and CCR5 Coreceptors by a Bispecific Lentiviral Vector," Aids Research and Therapy, 2:1, pp. 1-12, 2005.
Anderson et al., Specific Transduction of HIV-Susceptible Cells for CCR5 Knockdown and Resistance to HIV Infection: A Novel Method for Targeted Gene Therapy and Intracellular Immunization, J. Acquir, Immune. Defic. Syndr., vol. 52, No. 2 Oct. 1, 2009.
BR Office Action in App. No. BR112019014082-4, dated Jul. 26, 2022, 3 pages.
IL Office Action in App. No. 284348, dated Jun. 12, 2022, 3 pages.
JP Office Action in Japanese Application No. 2019-536901, dated Jul. 27, 2022, 12 pages.
Cronin et al., "Altering the Tropism of Lentiviral Vectors through Pseudotyping", Curr Gene Ther, Aug. 2005, vol. 5(4), pp. 687-398.

(56) References Cited

OTHER PUBLICATIONS

Cannon et al., "Pseudotype-Dependent Lentiviral Transduction of Astrocytes or Neurons in the Rat Substantia Nigra", Experimental Neurology, vol. 228, (Year: 2011), pp. 41-52, doi:10.1016/J.expneurol.2010.10.016.
USPTO; Non-Final Office Action dated Nov. 18, 2020 in the U.S. Appl. No. 16/318,345.
USPTO; Restriction Requirement dated Nov. 19, 2020 in the U.S. Appl. No. 16/593,882.
USPTO; Non-Final Office Action dated Nov. 25, 2020 in the U.S. Appl. No. 16/943,800.
USPTO; Notice of Allowance dated Dec. 2, 2020 in the U.S. Appl. No. 16/076,655.
USPTO; Restriction Requirement dated Dec. 8, 2020 in the U.S. Appl. No. 16/563,738.
USPTO; Notice of Allowance dated Jul. 10, 2020 in the U.S. Appl. No. 16/530,908.
USPTO; Final Office Action dated Jul. 27, 2020 in the U.S. Appl. No. 16/076,655.
JP; Japanese Office Action in the Application No. 2018-536892 dated Jun. 26, 2020.
USPTO; Non-Final Office Action dated Jan. 13, 2020 in the U.S. Appl. No. 15/580,661.
Brites, C., M. Abrahao, P. Bozza, E. M. Netto, A. Lyra and F. Bahia (2018). "Infection by HTLV-1 Is Associated with High Levels of Proinflammatory Cytokines in HIV-HCV-Coinfected Patients." J Acquir Immune Defic Syndr 77(2): 230-234.
Douek, D. C., J. M. Brenchley, M. R. Betts, D. R. Ambrozak, B. J. Hill, et al. (2002). "HIV preferentially infects HIV-specific CD4+ T cells." Nature 417(6884): 95-98.
Eguchi, K., N. Matsuoka, H. Ida, M. Nakashima, M. Sakai, et al. (1992). "Primary Sjogren's syndrome with antibodies to HTLV-I: clinical and laboratory features." Ann Rheum Dis 51(6): 769-776.
Futsch, N., R. Mahieux and H. Dutartre (2017). "HTLV-1, the Other Pathogenic Yet Neglected Human Retrovirus: From Transmission to Therapeutic Treatment." Viruses, 10, 1; doi: 10.3390/v10010001.
Gessain, A., F. Barin, J. C. Vernant, O. Gout, L. Maurs, A. Calender and G. de The (1985). "Antibodies to human T-lymphotropic virus type-I in patients with tropical spastic paraparesis." Lancet 2(8452): 407-410.
Gessain, A. and O. Cassar (2012). "Epidemiological Aspects and World Distribution of HTLV-1 Infection." Front Microbiol 3: 388.
Goncalves, D. U., F. A. Proietti, J. G. Ribas, M. G. Araujo, S. R. Pinheiro, A. C. Guedes and A. B. Carneiro-Proietti (2010). "Epidemiology, treatment, and prevention of human T-cell leukemia virus type 1-associated diseases." Clin Microbiol Rev 23(3): 577-589.
Kagdi, H., M. A. Demontis, J. C. Ramos and G. P. Taylor (2018). "Switching and loss of cellular cytokine producing capacity characterize in vivo viral infection and malignant transformation in human T- lymphotropic virus type 1 infection. " PLoS Pathog 14(2): e1006861.
Kagdi, H. H., M. A. Demontis, P. A. Fields, J. C. Ramos, C. R. Bangham and G. P. Taylor (2017). "Risk stratification of adult T-cell leukemia/lymphoma using immunophenotyping." Cancer Med 6(1): 298-309.
Macnamara, A., A. Rowan, S. Hilburn, U. Kadolsky, H. Fujiwara, et al. (2010). "HLA class I binding of HBZ determines outcome in HTLV-1 infection." PLoS Pathog 6(9): e1001117.
Manel, N., F. J. Kim, S. Kinet, N. Taylor, M. Sitbon and J. L. Battini (2003). "The ubiquitous glucose transporter GLUT-1 is a receptor for HTLV." Cell 115(4): 449-459.
Martinez, M. P., J. Al-Saleem and P. L. Green (2019). "Comparative virology of HTLV-1 and HTLV-2." Retrovirology 16(1): 21.
Mochizuki, M., T. Watanabe, K. Yamaguchi, K. Takatsuki, K. Yoshimura, et al. (1992). "HTLV-I uveitis: a distinct clinical entity caused by HTLV-I." Jpn J Cancer Res 83(3): 236-239.
Mosley, A. J., B. Asquith and C. R. Bangham (2005). "Cell-mediated immune response to human T-lymphotropic virus type I." Viral Immunol 18(2): 293-305.
Nagai, M. and M. Osame (2003). "Human T-cell lymphotropic virus type I and neurological diseases." J Neurovirol 9(2): 228-235.
Yamano, Y. and T. Sato (2012). "Clinical pathophysiology of human T-lymphotropic virus-type 1-associated myelopathy/tropical spastic paraparesis." Front Microbiol 3: 389.
Nishioka, K., I. Maruyama, K. Sato, I. Kitajima, Y. Nakajima and M. Osame (1989). "Chronic inflammatory arthropathy associated with HTLV-I." Lancet 1(8635): 441.
Osame, M., K. Usuku, S. Izumo, N. Ijichi, H. Amitani, et al. (1986). "HTLV-I associated myelopathy, a new clinical entity." Lancet 1(8488): 1031-1032.
Poiesz, B. J., F. W. Ruscetti, A. F. Gazdar, P. A. Bunn, J. D. Minna and R. C. Gallo (1980). "Detection and isolation of type C retrovirus particles from fresh and cultured lymphocytes of a patient with cutaneous T-cell lymphoma." Proc Natl Acad Sci U S A 77(12): 7415-7419.
Poiesz, B. J., F. W. Ruscetti, J. W. Mier, A. M. Woods and R. C. Gallo (1980). "T-cell lines established from human T-lymphocytic neoplasias by direct response to T-cell growth factor." Proc Natl Acad Sci U S A 77(11): 6815-6819.
Roc, L., C. de Mendoza, M. Fernandez-Alonso, G. Reina, V. Soriano and H. N. Spanish (2019). "Rapid subacute myelopathy following kidney transplantation from HTLV-1 donors: role of immunosuppresors and failure of antiretrovirals." Ther Adv Infect Dis 6: 2049936119868028.
Soker, S., S. Takashima, H. Q. Miao, G. Neufeld and M. Klagsbrun (1998). "Neuropilin-1 is expressed by endothelial and tumor cells as an isoform-specific receptor for vascular endothelial growth factor." Cell 92(6): 735-745.
Uchiyama, T., J. Yodoi, K. Sagawa, K. Takatsuki and H. Uchino (1977). "Adult T-cell leukemia: clinical and hematologic features of 16 cases." Blood 50(3): 481-492.
Dickler, H. B., et al. (1973). "Lymphocyte binding of aggregated IgG and surface Ig staining in chronic lymphocytic leukaemia." Clin Exp Immunol 14(1): 97-106.
USPTO; Notice of Allowance dated May 18, 2020 in the U.S. Appl. No. 16/083,384.
USPTO; Final Office Action dated Jun. 2, 2020 in the U.S. Appl. No. 15/580,661.
USPTO; Non-Final Office Action dated Jun. 1, 2020 in the U.S. Appl. No. 16/530,908.
CN; 1st Office Action in the CN Application No. 20170017712.6 dated May 8, 2020.
EPO; Office Action in the EPO Application No. 16808223.8 dated May 11, 2020.
JP Notice of Allowance in Japanese Application No. 2018-541270, dated Aug. 31, 2022, 6 pages (with English translation).
Wang et al., "HIV Vaccine Research: The Challenge and the Way Forward," Journal of Immunology Research, vol. 2015, Article ID 503978, 5 pages.
Bourguigon et al., "Processing of blood samples influences PBMC viability and outcome of cell-mediated immune responses in antiretroviral therapy-naïve HIV-1-infected patients," Journal of Immunological Methods, vol. 414, p. 1-10 (2014).
Briz et al., "Validation of Generation 4 Phosphorus-Containing Polycationic Dendrimer for Gene Delivery Against HIV-1," Current Medical Chemistry, vol. 19, p. 5044-5051, (2012).
Anderson et al., "Preintegration HIV-1 Inhibition by a Combination Lentiviral Vector Containing a Chimeric TRIM5a Protein, a CCR5 shRNA, and TAR Decoy," Molecular Therapy, vol. 17, No. 12, p. 2103-2114, Dec. 2009.
JP; Japanese Office Action in the Application No. 2017-567175 dated Jun. 15, 2020.
EPO; Extended European Search Report in the Application No. 18736295.9 dated Aug. 20, 2020.
USPTO; Final Office Action dated May 27, 2021 in the U.S. Appl. No. 15/736,384.
JP; Office Action in the JP Application No. 2019-500475 dated Mar. 4, 2021.
JP; Office Action in the JP Application No. 2019-500423 dated Jun. 2, 2021.

(56) References Cited

OTHER PUBLICATIONS

Hee Yeon Kim., "Farnesyl Diphosphate Synthase is Important for the Maintenance of Glioblastoma Stemness," Experimental & Molecular Medicine, (2018).
Hong Wang., "Indirect Stimulation of Human V2V2 Cells Through Alterations in Isoprenoid Metabolism," The Journal of Immunology, (2011).
Z. Li, "Inhibition of farnesyl pyrophosphate synthase prevents angiotensin II-induced cardiac fibrosis in vitro," Clinical & Experimental Immunology, (2014).
Xiaofeng Jiang, "A novel EST-derived RNAi screen reveals a critical role for farnesyl diphosphate in B2-adrenerigic receptor internalization and down-regulation," The FASEB Journal, vol. 26, pp. 1-13(1995).
Jian Yang, "Lentiviral-Mediated Silencing of Farnesyl Pyrophosphate Synthase through RNA Interference in Mice," Biomed Research International, vol. 2015, Article ID 914026, 6 pages, (2015).
Yang Ye, "Knockdown of farnesyl pyrophosphate synthase prevents angiotensin II-medicated cardiac hypertrophy," The International Journal of Biochemistry & Cell Biology, vol. 42, pp. 2056-2064, (2010).
Jianqiang Li, "Reduced Expression of Mevalonate Pathway Enzyme Farnesyl Pyrophosphate Synthase Unveils Recognition of Tumor Cells by V9V2 Cells," The Journal of Immunology, pp. 8118-8124, (2019).
Daryl S. Schiller, "Parameters Influencing Measurement of the Gag Antigen-Specific T-Proliferative Response to HIV Type 1 Infection," AIDS Research and Human Retroviruses, vol. 16, No. 3, pp. 259-271, (2000).
PCT; International Search Report dated Jul. 22, 2019 in the Application No. PCT/US2019/24410.
PCT; Written Opinion of the International Search Report dated Jul. 22, 2019 in the Application No. PCT/US2019/24410.
PCT; International Preliminary Report on Patentability dated Jul. 9, 2019 in the Application No. PCT/US2018/012998.
USPTO; Notice of Allowance dated Jun. 18, 2019 in the U.S. Appl. No. 16/182,443.
USPTO; Notice of Allowance dated Jul. 3, 2019 in U.S. Appl. No. 16/182,443.
USPTO; Restriction Requirement dated Jul. 12, 2019 in the U.S. Appl. No. 15/736,284.
USPTO; Advisory Action dated Jul. 23, 2019 in the U.S. Appl. No. 15/736,284.
USPTO; Notice of Allowance dated Aug. 14, 2019 in the U.S. Appl. No. 16/008,991.
USPTO; Notice of Allowance dated Sep. 25, 2019 in the U.S. Appl. No. 16/218,010.
USPTO; Final Office Action dated Jul. 1, 2019 in the U.S. Appl. No. 16/132,247.
USPTO; Notice of Allowance dated Jul. 19, 2019 in the U.S. Appl. No. 16/132,247.
EPO; European Search Report dated Aug. 12, 2019 in the EP Application No. 17764128.9.
EPO; Supplementary European Search Report dated Sep. 6, 2019 in the Application No. 17750547.6.
Hassan et al., "Isolation of umbilical cord mesenchymal stem cells using human blood derivative accompanied with explant method," Stem Cell Investigation, pp. 1-8, (2019).
Huang et al., "An Efficient protocol to generate placental chorionic plate-derived mesenchymal stem cells with superior proliferative and immunomodulatory properties," Stem Cell Research & Therapy, pp. 1-15, (2019).
USPTO; Restriction Requirement dated Oct. 22, 2019 in the U.S. Appl. No. 15/580,661.
USPTO; Restriction Requirement dated Nov. 4, 2019 in the U.S. Appl. No. 16/076,655.
USPTO; Notice of Allowance mailed Oct. 29, 2019 in the U.S. Appl. No. 13/333,882.
USPTO; Restriction Requirement dated Nov. 7, 2019 in the U.S. Appl. No. 16/083,384.
Zhang et al. "Uracils at Nucleotide Position 9-11 are Required for the Rapid Turnover of miR-29 Family," Nucleic Acids Research, vol. 39, No. 10, pp. 4387-4398, 2011.
USPTO; Non-Final Office Action issued on Jun. 27, 2022 in U.S. Appl. No. 15/736,284.
Nada et al., "Enhancing adoptive cancer immunotherapy with Vy2V82 T cells through pulse zoledronate stimulation", Journal for Immunotherapy of Cancer, vol. 5, No. 1, (Feb. 21, 2017), pp. 1-23, (2017) DOI 10.1186/s40425-017-0209-6 *the whole document*.
Benyamine et al., "BTN3A molecules considerably improve Vy9V82T cells-based immunotherapy in acute myeloid leukemia," OncoImmunology, vol. 5, No. 10, 10 pages, (Oct. 2, 2016), E1146843 *the whole document*.
Harly et al., "Key implication of CD277/butyrophilin-3 (BTN3A) in cellular stress sensing by a major human γδ T-cell subset," American Society of Hematology , vol. 120, No. 11, (Sep. 13, 2012), pp. 2269-2279, XP055081172, ISSN: 0006-4971, DOI: 10.1182/blood-2012-05-430470 *the whole document*.
Wang et al., "Intravenous Delivery of SiRNA Targeting CD47 Effectively Inhibits Melanoma Tumor Growth and Lung Metastasis", Molecular Therapy, pp. 1919-1929, vol. 21, No. 10, Oct. 2013.
USPTO; Notice of Allowance dated Feb. 10, 2021 in the U.S. Appl. No. 16/943,800.
USPTO; Non-Final Office Action dated Feb. 19, 2021 in the U.S. Appl. No. 15/580,661.
USPTO; Final Office Action dated Feb. 26, 2021 in the U.S. Appl. No. 16/312,056.
USPTO; Corrected Notice of Allowance dated Mar. 3, 2021 in the U.S. Appl. No. 16/687,525.
USPTO; Non-Final Office Action dated Mar. 12, 2021 in the U.S. Appl. No. 16/563,738.
CN; 1st Office Action in the CN Application No. 202010396594.8 dated Jan. 15, 2021.
EP; Supplementary Search Report in the EP Application No. 18817253 dated Feb. 10, 2021.
JP; Office Action in the JP Application No. 2018-547354 dated Feb. 16, 2021.
JP; Office Action in the JP Application No. 2018-541270 mailed Jan. 8, 2021.
Oh et al. "Lentiviral Vector Design Using Alternative RNA Export Elements," Retrovirology, vol. 4:38, pp. 1-10, (2007).
PCT; International Preliminary Report on Patentability dated Oct. 8, 2019 in the Application No. PCT/ US2018/025733.
PCT; International Search Report and Written Opinion of the International Search Report dated Jul. 22, 2019 in the Application No. PCT/US2019/024410.
USPTO; Notice of Allowance dated Nov. 27, 2019 in the U.S. Appl. No. 13/333,882.
Lee et al., "Lentiviral delivery of short hairpin RNAs protects CD4 cells from multiple clades and primary isolates of HIV." Blood, 2005, vol. 106(3):818-826. (Year: 2005).
Choi et al., "Multiplexing Seven miRNA-Based shRNAs to Suppress HIV Replication." Molecular Therapy, 2015, vol. 23(2):310-320. Supplementary materials.
Spartevello et al., Development of Lentiviral Vectors Simultaneously Expressing Multiple siRNAs Against CCR5, vif and tat/rev Genes for an HIV-1 Gene Therapy Approach, Molecular Therapy—Nucleic Acids, 2016, vol. 5:1-12.
USPTO; Restriction Requirement dated Jun. 15, 2020 in the U.S. Appl. No. 16/308,373.
USPTO; Restriction Requirement dated Jun. 26, 2020 in the U.S. Appl. No. 16/318,345.
USPTO; Office Action dated Jul. 6, 2020 in the U.S. Appl. No. 16/312,056.
JP; Japanese Office Action in the Application No. 2019-500475 dated Jun. 12, 2020.
USPTO; Non-Final Office Action dated Oct. 29, 2020 in the U.S. Appl. No. 15/736,284.
JP; Japanese Office Action in the JP Application No. 2018-563892 dated Oct. 14, 2020.
EP Office Action in European U.S. Appl. No. 16/822,021, dated Oct. 7, 2021, 4 pages.

(56) References Cited

OTHER PUBLICATIONS

JP Office Action in Japanese Application No. 2018-541270, dated Dec. 23, 2021, 19 pages (with English translation).
US Non-Final Office Action in United States U.S. Appl. No. 16/312,056, dated Nov. 17, 2021, 32 pages.
Yokota, "Gene therapy of virus replication with RNAi", Virus, vol. 55, No. 1, pp. 1-8.
Pallikkuth et al., "Human Immunodeficiency Virus (HIV) gag Anti-Specific T-Helper and Granule-Dependent CD8 T-Cell Activities in Exposed but Uninfected Heterosexual Partners of HIV Type 1-Infected Individuals in North India," Clinical and Vaccine Immunology, vol. 14(9) pp. 1196-1202, (2007).
USPTO; Non-Final Office Action dated Feb. 21, 2020 in the U.S. Appl. No. 16/076,655.
EPO; Extended European Supplementary Search Report dated Feb. 6, 2020 in the Application No. 17825011.4.
EPO; Extended European Supplementary Search Report dated Feb. 6, 2020 in the Application No. 17824652.6.
EPO; Examination Report dated Oct. 7, 2021 in App. No. 16822021.8.
EP Office Action in European Application No. 17750547.6, dated Apr. 29, 2022, 4 pages.
JP Office Action in Japanese Application No. 2019-500423, dated Apr. 27, 2022, 9 pages (with English translation).
Yang et al., "Construction of PARP-1 gene silencing cell lines by lentiviral-mediated RNA interference," School of Public Health, Guangdong Medical College, ABSTRACT (2006).
Zhaobing Ding et al., "Liver -Directed, AAV-and Lentivirus-Mediated Gene Therapy in the Phenylketonuria Mouse Model Pah-enu2", Molecular Therapy, vol. 11, Supp. 1. (May 2005) XP055751452.
Ledley et al., "Retroviral-mediated gene transfer of human phenylalanine hydroxylase into Nih 3T3 and hepatoma cells", Proceedings of the National Academy of Sciences, vol. 83, No. 2. (Jan. 1, 1986), pp. 409-413, XP002583115.
Ledley et al., "Molecular biology of phenylalanine hydroxylase and phenylketonurina", Trends in Genetics, Elsevier Science Publishers B.V. Amsterdam, NL, vol. 1. (Jan. 1, 1985), pp. 309-313, XP025943064.
USPTO; Notice of Allowance dated Jan. 13, 2021 in the U.S. Appl. No. 16/687,525.
EP; Supplementary Search Report in the EP Application No. 18781288.8 dated Dec. 8, 2020.
JP; Final Office Action in the JP Application No. 2018-536892 dated Nov. 16, 2020.
USPTO; Notice of Allowance dated Jan. 26, 2021 in the U.S. Appl. No. 16/593,882.
Vargas, J. Jr. et al., "Conditionally replicating lentiviral-hybrid episomal vectors for suicide gene therapy," Antiviral Res. Dec. 2008 vol. 80 No. 3, pp. 288-294.
Thompson et al., "Alkylamines cause Vγ9Vδ2 T-cell activation and proliferation by inhibiting the mevalonate pathway," Blood, Jan. 15, 2006, vol. 107, pp. 651-654.
Gober et al., "Human T Cell Receptor γδ Cells Recognize Endogenous Mevalonate Metabolites in Tumor Cells," J. of Experimental Med., Jan. 20, 2003, vol. 197, pp. 163-168.
Goepfert, et al., "Specificity and 6-Month Durability of Immune Responses Induced by DNA and Recombinant Modified Vaccinia Ankara Vaccines Expressing HIV-2 Virus-Like Particles," J. Infectious Diseases, Jul. 1, 2014, vol. 210, pp. 99-110.
Human papillomavirus type 16 (HPV16), complete genome; GenBank: K02718.1; Publication [online], Mar. 18, 1994, https://www.ncbi.nlm.nih.gov/nucleotide/333031?report=genbank&log$=nucltop&blast_rank=22&RID=H3E1THFU014; pp. 1-4.
{Long control region} [human papillomavirus, type 16, Genomic, 860 nt]; Accession S60559. Publication [online]. May 7, 1993, https://www.ncbi.nlm.nih.gov/nucleotide/237343?report=genbank&log$=nucltop&blast_rank=1&R ID=H3FCKA00014; pp. 1.
Tebas, P. et al., "Antiviral effects of autologous CD4 T cells genetically modified with a conditionally replicating lentiviral vector expressing long antisense to HIV," Blood, 2013, vol. 121, No. 9, pp. 1524-1533.
Tebas, p. et al., "Gene Editing of CCR5 in Autologous CD4 T Cells of Persons Infected with HIV," The New England Journal of Medicine, vol. 370 (10), pp. 901-910, Mar. 6, 2014.
Li et al., "Reduced Expression of the Mevalonate Pathway Enzyme Farnesyl Pyrophosphate Synthase Unveils Recognition of Tumor Cells by Vy2Vδ2 T Cells," J. of Immunology, 2009, vol. 182, pp. 8118-8124.
Wang et al., "Indirect Stimulation of Human Vy2Vδ2 T Cells through Alterations in Isoprenoid Metabolism," J. of Immunology, vol. 187 pp. 5099-5113, (Nov. 15, 2011).
Stunkel et al., "The Chromatin Structure of the Long Control Region of Human Papillomavirus Type 16 Repress Viral Oncoprotein Expression," Journal of Virology, vol. 73, No. 3, pp. 1918-1930 (Mar. 1999).
Lu et al., "Anti-sense-Mediated Inhibition of Human Immunodeficiency Virus (HIV) Replication by Use of an HIV Type 1-Based Vector Results in Severely Attenuated Mutants Incapable of Developing Resistance," Journal of Virology, vol. 79, No. 13, pp. 7079-7088 (Jul. 2004).
Dieli et al., "Targeting Human yδ T Cells with Zoledronate and Interleukin-2 for Immunotherapy of Hormone-Refractory Prostate Cancer, " Europe PMC Funders Group, Cancer Research, vol. 67(15), pp. 7450-1451, (Aug. 1, 2007).
GenBank Accession No. S60559 "(long control region) [human papillomavirus, type 16, Genomic, 860 nt]" May 7, 1993 [located online Nov. 21, 2017 at https://ncbi.nlm.nih.gov/nuccore/S60559] entire DNA sequence.
GenBank Accession No. JG619773, MNESCING-T3-001_L15_6FEB2009_054 Mnescing cell culture from Mahonia nervosa Berberis nervosa cDNA, mRNA sequence, Feb. 13, 2014 (online). [Retrieved on Dec. 5, 2017]. Retrieved from the internet:<URL:https://www.ncbi.nlm.nih.gov/nucest/JG619773 > entire document.
Moser et al., "yd T cells: novel initiators of adaptive immunity," Immunological Reviews, vol. 215, pp. 89-102 (Feb. 2, 2007).
Capietto, A. H. et al., "Stimulated yδ T Cells Increase the in Vivo Efficacy of Trastuzumab in HER-2+ Breast Cancer," J Immunology, vol. 187(2), pp. 1031-1038, (2011).
Chen, Z. and M. S. Freedman, "CD16+ yδ T Cells Mediate Antibody Dependent Cellular Cytotoxicity: Potential Mechanism in the Pathogenesis of Multiple Sclerosis," Clin Immunology, vol. 128(2), pp. 219-227, (2008).
Couzi, L. et al., "Antibody-Dependent Anti-Cytomegalovirus Activity of Human yδ T Cells Expressing CD16 (FcyRIIIa)," Blood, vol. 119(6), pp. 1418-1427, (2012).
Fisher, J. P. et al., "Effective Combination Treatment of GD2-Expressing Neuroblastoma and Ewing's Sarcoma Using Anti-GD2 ch14.18/CHO Antibody with Vy9V82+ y&T Cells," OncoImmunology, vol. 5(1), pp. e1025194, (2016).
Gertner-Dardenne, J et al., "Bromohydrin pyrophosphate enhances antibody-dependent cell-mediated cytotoxicity induced by therapeutic antibodies," Blood 113(20): 4875-4884, (2009).
Poonia, B. and C. D. Pauza, "Gamma delta T cells from HIV+ donors can be expanded in vitro by zoledronate/interleukin-2 to become cytotoxic effectors for antibody-dependent cellular cytotoxicity," Cytotherapy 14(2): 173-181, (2012).
Schiller, C. B. et al., "CD19-Specific Triplebody SPM-1 Engages NK and yδ T Cells for Rapid and Efficient Lysis of Malignant B-Lymphoid Cells," Oncotarget, vol. 7(50), pp. 83392-83408, (2016).
Tokuyama, H. et al., "Vy9Vδ2 T Cell Cytotoxicity Against Tumor Cells is Enhanced by Monoclonal Antibody Drugs—Rituximab and Trastuzumab," Int J Cancer, vol. 122(11), pp. 2526-2534, (2008).
Zufferey et al., "Self-Inactivating Lentivirus Vector for Safe and Efficient In Vivo Gene Delivery," Journal of Virology, vol. 72(12), pp. 9873-9880, (1998).
Ostertag et al., "Brain Tumor Eradication and Prolonged Survival from Intratumoral Conversion of 5-Fluorocytosine to 5-fluorouracil Using a Nonlytic Retroviral Replicating Vector," Neoro-Oncology 14(2), pp. 145-159, Feb. 2012.

(56) References Cited

OTHER PUBLICATIONS

Twitty et al., "Retroviral Replicating Vectors Deliver Cytosine Deaminase Leading to Targeted 5-Fluorouracil-Mediated Cytotoxicity in Multiple Human Cancer Types," Human Gene Therapy Methods, 27(1), pp. 17-31, Feb. 1, 2016.
Charron et al., "Dominant-Negative Interference in the Pahenu2 Mouse Model of PKU: Effectiveness of Vectors Expressing Either Modified Forms of Phenylalanine Hydroxylase (PAH) or Ribozymes Plus a Hardened PAH mRNA," Molecular Therapy, vol. 11, pp. S163-S164, (2005).
Fusetti, et al., "Structure of Tetrameric Human Phenylalanine Hydroxylase and Its Implications for Phenylketonuria," J. Bio. Chem., vol. 273, No. 27, pp. 16962-16967 (1998).
Hafid et al., "Phenylketonuria: A Review of Current and Future Treatments," Translational Pediatrics, vol. 4(4), pp. 304-317, (2015).
Blau et al., "Phenylketonuria," The Lancet, vol. 376(9750), pp. 1417-1427, (2010).
Chandler et al., "Vector Design Influences Hepatic Genotoxicity After Adeno-Associated Virus Gene Therapy," Journal of Clinical Investigation, vol. 125(2), pp. 870-880, (2015).
Christophersen et al., "A Technique of Transumbilical Portal Vein Catheterization in Adults," The Archives of Surgery, vol. 95(6), pp. 960-963, (1967). (Abstract Only).
Bartholome, "Genetics and Biochemistry of the Phenylketonuria-Present State," Human Genetics, vol. 51(3), pp. 241-245, (1979).
Donsante et al., "AAV Vector Integration Sites in Mouse Hepatocellular Carcinoma," Science, vol. 317(5837, p. 477, (2007).
Eisensmith et al., "Multiple Origins for Phenylketonuria in Europe," American Journal of Human Genetics, vol. 51(6), pp. 1355-1365, (1992).
Fisher et al., "The Inhibition of Phenylalanine and Tyrosine Hydroxylases by High Oxygen Levels," Journal of Neurochemistry, vol. 19(5), pp. 1359-1365, (1972). (Abstract Only).
Grisch-Chan et al., "Low-Dose Gene Therapy for Murine PKU Using Episomal Naked DNA Vectors Expressing PAH from Its Endogenous Liver Promoter," Molecular Therapy Nucleic Acids, vol. 7, pp. 339-349, (2017).
Guldberg et al., "Aberrant Phenylalanine Metabolism in Phenylketonuria Heterozygotes," Journal of Inherited Metabolic Disease, vol. 21(4), pp. 365-372, (1998).
Kaufman et al., "A Model of Human Phenylalanine Metabolism in Normal Subjects and in Phenylketonuric Patients," Proceedings of the National Academy of Sciences USA, vol. 96(6), pp. 3160-3164, (1999).
Kaufman et al., "Phenylalanine Hydroxylase Activity in Liver Biopsies from Hyperphenylalaninemia Heterozygotes: Deviation from Proportionality with Gene Dosage," Pediatric Research, vol. 9(8), pp. 632-634, (1975).
Longo et al., "Single-Dose, Subcutaneous Recombinant Phenylalanine Ammonia Lyase Conjugated with Polyethylene Glycol in Adult Patients with Phenylketonuria: An Open-Label, Multicentre, Phase 1 Dose-Escalation Trial, " The Lancet, vol. 384(9937), pp. 37-44, (2014).
Mochizuki et al., "Long-Term Correction of Hyperphenylalaninemia by AAV-Mediated Gene Transfer Leads to Behavioral Recovery in Phenylketonuria Mice," Gene Therapy, vol. 11(13), pp. 1081-1086, (2004).
Nault et al., "Adeno-Associated Virus Type 2 as an Oncogenic Virus in Human Hepatocellular Carcinoma," Molecular & Cellular Oncology, vol. 3(2), p. e1095271, (2016).
Oh et al., "Reversal of Gene Expression Profile in the Phenylketonuria Mouse Model After Adeno-Associated Virus Vector-Mediated Gene Therapy," Molecular Genetics and Metabolism, vol. 86(Supp. 1), pp. S124-132, (2005).
Oh et al., "Long-Term Enzymatic and Phenotypic Correction in the Phenylketonuria Mouse Model by Adeno-Associated Virus Vector-Mediated Gene Transfer," Pediatric Research, vol. 56(2), pp. 278-284, (2004).
Pan et al., "Biodistribution and Toxicity Studies of VSVG-Pseudotyped Lentiviral Vector After Intravenous Administration in Mice with the Observation of in Vivo Transduction of Bone Marrow," Molecular Therapy, vol. 6(1), pp. 19-29, (2002).
Shedlovsky et al., "Mouse Models of Human Phenylketonuria," Genetics, vol. 134(4), pp. 1205-1210, (1993).
Yagi et al., "Complete Restoration of Phenylalanine Oxidation in Phenylketonuria Mouse by a Self-Complementary Adeno-Associated Virus Vector," Journal of Gene Medicine, vol. 13(2), pp. 114-122, (2011).
Yano et al., "Evaluation of Tetrahydrobiopterin Therapy with Large Neutral Amino Acid Supplementation in Phenylketonuria: Effects on Potential Peripheral Biomarkers, Melatonin and Dopamine, for Brain Monoamine Neurotransmitters," PLoS One, vol. 11(8), p. e0160892, (2016).
Mason et al., "Inactivated Simian Immunodeficiency Virus-Pulsed Autologous Fresh Blood Cells as an Immunotherapy Strategy," Journal of Virology, vol. 83(3), pp. 1501-1510, (2009).
Blick et al., "Cyclophosphamide Enhances SB-728-T Engraftment to Levels Associated with Hiv-RNA Control," CROI Conference on Retroviruses and Opportunistic Infections, Boston, Massachusetts, p. 141, (2014), (Abstract Only).
De Rose et al., "Safety, Immunogenicity and Efficacy of Peptide-Pulsed Cellular Immunotherapy in Macaques," Journal of Medical Primatology, vol. 27(2), pp. 69-78, (2008).
Smith et al., "Developments in HIV-1 Immunotherapy and therapeutic Vaccination," F1000Prime Reports, vol. 6, p. 42, (2014).
Charron, "Gene Therapy for Phenylketonuria: Dominant-Negative Interference in a Recessive Disease," Dissertation, University of Florida 2005, http://etd.fcla.edu/UF/UFE0011392/charron_c.pdf>, (retrieved Jul. 26, 2018) (2005).
Ding et al., "Administration-Route and Gender-Independent Longterm Therapeutic Correction of Phenylketonuria (PKU) in a Mouse Model by Recombinant Adeno-Associated Virus 8 Pseudotyped Vector-Mediated Gene Transfer," Gene Therapy, vol. 13, pp. 583-587, (Dec. 1, 2005).
Nowacki et al., "The PAH Mutation Analysis Consortium Database: Update 1996," Nucleic Acid Research, vol. 25(1), pp. 139-142, (Jan. 1, 1997).
Condiotti et al., "Prolonged Liver-Specific Transgene Expression by a Non-Primate Lentiviral Vector," Biochemical and Biophysical Research Communications, vol. 320(3), pp. 998-1006, (Jul. 30, 2004).
Wang et al., "Butyrophilin 3A1 Plays an Essential Role in Prenyl Pyrophosphate Stimulation of Human Vg2Vd2 T Cells," Journal of Immunology, vol. 191(3), pp. 1029-1042, (Jul. 5, 2013).
Jiang et al., "A Novel EST-Derived RNAi Screen Reveals a Critical Role for Farnesyl Diphosphate Synthase in Beta2-Adrenergic Receptor Internalization and Down-Regulation," FASEB Journal, vol. 26(5), pp. 1-13, (Jan. 25, 2012).
Miettinen et al., "Mevalonate Pathway Regulates Cell Size Homeostasis and Proteostasis Through Autophagy," Cell Reports, vol. 13(11), pp. 2610-2620, (Dec. 2015).
Tolmachov, "Designing Lentiviral Gene Vectors," Viral Gene Therapy, Chapter 13, pp. 263-284, (2011).
Tracey, "Human DNA Sequence from Clone RP1-288M22 on Chromosome 6q 12-13," Complete Sequence, National Center for Biotechnology. GenBank Entry. Retrieved from the internet: <https://www.ncbi.nlm.nih.gov/nucleotide/AL035467.23?report=genbank&log$=nucltop&blast_rank=1&RID=UUD4GX2D014>; pp. 1-34, (Jan. 24, 2013).
Gorziglia et al., "Elimination of Both E1 and E2A from Adenovirus Vectors Further Improves Prospects for In Vivo Human gene Therapy," Journal of Virology, vol. 70(6), pp. 4173-4178, (1996).
Vargas et al., "Novel Integrase-Defective Lentiviral Episomal Vectors for Gene Transfer," Human Gene Therapy, vol. 15(4), pp. 361-372, (Apr. 2004).
Wendelburg et al., "An Enhanced EBNA1 Variant with reduced IR3 Domain for Long-Term Episomal Maintenance and Transgene Expression of ORIP-Based Plasmids in Human Cells," Gene Therapy, vol. 5, pp. 1389-1399, (Oct. 1998).
Westerhout et al., "A Conditionally Replicating HIV-Based Vector that Stably Expresses an Antiviral shRNA Against HIV-1 Replication," Molecular Therapy: The Journal of the American Society of Gene Therapy, vol. 14(2), pp. 268-275, (May 2006).

(56) References Cited

OTHER PUBLICATIONS

Lam et al., "T-Cell Therapies for HIV," Immunotherapy, Future Medicine, vol. 5(4), pp. 407-414, (Apr. 2013).
Munoz et al., "Ex Vivo Expansion and Lentiviral Transduction of Macaca Nemestrina CD4 + T Cells," Journal of Medical Primatology, vol. 38(6), pp. 438-443, (Dec. 2009).
Porichis et al., "HIV-Specific CD4 T Cells and Immune Control of Viral Replication," Current Opinion in HIV and Aids, vol. 6(3), pp. 174-180, (May 2011).
Kavanagh et al., "Expansion of HIV-Specific CD4+ and CD8+ T Cells by Dendritic Cells Transfected with mRNA Encoding Cytoplasm- or Lysosome- Targeted Nef," Blood, American Society of Hematology, vol. 107(5), pp. 1963-1969, (Mar. 2006).
Akinsheye et al., "Fetal Hemoglobin in Sickle Cell Anemia," Blood, vol. 118(1), pp. 19-27, (2011).
Lin et al., "Up-Regulation of Bcl-2 is Required for the Progression of Prostate Cancer Cells from an Androgen-Dependent to an Androgen-Independent Growth Stage," Cell Research, vol. 17, pp. 531-536, (2007).
GenBank Sequence M65141.1 Retrieved from the Internet <URL: https://www.ncbi.ntm.nih.gov/nuccore/M65141.1. Especially Sequence, nt 301-420, (Retrieved Mar. 31, 2019).
PCT: International Search Report dated Nov. 7, 2016 in Application No. PCT/US2016/036519.
PCT: Written Opinion dated Nov. 7, 2016 in Application No. PCT/US2016/036519.
PCT: International Search Report dated Oct. 19, 2016 in Application No. PCT/US2016/041456.
PCT: Written Opinion dated Oct. 19, 2016 in Application No. PCT/US2016/041456.
PCT: International Search Report dated Jul. 20, 2017 in Application No. PCT/US2017/043157.
PCT: Written Opinion dated Jul. 20, 2017 in application No. PCT/US2017/043157.
PCT: International Search Report dated Jun. 9, 2017 in Application No. PCT/US2016/066185.
PCT: Written Opinion dated Jun. 9, 2017 in Application No. PCT/US2016/066185.
PCT: International Search Report dated Jul. 17, 2017 in Application No. PCT/US2017/013019.
PCT: Written Opinion dated Jul. 17, 2017 in Application No. PCT/US2017/013019.
PCT: International Search Report dated May 26, 2017 in Application No. PCT/US2017/013399.
PCT: Written Opinion dated May 26, 2017 in Application No. PCT/US2017/013399.
PCT: International Search report dated Aug. 25, 2017 in Application No. PCT/US2017/021639.
PCT: Written Opinion dated Aug. 25, 2017 Application No. PCT/US2017/021639.
PCT: International Search Report dated Nov. 8, 2017 Application No. PCT/US2017/041168.
PCT: Written Opinion dated Nov. 8, 2017 in Application No. PCT/US2017/041168.
PCT: International Search Report dated Dec. 15, 2017 in Application No. PCT/US2017/36433.
PCT: Written Opinion dated Dec. 15, 2017 in Application No. PCT/US2017/36433.
PCT: International Search Report date Jul. 14, 2017 in Application No. PCT/US2017/013024.
PCT: Written Opinion dated Jul. 14, 2017 in application No. PCT/US2017/013024.
PCT: International Search Report dated May 29, 2018 in Application No. PCT/US2018/012998.
PCT: Written Opinion dated May 29, 2018 in Application No. PCT/US2018/012998.
PCT; International Search Report dated Sep. 24, 2018 in Application No. PCT/US2018/025733.
PCT; Written Opinion dated Sep. 24, 2018 in Application No. PCT/US2018/025733.
PCT; International Search Report dated Nov. 9, 2018 in Application No. PCT/US2018/037924.
PCT; Written Opinion dated Nov. 9, 2018 in Application No. PCT/US2018/037924.
PCT; Invitation to Pay Additional Fees in Application No. PCT/US2018/053919 dated Feb. 22, 2019.
PCT; Written Opinion dated Apr. 12, 2019 in Application No. PCT/US2018/053919.
PCT; International Search Report dated Apr. 12, 2019 in Application No. PCT/ US2018/053919.
USPTO; Notice of Allowance dated Oct. 13, 2017 in U.S. Appl. No. 14/706,481.
USPTO; Requirement for Restriction dated Oct. 23, 2017 in U.S. Appl. No. 15/668,223.
USPTO; Notice of Allowance dated Nov. 2, 2017 in U.S. Appl. No. 15/652,080.
USPTO; Non-Final Office Action dated Feb. 22, 2018 in U.S. Appl. No. 15/850,937.
USPTO; Non-Final Office Action dated Feb. 22, 2018 in U.S. Appl. No. 15/849,062.
USPTO; Non-Final Office Action dated Feb. 22, 2018 in U.S. Appl. No. 13/333,882.
USPTO; Notice of Allowance dated Mar. 26, 2018 in U.S. Appl. No. 15/668,223.
USPTO; Notice of Allowance dated Apr. 23, 2018 in U.S. Appl. No. 15/850,937.
USPTO; Notice Allowance dated Apr. 26, 2018 in U.S. Appl. No. 15/849,062.
USPTO; Requirement for Restriction dated Jul. 12, 2018 in U.S. Appl. No. 15/736,284.
USPTO; Invitation to Pay Additional Fees And, Where Applicable, Protest Fee dated Jul. 17, 2018 in Application No. PCT/US2018/25733.
USPTO; Requirement for Restriction dated Aug. 3, 2018 in U.S. Appl. No. 16/011,550.
USPTO; Non-Final Office Action dated Jun. 15, 2018 in U.S. Appl. No. 15/904,131.
USPTO; Notice of Allowance dated Aug. 10, 2018 in U.S. Appl. No. 15/904,131.
USPTO; Final Office Action dated Aug. 27, 2018 in U.S. Appl. No. 13/333,882.
USPTO; Non-Final Office Action dated Sep. 19, 2018 in U.S. Appl. No. 16/011,550.
USPTO; Invitation to Pay Additional Fees And, Where Applicable, Protest Fee dated Sep. 11, 2018 in Application No. PCT/US2018/37924.
USPTO; Non-Final Office Action dated Oct. 19, 2018 in U.S. Appl. No. 15/736,284.
USPTO; Notice of Allowance dated Oct. 31, 2018 in U.S. Appl. No. 16/011,550.
USPTO; Advisory Action dated Nov. 16, 2018 in U.S. Appl. No. 13/333,882.
USPTO; Non-Final Office Action dated Dec. 31, 2018 in U.S. Appl. No. 16/182,443.
USPTO; Non-Final Office Action dated Apr. 18, 2019 in U.S. Appl. No. 13/333,882.
USPTO; Final Office Action dated May 2, 2019 in U.S. Appl. No. 15/736,284.
USPTO; Final Office Action dated May 2, 2019 in U.S. Appl. No. 16/182,443.
USPTO; Non-Final Office Action dated May 7, 2019 in U.S. Appl. No. 16/008,991.
USPTO; Non-Final Office Action dated May 16, 2019 in U.S. Appl. No. 16/132,247.
USPTO; Non-Final Office Action dated May 24, 2019 in U.S. Appl. No. 16/218,010.
EPO; Extended Search Report dated Dec. 12, 2018 in EP Application No. 16808223.8.
EPO; Extended Search Report dated Dec. 11, 2018 in EP Application No. 16822021.8.
EPO; Extended Search Report dated Jun. 6, 2019 in EP Application No. 17739028.3.

(56) References Cited

OTHER PUBLICATIONS

EP Office Action in European Application No. 18736295, dated Jan. 25, 2023, 10 pages.
US Final Office Action in U.S. Appl. No. 16/312,056, dated Jan. 31, 2023, 36 pages.
[Online], "CD4+ T Cell Isolation Kit Human," Miltenyi Biotec, published online in 2015, 3 pages.
AU Office Action in Australian Application No. 2018205388, dated Mar. 3, 2023, 5 pages.
JP Office Action in Japanese Application No. 2020-551499, dated Mar. 10, 2023, 10 pages (with English translation).
Anderson et al., Safety and Efficacy of a Lentiviral Vector Containing Three Anti-HIV Genes-CCR5 Ribozyme, Tat-Rev siRNA, and TAR Decoy-in SCID-hu Mouse-Derived T Cells, Mol. Ther., vol. 15, pp. 1182-1188,2007.
JP Notice of Allowance in Japanese Application No. 2019-536901, dated Mar. 3, 2023, 6 pages (with English translation).
JP Office Action in Japanese Application No. 2021-084813, dated Feb. 10, 2023, 10 pages (with English translation).
Kretova et al., Generation of Genetic Constructs that Simultaneously Express Several shRNAs, Biotechniques, vol. 52, 3 pages, 2012.
Spanevello et al., "Combinatorial RNA Interference as a Gene Therapy Strategy for HIV-1 Infection," Retrovirology, vol. 10, 2013.
Office Action for Japanese Patent Application No. 2022133225, mailed Jun. 26, 2023, 10 Pages.
AU, Examination Report issued in Application No. 2021200210 on Jul. 13, 2023, 3 pages.
Chavez L., et al., "HIV Latency Is Established Directly and Early in Both Resting and Activated Primary CD4 T Cells," PLoS Pathogens, Jun. 11, 2015, vol. 11, No. 6, e1004955, 21 Pages.
Curriu M., et al., "Viremic HIV Infected Individuals with High CD4 T Cells and Functional Envelope Proteins Show Anti-gp41 Antibodies with Unique Specificity and Function," PLoS ONE, Feb. 2012, vol. 7, No. 2, e30330, 11 Pages.
Davis-Gardner M.E., et al., "eCD4-Ig promotes ADCC activity of sera from HIV-1-infected patients", Department of Immunology and Microbiology, The Scripps Research Institute, PLOS Pathogen, Dec. 18, 2017, 19 Pages, Retrieved from URL: https://doi.org/10.1371/journal.ppat.1006786.
Office Action for Japanese Patent Application No. 2021174409, mailed Apr. 25, 2023, 13 pages.
Office Action for U.S. Appl. No. 16/476,529, mailed Dec. 23, 2022, 65 pages.
Rana S., et al., "Role of CCR5 in Infection of Primary Macrophages and Lymphocytes by Macrophage-Tropic Strains of Human Immunodeficiency Virus: Resistance to Patient-Derived and Prototype Isolates Resulting from the delta ccr5 Mutation," Journal of Virology, Apr. 1997, vol. 71, No. 4, pp. 3219-3227.
Japan Office Action dated Apr. 4, 2023 issued in Application No. 2022-071538.
Canada; Office Action dated May 17, 2023 issued in Application No. 3028982.
Korea; Office Action dated Apr. 21, 2023 issued in Application No. 10-2019-7023287.
CN Office Action in Chinese Application No. 201880016715, dated Nov. 15, 2022, 13 pages (with English translation).
EP Office Action in European U.S. Appl. No. 18/736,295, dated Dec. 20, 2022, 10 pages.
IL Office Action in Application No. 266188.3, dated Nov. 21, 2022, 6 pages.
JP Office Action in Japanese Application No. 2021-174409, dated Nov. 7, 2022, 4 pages (with English translation).
JP; Office Action issued in Application No. 2022-071538 on Dec. 21, 2023.
CA; Office Action issued in Application No. 3048634 on Jan. 11, 2024.
CN; Office Action issued in Application No. 201880016715.2 on Jan. 23, 2024.
JP; Office Action issued in Application No. 2021-174409 on Jan. 17, 2024.
CN; Office Action issued in Application No. 201880016715.2 on Sep. 21, 2023.
KR; Office Action issued in Application No. 10-2023-7020872 on Sep. 26, 2023.
KR; Office Action issued in Application No. 10-2019-7023287 on Oct. 11, 2023.
Prebensen et al., "Regulation of Gag- and Env-Specific CD8* T Cell Responses in ART-Naïve HIV-Infected Patients: Potential Implications for Individualized Immunotherapy," PloS ONE 9(12), e115241, pp. 1-13, Dec. 2014.
Lam et al., "Broadly-Specific Cytotoxic T Cells Targeting Multiple HIV Antigens Are Expanded From HIV+ Patients: Implications for Immunotherapy," Molecular Therapy, vol. 23, No. 2, pp. 387-295. Feb. 2015.
US; Office Action issued in U.S. Appl. No. 17/042,043 on Dec. 6, 2023.
JP; Office Action issued in Application No. 2021-84813 on Oct. 31, 2023.
JP; Office Action issued in Application No. 2020-551499 on Nov. 22, 2023.
JP; Office Action issued in Application No. 2022-189475 on Oct. 10, 2023.
Altschul S.F., et al. "Basic Local Alignment Search Tool," Journal Molecular Biology. Oct. 5, 1990; 215(3):403-10.
Altschul, S.F. et al., "Gapped BLAST and Psi-Blast: A New Generation of Protein Database Search Programs," Nucleic Acids Research. Sep. 1, 1997; 25(17):3389-402.
Bancroft J.D., et al. "Characterization of the Alu-rich 5'-flanking Region of the Human Prothrombin-Encoding Gene: Identification of a Positive Cis-acting Element That Regulates Liver-Specific Expression," Gene. Nov. 15, 1990;95(2):253-60.
Berge et al. "Pharmaceutical Salts" Jan. 1977, Journal of Pharmaceutical Sciences, 66(1):1-19.
Boden et al. "Promoter choice affects the potency of HIV-1 specific RNA interference", Nucleic Acids Research. Sep. 1, 2003; 31(17):5033-5038.
Broad Institute, "Gene: Human PARP1 (142)," GPP Web Portal, Sep. 16, 2019 [online]. Retrieved from: https://portals.broadinstitute.org/gpp/public/gene/details?geneId=142; 2 pages.
Bulla, G.A. et al. "Genome-wide analysis of hepatic gene silencing in hepatoma cell variants", Genomics, Sep. 2012; 100(3):176-183.
Ceska et al., "The X-ray structure of an atypical homeodomain present in the rat liver transcription factor LFB1/HNF1 and implications for DNA binding," EMBO J., 1993; 12(5):1805-1810.
Chen H.C., et al. "An Unconventional TRAIL to Cancer Therapy," European Journal of Immunology. Dec. 2013; 43(12):3159-3162.
Cheng M., et al. "Establishment, Characterization, and Successful Adaptive Therapy Against Human Tumors of NKG Cell, a New Human NK Cell Line", Cell Transplantation, 2011; 20(11-12):1731-1746.
Chow et al. "Characterization of a Novel Liver-specific Enhancer in the Human Prothrombin Gene", The Journal of Biological Chemistry, Oct. 5, 1991; 266(28):18927-18933.
Clontech Laboratories, Inc., "High-Efficiency Lentiviral Packaging System," Product Overview. Clontechniques, Jan. 2008, pp. 8-9 [online]. Retrieved from URL: https://catalog.takara-bio.co.jp/PDFFiles/200802_08.pdf.
Clontech Laboratories, "pLVX-shRNA1 Vector Information," PT4051-5 Catalog No. 632177. PR852544, Jul. 15, 2008, Retrieved from the Internet: http://www.takara.eo.kr/file/manual/pdf/PT4051-5.pdf, 3 pages.
Decision of Refusal for Japanese Application No. 2022-189475 mailed Feb. 22, 2024, with English translation, 2 pages.
Devereux et al. "A comprehensive set of sequence analysis programs for the VAX" Nucleic Acids Research 12(1):387-395 (Jan. 11, 1984).
Dorsey, E.R. et al., "Projected No. of people with Parkinson disease in the most populous nations, 2005 through 2030", Neurology, Jan. 30, 2007;68(5):384-386.

(56) References Cited

OTHER PUBLICATIONS

Eberling, et al., "Results from a phase I safety trial of hAADC gene therapy for Parkinson disease", Neurology, May 2, 20080; 70(21):1980-1993. Epub Apr. 9, 2008.
Erdelyi K., et al. "Dual Role of Poly(ADP-ribose) Glycohydrolase in the Regulation of Cell Death in Oxidatively Stressed A549 cells," FASEB Journal, Oct. 2009;23(10):3553-3563.
Flotte et al. "Phase I trial of intramuscular injection of a recombinant adeno-associated virus alpha 1-antitrypsin (rAAV2-CB-hAAT) gene vector to AAT-deficient adults". Hum Gene Ther. Jan. 2004; 15(1): 93-128.
Friedman et al., "Cloning and characterization of cyclophilin C-associated protein: a candidate natural cellular ligand for cyclophilin C," PNAS, Jul. 1993, 90:6815-6819.
Fujiwara et al. "A Nucleolar Stress-Specific p53-miR-101 Molecular Circuit Functions as an Intrinsic Tumor-Suppressor Network", EBioMedicine Jul. 2018: 33:33-48.
Gagniuc et al. "Eukaryotic genomes may exhibit up to 10 generic classes of gene promoters," BMC Genomics, Sep. 28, 2012:13:512, 16 pages.
GenBank Accession No. AB236435.1, "Cloning vector p3216PCbeta DNA, complete genome," Sep. 15, 2007 [online]. Retrieved from: www.ncbi.nlm.nih.gov/nuccore/AB236435; 5 pages.
GenBank Accession No. K03020, Human phenylalanine hydroxylase mRNA, complete cds, Jan. 7, 1995 [online]. Retrieved from: https://www.ncbi.nlm.nih.gov/nuccore/K03020.1?report=gbwithparts&log$=seqview; 3 pages.
GenBank Accession No. M65141.1, "Human Prothrombin Gene Liver-specific Enhancer," NCBI, Nucleotide Database, Apr. 1993, 1 page [online]. [Retrieved on Mar. 31, 2019] Retrieved from URL: https://www.ncbi.ntm.nih.gov/nuccore/M65141.1.
GenBank Accession No. NM_001354304.2, "*Homo sapiens* phenylalanine hydroxylase (PAH), transcript variant 2, mRNA," Oct. 12, 2024; National Library of Medicine, NCBI. Retrieved from: https://www.ncbi.nlm.nih.gov/nuccore/NM_001354304, 7 pages.
GenBank Accession No. NP_001341233, "phenylalanine-4-hydroxylase [*Homo sapiens*]," Oct. 12, 2024; National Library of Medicine, NCBI. Retrieved from: https://www.ncbi.nlm.nih.gov/protein/NP_001341233; 4 pages.
GenBank Accession No. U49897.1 "*Homo sapiens* phenylalanine hydroxylase (PAH) mRNA, complete cds" Oct. 2, 1997 [online]. Retrieved from: https://www.ncbi.nlm.nih.gov/nuccore/2462721, 2 pages.
Gennaro A.R., Remington's Pharmaceutical Sciences, 17th Edition. Mack Publishing Company, Easton, PA., 1985 [Review]. Journal of Pharmaceutical Sciences, Oct. 1985; 74(10):1143-1144.
Grisch-Chan et al., "State-of-the-Art 2019 on Gene Therapy for Phenylketonuria," Human Gene Therapy, Oct. 1, 2019; 30(10):1274-1283.
Harding C.O., et al. "Complete Correction of Hyperphenylalaninemia Following Liver-directed, Recombinant AAV2/8 Vector-mediated Gene Therapy In Murine Phenylketonuria," Gene Therapy, Mar. 2006;13(5):457-462.
Hedley, "Gene therapy of chronic inflammatory disease.", Advanced Drug Delivery Reviews, Nov. 15, 2000; 44(2-3):195-207.
Hellstrom M., et al. "Cellular Tropism and Transduction Properties of Seven Adena-Associated Viral Vector Serotypes in Adult Retina After Intravitreal Injection," Gene Therapy, Apr. 2009; 16(4):521-532.
Hermodson, M., Current Protocols in Protein Science. J.E. Coligan et al. (Eds.) New York: Wiley, 1995 [Review]. PROTEINS: Structure, Function, and Genetics. 1996;24:409, 1 page.
Herrera et al. "Adult peripheral blood and umbilical cord blood NK cells are good sources for effective CAR therapy against CD19 positive leukemic cells", Scientific Reports, Dec. 10, 2019;9(1):18729, 10 pages.
Hirsch-Behnam, A. et al., "A comparative sequence analysis of two human papillomavirus (HPV) types 2a and 57," Virus Res. Dec. 1990;18(1):81-97. doi: 10.1016/0168-1702(90)90091-0.
Ho, et al. "Phenylketonuria: Translating Research into Novel Therapies," Translational Pediatrics, Apr. 2014; 3(2):49-62.
Ho et al. "Synthetic Protein Transduction Domains: Enhanced Transduction Potential in Vitro and in Vivo.", Cancer Research, Jan. 15, 2001;61(2):474-477.
Hui Y., et al. "Construction of PARP-1 Gene Silencing Cell Lines by Lentiviral-Mediated RNA Interference Technology," Journal of Environmental Health, Apr. 2014; (31):288-291, English abstract only, 1 page.
Invitation to Pay Additional fees for International Application No. PCT/US2018/012998 mailed Apr. 2, 2018, 2 pages.
Kaalund S.S., et al. "Untreated Patients Dying With AIDS have Loss of Neocortical Neurons and Glia Cells," Frontiers in Neuroscience, Jan. 15, 2020; 13:1398, 10 pages.
Kaplitt et al., "Safety and tolerability of gene therapy with an adeno-associated virus (AAV) borne GAD gene for Parkinson's disease: an open label, phase I trial," Lancet, Jun. 2, 20073;369(9579):2097-2105.
Kaur, S. et al., "Thrombospondin-1 signaling through CD47 inhibits self-renewal by regulating c-Myc and other stem cell transcription factors." Scientific Reports, 2013;3:1673, DOI:10.1038/srep01673, 12 pages.
Kopin and Markey, "Mptp toxicity: implications for research in Parkinson's disease", Annu. Rev. Neurosci, 1988; 11:81-96.
Lü, X. et al. "A novel amplification method of γδT cells," Chinese Journal of Immunology, Aug. 20, 2011; 8:739-747, doi: 10.3969/j.issn.1000-484X.2011.08.014 (Chinese with English abstract on p. 739).
Lafountaine J.S., et al. "Delivery and Therapeutic Applications of Gene Editing Technologies ZFNs, TALENs, and CRISPR/Cas9," International Journal of Pharmaceutics, Oct. 15, 2015; 494(1):180-194.
Li, Z et al., "Amplification of γδT cells in PBMCs of healthy donors and osteosarcoma patients stimulated by zoledronate," Chinese Journal of Cell and Molecular Immunology, Aug. 18, 2012; 28(8):822-824, DOI:10.13423/j.cnki.cjcmi.006529. (Chinese with English Abstract on p. 822).
Lichter-Koneck, U. and J. Vockley, "Phenylketonuria: Current Treatments and Future Developments," Drugs. Apr. 2019; 79:495-500.
Lin, et al. "Clinical Effects of Intra-arterial Infusion Chemotherapy with Cisplatin, Mitomycin C, Leucovor and 5-Fluorouracil for Unresectable Advanced Hepatocellular Carcinoma", J. Chin. Med. Assoc., Dec. 2004;67(12):602-610.
Liou, M-L. et al. "Reducing farnesyl diphosphate synthase levels activates Vγ9Vδ2 T cells and improves tumor suppression in murine xenograft cancer models", Front Immunol. Oct. 5, 2022:13:1012051, 15 pages.
List, H.-J. et al. "Methylation sensitivity of the enhancer from the human papillomavirus type 16", J Biol Chem. Apr. 22, 1994; 269(16):11902-11.
Liu F., et al. "Effects of Poly (ADP-ribose) Polymerase- 1 (PARP-1) Inhibition on Sulfur Mustard- Induced Cutaneous Injuries in Vitro and in Vivo", PeerJ, Apr. 4, 2016; 4:e1890, 30 pages.
Liu, N. et al. "Prenatal diagnosis of Chinese families with phenylketonuria," Genetics and Molecular Research. 2015; 14(4):14615-14628.
Ma et al. "Pol III Promoters to Express Small RNAs: Delineation of Transcription Initiation", Molecular Therapy-Nucleic Acids, May 6, 2014; 3(5):e161, 11 pages.
Mandir A.S., et al. "Poly (ADP-ribose) Polymerase Activation Mediates 1-methyl-4-phenyl-1, 2,3,6- tetrahydropyridine (MPTP)-induced Parkinsonism," Proceedings of the National Academy of Sciences of the United States of America, May 11, 1999;96(10):5774-5779.
Marks, JR. et al., "Gene delivery of AAV2-neurturin for Parkinson's disease: a double-blind, randomised, controlled trial," Lancet Neurol. Dec. 2010; 9(12):1164-1172.
Martin, K.A. et al., "Global Transcriptome Analysis Reveals That Poly(ADP-Ribose) Polymerase 1 Regulates Gene Expression through EZH2," Molecular and Cellular Biology, Dec. 2015; 35(23):3934-3944.
Mensali, N. et al. "NK Cells Specifically TCR-dressed to Kill Cancer Cells", EBioMedicine, Feb. 2019:40:106-117.

(56) References Cited

OTHER PUBLICATIONS

Miyoshi, H., "Transduction of hematopoietic stem cells by lentiviral vectors," Virus, 2002; 52(2):225-231 (Japanese with English Abstract, 1 page).
Mäkinen et al. "Stable RNA interference: comparison of U6 and H1 promoters in endothelial cells and in mouse brain", J Gene Med. Apr. 2006;8(4):433-441.
Muvarak, N. et al. "Safety and durability of AGT103-T autologous T cell therapy for HIV infection in a Phase 1 trial", Front Med. Nov. 14, 2022:9:1044713, DOI: 10.3389/fmed.2022.1044713, 12 pages.
Myburgh, R. et al. "Optimization of Critical Hairpin Features Allows miRNA-based Gene Knockdown Upon Single-copy Transduction", Mol Ther Nucleic Acids. Oct. 28, 2014;3(10):e207; 13 pages.
Myers and Miller "Optimal alignments in linear space," CABIOS, Mar. 1988;4(1):11-17.
Nakahara et al. "Regulation of Human Papillomavirus (HPV) Genome Replication in the Viral Life Cycle and Its Association with the Viral Persistence and Cancer Development," Virus, 2014; 64(1):57-66. (Japanese; English abstract on p. 65).
Needleman et al., "A General Method Applicable to the Search for Similarities in the Amino Acid Sequence of Two Proteins," Journal of Molecular Biology, 1970, vol. 48, pp. 443-453.
Nie, J. "DNA Repair Proteins Metnase and PARP1 Regulate DNA Integration," 2000-2019—CSU Theses and Dissertations [online]. 2015, Chapter 3; p. 95-141. Retrieved from: http://hdl.handle.net/10217/1898; on May 23, 2021, 49 pages.
Nielsen et al. "Lentiviral RNAi-Vectors Utilizing Pol II-Promoters for Use in the Brain," Molecular Therapy, May 2007; 15(1):S270, Abstract 705, 1 page.
Notice of Reasons for Refusal for Japanese Application No. 2019-536901 mailed Jan. 20, 2023, with English translation, 6 pages.
Notice of Reasons for Refusal for Japanese Application No. 2022-189475 mailed Jun. 4, 2024, with English translation, 17 pages.
O'connor, M. et al., "Transcription Factor Binding Sites in the Long Control Region of Genital HPVs," In Human Papillomaviruses; 1995 compendium, part III-A; Los Alamos National Laboratory: Los Alamos, NM, USA, 1995; pp. 21-40. Retrieved from the Internet: https://pave.niaid.nih.gov/lanl-archives/compendium/95PDF/3/oconnor.pdf.
Office Action for Israel Patent Application No. 267794, mailed Nov. 21, 2022, 11 pages.
Ory, B, et al. "Farnesyl diphosphate synthase is involved in the resistance to zoledronic acid of osteosarcoma cells." J. Cell. Mol. Med. Jun. 2008;12(3):928-941.
Pauza et al. "δ T cells in HIV disease: past, present, and future," Frontiers in Immunol., Jan. 30, 2015:5:687, 12 pages.
Pauza et al. "Evolution and function of the TCR Vgamma9 chain repertoire: It's good to be public," Cell Immunol., Jul. 2015;296(1):22-30.
Pearson et al. "Improved tools for biological sequence comparison," Proc. Nat'l. Acad. Sci., Apr. 1988;85(8):2444-2448.
Peng et al. Retroviral-mediated gene transfer and expression of human phenylalanine hydroxylase in primary mouse hepatocytes, Proc. Natl. Acad. Sci. USA, Nov. 1988; 85(21):8146-8150.
Przedborski, S. et al. "Role of neuronal nitric oxide in 1-methyl-4-phenyl-1,2,3,6-tetrahydropyridine (MPTP)-induced dopaminergic neurotoxicity," Proc. Natl. Acad. Sci. U.S.A., May 1996; 93(10):4565-44571.
Qiu, Jian-ping et al. "Stimulation of γδT Cell in Peripheral Blood by Zoledronic Acid and Its Cytotoxic Effect on Nonspecific Immunity of Hepatoma," Suzhou University Journal of Medical Science, 2010; 30(4):808-830 with 1 page of figures. (Chinese with English abstract on p. 808).
Qiu, P., "Hepatocyte-mediated somatic gene therapy," Foreign Medicine (Genetics). Aug. 12, 1996; 19(4):194-199 (Chinese with English summary, 1 page).
Riano, F. et al. "Vγ9Vδ2 TCR-activation by phosphorylated antigens requires butyrophilin 3 A1 (BTN3A1) and additional genes on human chromosome 6," Eur J Immunol, Sep. 2014, 44(9):2571-2576. [Epub Jun. 30, 2014].
Ribeiro, A.L. et al. "Regulation of HPV transcription", Clinics (Sao Paulo). Oct. 11, 2018;73(suppl 1):e486s, doi: 10.6061/clinics/2018/e486s, 8 pages.
Roden, C. et al., "Novel determinants of mammalian primary microRNA processing revealed by systematic evaluation of hairpin-containing transcripts and human genetic variation," Genome Res. Mar. 2017;27(3):374-384. doi: 10.1101/gr.208900.116. Epub Jan. 13, 2017.
Sailaja et al. "Many Different Papillomaviruses Have Low Transcriptional Activity in Spite of Strong Epithelial Specific Enhancers," Journal of General Virology, Jul. 1999; 80(7):1715-1724.
Samadani, U. et al. "Identification of a transthyretin enhancer site that selectively binds the hepatocyte nuclear factor-3 beta isoform", Gene Expression, 1996; 6(1):23-33.
Sambrook et al. "Molecular Cloning: A Laboratory Manual", 3rd. ed. Cold Spring Harbor Laboratory Press; 2001; 2272 pages.
Sandstrom et al. "The Intracellular B30.2 Domain of Butrophilin 3A1 Binds Phosphoantigens to Mediate Activation of Human Vγ9Vδ2 T Cells", Immunity, Apr. 17, 2014; 40(4):490-500.
Sangro, et al. "A Phase I Clinic Trial of Thymidine Kinase-based Gene Therapy in Advanced Hepatocellular Carcinoma", Cancer Gene Ther., Dec. 2010;17(12):837-843.
Selbach, M. et al. "Widespread changes in protein synthesis induced by microRNAs", Nature. Sep. 4, 2008 Sep 4;455(7209):58-63.
Shalova I.N., et al., "CD16 Regulates TRIF-Dependent TLR4 Response in Human Monocytes and Their Subsets", The Journal of Immunology, Apr. 12, 2012;188(8):3584-3593.
Smith et al. "Comparison of Biosequences," Adv. Appl. Math., 1981, 2:482-489.
Soneoka, Y. et al. "A transient three-plasmid expression system for the production of high titer retroviral vectors", Nucleic Acids Research, Feb. 25, 1995;23(4):628-633.
Sun, J. and Sampson, N.S., Short Protocols in Molecular Biology. Third Edition. A Compendium of Methods from Current Protocols in Molecular Biology. Frederic M. Ausubel et al. (Eds.) New York: Wiley John & Sons, Inc., 1995 [Review]. Quart. Rev. Biol., Mar. 1997; 72:71, 1 page.
System Biosciences, "Enhances Episomal Vectors (EEV)," Feb. 16, 2017 [online]. Retrieved from: https://www.funakoshi.co.jp/contents/63198; retrieved Mar. 2020; 2 pages.
Technical Examination Report for Brazilian Application No. BR112019014082-4 mailed Mar. 25, 2025, with English Translation, 16 pages.
Ter Brake, O. et al. "Lentiviral vector design for multiple shRNA expression and durable HIV-1 inhibition", Mol Ther. Mar. 2008;16(3):557-64.
Tian et al. "MicroRNA-30a Promotes Chondrogenic Differentiation of Mesenchymal Stem Cells Through Inhibiting Delta-Like 4 Expression" Life Sciences, Mar. 1, 2016:148:220-228; accepted manuscript, 36 pages.
Ueda et al. "CD47-dependent molecular mechanisms of blood outgrowth endothelial cell attachment on cholesterol-modified polyurethane", Biomaterials. Sep. 2010;31(25):6394-9. Epub Jun. 9, 2010.
Waddington et al. "Fetal and neonatal gene therapy: benefits and pitfalls", Gene Ther. Oct. 2004; 11(Suppl 1):S92-7.
Waddington et al., "In utero gene therapy: current challenges and perspectives," Mol Ther., 2005; 11(5):661-676.
Wang et al. "Kinesin Family Member 11 is a Potential Therapeutic Target and is Suppressed by MicroRNA-30a in Breast Cancer," Molecular Carcinogensis, Aug. 2020;59(8):908-922.
Wang et al. "The interferon-inducible protein viperin inhibits influenza virus release by perturbing lipid rafts", Cell Host Microbe. Aug. 16, 2007;2(2):96-105.
Weintraub, "Antisense RNA and DNA", 1990, Scientific American 262(1):40-6.
Welch, M. et al. "Design parameters to control synthetic gene expression in Escherichia coli", PLoS One. Sep. 14, 2009;4(9):e7002, 10 pages.
Wikipedia, Phenylalanine hydroxylase. Oct. 18, 2022 [online]. Retrieved from: https://en.wikipedia.org/w/index.php?title=Phenylalanine_hydroxylase&oldid=1116722 687; 8 pages.

(56) References Cited

OTHER PUBLICATIONS

Wilkin et al. "Isolation and Sequence of the Human Farnesyl Pyrophosphate Synthetase cDNA", The Journal of Biological Chemistry, Mar. 15, 1990;265(8):4607-4614.
Wong, L.-F. et al. (Jan. 2004). "Transduction Patterns of Pseudotyped Lentiviral Vectors in the Nervous System," Mol. Ther. 9:101-111.
Wright, K. "Antibodies. A Laboratory Manual. by E. Harlow and D. Lane," [Review] Biochemical Education. 1989;17(4):220, 1 page.
Wu et al. "Development of a novel trans-lentiviral vector that affords predictable safety", Mol Ther. Jul. 2000;2(1):47-55.
Yu, M. et al., "Proteomic screen defines the hepatocyte nuclear factor 1alpha-binding partners and identifies HMGB1 as a new cofactor of HNF1alpha," Nucleic Acids Research, Mar. 2008;36(4):1209-1219.
Zhang, F. et al. "Research Progress on the Mechanism of Antitumor Action of Bisphosphonates," Chinese Journal of Hospital Pharmacy. Sep. 30, 2008; 28(18):1590-1593 (Chinese with English abstract, 1 page).
Zhang, Y. et al., "Combinational delivery of c-myc siRNA and nucleoside analogs in a single, synthetic nanocarrier for targeted cancer therapy," Biomaterials. 2013; 34(33):8459-8468.
Kuhlmann et al. "Long-Term Persistence of Anti-HIV Broadly Neutralizing Antibody-Secreting Hematopoietic Cells in Humanized Mice," Molecular Therapy, vol. 27, No. 1, pp. 164-177, Jan. 1, 2019.
Yongjiao et al., "Expression of HIV-1 Broadly Neutralizing Antibodies Mediated by Recobinant Adeno-Associated Virus 8 In Vitro and In Vivo," Molecular Immunology, vol. 80, pp. 68-77, 2016.
Falkenhagen et al., "Control of HIV Infection In Vivo Using Gene Therapy with a Secreted Entry Inhibitor," Molecular Therapy-Nucleic Acids, vol. 9, pp. 132-144, Dec. 1, 2017.
EP; Office Action issued in Application No. 17750547.6 on Feb. 23, 2024.
IN; Office Action issued in Application No. 201947031955 on Feb. 23, 2024.
AU; Office Action issued in Application No. 2018205388 on Mar. 1, 2024.
KR; Decision for Grant issued in Application No. 10-2019-7023287 on Feb. 28, 2024.
JP; Office Action issued in Application No. 2022-133225 on Feb. 29, 2024.
AU; Office Action issued in Application No. 2018205388 on Feb. 26, 2024.

* cited by examiner

Elongation Factor-1 alpha (EF1-alpha) promoter (SEQ ID NO: 105)

*CCGGTGCCTAGAGAAGGTGGCGCGGGGTAAACTGGGAAAGTGATGTCGTGTACTGGCTCCGCCTT*
*TTTCCCGAGGGTGGGGGAGAACCGTATATAAGTGCAGTAGTCGCCGTGAACGTTCTTTTTCGCAA*
*CGGGTTTGCCGCCAGAACACAGGTAAGTGCCGTGTGTGGTTCCCGCGGGCCTGGCCTCTTTACGG*
*GTTATGGCCCTTGCGTGCCTTGAATTACTTCCACGCCCCTGGCTGCAGTACGTGATTCTTGATCC*
*CGAGCTTCGGGTTGGAAGTGGGTGGGAGAGTTCGAGGCCTTGCGCTTAAGGAGCCCCTTCGCCTC*
*GTGCTTGAGTTGAGGCCTGGCCTGGGCGCTGGGGCCGCCGCGTGCGAATCTGGTGGCACCTTCGC*
*GCCTGTCTCGCTGCTTTCGATAAGTCTCTAGCCATTTAAAATTTTTGATGACCTGCTGCGACGCT*
*TTTTTTCTGGCAAGATAGTCTTGTAAATGCGGGCCAAGATCTGCACACTGGTATTTCGGTTTTTG*
*GGGCCGCGGGCGGCGACGGGGCCCGTGCGTCCCAGCGCACATGTTCGGCGAGGCGGGGCCTGCGA*
*GCGCGGCCACCGAGAATCGGACGGGGGTAGTCTCAAGCTGGCCGGCCTGCTCTGGTGCCTGGCCT*
*CGCGCCGCCGTGTATCGCCCCGCCCTGGGCGGCAAGGCTGGCCCGGTCGGCACCAGTTGCGTGAG*
*CGGAAAGATGGCCGCTTCCCGGCCCTGCTGCAGGGAGCTCAAAATGGAGGACGCGGCGCTCGGGA*
*GAGCGGGCGGGTGAGTCACCCACACAAAGGAAAAGGGCCTTTCCGTCCTCAGCCGTCGCTTCATG*
*TGACTCCACGGAGTACCGGGCGCCGTCCAGGCACCTCGATTAGTTCTCGAGCTTTTGGAGTACGT*
*CGTCTTTAGGTTGGGGGGAGGGGTTTTATGCGATGGAGTTTCCCCACACTGAGTGGGTGGAGACT*
*GAAGTTAGGCCAGCTTGGCACTTGATGTAATTCTCCTTGGAATTTGCCCTTTTTGAGTTTGGATC*
*TTGGTTCATTCTCAAGCCTCAGACAGTGGTTCAAAGTTTTTTTCTTCCATTTCAGGTGTCGTGAT*
GTACA miR30 CCR5 (SEQ ID NO: 1)

AGGTATATTGCTGTTGACAGTGAGCGACTGTAAACTGAGCTTGCTCTACTGTGAAGCCACAGATG
GGTAGAGCAAGCACAGTTTACCGCTGCCTACTGCCTCGGACTTCAAGGGGCTT miR21 Vif (SEQ ID NO: 106)

CCCGGG*CATCTCCATGGCTGTACCACCTTGTCGGGGGATGTGTACTTCTGAACTTGTGTTGAATC*
*TCATGGAGTTCAGAAGAACACATCCGCACTGACATTTTGGTATCTTTCATCTGACCA* miR185 Tat (SEQ ID NO: 107; SEQ ID NO: 108 (underlined portion))

GCTAGCGGGCCTGGCTCGAGCAGGGGGCGAGGGATTCCGCTTCTTCCTGCCATAGCGTGGTCCCC
TCCCCTATGGCAGGCAGAAGCGGCACCTTCCCTCCCAATGACCGCGTCTTCGTC

FIG. 6

| | Sample Name | Geometric Mean : FL4-H |
|---|---|---|
| | ISO.001 | 12.9 |
| | LVMOI=0.002 | 124 |
| | LVMOI=0.008.003 | 121 |
| | LVMOI=0.04.004 | 90.2 |
| | LVMOI=0.2.005 | 58.4 |
| | LVMOI=1.006 | 22.5 |
| | LVMOI=5.007 | 13.0 |

```
SEQUENCE LISTING


<160> NUMBER OF SEQ ID NOS: 108

<210> SEQ ID NO 1
<211> LENGTH: 118
<212> TYPE: DNA
<213> ORGANISM: Artificial Sequence
<220> FEATURE:
<223> OTHER INFORMATION: miR30 CCR5

<400> SEQUENCE: 1

aggtatattg ctgttgacag tgagcgactg taaactgagc ttgctctact gtgaagccac     60

agatgggtag agcaagcaca gtttaccgct gcctactgcc tcggacttca aggggctt      118


<210> SEQ ID NO 2
<211> LENGTH: 116
<212> TYPE: DNA
<213> ORGANISM: Artificial Sequence
<220> FEATURE:
<223> OTHER INFORMATION: miR21 Vif

<400> SEQUENCE: 2
```

catctccatg gctgtaccac cttgtcgggg gatgtgtact tctgaacttg tgttgaatct 60
catggagttc agaagaacac atccgcactg acattttggt atctttcatc tgacca 116

<210> SEQ ID NO 3
<211> LENGTH: 114
<212> TYPE: DNA
<213> ORGANISM: Artificial Sequence
<220> FEATURE:
<223> OTHER INFORMATION: miR185 Tat

<400> SEQUENCE: 3
gggcctggct cgagcagggg gcgagggatt ccgcttcttc ctgccatagc gtggtcccct 60
cccctatggc aggcagaagc ggcaccttcc ctcccaatga ccgcgtcttc gtcg 114

<210> SEQ ID NO 4
<211> LENGTH: 1194
<212> TYPE: DNA
<213> ORGANISM: Artificial Sequence
<220> FEATURE:
<223> OTHER INFORMATION: Elongation Factor-1 alpha (EF1-alpha) promoter

<400> SEQUENCE: 4
ccggtgccta gagaaggtgg cgcggggtaa actgggaaag tgatgtcgtg tactggctcc 60
gcctttttcc cgagggtggg ggagaaccgt atataagtgc agtagtcgcc gtgaacgttc 120
tttttcgcaa cgggtttgcc gccagaacac aggtaagtgc cgtgtgtggt tcccgcgggc 180
ctggcctctt tacgggttat ggcccttgcg tgccttgaat tacttccacg cccctggctg 240
cagtacgtga ttcttgatcc cgagcttcgg gttggaagtg ggtgggagag ttcgaggcct 300
tgcgcttaag gagccccttc gcctcgtgct tgagttgagg cctggcctgg gcgctggggc 360
cgccgcgtgc gaatctggtg gcaccttcgc gcctgtctcg ctgctttcga taagtctcta 420
gccatttaaa atttttgatg acctgctgcg acgctttttt tctggcaaga tagtcttgta 480
aatgcgggcc aagatctgca cactggtatt tcggtttttg gggccgcggg cggcgacggg 540
gcccgtgcgt cccagcgcac atgttcggcg aggcggggcc tgcgagcgcg gccaccgaga 600
atcggacggg ggtagtctca agctggccgg cctgctctgg tgcctggcct cgcgccgccg 660
tgtatcgccc cgccctgggc ggcaaggctg gcccggtcgg caccagttgc gtgagcggaa 720
agatggccgc ttcccggccc tgctgcaggg agctcaaaat ggaggacgcg gcgctcggga 780
gagcgggcgg gtgagtcacc cacacaaagg aaaagggcct ttccgtcctc agccgtcgct 840
tcatgtgact ccacggagta ccgggcgccg tccaggcacc tcgattagtt ctcgagcttt 900
tggagtacgt cgtctttagg ttggggggag gggttttatg cgatggagtt tccccacact 960
gagtgggtgg agactgaagt taggccagct tggcacttga tgtaattctc cttggaattt 1020
gccctttttg agtttggatc ttggttcatt ctcaagcctc agacagtggt tcaaagtttt 1080
tttcttccat ttcaggtgtc gtgagccctt tttgagtttg gatcttggtt cattctcaag 1140
cctcagacag tggttcaaag ttttttcctt ccatttcagg tgtcgtgatg taca 1194

<210> SEQ ID NO 5
<211> LENGTH: 18
<212> TYPE: DNA
<213> ORGANISM: Artificial Sequence
<220> FEATURE:
<223> OTHER INFORMATION: CCR5 target sequence

<400> SEQUENCE: 5
gagcaagctc agtttaca 18

<210> SEQ ID NO 6
<211> LENGTH: 21
<212> TYPE: DNA
<213> ORGANISM: Artificial Sequence
<220> FEATURE:
<223> OTHER INFORMATION: Vif target sequence

<400> SEQUENCE: 6
gggatgtgta cttctgaact t 21

<210> SEQ ID NO 7
<211> LENGTH: 20
<212> TYPE: DNA
<213> ORGANISM: Artificial Sequence
<220> FEATURE:
<223> OTHER INFORMATION: Tat target sequence

<400> SEQUENCE: 7
tccgcttctt cctgccatag 20

<210> SEQ ID NO 8
<211> LENGTH: 126
<212> TYPE: DNA
<213> ORGANISM: Artificial Sequence
<220> FEATURE:
<223> OTHER INFORMATION: TAR decoy sequence

<400> SEQUENCE: 8
cttgcaatga tgtcgtaatt tgcgtcttac ctcgttctcg acagcgacca gatctgagcc 60
tgggagctct ctggctgtca gtaagctggt acagaaggtt gacgaaaatt cttactgagc 120
aagaaa 126

<210> SEQ ID NO 9
<211> LENGTH: 21
<212> TYPE: DNA
<213> ORGANISM: Artificial Sequence
<220> FEATURE:
<223> OTHER INFORMATION: Rev/Tat target sequence

<400> SEQUENCE: 9
gcggagacag cgacgaagag c 21

<210> SEQ ID NO 10
<211> LENGTH: 56
<212> TYPE: DNA
<213> ORGANISM: Artificial Sequence
<220> FEATURE:
<223> OTHER INFORMATION: Rev/Tat shRNA sequence

<400> SEQUENCE: 10
gcggagacag cgacgaagag cttcaagaga gctcttcgtc gctgtctccg cttttt 56

<210> SEQ ID NO 11
<211> LENGTH: 19
<212> TYPE: DNA
<213> ORGANISM: Artificial Sequence
<220> FEATURE:
<223> OTHER INFORMATION: Gag target sequence

<400> SEQUENCE: 11
gaagaaatga tgacagcat 19

<210> SEQ ID NO 12

-continued

<211> LENGTH: 52
<212> TYPE: DNA
<213> ORGANISM: Artificial Sequence
<220> FEATURE:
<223> OTHER INFORMATION: Gag shRNA sequence

<400> SEQUENCE: 12
gaagaaatga tgacagcatt tcaagagaat gctgtcatca tttcttcttt tt 52

<210> SEQ ID NO 13
<211> LENGTH: 18
<212> TYPE: DNA
<213> ORGANISM: Artificial Sequence
<220> FEATURE:
<223> OTHER INFORMATION: Pol target sequence

<400> SEQUENCE: 13
caggagcaga tgatacag 18

<210> SEQ ID NO 14
<211> LENGTH: 47
<212> TYPE: DNA
<213> ORGANISM: Artificial Sequence
<220> FEATURE:
<223> OTHER INFORMATION: Pol shRNA sequence

<400> SEQUENCE: 14
caggagatga tacagttcaa gagactgtat catctgctcc tgttttt 47

<210> SEQ ID NO 15
<211> LENGTH: 19
<212> TYPE: DNA
<213> ORGANISM: Artificial Sequence
<220> FEATURE:
<223> OTHER INFORMATION: CCR5 target sequence #1

<400> SEQUENCE: 15
gtgtcaagtc caatctatg 19

<210> SEQ ID NO 16
<211> LENGTH: 52
<212> TYPE: DNA
<213> ORGANISM: Artificial Sequence
<220> FEATURE:
<223> OTHER INFORMATION: CCR5 shRNA sequence #1

<400> SEQUENCE: 16
gtgtcaagtc caatctatgt tcaagagaca tagattggac ttgacacttt tt 52

<210> SEQ ID NO 17
<211> LENGTH: 19
<212> TYPE: DNA
<213> ORGANISM: Artificial Sequence
<220> FEATURE:
<223> OTHER INFORMATION: CCR5 target sequence #2

<400> SEQUENCE: 17
gagcatgact gacatctac 19

<210> SEQ ID NO 18
<211> LENGTH: 52
<212> TYPE: DNA
<213> ORGANISM: Artificial Sequence
<220> FEATURE:
<223> OTHER INFORMATION: CCR5 shRNA sequence #2

<400> SEQUENCE: 18
gagcatgact gacatctact tcaagagagt agatgtcagt catgctcttt tt 52

<210> SEQ ID NO 19
<211> LENGTH: 19
<212> TYPE: DNA
<213> ORGANISM: Artificial Sequence
<220> FEATURE:
<223> OTHER INFORMATION: CCR5 target sequence #3

<400> SEQUENCE: 19
gtagctctaa caggttgga 19

<210> SEQ ID NO 20
<211> LENGTH: 52
<212> TYPE: DNA
<213> ORGANISM: Artificial Sequence
<220> FEATURE:
<223> OTHER INFORMATION: CCR5 shRNA sequence #3

<400> SEQUENCE: 20
gtagctctaa caggttggat tcaagagatc caacctgtta gagctacttt tt 52

<210> SEQ ID NO 21
<211> LENGTH: 19
<212> TYPE: DNA
<213> ORGANISM: Artificial Sequence
<220> FEATURE:
<223> OTHER INFORMATION: CCR5 target sequence #4

<400> SEQUENCE: 21
gttcagaaac tacctctta 19

<210> SEQ ID NO 22
<211> LENGTH: 52
<212> TYPE: DNA
<213> ORGANISM: Artificial Sequence
<220> FEATURE:
<223> OTHER INFORMATION: CCR5 shRNA sequence #4

<400> SEQUENCE: 22
gttcagaaac tacctcttat tcaagagata agaggtagtt tctgaacttt tt 52

<210> SEQ ID NO 23
<211> LENGTH: 20
<212> TYPE: DNA
<213> ORGANISM: Artificial Sequence
<220> FEATURE:
<223> OTHER INFORMATION: CCR5 target sequence #5

<400> SEQUENCE: 23
gagcaagctc agtttacacc 20

<210> SEQ ID NO 24
<211> LENGTH: 54
<212> TYPE: DNA
<213> ORGANISM: Artificial Sequence
<220> FEATURE:
<223> OTHER INFORMATION: CCR5 shRNA sequence #5

<400> SEQUENCE: 24
gagcaagctc agtttacacc ttcaagagag gtgtaaactg agcttgctct tttt 54

<210> SEQ ID NO 25
<211> LENGTH: 141
<212> TYPE: DNA

<213> ORGANISM: Artificial Sequence
<220> FEATURE:
<223> OTHER INFORMATION: Homo sapiens CCR5 gene, sequence 1

<400> SEQUENCE: 25
atggattatc aagtgtcaag tccaatctat gacatcaatt attatacatc ggagccctgc 60
caaaaaatca atgtgaagca aatcgcagcc cgcctcctgc ctccgctcta ctcactggtg 120
ttcatctttg gttttgtggg c 141

<210> SEQ ID NO 26
<211> LENGTH: 633
<212> TYPE: DNA
<213> ORGANISM: Artificial Sequence
<220> FEATURE:
<223> OTHER INFORMATION: Homo sapiens CCR5 gene, sequence 2

<400> SEQUENCE: 26
aacatgctgg tcatcctcat cctgataaac tgcaaaaggc tgaagagcat gactgacatc 60
tacctgctca acctggccat ctctgacctg tttttccttc ttactgtccc cttctgggct 120
cactatgctg ccgcccagtg ggactttgga aatacaatgt gtcaactctt gacagggctc 180
tattttatag gcttcttctc tggaatcttc ttcatcatcc tcctgacaat cgataggtac 240
ctggctgtcg tccatgctgt gtttgcttta aaagccagga cggtcacctt tggggtggtg 300
acaagtgtga tcacttgggt ggtggctgtg tttgcgtctc tcccaggaat catctttacc 360
agatctcaaa aagaaggtct tcattacacc tgcagctctc attttccata cagtcagtat 420
caattctgga agaatttcca gacattaaag atagtcatct tggggctggt cctgccgctg 480
cttgtcatgg tcatctgcta ctcgggaatc ctaaaaactc tgcttcggtg tcgaaatgag 540
aagaagaggc acagggctgt gaggcttatc ttcaccatca tgattgttta ttttctcttc 600
tgggctccct acaacattgt ccttctcctg aac 633

<210> SEQ ID NO 27
<211> LENGTH: 70
<212> TYPE: DNA
<213> ORGANISM: Artificial Sequence
<220> FEATURE:
<223> OTHER INFORMATION: Homo sapiens CCR5 gene, sequence 3

<400> SEQUENCE: 27
accttccagg aattctttgg cctgaataat tgcagtagct ctaacaggtt ggaccaagct 60
atgcaggtga 70

<210> SEQ ID NO 28
<211> LENGTH: 140
<212> TYPE: DNA
<213> ORGANISM: Artificial Sequence
<220> FEATURE:
<223> OTHER INFORMATION: Homo sapiens CCR5 gene, sequence 4

<400> SEQUENCE: 28
cagagactct tgggatgacg cactgctgca tcaaccccat catctatgcc tttgtcgggg 60
agaagttcag aaactacctc ttagtcttct tccaaaagca cattgccaaa cgcttctgca 120
aatgctgttc tattttccag 140

<210> SEQ ID NO 29
<211> LENGTH: 75
<212> TYPE: DNA
<213> ORGANISM: Artificial Sequence
<220> FEATURE:
<223> OTHER INFORMATION: Homo sapiens CCR5 gene, sequence 5

<400> SEQUENCE: 29
caagaggctc ccgagcgagc aagctcagtt tacacccgat ccactgggga gcaggaaata 60
tctgtgggct tgtga 75

<210> SEQ ID NO 30
<211> LENGTH: 541
<212> TYPE: DNA
<213> ORGANISM: Artificial Sequence
<220> FEATURE:
<223> OTHER INFORMATION: CD4 promoter sequence

<400> SEQUENCE: 30
tgttggggtt caaatttgag ccccagctgt tagccctctg caaagaaaaa aaaaaaaaaa 60
aaagaacaaa gggcctagat ttcccttctg agccccaccc taagatgaag cctcttcttt 120
caagggagtg gggttggggt ggaggcggat cctgtcagct ttgctctctc tgtggctggc 180
agtttctcca aagggtaaca ggtgtcagct ggctgagcct aggctgaacc ctgagacatg 240
ctacctctgt cttctcatgg ctggaggcag cctttgtaag tcacagaaag tagctgaggg 300
gctctggaaa aaagacagcc agggtggagg tagattggtc tttgactcct gatttaagcc 360
tgattctgct taactttttc ccttgacttt ggcattttca ctttgacatg ttccctgaga 420
gcctgggggg tggggaaccc agctccagct ggtgacgttt ggggccggcc caggcctagg 480
gtgtggagga gccttgccat cgggcttcct gtctctcttc atttaagcac gactctgcag 540
a 541

<210> SEQ ID NO 31
<211> LENGTH: 359
<212> TYPE: DNA
<213> ORGANISM: Artificial Sequence
<220> FEATURE:
<223> OTHER INFORMATION: miR30-CCR5/miR21-Vif/miR185 Tat microRNA
cluster sequence

<400> SEQUENCE: 31
aggtatattg ctgttgacag tgagcgactg taaactgagc ttgctctact gtgaagccac 60
agatgggtag agcaagcaca gtttaccgct gcctactgcc tcggacttca aggggcttcc 120
cgggcatctc catggctgta ccaccttgtc gggggatgtg tacttctgaa cttgtgttga 180
atctcatgga gttcagaaga acacatccgc actgacattt tggtatcttt catctgacca 240
gctagcgggc ctggctcgag cagggggcga gggattccgc ttcttcctgc catagcgtgg 300
tcccctcccc tatggcaggc agaagcggca ccttccctcc caatgaccgc gtcttcgtc 359

<210> SEQ ID NO 32
<211> LENGTH: 590
<212> TYPE: DNA
<213> ORGANISM: Artificial Sequence
<220> FEATURE:
<223> OTHER INFORMATION: Long WPRE sequence

<400> SEQUENCE: 32
aatcaacctc tgattacaaa atttgtgaaa gattgactgg tattcttaac tatgttgctc 60
cttttacgct atgtggatac gctgctttaa tgcctttgta tcatgctatt gcttcccgta 120
tggctttcat tttctcctcc ttgtataaat cctggttgct gtctctttat gaggagttgt 180
ggcccgttgt caggcaacgt ggcgtggtgt gcactgtgtt tgctgacgca acccccactg 240
gttggggcat tgccaccacc tgtcagctcc tttccgggac tttcgctttc cccctcccta 300
ttgccacggc ggaactcatc gccgcctgcc ttgcccgctg ctggacaggg gctcggctgt 360
tgggcactga caattccgtg gtgttgtcgg ggaaatcatc gtcctttcct tggctgctcg 420
cctgtgttgc cacctggatt ctgcgcggga cgtccttctg ctacgtccct tcggccctca 480
atccagcgga ccttccttcc cgcggcctgc tgccggctct gcggcctctt ccgcgtcttc 540
gccttcgccc tcagacgagt cggatctccc tttgggccgc ctccccgcct 590

<210> SEQ ID NO 33
<211> LENGTH: 1469
<212> TYPE: DNA
<213> ORGANISM: Artificial Sequence
<220> FEATURE:
<223> OTHER INFORMATION: Elongation Factor?1 alpha (EF1?alpha) promoter; miR30CCR5; miR21Vif; miR185 Tat

<400> SEQUENCE: 33
ccggtgccta gagaaggtgg cgcggggtaa actgggaaag tgatgtcgtg tactggctcc 60
gcctttttcc cgagggtggg ggagaaccgt atataagtgc agtagtcgcc gtgaacgttc 120
tttttcgcaa cgggtttgcc gccagaacac aggtaagtgc cgtgtgtggt tcccgcgggc 180
ctggcctctt tacgggttat ggcccttgcg tgccttgaat tacttccacg cccctggctg 240
cagtacgtga ttcttgatcc cgagcttcgg gttggaagtg ggtgggagag ttcgaggcct 300
tgcgcttaag gagccccttc gcctcgtgct tgagttgagg cctggcctgg gcgctggggc 360
cgccgcgtgc gaatctggtg gcaccttcgc gcctgtctcg ctgctttcga taagtctcta 420
gccatttaaa atttttgatg acctgctgcg acgctttttt tctggcaaga tagtcttgta 480
aatgcgggcc aagatctgca cactggtatt tcggtttttg gggccgcggg cggcgacggg 540
gcccgtgcgt cccagcgcac atgttcggcg aggcggggcc tgcgagcgcg gccaccgaga 600
atcggacggg ggtagtctca agctggccgg cctgctctgg tgcctggcct cgcgccgccg 660
tgtatcgccc cgccctgggc ggcaaggctg gcccggtcgg caccagttgc gtgagcggaa 720
agatggccgc ttcccggccc tgctgcaggg agctcaaaat ggaggacgcg gcgctcggga 780
gagcgggcgg gtgagtcacc cacacaaagg aaaagggcct ttccgtcctc agccgtcgct 840
tcatgtgact ccacggagta ccgggcgccg tccaggcacc tcgattagtt ctcgagcttt 900
tggagtacgt cgtctttagg ttggggggag gggttttatg cgatggagtt tccccacact 960
gagtgggtgg agactgaagt taggccagct tggcacttga tgtaattctc cttggaattt 1020
gccctttttg agtttggatc ttggttcatt ctcaagcctc agacagtggt tcaaagtttt 1080
tttcttccat ttcaggtgtc gtgatgtaca aggtatattg ctgttgacag tgagcgactg 1140
taaactgagc ttgctctact gtgaagccac agatgggtag agcaagcaca gtttaccgct 1200
gcctactgcc tcggacttca aggggcttcc cgggcatctc catggctgta ccaccttgtc 1260
gggggatgtg tacttctgaa cttgtgttga atctcatgga gttcagaaga acacatccgc 1320
actgacattt tggtatcttt catctgacca gctagcgggc ctggctcgag caggggggcga 1380 gggattccgc ttcttcctgc catagcgtgg tcccctcccc tatggcaggc agaagcggca 1440
ccttccctcc caatgaccgc gtcttcgtc 1469

<210> SEQ ID NO 34
<211> LENGTH: 228
<212> TYPE: DNA
<213> ORGANISM: Artificial Sequence
<220> FEATURE:
<223> OTHER INFORMATION: Rous Sarcoma virus (RSV) promoter

<400> SEQUENCE: 34
gtagtcttat gcaatactct tgtagtcttg caacatggta acgatgagtt agcaacatgc 60
cttacaagga gagaaaaagc accgtgcatg ccgattggtg gaagtaaggt ggtacgatcg 120
tgccttatta ggaaggcaac agacgggtct gacatggatt ggacgaacca ctgaattgcc 180
gcattgcaga gatattgtat ttaagtgcct agctcgatac aataaacg 228

<210> SEQ ID NO 35
<211> LENGTH: 180
<212> TYPE: DNA
<213> ORGANISM: Artificial Sequence
<220> FEATURE:
<223> OTHER INFORMATION: 5' Long terminal repeat (LTR)

<400> SEQUENCE: 35
ggtctctctg gttagaccag atctgagcct gggagctctc tggctaacta gggaacccac 60
tgcttaagcc tcaataaagc ttgccttgag tgcttcaagt agtgtgtgcc cgtctgttgt 120
gtgactctgg taactagaga tccctcagac ccttttagtc agtgtggaaa atctctagca 180

<210> SEQ ID NO 36
<211> LENGTH: 41
<212> TYPE: DNA
<213> ORGANISM: Artificial Sequence
<220> FEATURE:
<223> OTHER INFORMATION: Psi Packaging signal

<400> SEQUENCE: 36
tacgccaaaa attttgacta gcggaggcta gaaggagaga g 41

<210> SEQ ID NO 37
<211> LENGTH: 233
<212> TYPE: DNA
<213> ORGANISM: Artificial Sequence
<220> FEATURE:
<223> OTHER INFORMATION: Rev response element (RRE)

<400> SEQUENCE: 37
aggagctttg ttccttgggt tcttgggagc agcaggaagc actatgggcg cagcctcaat 60
gacgctgacg gtacaggcca gacaattatt gtctggtata gtgcagcagc agaacaattt 120
gctgagggct attgaggcgc aacagcatct gttgcaactc acagtctggg gcatcaagca 180
gctccaggca agaatcctgg ctgtggaaag atacctaaag gatcaacagc tcc 233

<210> SEQ ID NO 38
<211> LENGTH: 118
<212> TYPE: DNA
<213> ORGANISM: Artificial Sequence
<220> FEATURE:
<223> OTHER INFORMATION: Central polypurine tract (cPPT)

<400> SEQUENCE: 38
ttttaaaaga aaagggggga ttggggggta cagtgcaggg gaaagaatag tagacataat 60
agcaacagac atacaaacta aagaattaca aaaacaaatt acaaaattca aaatttta 118

<210> SEQ ID NO 39
<211> LENGTH: 250
<212> TYPE: DNA
<213> ORGANISM: Artificial Sequence
<220> FEATURE:

-continued

<223> OTHER INFORMATION: 3' delta LTR

<400> SEQUENCE: 39
tggaagggct aattcactcc caacgaagat aagatctgct tttgcttgt actgggtctc 60 tctggttaga ccagatctga gcctgggagc tctctggcta actagggaac ccactgctta 120
agcctcaata aagcttgcct tgagtgcttc aagtagtgtg tgcccgtctg ttgtgtgact 180
ctggtaacta gagatccctc agaccctttt agtcagtgtg gaaaatctct agcagtagta 240
gttcatgtca 250

<210> SEQ ID NO 40
<211> LENGTH: 352
<212> TYPE: DNA
<213> ORGANISM: Artificial Sequence
<220> FEATURE:
<223> OTHER INFORMATION: Helper/Rev; CMV early (CAG) enhancer; Enhance Transcription

<400> SEQUENCE: 40
tagttattaa tagtaatcaa ttacggggtc attagttcat agcccatata tggagttccg 60
cgttacataa cttacggtaa atggcccgcc tggctgaccg cccaacgacc cccgcccatt 120
gacgtcaata atgacgtatg ttcccatagt aacgccaata gggactttcc attgacgtca 180
atgggtggac tatttacggt aaactgccca cttggcagta catcaagtgt atcatatgcc 240
aagtacgccc cctattgacg tcaatgacgg taaatggccc gcctggcatt atgcccagta 300
catgacctta tgggactttc ctacttggca gtacatctac gtattagtca tc 352

<210> SEQ ID NO 41
<211> LENGTH: 290
<212> TYPE: DNA
<213> ORGANISM: Artificial Sequence
<220> FEATURE:
<223> OTHER INFORMATION: Helper/Rev; Chicken beta actin (CAG) promoter; Transcription

<400> SEQUENCE: 41
gctattacca tgggtcgagg tgagccccac gttctgcttc actctcccca tctccccccc 60
ctccccaccc ccaattttgt atttatttat tttttaatta ttttgtgcag cgatgggggc 120
gggggggggg ggggcgcgcg ccaggcgggg cggggcgggg cgaggggcgg ggcggggcga 180
ggcggagagg tgcggcggca gccaatcaga gcggcgcgct ccgaaagttt ccttttatgg 240
cgaggcggcg gcggcggcgg ccctataaaa agcgaagcgc gcggcgggcg 290

<210> SEQ ID NO 42
<211> LENGTH: 960
<212> TYPE: DNA
<213> ORGANISM: Artificial Sequence
<220> FEATURE:
<223> OTHER INFORMATION: Helper/Rev; Chicken beta actin intron; Enhance gene expression

<400> SEQUENCE: 42
ggagtcgctg cgttgccttc gccccgtgcc ccgctccgcg ccgcctcgcg ccgcccgccc 60
cggctctgac tgaccgcgtt actcccacag gtgagcgggc gggacggccc ttctcctccg 120
ggctgtaatt agcgcttggt ttaatgacgg ctcgtttctt ttctgtggct gcgtgaaagc 180
cttaaagggc tccgggaggg ccctttgtgc ggggggggagc ggctcggggg gtgcgtgcgt 240
gtgtgtgtgc gtggggagcg ccgcgtgcgg cccgcgctgc ccggcggctg tgagcgctgc 300

```
gggcgcggcg cggggctttg tgcgctccgc gtgtgcgcga ggggagcgcg gccgggggcg    360

gtgccccgcg gtgcgggggg gctgcgaggg gaacaaaggc tgcgtgcggg gtgtgtgcgt    420

gggggggtga gcagggggtg tgggcgcggc ggtcgggctg taaccccccc ctgcaccccc    480

ctccccgagt tgctgagcac ggcccggctt cgggtgcggg gctccgtgcg gggcgtggcg    540

cggggctcgc cgtgccgggc gggggggtggc ggcaggtggg ggtgccgggc ggggcggggc    600

cgcctcgggc cggggagggc tcgggggagg ggcgcggcgg ccccggagcg ccggcggctg    660

tcgaggcgcg gcgagccgca gccattgcct tttatggtaa tcgtgcgaga gggcgcaggg    720

acttcctttg tcccaaatct ggcggagccg aaatctggga ggcgccgccg cacccctct    780

agcgggcgcg ggcgaagcgg tgcggcgccg gcaggaagga aatgggcggg gagggccttc    840

gtgcgtcgcc gcgccgccgt ccccttctcc atctccagcc tcggggctgc cgcaggggga    900

cggctgcctt cggggggac ggggcagggc ggggttcggc ttctggcgtg tgaccggcgg    960
```

<210> SEQ ID NO 43
<211> LENGTH: 1503
<212> TYPE: DNA
<213> ORGANISM: Artificial Sequence
<220> FEATURE:
<223> OTHER INFORMATION: Helper/Rev; HIV Gag; Viral capsid

<400> SEQUENCE: 43

```
atgggtgcga gagcgtcagt attaagcggg ggagaattag atcgatggga aaaaattcgg     60

ttaaggccag ggggaaagaa aaaatataaa ttaaaacata tagtatgggc aagcagggag    120

ctagaacgat tcgcagttaa tcctggcctg ttagaaacat cagaaggctg tagacaaata    180

ctgggacagc tacaaccatc ccttcagaca ggatcagaag aacttagatc attatataat    240

acagtagcaa ccctctattg tgtgcatcaa aggatagaga taaaagacac caaggaagct    300

ttagacaaga tagaggaaga gcaaaacaaa agtaagaaaa aagcacagca agcagcagct    360

gacacaggac acagcaatca ggtcagccaa aattacccta tagtgcagaa catccagggg    420

caaatggtac atcaggccat atcacctaga actttaaatg catgggtaaa agtagtagaa    480

gagaaggctt tcagcccaga agtgataccc atgttttcag cattatcaga aggagccacc    540

ccacaagatt taaacaccat gctaaacaca gtgggggac atcaagcagc catgcaaatg    600

ttaaaagaga ccatcaatga ggaagctgca gaatgggata gagtgcatcc agtgcatgca    660

gggcctattg caccaggcca gatgagagaa ccaaggggaa gtgacatagc aggaactact    720

agtacccttc aggaacaaat aggatggatg acacataatc cacctatccc agtaggagaa    780

atctataaaa gatggataat cctgggatta aataaaatag taagaatgta tagccctacc    840

agcattctgg acataagaca aggaccaaag gaacccttta gagactatgt agaccgattc    900

tataaaactc taagagccga gcaagcttca caagaggtaa aaaattggat gacagaaacc    960

ttgttggtcc aaaatgcgaa cccagattgt aagactattt taaaagcatt gggaccagga   1020

gcgacactag aagaaatgat gacagcatgt cagggagtgg ggggacccgg ccataaagca   1080

agagttttgg ctgaagcaat gagccaagta acaaatccag ctaccataat gatacagaaa   1140

ggcaatttta ggaaccaaag aaagactgtt aagtgtttca attgtggcaa agaagggcac   1200

atagccaaaa attgcagggc ccctaggaaa aagggctgtt ggaaatgtgg aaaggaagga   1260

caccaaatga aagattgtac tgagagacag gctaattttt tagggaagat ctggccttcc   1320

cacaagggaa ggccagggaa ttttcttcag agcagaccag agccaacagc cccaccagaa   1380

gagagcttca ggtttgggga agagacaaca actccctctc agaagcagga gccgatagac   1440
```

aaggaactgt atcctttagc ttccctcaga tcactctttg gcagcgaccc ctcgtcacaa 1500
taa 1503

<210> SEQ ID NO 44
<211> LENGTH: 1872
<212> TYPE: DNA
<213> ORGANISM: Artificial Sequence
<220> FEATURE:
<223> OTHER INFORMATION: Helper/Rev; HIV Pol; Protease and reverse transcriptase

<400> SEQUENCE: 44
atgaatttgc caggaagatg gaaaccaaaa atgatagggg gaattggagg ttttatcaaa 60
gtaggacagt atgatcagat actcatagaa atctgcggac ataaagctat aggtacagta 120
ttagtaggac ctacacctgt caacataatt ggaagaaatc tgttgactca gattggctgc 180
actttaaatt ttcccattag tcctattgag actgtaccag taaaattaaa gccaggaatg 240
gatggcccaa aagttaaaca atggccattg acagaagaaa aaataaaagc attagtagaa 300
atttgtacag aaatggaaaa ggaaggaaaa atttcaaaaa ttgggcctga aaatccatac 360
aatactccag tatttgccat aaagaaaaaa gacagtacta aatggagaaa attagtagat 420
ttcagagaac ttaataagag aactcaagat ttctgggaag ttcaattagg aataccacat 480
cctgcagggt taaaacagaa aaaatcagta acagtactgg atgtgggcga tgcatatttt 540
tcagttccct tagataaaga cttcaggaag tatactgcat ttaccatacc tagtataaac 600
aatgagacac cagggattag atatcagtac aatgtgcttc cacagggatg gaaaggatca 660
ccagcaatat tccagtgtag catgacaaaa atcttagagc cttttagaaa acaaaatcca 720
gacatagtca tctatcaata catggatgat ttgtatgtag gatctgactt agaaataggg 780
cagcatagaa caaaaataga ggaactgaga caacatctgt tgaggtgggg atttaccaca 840
ccagacaaaa aacatcagaa agaacctcca ttcctttgga tgggttatga actccatcct 900
gataaatgga cagtacagcc tatagtgctg ccagaaaagg acagctggac tgtcaatgac 960
atacagaaat tagtgggaaa attgaattgg gcaagtcaga tttatgcagg gattaaagta 1020
aggcaattat gtaaacttct taggggaacc aaagcactaa cagaagtagt accactaaca 1080
gaagaagcag agctagaact ggcagaaaac agggagattc taaaagaacc ggtacatgga 1140
gtgtattatg acccatcaaa agacttaata gcagaaatac agaagcaggg gcaaggccaa 1200
tggacatatc aaatttatca agagccattt aaaaatctga aaacaggaaa atatgcaaga 1260
atgaagggtg cccacactaa tgatgtgaaa caattaacag aggcagtaca aaaaatagcc 1320
acagaaagca tagtaatatg gggaaagact cctaaattta aattacccat acaaaaggaa 1380
acatgggaag catggtggac agagtattgg caagccacct ggattcctga gtgggagttt 1440
gtcaataccc ctcccttagt gaagttatgg taccagttag agaaagaacc cataatagga 1500
gcagaaactt tctatgtaga tggggcagcc aatagggaaa ctaaattagg aaaagcagga 1560
tatgtaactg acagaggaag acaaaaagtt gtccccctaa cggacacaac aaatcagaag 1620
actgagttac aagcaattca tctagctttg caggattcgg gattagaagt aaacatagtg 1680
acagactcac aatatgcatt gggaatcatt caagcacaac cagataagag tgaatcagag 1740
ttagtcagtc aaataataga gcagttaata aaaaaggaaa aagtctacct ggcatgggta 1800
ccagcacaca aaggaattgg aggaaatgaa caagtagatg ggttggtcag tgctggaatc 1860
aggaaagtac ta 1872

<210> SEQ ID NO 45
<211> LENGTH: 867
<212> TYPE: DNA
<213> ORGANISM: Artificial Sequence
<220> FEATURE:
<223> OTHER INFORMATION: Helper Rev; HIV Integrase; Integration of viral RNA

<400> SEQUENCE: 45

```
tttttagatg gaatagataa ggcccaagaa gaacatgaga aatatcacag taattggaga     60

gcaatggcta gtgattttaa cctaccacct gtagtagcaa aagaaatagt agccagctgt    120

gataaatgtc agctaaaagg ggaagccatg catggacaag tagactgtag cccaggaata    180

tggcagctag attgtacaca tttagaagga aaagttatct tggtagcagt tcatgtagcc    240

agtggatata tagaagcaga agtaattcca gcagagacag ggcaagaaac agcatacttc    300

ctcttaaaat tagcaggaag atggccagta aaaacagtac atacagacaa tggcagcaat    360

ttcaccagta ctacagttaa ggccgcctgt tggtgggcgg ggatcaagca ggaatttggc    420

attccctaca atccccaaag tcaaggagta atagaatcta tgaataaaga attaaagaaa    480

attataggac aggtaagaga tcaggctgaa catcttaaga cagcagtaca aatggcagta    540

ttcatccaca attttaaaag aaaagggggg attggggggt acagtgcagg ggaaagaata    600

gtagacataa tagcaacaga catacaaact aaagaattac aaaaacaaat tacaaaaatt    660

caaaattttc gggtttatta cagggacagc agagatccag tttggaaagg accagcaaag    720

ctcctctgga aaggtgaagg ggcagtagta atacaagata atagtgacat aaaagtagtg    780

ccaagaagaa aagcaaagat catcagggat tatggaaaac agatggcagg tgatgattgt    840

gtggcaagta gacaggatga ggattaa                                         867
```

<210> SEQ ID NO 46
<211> LENGTH: 234
<212> TYPE: DNA
<213> ORGANISM: Artificial Sequence
<220> FEATURE:
<223> OTHER INFORMATION: Helper/Rev; HIV RRE; Binds Rev element

<400> SEQUENCE: 46

```
aggagctttg ttccttgggt tcttgggagc agcaggaagc actatgggcg cagcgtcaat     60

gacgctgacg gtacaggcca gacaattatt gtctggtata gtgcagcagc agaacaattt    120

gctgagggct attgaggcgc aacagcatct gttgcaactc acagtctggg gcatcaagca    180

gctccaggca agaatcctgg ctgtggaaag atacctaaag gatcaacagc tcct          234
```

<210> SEQ ID NO 47
<211> LENGTH: 351
<212> TYPE: DNA
<213> ORGANISM: Artificial Sequence
<220> FEATURE:
<223> OTHER INFORMATION: Helper/Rev; HIV Rev; Nuclear export and stabilize viral mRNA

<400> SEQUENCE: 47

```
atggcaggaa gaagcggaga cagcgacgaa gaactcctca aggcagtcag actcatcaag     60

tttctctatc aaagcaaccc acctcccaat cccgagggga cccgacaggc ccgaaggaat    120

agaagaagaa ggtggagaga gagacagaga cagatccatt cgattagtga acggatcctt    180

agcacttatc tgggacgatc tgcggagcct gtgcctcttc agctaccacc gcttgagaga    240
```

-continued

```
cttactcttg attgtaacga ggattgtgga acttctggga cgcagggggt gggaagccct    300

caaatattgg tggaatctcc tacaatattg gagtcaggag ctaaagaata g             351


<210> SEQ ID NO 48
<211> LENGTH: 448
<212> TYPE: DNA
<213> ORGANISM: Artificial Sequence
<220> FEATURE:
<223> OTHER INFORMATION: Helper/Rev; Rabbit beta globin poly A; RNA
      stability

<400> SEQUENCE: 48

agatcttttt ccctctgcca aaaattatgg ggacatcatg aagccccttg agcatctgac     60

ttctggctaa taaaggaaat ttattttcat tgcaatagtg tgttggaatt ttttgtgtct    120

ctcactcgga aggacatatg ggagggcaaa tcatttaaaa catcagaatg agtatttggt    180

ttagagtttg gcaacatatg ccatatgctg gctgccatga acaaaggtgg ctataaagag    240

gtcatcagta tatgaaacag ccccctgctg tccattcctt attccataga aaagccttga    300

cttgaggtta gattttttt atattttgtt ttgtgttatt tttttcttta acatccctaa    360

aattttcctt acatgtttta ctagccagat ttttcctcct ctcctgacta ctcccagtca    420

tagctgtccc tcttctctta tgaagatc                                      448


<210> SEQ ID NO 49
<211> LENGTH: 352
<212> TYPE: DNA
<213> ORGANISM: Artificial Sequence
<220> FEATURE:
<223> OTHER INFORMATION: Helper/Rev; CMV early (CAG) enhancer; Enhance
      Transcription

<400> SEQUENCE: 49

tagttattaa tagtaatcaa ttacggggtc attagttcat agcccatata tggagttccg     60

cgttacataa cttacggtaa atggcccgcc tggctgaccg cccaacgacc cccgcccatt    120

gacgtcaata atgacgtatg ttcccatagt aacgccaata gggactttcc attgacgtca    180

atgggtggac tatttacggt aaactgccca cttggcagta catcaagtgt atcatatgcc    240

aagtacgccc cctattgacg tcaatgacgg taaatggccc gcctggcatt atgcccagta    300

catgacctta tgggactttc ctacttggca gtacatctac gtattagtca tc            352


<210> SEQ ID NO 50
<211> LENGTH: 290
<212> TYPE: DNA
<213> ORGANISM: Artificial Sequence
<220> FEATURE:
<223> OTHER INFORMATION: Helper/Rev; Chicken beta actin (CAG) promoter;
      Transcription

<400> SEQUENCE: 50

gctattacca tgggtcgagg tgagccccac gttctgcttc actctcccca tctccccccc     60

ctccccaccc ccaattttgt atttatttat tttttaatta ttttgtgcag cgatgggggc    120

gggggggggg ggggcgcgcg ccaggcgggg cggggcgggg cgaggggcgg ggcggggcga    180

ggcggagagg tgcggcggca gccaatcaga gcggcgcgct ccgaaagttt ccttttatgg    240

cgaggcggcg gcggcggcgg ccctataaaa agcgaagcgc gcggcgggcg               290


<210> SEQ ID NO 51
<211> LENGTH: 960
<212> TYPE: DNA
```

<213> ORGANISM: Artificial Sequence
<220> FEATURE:
<223> OTHER INFORMATION: Helper/Rev; Chicken beta actin intron; Enhance gene expression

<400> SEQUENCE: 51
ggagtcgctg cgttgccttc gccccgtgcc ccgctccgcg ccgcctcgcg ccgcccgccc 60
cggctctgac tgaccgcgtt actcccacag gtgagcgggc gggacggccc ttctcctccg 120
ggctgtaatt agcgcttggt ttaatgacgg ctcgtttctt ttctgtggct gcgtgaaagc 180
cttaaagggc tccgggaggg ccctttgtgc ggggggagc ggctcggggg gtgcgtgcgt 240
gtgtgtgtgc gtggggagcg ccgcgtgcgg cccgcgctgc ccggcggctg tgagcgctgc 300
gggcgcggcg cggggctttg tgcgctccgc gtgtgcgcga ggggagcgcg gccgggggcg 360
gtgccccgcg gtgcgggggg gctgcgaggg gaacaaaggc tgcgtgcggg gtgtgtgcgt 420
gggggggtga gcagggggtg tgggcgcggc ggtcgggctg taaccccccc ctgcaccccc 480
ctccccgagt tgctgagcac ggcccggctt cgggtgcggg gctccgtgcg gggcgtggcg 540
cggggctcgc cgtgccgggc ggggggtggc ggcaggtggg ggtgccgggc ggggcggggc 600
cgcctcgggc cggggagggc tcgggggagg ggcgcggcgg ccccggagcg ccggcggctg 660
tcgaggcgcg gcgagccgca gccattgcct tttatggtaa tcgtgcgaga gggcgcaggg 720
acttcctttg tcccaaatct ggcggagccg aaatctggga ggcgccgccg caccccctct 780
agcgggcgcg ggcgaagcgg tgcggcgccg gcaggaagga aatgggcggg gagggccttc 840
gtgcgtcgcc gcgccgccgt ccccttctcc atctccagcc tcggggctgc cgcaggggga 900
cggctgcctt cgggggggac ggggcagggc ggggttcggc ttctggcgtg tgaccggcgg 960

<210> SEQ ID NO 52
<211> LENGTH: 1503
<212> TYPE: DNA
<213> ORGANISM: Artificial Sequence
<220> FEATURE:
<223> OTHER INFORMATION: Helper/Rev; HIV Gag; Viral capsid

<400> SEQUENCE: 52
atgggtgcga gagcgtcagt attaagcggg ggagaattag atcgatggga aaaaattcgg 60
ttaaggccag ggggaaagaa aaaatataaa ttaaaacata tagtatgggc aagcagggag 120
ctagaacgat tcgcagttaa tcctggcctg ttagaaacat cagaaggctg tagacaaata 180
ctgggacagc tacaaccatc ccttcagaca ggatcagaag aacttagatc attatataat 240
acagtagcaa ccctctattg tgtgcatcaa aggatagaga taaaagacac caaggaagct 300
ttagacaaga tagaggaaga gcaaaacaaa agtaagaaaa aagcacagca agcagcagct 360
gacacaggac acagcaatca ggtcagccaa aattacccta tagtgcagaa catccagggg 420
caaatggtac atcaggccat atcacctaga actttaaatg catgggtaaa agtagtagaa 480
gagaaggctt tcagcccaga agtgataccc atgttttcag cattatcaga aggagccacc 540
ccacaagatt taaacaccat gctaaacaca gtggggggac atcaagcagc catgcaaatg 600
ttaaaagaga ccatcaatga ggaagctgca gaatgggata gagtgcatcc agtgcatgca 660
gggcctattg caccaggcca gatgagagaa ccaaggggaa gtgacatagc aggaactact 720
agtacccttc aggaacaaat aggatggatg acacataatc cacctatccc agtaggagaa 780
atctataaaa gatggataat cctgggatta aataaaatag taagaatgta tagccctacc 840
agcattctgg acataagaca aggaccaaag gaacccttta gagactatgt agaccgattc 900

```
tataaaactc taagagccga gcaagcttca caagaggtaa aaaattggat gacagaaacc     960

ttgttggtcc aaaatgcgaa cccagattgt aagactattt taaaagcatt gggaccagga    1020

gcgacactag aagaaatgat gacagcatgt cagggagtgg ggggacccgg ccataaagca    1080

agagttttgg ctgaagcaat gagccaagta acaaatccag ctaccataat gatacagaaa    1140

ggcaatttta ggaaccaaag aaagactgtt aagtgtttca attgtggcaa agaagggcac    1200

atagccaaaa attgcagggc ccctaggaaa aagggctgtt ggaaatgtgg aaaggaagga    1260

caccaaatga aagattgtac tgagagacag gctaattttt tagggaagat ctggccttcc    1320

cacaagggaa ggccagggaa ttttcttcag agcagaccag agccaacagc cccaccagaa    1380

gagagcttca ggtttgggga agagacaaca actccctctc agaagcagga gccgatagac    1440

aaggaactgt atcctttagc ttccctcaga tcactctttg gcagcgaccc ctcgtcacaa    1500

taa                                                                  1503
```

<210> SEQ ID NO 53
<211> LENGTH: 1872
<212> TYPE: DNA
<213> ORGANISM: Artificial Sequence
<220> FEATURE:
<223> OTHER INFORMATION: Helper/Rev; HIV Pol; Protease and reverse transcriptase

<400> SEQUENCE: 53

```
atgaatttgc caggaagatg gaaaccaaaa atgatagggg gaattggagg ttttatcaaa      60

gtaggacagt atgatcagat actcatagaa atctgcggac ataaagctat aggtacagta     120

ttagtaggac ctacacctgt caacataatt ggaagaaatc tgttgactca gattggctgc     180

actttaaatt ttcccattag tcctattgag actgtaccag taaaattaaa gccaggaatg     240

gatggcccaa aagttaaaca atggccattg acagaagaaa aaataaaagc attagtagaa     300

atttgtacag aaatggaaaa ggaaggaaaa atttcaaaaa ttgggcctga aaatccatac     360

aatactccag tatttgccat aaagaaaaaa gacagtacta aatggagaaa attagtagat     420

ttcagagaac ttaataagag aactcaagat ttctgggaag ttcaattagg aataccacat     480

cctgcagggt taaaacagaa aaaatcagta acagtactgg atgtgggcga tgcatatttt     540

tcagttccct tagataaaga cttcaggaag tatactgcat ttaccatacc tagtataaac     600

aatgagacac cagggattag atatcagtac aatgtgcttc cacagggatg gaaaggatca     660

ccagcaatat tccagtgtag catgacaaaa atcttagagc cttttagaaa acaaaatcca     720

gacatagtca tctatcaata catggatgat ttgtatgtag gatctgactt agaaataggg     780

cagcatagaa caaaaataga ggaactgaga caacatctgt tgaggtgggg atttaccaca     840

ccagacaaaa aacatcagaa agaacctcca ttcctttgga tgggttatga actccatcct     900

gataaatgga cagtacagcc tatagtgctg ccagaaaagg acagctggac tgtcaatgac     960

atacagaaat tagtgggaaa attgaattgg gcaagtcaga tttatgcagg gattaaagta    1020

aggcaattat gtaaacttct taggggaacc aaagcactaa cagaagtagt accactaaca    1080

gaagaagcag agctagaact ggcagaaaac agggagattc taaaagaacc ggtacatgga    1140

gtgtattatg acccatcaaa agacttaata gcagaaatac agaagcaggg gcaaggccaa    1200

tggacatatc aaatttatca agagccattt aaaaatctga aaacaggaaa atatgcaaga    1260

atgaagggtg cccacactaa tgatgtgaaa caattaacag aggcagtaca aaaaatagcc    1320

acagaaagca tagtaatatg gggaaagact cctaaattta aattacccat acaaaaggaa    1380
```

```
acatgggaag catggtggac agagtattgg caagccacct ggattcctga gtgggagttt   1440

gtcaataccc ctcccttagt gaagttatgg taccagttag agaaagaacc cataatagga   1500

gcagaaactt tctatgtaga tggggcagcc aatagggaaa ctaaattagg aaaagcagga   1560

tatgtaactg acagaggaag acaaaaagtt gtccccctaa cggacacaac aaatcagaag   1620

actgagttac aagcaattca tctagctttg caggattcgg gattagaagt aaacatagtg   1680

acagactcac aatatgcatt gggaatcatt caagcacaac cagataagag tgaatcagag   1740

ttagtcagtc aaataataga gcagttaata aaaaaggaaa aagtctacct ggcatgggta   1800

ccagcacaca aaggaattgg aggaaatgaa caagtagatg ggttggtcag tgctggaatc   1860

aggaaagtac ta                                                       1872


<210> SEQ ID NO 54
<211> LENGTH: 867
<212> TYPE: DNA
<213> ORGANISM: Artificial Sequence
<220> FEATURE:
<223> OTHER INFORMATION: Helper Rev; HIV Integrase; Integration of viral
      RNA

<400> SEQUENCE: 54

tttttagatg gaatagataa ggcccaagaa gaacatgaga aatatcacag taattggaga     60

gcaatggcta gtgattttaa cctaccacct gtagtagcaa aagaaatagt agccagctgt    120

gataaatgtc agctaaaagg ggaagccatg catggacaag tagactgtag cccaggaata    180

tggcagctag attgtacaca tttagaagga aaagttatct tggtagcagt tcatgtagcc    240

agtggatata tagaagcaga agtaattcca gcagagacag ggcaagaaac agcatacttc    300

ctcttaaaat tagcaggaag atggccagta aaaacagtac atacagacaa tggcagcaat    360

ttcaccagta ctacagttaa ggccgcctgt tggtgggcgg ggatcaagca ggaatttggc    420

attccctaca atccccaaag tcaaggagta atagaatcta tgaataaaga attaaagaaa    480

attataggac aggtaagaga tcaggctgaa catcttaaga cagcagtaca aatggcagta    540

ttcatccaca attttaaaag aaaagggggg attggggggt acagtgcagg ggaaagaata    600

gtagacataa tagcaacaga catacaaact aaagaattac aaaaacaaat tacaaaaatt    660

caaaattttc gggtttatta cagggacagc agagatccag tttggaaagg accagcaaag    720

ctcctctgga aaggtgaagg ggcagtagta atacaagata atagtgacat aaaagtagtg    780

ccaagaagaa aagcaaagat catcagggat tatggaaaac agatggcagg tgatgattgt    840

gtggcaagta gacaggatga ggattaa                                        867


<210> SEQ ID NO 55
<211> LENGTH: 234
<212> TYPE: DNA
<213> ORGANISM: Artificial Sequence
<220> FEATURE:
<223> OTHER INFORMATION: Helper/Rev; HIV RRE; Binds Rev element

<400> SEQUENCE: 55

aggagctttg ttccttgggt tcttgggagc agcaggaagc actatgggcg cagcgtcaat     60

gacgctgacg gtacaggcca gacaattatt gtctggtata gtgcagcagc agaacaattt    120

gctgagggct attgaggcgc aacagcatct gttgcaactc acagtctggg gcatcaagca    180

gctccaggca agaatcctgg ctgtggaaag atacctaaag gatcaacagc tcct          234


<210> SEQ ID NO 56
```

```
<211> LENGTH: 448
<212> TYPE: DNA
<213> ORGANISM: Artificial Sequence
<220> FEATURE:
<223> OTHER INFORMATION: Helper/Rev; Rabbit beta globin poly A; RNA
      stability

<400> SEQUENCE: 56

agatcttttt ccctctgcca aaaattatgg ggacatcatg aagccccttg agcatctgac     60

ttctggctaa taaaggaaat ttattttcat tgcaatagtg tgttggaatt ttttgtgtct    120

ctcactcgga aggacatatg ggagggcaaa tcatttaaaa catcagaatg agtatttggt    180

ttagagtttg gcaacatatg ccatatgctg gctgccatga acaaaggtgg ctataaagag    240

gtcatcagta tatgaaacag ccccctgctg tccattcctt attccataga aaagccttga    300

cttgaggtta gatttttttt atattttgtt ttgtgttatt tttttcttta acatccctaa    360

aattttcctt acatgtttta ctagccagat ttttcctcct ctcctgacta ctcccagtca    420

tagctgtccc tcttctctta tgaagatc                                       448


<210> SEQ ID NO 57
<211> LENGTH: 351
<212> TYPE: DNA
<213> ORGANISM: Artificial Sequence
<220> FEATURE:
<223> OTHER INFORMATION: Helper/Rev; HIV Rev; Nuclear export and
      stabilize viral mRNA

<400> SEQUENCE: 57

atggcaggaa gaagcggaga cagcgacgaa gaactcctca aggcagtcag actcatcaag     60

tttctctatc aaagcaaccc acctcccaat cccgagggga cccgacaggc ccgaaggaat    120

agaagaagaa ggtggagaga gagacagaga cagatccatt cgattagtga acggatcctt    180

agcacttatc tgggacgatc tgcggagcct gtgcctcttc agctaccacc gcttgagaga    240

cttactcttg attgtaacga ggattgtgga acttctggga cgcagggggt gggaagccct    300

caaatattgg tggaatctcc tacaatattg gagtcaggag ctaaagaata g             351


<210> SEQ ID NO 58
<211> LENGTH: 351
<212> TYPE: DNA
<213> ORGANISM: Artificial Sequence
<220> FEATURE:
<223> OTHER INFORMATION: Helper/Rev; HIV Rev; Nuclear export and
      stabilize viral mRNA

<400> SEQUENCE: 58

atggcaggaa gaagcggaga cagcgacgaa gaactcctca aggcagtcag actcatcaag     60

tttctctatc aaagcaaccc acctcccaat cccgagggga cccgacaggc ccgaaggaat    120

agaagaagaa ggtggagaga gagacagaga cagatccatt cgattagtga acggatcctt    180

agcacttatc tgggacgatc tgcggagcct gtgcctcttc agctaccacc gcttgagaga    240

cttactcttg attgtaacga ggattgtgga acttctggga cgcagggggt gggaagccct    300

caaatattgg tggaatctcc tacaatattg gagtcaggag ctaaagaata g             351


<210> SEQ ID NO 59
<211> LENGTH: 450
<212> TYPE: DNA
<213> ORGANISM: Artificial Sequence
<220> FEATURE:
<223> OTHER INFORMATION: Rev; Rabbit beta globin poly A; RNA stability
```

<400> SEQUENCE: 59
agatcttttt ccctctgcca aaaattatgg ggacatcatg aagccccttg agcatctgac 60
ttctggctaa taaaggaaat ttattttcat tgcaatagtg tgttggaatt ttttgtgtct 120
ctcactcgga aggacatatg ggagggcaaa tcatttaaaa catcagaatg agtatttggt 180
ttagagtttg gcaacatatg cccatatgct ggctgccatg aacaaaggtt ggctataaag 240
aggtcatcag tatatgaaac agccccctgc tgtccattcc ttattccata gaaaagcctt 300
gacttgaggt tagatttttt ttatattttg ttttgtgtta ttttttttctt taacatccct 360 aaaattttcc ttacatgttt tactagccag atttttcctc ctctcctgac tactcccagt 420
catagctgtc cctcttctct tatggagatc 450

<210> SEQ ID NO 60
<211> LENGTH: 577
<212> TYPE: DNA
<213> ORGANISM: Artificial Sequence
<220> FEATURE:
<223> OTHER INFORMATION: Envelope; CMV promoter; Transcription

<400> SEQUENCE: 60
acattgatta ttgactagtt attaatagta atcaattacg gggtcattag ttcatagccc 60
atatatggag ttccgcgtta cataacttac ggtaaatggc ccgcctggct gaccgcccaa 120
cgacccccgc ccattgacgt caataatgac gtatgttccc atagtaacgc caatagggac 180
tttccattga cgtcaatggg tggagtattt acggtaaact gcccacttgg cagtacatca 240
agtgtatcat atgccaagta cgccccctat tgacgtcaat gacggtaaat ggcccgcctg 300
gcattatgcc cagtacatga ccttatggga ctttcctact tggcagtaca tctacgtatt 360
agtcatcgct attaccatgg tgatgcggtt ttggcagtac atcaatgggc gtggatagcg 420
gtttgactca cggggatttc caagtctcca ccccattgac gtcaatggga gtttgttttg 480
gcaccaaaat caacgggact ttccaaaatg tcgtaacaac tccgccccat tgacgcaaat 540
gggcggtagg cgtgtacggt gggaggtcta tataagc 577

<210> SEQ ID NO 61
<211> LENGTH: 573
<212> TYPE: DNA
<213> ORGANISM: Artificial Sequence
<220> FEATURE:
<223> OTHER INFORMATION: Envelope; Beta globin intron; Enhance gene expression

<400> SEQUENCE: 61
gtgagtttgg ggacccttga ttgttctttc tttttcgcta ttgtaaaatt catgttatat 60
ggagggggca aagttttcag ggtgttgttt agaatgggaa gatgtccctt gtatcaccat 120
ggaccctcat gataattttg tttctttcac tttctactct gttgacaacc attgtctcct 180
cttattttct tttcattttc tgtaactttt tcgttaaact ttagcttgca tttgtaacga 240
atttttaaat tcacttttgt ttatttgtca gattgtaagt actttctcta atcacttttt 300
tttcaaggca atcagggtat attatattgt acttcagcac agttttagag aacaattgtt 360
ataattaaat gataaggtag aatatttctg catataaatt ctggctggcg tggaaatatt 420
cttattggta gaaacaacta caccctggtc atcatcctgc ctttctcttt atggttacaa 480
tgatatacac tgtttgagat gaggataaaa tactctgagt ccaaaccggg cccctctgct 540
aaccatgttc atgccttctt ctctttccta cag 573

<210> SEQ ID NO 62
<211> LENGTH: 1519
<212> TYPE: DNA
<213> ORGANISM: Artificial Sequence
<220> FEATURE:
<223> OTHER INFORMATION: Envelope; VSV-G; Glycoprotein envelope-cell entry

<400> SEQUENCE: 62
atgaagtgcc ttttgtactt agccttttta ttcattgggg tgaattgcaa gttcaccata 60
gtttttccac acaaccaaaa aggaaactgg aaaaatgttc cttctaatta ccattattgc 120
ccgtcaagct cagatttaaa ttggcataat gacttaatag gcacagcctt acaagtcaaa 180
atgcccaaga gtcacaaggc tattcaagca gacggttgga tgtgtcatgc ttccaaatgg 240
gtcactactt gtgatttccg ctggtatgga ccgaagtata taacacattc catccgatcc 300
ttcactccat ctgtagaaca atgcaaggaa agcattgaac aaacgaaaca aggaacttgg 360
ctgaatccag gcttccctcc tcaaagttgt ggatatgcaa ctgtgacgga tgccgaagca 420
gtgattgtcc aggtgactcc tcaccatgtg ctggttgatg aatacacagg agaatgggtt 480
gattcacagt tcatcaacgg aaaatgcagc aattacatat gccccactgt ccataactct 540
acaacctggc attctgacta taaggtcaaa gggctatgtg attctaacct catttccatg 600
gacatcacct tcttctcaga ggacggagag ctatcatccc tgggaaagga gggcacaggg 660
ttcagaagta actactttgc ttatgaaact ggaggcaagg cctgcaaaat gcaatactgc 720
aagcattggg gagtcagact cccatcaggt gtctggttcg agatggctga taaggatctc 780
tttgctgcag ccagattccc tgaatgccca gaagggtcaa gtatctctgc tccatctcag 840
acctcagtgg atgtaagtct aattcaggac gttgagagga tcttggatta ttccctctgc 900
caagaaacct ggagcaaaat cagagcgggt cttccaatct ctccagtgga tctcagctat 960
cttgctccta aaaacccagg aaccggtcct gctttcacca taatcaatgg taccctaaaa 1020
tactttgaga ccagatacat cagagtcgat attgctgctc caatcctctc aagaatggtc 1080
ggaatgatca gtggaactac cacagaaagg gaactgtggg atgactgggc accatatgaa 1140
gacgtggaaa ttggacccaa tggagttctg aggaccagtt caggatataa gtttccttta 1200
tacatgattg gacatggtat gttggactcc gatcttcatc ttagctcaaa ggctcaggtg 1260
ttcgaacatc ctcacattca agacgctgct tcgcaacttc ctgatgatga gagtttattt 1320
tttggtgata ctgggctatc caaaaatcca atcgagcttg tagaaggttg gttcagtagt 1380
tggaaaagct ctattgcctc ttttttcttt atcatagggt taatcattgg actattcttg 1440
gttctccgag ttggtatcca tctttgcatt aaattaaagc acaccaagaa aagacagatt 1500
tatacagaca tagagatga 1519

<210> SEQ ID NO 63
<211> LENGTH: 450
<212> TYPE: DNA
<213> ORGANISM: Artificial Sequence
<220> FEATURE:
<223> OTHER INFORMATION: Rev; Rabbit beta globin poly A; RNA stability

<400> SEQUENCE: 63
agatcttttt ccctctgcca aaaattatgg ggacatcatg aagccccttg agcatctgac 60
ttctggctaa taaaggaaat ttattttcat tgcaatagtg tgttggaatt ttttgtgtct 120
ctcactcgga aggacatatg ggagggcaaa tcatttaaaa catcagaatg agtatttggt 180
ttagagtttg gcaacatatg cccatatgct ggctgccatg aacaaaggtt ggctataaag 240
aggtcatcag tatatgaaac agccccctgc tgtccattcc ttattccata gaaaagcctt 300
gacttgaggt tagatttttt ttatattttg ttttgtgtta tttttttctt taacatccct 360
aaaattttcc ttacatgttt tactagccag atttttcctc ctctcctgac tactcccagt 420
catagctgtc cctcttctct tatggagatc 450

<210> SEQ ID NO 64
<211> LENGTH: 1104
<212> TYPE: DNA
<213> ORGANISM: Artificial Sequence
<220> FEATURE:
<223> OTHER INFORMATION: Elongation Factor-1 alpha (EF1-alpha) promoter

<400> SEQUENCE: 64
ccggtgccta gagaaggtgg cgcggggtaa actgggaaag tgatgtcgtg tactggctcc 60
gcctttttcc cgagggtggg ggagaaccgt atataagtgc agtagtcgcc gtgaacgttc 120
tttttcgcaa cgggtttgcc gccagaacac aggtaagtgc cgtgtgtggt tcccgcgggc 180
ctggcctctt tacgggttat ggcccttgcg tgccttgaat tacttccacg cccctggctg 240
cagtacgtga ttcttgatcc cgagcttcgg gttggaagtg ggtgggagag ttcgaggcct 300
tgcgcttaag gagccccttc gcctcgtgct tgagttgagg cctggcctgg gcgctggggc 360
cgccgcgtgc gaatctggtg gcaccttcgc gcctgtctcg ctgctttcga taagtctcta 420
gccatttaaa atttttgatg acctgctgcg acgctttttt tctggcaaga tagtcttgta 480
aatgcgggcc aagatctgca cactggtatt tcggtttttg gggccgcggg cggcgacggg 540
gcccgtgcgt cccagcgcac atgttcggcg aggcggggcc tgcgagcgcg gccaccgaga 600
atcggacggg ggtagtctca agctggccgg cctgctctgg tgcctggcct cgcgccgccg 660
tgtatcgccc cgccctgggc ggcaaggctg gcccggtcgg caccagttgc gtgagcggaa 720
agatggccgc ttcccggccc tgctgcaggg agctcaaaat ggaggacgcg gcgctcggga 780
gagcgggcgg gtgagtcacc cacacaaagg aaaagggcct ttccgtcctc agccgtcgct 840
tcatgtgact ccacggagta ccgggcgccg tccaggcacc tcgattagtt ctcgagcttt 900
tggagtacgt cgtctttagg ttggggggag gggttttatg cgatggagtt tccccacact 960
gagtgggtgg agactgaagt taggccagct tggcacttga tgtaattctc cttggaattt 1020
gccctttttg agtttggatc ttggttcatt ctcaagcctc agacagtggt tcaaagtttt 1080
tttcttccat ttcaggtgtc gtga 1104

<210> SEQ ID NO 65
<211> LENGTH: 511
<212> TYPE: DNA
<213> ORGANISM: Artificial Sequence
<220> FEATURE:
<223> OTHER INFORMATION: Promoter; PGK

<400> SEQUENCE: 65
ggggttgggg ttgcgccttt tccaaggcag ccctgggttt gcgcagggac gcggctgctc 60
tgggcgtggt tccgggaaac gcagcggcgc cgaccctggg tctcgcacat tcttcacgtc 120
cgttcgcagc gtcacccgga tcttcgccgc taccettgtg ggcccccegg cgacgcttcc 180 tgctccgccc ctaagtcggg aaggttcctt gcggttcgcg gcgtgccgga cgtgacaaac 240
ggaagccgca cgtctcacta gtaccctcgc agacggacag cgccagggag caatggcagc 300
gcgccgaccg cgatgggctg tggccaatag cggctgctca gcagggcgcg ccgagagcag 360

-continued

```
cggccgggaa ggggcggtgc gggaggcggg gtgtggggcg gtagtgtggg ccctgttcct    420

gcccgcgcgg tgttccgcat tctgcaagcc tccggagcgc acgtcggcag tcggctccct    480

cgttgaccga atcaccgacc tctctcccca g                                   511
```

<210> SEQ ID NO 66
<211> LENGTH: 1162
<212> TYPE: DNA
<213> ORGANISM: Artificial Sequence
<220> FEATURE:
<223> OTHER INFORMATION: Promoter; UbC

<400> SEQUENCE: 66

```
gcgccgggtt ttggcgcctc ccgcgggcgc ccccctcctc acggcgagcg ctgccacgtc     60

agacgaaggg cgcaggagcg ttcctgatcc ttccgcccgg acgctcagga cagcggcccg    120

ctgctcataa gactcggcct tagaacccca gtatcagcag aaggacattt taggacggga    180

cttgggtgac tctagggcac tggttttctt tccagagagc ggaacaggcg aggaaaagta    240

gtcccttctc ggcgattctg cggagggatc tccgtggggc ggtgaacgcc gatgattata    300

taaggacgcg ccgggtgtgg cacagctagt tccgtcgcag ccgggatttg ggtcgcggtt    360

cttgtttgtg gatcgctgtg atcgtcactt ggtgagttgc gggctgctgg gctggccggg    420

gctttcgtgg ccgccgggcc gctcggtggg acggaagcgt gtggagagac cgccaagggc    480

tgtagtctgg gtccgcgagc aaggttgccc tgaactgggg gttgggggga gcgcacaaaa    540

tggcggctgt tcccgagtct tgaatggaag acgcttgtaa ggcgggctgt gaggtcgttg    600

aaacaaggtg gggggcatgg tgggcggcaa gaacccaagg tcttgaggcc ttcgctaatg    660

cgggaaagct cttattcggg tgagatgggc tggggcacca tctggggacc ctgacgtgaa    720

gtttgtcact gactggagaa ctcgggtttg tcgtctggtt gcgggggcgg cagttatgcg    780

gtgccgttgg gcagtgcacc cgtacctttg ggagcgcgcg cctcgtcgtg tcgtgacgtc    840

acccgttctg ttggcttata atgcagggtg gggccacctg ccggtaggtg tgcggtaggc    900

ttttctccgt cgcaggacgc agggttcggg cctagggtag gctctcctga atcgacaggc    960

gccggacctc tggtgagggg agggataagt gaggcgtcag tttctttggt cggttttatg   1020

tacctatctt cttaagtagc tgaagctccg gttttgaact atgcgctcgg ggttggcgag   1080

tgtgttttgt gaagtttttt aggcaccttt tgaaatgtaa tcatttgggt caatatgtaa   1140

ttttcagtgt tagactagta aa                                            1162
```

<210> SEQ ID NO 67
<211> LENGTH: 120
<212> TYPE: DNA
<213> ORGANISM: Artificial Sequence
<220> FEATURE:
<223> OTHER INFORMATION: Poly A; SV40

<400> SEQUENCE: 67

```
gtttattgca gcttataatg gttacaaata aagcaatagc atcacaaatt tcacaaataa     60

agcatttttt tcactgcatt ctagttgtgg tttgtccaaa ctcatcaatg tatcttatca    120
```

<210> SEQ ID NO 68
<211> LENGTH: 227
<212> TYPE: DNA
<213> ORGANISM: Artificial Sequence
<220> FEATURE:
<223> OTHER INFORMATION: Poly A; bGH -continued

<400> SEQUENCE: 68
gactgtgcct tctagttgcc agccatctgt tgtttgcccc tcccccgtgc cttccttgac 60
cctggaaggt gccactccca ctgtcctttc ctaataaaat gaggaaattg catcgcattg 120
tctgagtagg tgtcattcta ttctgggggg tggggtgggg caggacagca agggggagga 180
ttgggaagac aatagcaggc atgctgggga tgcggtgggc tctatgg 227

<210> SEQ ID NO 69
<211> LENGTH: 1512
<212> TYPE: DNA
<213> ORGANISM: Artificial Sequence
<220> FEATURE:
<223> OTHER INFORMATION: HIV Gag; Bal

<400> SEQUENCE: 69
atgggtgcga gagcgtcagt attaagcggg ggagaattag ataggtggga aaaaattcgg 60
ttaaggccag ggggaaagaa aaaatataga ttaaaacata tagtatgggc aagcagggaa 120
ctagaaagat tcgcagtcaa tcctggcctg ttagaaacat cagaaggctg cagacaaata 180
ctgggacagc tacaaccatc ccttcagaca ggatcagaag aacttagatc attatataat 240
acagtagcaa ccctctattg tgtacatcaa aagatagagg taaaagacac caaggaagct 300
ttagacaaaa tagaggaaga gcaaaacaaa tgtaagaaaa aggcacagca agcagcagct 360
gacacaggaa acagcggtca ggtcagccaa aatttcccta tagtgcagaa cctccagggg 420
caaatggtac atcaggccat atcacctaga actttaaatg catgggtaaa agtaatagaa 480
gagaaagctt tcagcccaga agtaataccc atgttttcag cattatcaga aggagccacc 540
ccacaagatt taaacaccat gctaaacaca gtggggggac atcaagcagc catgcaaatg 600
ttaaaagaac ccatcaatga ggaagctgca agatgggata gattgcatcc cgtgcaggca 660
gggcctgttg caccaggcca gataagagat ccaaggggaa gtgacatagc aggaactacc 720
agtacccttc aggaacaaat aggatggatg acaagtaatc cacctatccc agtaggagaa 780
atctataaaa gatggataat cctgggatta aataaaatag taaggatgta tagccctacc 840
agcattttgg acataagaca aggaccaaag gaacccttta gagactatgt agaccggttc 900
tataaaactc taagagccga gcaagcttca caggaggtaa aaaattggat gacagaaacc 960
ttgttggtcc aaaatgcgaa cccagattgt aagactattt taaaagcatt gggaccagca 1020
gctacactag aagaaatgat gacagcatgt cagggagtgg gaggacccag ccataaagca 1080
agaattttgg cagaagcaat gagccaagta acaaattcag ctaccataat gatgcagaaa 1140
ggcaatttta ggaaccaaag aaagattgtt aaatgtttca attgtggcaa agaagggcac 1200
atagccagaa actgcagggc ccctaggaaa aggggctgtt ggaaatgtgg aaaggaagga 1260
caccaaatga aagactgtac tgagagacag gctaattttt tagggaaaat ctggccttcc 1320
cacaaaggaa ggccagggaa tttccttcag agcagaccag agccaacagc cccaccagcc 1380
ccaccagaag agagcttcag gtttggggaa gagacaacaa ctccctctca gaagcaggag 1440
ctgatagaca aggaactgta tcctttagct tccctcagat cactctttgg caacgacccc 1500
tcgtcacaat aa 1512

<210> SEQ ID NO 70
<211> LENGTH: 1872
<212> TYPE: DNA
<213> ORGANISM: Artificial Sequence
<220> FEATURE:
<223> OTHER INFORMATION: HIV Pol; Bal

<400> SEQUENCE: 70
atgaatttgc caggaagatg gaaaccaaaa atgatagggg gaattggagg ttttatcaaa 60
gtaagacagt atgatcagat actcatagaa atctgtggac ataaagctat aggtacagta 120
ttaataggac ctacacctgt caacataatt ggaagaaatc tgttgactca gattggttgc 180
actttaaatt ttcccattag tcctattgaa actgtaccag taaaattaaa accaggaatg 240
gatggcccaa aagttaaaca atggccactg acagaagaaa aaataaaagc attaatggaa 300
atctgtacag aaatggaaaa ggaagggaaa atttcaaaaa ttgggcctga aaatccatac 360
aatactccag tatttgccat aaagaaaaaa gacagtacta aatggagaaa attagtagat 420
ttcagagaac ttaataagaa aactcaagac ttctgggaag tacaattagg aatacacatc 480
ccgcaggggt taaaaaagaa aaaatcagta acagtactgg atgtgggtga tgcatatttt 540
tcagttccct tagataaaga attcaggaag tatactgcat ttaccatacc tagtataaac 600
aatgaaacac cagggatcag atatcagtac aatgtacttc cacagggatg gaaaggatca 660
ccagcaatat ttcaaagtag catgacaaga atcttagagc cttttagaaa acaaaatcca 720
gaaatagtga tctatcaata catggatgat ttgtatgtag gatctgactt agaaataggg 780
cagcatagaa caaaaataga ggaactgaga caacatctgt tgaggtgggg atttaccaca 840
ccagacaaaa aacatcagaa agaacctcca ttcctttgga tgggttatga actccatcct 900
gataaatgga cagtacagcc tatagtgctg ccagaaaaag acagctggac tgtcaatgac 960
atacagaagt tagtgggaaa attgaattgg gcaagtcaga tttacccagg aattaaagta 1020
aagcaattat gtaggctcct taggggaacc aaggcattaa cagaagtaat accactaaca 1080
aaagaaacag agctagaact ggcagagaac agggaaattc taaaagaacc agtacatggg 1140
gtgtattatg acccatcaaa agacttaata gcagaaatac agaagcaggg gcaaggccaa 1200
tggacatatc aaatttatca agagccattt aaaaatctga aaacaggaaa atatgcaaga 1260
atgaggggtg cccacactaa tgatgtaaaa caattaacag aggcagtgca aaaaataacc 1320
acagaaagca tagtaatatg gggaaagact cctaaattta aactacccat acaaaaagaa 1380
acatgggaaa catggtggac agagtattgg caagccacct ggattcctga gtgggagttt 1440
gtcaataccc ctcccttagt gaaattatgg taccagttag agaaagaacc cataatagga 1500
gcagaaacat tctatgtaga tggagcagct aaccgggaga ctaaattagg aaaagcagga 1560
tatgttacta acagaggaag acaaaaagtt gtctccctaa ctgacacaac aaatcagaag 1620
actgagttac aagcaattca tctagcttta caagattcag gattagaagt aaacatagta 1680
acagactcac aatatgcatt aggaatcatt caagcacaac cagataaaag tgaatcagag 1740
ttagtcagtc aaataataga acagttaata aaaaaggaaa aggtctacct ggcatgggta 1800
ccagcgcaca aaggaattgg aggaaatgaa caagtagata aattagtcag tactggaatc 1860
aggaaagtac ta 1872

<210> SEQ ID NO 71
<211> LENGTH: 867
<212> TYPE: DNA
<213> ORGANISM: Artificial Sequence
<220> FEATURE:
<223> OTHER INFORMATION: HIV Integrase; Bal

<400> SEQUENCE: 71
tttttagatg gaatagatat agcccaagaa gaacatgaga aatatcacag taattggaga 60
gcaatggcta gtgattttaa cctgccacct gtggtagcaa aagaaatagt agccagctgt 120
gataaatgtc agctaaaagg agaagccatg catggacaag tagactgtag tccaggaata 180
tggcaactag attgtacaca tttagaagga aaaattatcc tggtagcagt tcatgtagcc 240
agtggatata tagaagcaga agttattcca gcagagacag ggcaggaaac agcatacttt 300
ctcttaaaat tagcaggaag atggccagta aaaacaatac atacagacaa tggcagcaat 360
ttcactagta ctacagtcaa ggccgcctgt tggtgggcgg ggatcaagca ggaatttggc 420
attccctaca atccccaaag tcagggagta gtagaatcta taaataaaga attaaagaaa 480
attataggac aggtaagaga tcaggctgaa catcttaaaa cagcagtaca aatggcagta 540
ttcatccaca attttaaaag aaaagggggg attggggggt atagtgcagg ggaaagaata 600
gtagacataa tagcaacaga catacaaact aaagaattac aaaaacaaat tacaaaaatt 660
caaaattttc gggtttatta cagggacagc agagatccac tttggaaagg accagcaaag 720
cttctctgga aaggtgaagg ggcagtagta atacaagata atagtgacat aaaagtagta 780
ccaagaagaa aagcaaagat cattagggat tatggaaaac agatggcagg tgatgattgt 840
gtggcaagta gacaggatga ggattag 867

<210> SEQ ID NO 72
<211> LENGTH: 1695
<212> TYPE: DNA
<213> ORGANISM: Artificial Sequence
<220> FEATURE:
<223> OTHER INFORMATION: Envelope; RD114

<400> SEQUENCE: 72
atgaaactcc caacaggaat ggtcatttta tgtagcctaa taatagttcg ggcagggttt 60
gacgaccccc gcaaggctat cgcattagta caaaaacaac atggtaaacc atgcgaatgc 120
agcggagggc aggtatccga ggccccaccg aactccatcc aacaggtaac ttgcccaggc 180
aagacggcct acttaatgac caaccaaaaa tggaaatgca gagtcactcc aaaaaatctc 240
acccctagcg gggagaact ccagaactgc ccctgtaaca ctttccagga ctcgatgcac 300
agttcttgtt atactgaata ccggcaatgc agggcgaata ataagacata ctacacggcc 360
accttgctta aaatacggtc tgggagcctc aacgaggtac agatattaca aaaccccaat 420
cagctcctac agtccccttg taggggctct ataaatcagc ccgtttgctg gagtgccaca 480
gcccccatcc atatctccga tggtggagga cccctcgata ctaagagagt gtggacagtc 540
caaaaaaggc tagaacaaat tcataaggct atgcatcctg aacttcaata ccacccctta 600
gccctgccca aagtcagaga tgaccttagc cttgatgcac ggacttttga tatcctgaat 660
accactttta ggttactcca gatgtccaat tttagccttg cccaagattg ttggctctgt 720
ttaaaactag gtacccctac ccctcttgcg atacccactc cctctttaac ctactcccta 780
gcagactccc tagcgaatgc ctcctgtcag attatacctc ccctcttggt tcaaccgatg 840
cagttctcca actcgtcctg tttatcttcc cctttcatta acgatacgga acaaatagac 900
ttaggtgcag tcacctttac taactgcacc tctgtagcca atgtcagtag tcctttatgt 960
gccctaaacg ggtcagtctt cctctgtgga aataacatgg catacaccta tttaccccaa 1020
aactggacag gactttgcgt ccaagcctcc ctcctccccg acattgacat catcccgggg 1080
gatgagccag tccccattcc tgccattgat cattatatac atagacctaa acgagctgta 1140
cagttcatcc ctttactagc tggactggga atcaccgcag cattcaccac cggagctaca 1200
ggcctaggtg tctccgtcac ccagtataca aaattatccc atcagttaat atctgatgtc 1260

```
caagtcttat ccggtaccat acaagattta caagaccagg tagactcgtt agctgaagta   1320

gttctccaaa ataggagggg actggaccta ctaacggcag aacaaggagg aatttgttta   1380

gccttacaag aaaaatgctg tttttatgct aacaagtcag gaattgtgag aaacaaaata   1440

agaaccctac aagaagaatt acaaaaacgc agggaaagcc tggcatccaa ccctctctgg   1500

accgggctgc agggcttct tccgtacctc ctacctctcc tgggacccct actcaccctc   1560

ctactcatac taaccattgg gccatgcgtt ttcaatcgat tggtccaatt tgttaaagac   1620

aggatctcag tggtccaggc tctggttttg actcagcaat atcaccagct aaaacccata   1680

gagtacgagc catga                                                    1695


<210> SEQ ID NO 73
<211> LENGTH: 2013
<212> TYPE: DNA
<213> ORGANISM: Artificial Sequence
<220> FEATURE:
<223> OTHER INFORMATION: Envelope; GALV

<400> SEQUENCE: 73

atgcttctca cctcaagccc gcaccacctt cggcaccaga tgagtcctgg gagctggaaa     60

agactgatca tcctcttaag ctgcgtattc ggagacggca aaacgagtct gcagaataag    120

aacccccacc agcctgtgac cctcacctgg caggtactgt cccaaactgg ggacgttgtc    180

tgggacaaaa aggcagtcca gccccttttgg acttggtggc cctctcttac acctgatgta    240

tgtgccctgg cggccggtct tgagtcctgg gatatcccgg gatccgatgt atcgtcctct    300

aaaagagtta gacctcctga ttcagactat actgccgctt ataagcaaat cacctgggga    360

gccatagggt gcagctaccc tcgggctagg accaggatgg caaattcccc cttctacgtg    420

tgtccccgag ctggccgaac ccattcagaa gctaggaggt gtggggggct agaatcccta    480

tactgtaaag aatggagttg tgagaccacg ggtaccgttt attggcaacc caagtcctca    540

tgggacctca taactgtaaa atgggaccaa aatgtgaaat gggagcaaaa atttcaaaag    600

tgtgaacaaa ccggctggtg taaccccctc aagatagact tcacagaaaa aggaaaactc    660

tccagagatt ggataacgga aaaaacctgg gaattaaggt tctatgtata tggacaccca    720

ggcatacagt tgactatccg cttagaggtc actaacatgc cggttgtggc agtgggccca    780

gaccctgtcc ttgcggaaca gggacctcct agcaagcccc tcactctccc tctctcccca    840

cggaaagcgc cgcccacccc tctacccccg gcggctagtg agcaaacccc tgcggtgcat    900

ggagaaactg ttaccctaaa ctctccgcct cccaccagtg gcgaccgact ctttggcctt    960

gtgcaggggg ccttcctaac cttgaatgct accaacccag gggccactaa gtcttgctgg   1020

ctctgtttgg gcatgagccc cccttattat gaagggatag cctcttcagg agaggtcgct   1080

tatacctcca accatacccg atgccactgg ggggcccaag gaaagcttac cctcactgag   1140

gtctccggac tcgggtcatg catagggaag gtgcctctta cccatcaaca tctttgcaac   1200

cagaccttac ccatcaattc ctctaaaaac catcagtatc tgctcccctc aaaccatagc   1260

tggtgggcct gcagcactgg cctcaccccc tgcctctcca cctcagtttt taatcagtct   1320

aaagacttct gtgtccaggt ccagctgatc ccccgcatct attaccattc tgaagaaacc   1380

ttgttacaag cctatgacaa atcacccccc aggtttaaaa gagagcctgc ctcacttacc   1440

ctagctgtct tcctggggtt agggattgcg gcaggtatag gtactggctc aaccgcccta   1500

attaaagggc ccatagacct ccagcaaggc ctaaccagcc tccaaatcgc cattgacgct   1560
```

-continued gacctccggg cccttcagga ctcaatcagc aagctagagg actcactgac ttccctatct 1620
gaggtagtac tccaaaatag gagaggcctt gacttactat tccttaaaga aggaggcctc 1680
tgcgcggccc taaaagaaga gtgctgtttt tatgtagacc actcaggtgc agtacgagac 1740
tccatgaaaa aacttaaaga aagactagat aaaagacagt tagagcgcca gaaaaaccaa 1800
aactggtatg aagggtggtt caataactcc ccttggttta ctaccctact atcaaccatc 1860
gctgggcccc tattgctcct ccttttgtta ctcactcttg ggccctgcat catcaataaa 1920
ttaatccaat tcatcaatga taggataagt gcagtcaaaa ttttagtcct tagacagaaa 1980
tatcagaccc tagataacga ggaaaacctt taa 2013

<210> SEQ ID NO 74
<211> LENGTH: 1530
<212> TYPE: DNA
<213> ORGANISM: Artificial Sequence
<220> FEATURE:
<223> OTHER INFORMATION: Envelope; FUG

<400> SEQUENCE: 74
atggttccgc aggttctttt gtttgtactc cttctgggtt tttcgttgtg tttcgggaag 60
ttccccattt acacgatacc agacgaactt ggtccctgga gccctattga catacaccat 120
ctcagctgtc caaataacct ggttgtggag gatgaaggat gtaccaacct gtccgagttc 180
tcctacatgg aactcaaagt gggatacatc tcagccatca aagtgaacgg gttcacttgc 240
acaggtgttg tgacagaggc agagacctac accaactttg ttggttatgt cacaaccaca 300
ttcaagagaa agcatttccg ccccaccca gacgcatgta gagccgcgta taactggaag 360
atggccggtg accccagata tgaagagtcc ctacacaatc cataccccga ctaccactgg 420
cttcgaactg taagaaccac caaagagtcc ctcattatca tatccccaag tgtgacagat 480
ttggacccat atgacaaatc ccttcactca agggtcttcc ctggcggaaa gtgctcagga 540
ataacggtgt cctctaccta ctgctcaact aaccatgatt acaccatttg gatgcccgag 600
aatccgagac caaggacacc ttgtgacatt tttaccaata gcagagggaa gagagcatcc 660
aacgggaaca agacttgcgg ctttgtggat gaaagaggcc tgtataagtc tctaaaagga 720
gcatgcaggc tcaagttatg tggagttctt ggacttagac ttatggatgg aacatgggtc 780
gcgatgcaaa catcagatga gaccaaatgg tgccctccag atcagttggt gaatttgcac 840
gactttcgct cagacgagat cgagcatctc gttgtggagg agttagttaa gaaaagagag 900
gaatgtctgg atgcattaga gtccatcatg accaccaagt cagtaagttt cagacgtctc 960
agtcacctga gaaaacttgt cccagggttt ggaaaagcat ataccatatt caacaaaacc 1020
ttgatggagg ctgatgctca ctacaagtca gtccggacct ggaatgagat catcccctca 1080
aaagggtgtt tgaaagttgg aggaaggtgc catcctcatg tgaacggggt gtttttcaat 1140
ggtataatat tagggcctga cgaccatgtc ctaatcccag agatgcaatc atccctcctc 1200
cagcaacata tggagttgtt ggaatcttca gttatccccc tgatgcaccc cctggcagac 1260
ccttctacag ttttcaaaga aggtgatgag gctgaggatt ttgttgaagt tcacctcccc 1320
gatgtgtaca aacagatctc aggggttgac ctgggtctcc cgaactgggg aaagtatgta 1380
ttgatgactg caggggccat gattggcctg gtgttgatat tttccctaat gacatggtgc 1440
agagttggta tccatctttg cattaaatta aagcacacca agaaaagaca gatttataca 1500
gacatagaga tgaaccgact tggaaagtaa 1530

<210> SEQ ID NO 75
<211> LENGTH: 1497
<212> TYPE: DNA
<213> ORGANISM: Artificial Sequence
<220> FEATURE:
<223> OTHER INFORMATION: Envelope; LCMV

<400> SEQUENCE: 75

```
atgggtcaga ttgtgacaat gtttgaggct ctgcctcaca tcatcgatga ggtgatcaac      60
attgtcatta ttgtgcttat cgtgatcacg ggtatcaagg ctgtctacaa ttttgccacc     120
tgtgggatat tcgcattgat cagtttccta cttctggctg gcaggtcctg tggcatgtac     180
ggtcttaagg gacccgacat ttacaaagga gtttaccaat ttaagtcagt ggagtttgat     240
atgtcacatc tgaacctgac catgcccaac gcatgttcag ccaacaactc ccaccattac     300
atcagtatgg ggacttctgg actagaattg accttcacca atgattccat catcagtcac     360
aacttttgca atctgacctc tgccttcaac aaaaagacct ttgaccacac actcatgagt     420
atagtttcga gcctacacct cagtatcaga gggaactcca actataaggc agtatcctgc     480
gacttcaaca atggcataac catccaatac aacttgacat tctcagatcg acaaagtgct     540
cagagccagt gtagaacctt cagaggtaga gtcctagata tgtttagaac tgccttcggg     600
gggaaataca tgaggagtgg ctggggctgg acaggctcag atggcaagac cacctggtgt     660
agccagacga gttaccaata cctgattata caaaatagaa cctgggaaaa ccactgcaca     720
tatgcaggtc cttttgggat gtccaggatt ctcctttccc aagagaagac taagttcttc     780
actaggagac tagcgggcac attcacctgg actttgtcag actcttcagg ggtggagaat     840
ccaggtggtt attgcctgac caaatggatg attcttgctg cagagcttaa gtgtttcggg     900
aacacagcag ttgcgaaatg caatgtaaat catgatgccg aattctgtga catgctgcga     960
ctaattgact acaacaaggc tgctttgagt aagttcaaag aggacgtaga atctgccttg    1020
cacttattca aaacaacagt gaattctttg atttcagatc aactactgat gaggaaccac    1080
ttgagagatc tgatgggggt gccatattgc aattactcaa agttttggta cctagaacat    1140
gcaaagaccg gcgaaactag tgtccccaag tgctggcttg tcaccaatgg ttcttactta    1200
aatgagaccc acttcagtga tcaaatcgaa caggaagccg ataacatgat tacagagatg    1260
ttgaggaagg attacataaa gaggcagggg agtacccccc tagcattgat ggaccttctg    1320
atgttttcca catctgcata tctagtcagc atcttcctgc accttgtcaa aataccaaca    1380
cacaggcaca taaaaggtgg ctcatgtcca aagccacacc gattaaccaa caaaggaatt    1440
tgtagttgtg gtgcatttaa ggtgcctggt gtaaaaaccg tctggaaaag acgctga       1497
```

<210> SEQ ID NO 76
<211> LENGTH: 1692
<212> TYPE: DNA
<213> ORGANISM: Artificial Sequence
<220> FEATURE:
<223> OTHER INFORMATION: Envelope; FPV

<400> SEQUENCE: 76

```
atgaacactc aaatcctggt tttcgccctt gtggcagtca tccccacaaa tgcagacaaa      60
atttgtcttg gacatcatgc tgtatcaaat ggcaccaaag taaacacact cactgagaga     120
ggagtagaag ttgtcaatgc aacggaaaca gtggagcgga caaacatccc caaaatttgc     180
tcaaaaggga aaagaaccac tgatcttggc caatgcggac tgttagggac cattaccgga     240
ccacctcaat gcgaccaatt tctagaattt tcagctgatc taataatcga gagacgagaa     300
```

```
ggaaatgatg tttgttaccc ggggaagttt gttaatgaag aggcattgcg acaaatcctc    360

agaggatcag gtgggattga caaagaaaca atgggattca catatagtgg aataaggacc    420

aacggaacaa ctagtgcatg tagaagatca gggtcttcat tctatgcaga aatggagtgg    480

ctcctgtcaa atacagacaa tgctgctttc ccacaaatga caaaatcata caaaaacaca    540

aggagagaat cagctctgat agtctgggga atccaccatt caggatcaac caccgaacag    600

accaaactat atgggagtgg aaataaactg ataacagtcg ggagttccaa atatcatcaa    660

tcttttgtgc cgagtccagg aacacgaccg cagataaatg gccagtccgg acggattgat    720

tttcattggt tgatcttgga tcccaatgat acagttactt ttagtttcaa tggggctttc    780

atagctccaa atcgtgccag cttcttgagg ggaaagtcca tggggatcca gagcgatgtg    840

caggttgatg ccaattgcga aggggaatgc taccacagtg gagggactat aacaagcaga    900

ttgccttttc aaaacatcaa tagcagagca gttggcaaat gcccaagata tgtaaaacag    960

gaaagtttat tattggcaac tgggatgaag aacgttcccg aaccttccaa aaaaaggaaa   1020

aaaagaggcc tgtttggcgc tatagcaggg tttattgaaa atggttggga aggtctggtc   1080

gacgggtggt acggtttcag gcatcagaat gcacaaggag aaggaactgc agcagactac   1140

aaaagcaccc aatcggcaat tgatcagata accggaaagt taaatagact cattgagaaa   1200

accaaccagc aatttgagct aatagataat gaattcactg aggtggaaaa gcagattggc   1260

aatttaatta actggaccaa agactccatc acagaagtat ggtcttacaa tgctgaactt   1320

cttgtggcaa tggaaaacca gcacactatt gatttggctg attcagagat gaacaagctg   1380

tatgagcgag tgaggaaaca attaagggaa aatgctgaag aggatggcac tggttgcttt   1440

gaaatttttc ataaatgtga cgatgattgt atggctagta taaggaacaa tacttatgat   1500

cacagcaaat acagagaaga agcgatgcaa aatagaatac aaattgaccc agtcaaattg   1560

agtagtggct acaaagatgt gatactttgg tttagcttcg ggcatcatg ctttttgctt    1620

cttgccattg caatgggcct tgttttcata tgtgtgaaga acggaaacat gcggtgcact   1680

atttgtatat aa                                                       1692
```

<210> SEQ ID NO 77
<211> LENGTH: 1266
<212> TYPE: DNA
<213> ORGANISM: Artificial Sequence
<220> FEATURE:
<223> OTHER INFORMATION: Envelope; RRV

<400> SEQUENCE: 77

```
agtgtaacag agcactttaa tgtgtataag gctactagac catacctagc acattgcgcc     60

gattgcgggg acgggtactt ctgctatagc ccagttgcta tcgaggagat ccgagatgag    120

gcgtctgatg gcatgcttaa gatccaagtc tccgcccaaa taggtctgga caaggcaggc    180

acccacgccc acacgaagct ccgatatatg gctggtcatg atgttcagga atctaagaga    240

gattccttga gggtgtacac gtccgcagcg tgctccatac atgggacgat gggacacttc    300

atcgtcgcac actgtccacc aggcgactac ctcaaggttt cgttcgagga cgcagattcg    360

cacgtgaagg catgtaaggt ccaatacaag cacaatccat tgccggtggg tagagagaag    420

ttcgtggtta gaccacactt tggcgtagag ctgccatgca cctcatacca gctgacaacg    480

gctcccaccg acgaggagat tgacatgcat acaccgccag atataccgga tcgcaccctg    540

ctatcacaga cggcgggcaa cgtcaaaata acagcaggcg gcaggactat caggtacaac    600

tgtacctgcg gccgtgacaa cgtaggcact accagtactg acaagaccat caacacatgc    660
```

```
aagattgacc aatgccatgc tgccgtcacc agccatgaca aatggcaatt tacctctcca    720

tttgttccca gggctgatca gacagctagg aaaggcaagg tacacgttcc gttccctctg    780

actaacgtca cctgccgagt gccgttggct cgagcgccgg atgccaccta tggtaagaag    840

gaggtgaccc tgagattaca cccagatcat ccgacgctct tctcctatag gagtttagga    900

gccgaaccgc acccgtacga ggaatgggtt gacaagttct ctgagcgcat catcccagtg    960

acggaagaag ggattgagta ccagtggggc aacaacccgc cggtctgcct gtgggcgcaa   1020

ctgacgaccg agggcaaacc ccatggctgg ccacatgaaa tcattcagta ctattatgga   1080

ctataccccg ccgccactat tgccgcagta tccggggcga gtctgatggc cctcctaact   1140

ctggcggcca catgctgcat gctggccacc gcgaggagaa agtgcctaac accgtacgcc   1200

ctgacgccag gagcggtggt accgttgaca ctggggctgc tttgctgcgc accgagggcg   1260

aatgca                                                              1266
```

<210> SEQ ID NO 78
<211> LENGTH: 1266
<212> TYPE: DNA
<213> ORGANISM: Artificial Sequence
<220> FEATURE:
<223> OTHER INFORMATION: Envelope; RRV

<400> SEQUENCE: 78

```
agtgtaacag agcactttaa tgtgtataag gctactagac catacctagc acattgcgcc     60

gattgcgggg acgggtactt ctgctatagc ccagttgcta tcgaggagat ccgagatgag    120

gcgtctgatg gcatgcttaa gatccaagtc tccgcccaaa taggtctgga caaggcaggc    180

acccacgccc acacgaagct ccgatatatg gctggtcatg atgttcagga atctaagaga    240

gattccttga gggtgtacac gtccgcagcg tgctccatac atgggacgat gggacacttc    300

atcgtcgcac actgtccacc aggcgactac ctcaaggttt cgttcgagga cgcagattcg    360

cacgtgaagg catgtaaggt ccaatacaag cacaatccat tgccggtggg tagagagaag    420

ttcgtggtta gaccacactt tggcgtagag ctgccatgca cctcatacca gctgacaacg    480

gctcccaccg acgaggagat tgacatgcat acaccgccag atataccgga tcgcaccctg    540

ctatcacaga cggcgggcaa cgtcaaaata acagcaggcg gcaggactat caggtacaac    600

tgtacctgcg gccgtgacaa cgtaggcact accagtactg acaagaccat caacacatgc    660

aagattgacc aatgccatgc tgccgtcacc agccatgaca aatggcaatt tacctctcca    720

tttgttccca gggctgatca gacagctagg aaaggcaagg tacacgttcc gttccctctg    780

actaacgtca cctgccgagt gccgttggct cgagcgccgg atgccaccta tggtaagaag    840

gaggtgaccc tgagattaca cccagatcat ccgacgctct tctcctatag gagtttagga    900

gccgaaccgc acccgtacga ggaatgggtt gacaagttct ctgagcgcat catcccagtg    960

acggaagaag ggattgagta ccagtggggc aacaacccgc cggtctgcct gtgggcgcaa   1020

ctgacgaccg agggcaaacc ccatggctgg ccacatgaaa tcattcagta ctattatgga   1080

ctataccccg ccgccactat tgccgcagta tccggggcga gtctgatggc cctcctaact   1140

ctggcggcca catgctgcat gctggccacc gcgaggagaa agtgcctaac accgtacgcc   1200

ctgacgccag gagcggtggt accgttgaca ctggggctgc tttgctgcgc accgagggcg   1260

aatgca                                                              1266
```

<210> SEQ ID NO 79

<211> LENGTH: 2030
<212> TYPE: DNA
<213> ORGANISM: Artificial Sequence
<220> FEATURE:
<223> OTHER INFORMATION: Envelope; Ebola

<400> SEQUENCE: 79
atgggtgtta caggaatatt gcagttacct cgtgatcgat tcaagaggac atcattcttt 60
ctttgggtaa ttatcctttt ccaaagaaca ttttccatcc cacttggagt catccacaat 120
agcacattac aggttagtga tgtcgacaaa ctggtttgcc gtgacaaact gtcatccaca 180
aatcaattga gatcagttgg actgaatctc gaagggaatg gagtggcaac tgacgtgcca 240
tctgcaacta aaagatgggg cttcaggtcc ggtgtcccac caaaggtggt caattatgaa 300
gctggtgaat gggctgaaaa ctgctacaat cttgaaatca aaaaacctga cgggagtgag 360
tgtctaccag cagcgccaga cgggattcgg ggcttccccc ggtgccggta tgtgcacaaa 420
gtatcaggaa cgggaccgtg tgccggagac tttgccttcc acaaagaggg tgctttcttc 480
ctgtatgacc gacttgcttc cacagttatc taccgaggaa cgactttcgc tgaaggtgtc 540
gttgcatttc tgatactgcc ccaagctaag aaggacttct tcagctcaca ccccttgaga 600
gagccggtca atgcaacgga ggacccgtct agtggctact attctaccac aattagatat 660
caagctaccg gttttggaac caatgagaca gagtatttgt tcgaggttga caatttgacc 720
tacgtccaac ttgaatcaag attcacacca cagtttctgc tccagctgaa tgagacaata 780
tatacaagtg ggaaaaggag caataccacg ggaaaactaa tttggaaggt caaccccgaa 840
attgatacaa caatcgggga gtgggccttc tgggaaacta aaaaaacctc actagaaaaa 900
ttcgcagtga agagttgtct ttcacagctg tatcaaacag agccaaaaac atcagtggtc 960
agagtccggc gcgaacttct tccgacccag ggaccaacac aacaactgaa gaccacaaaa 1020
tcatggcttc agaaaattcc tctgcaatgg ttcaagtgca cagtcaagga agggaagctg 1080
cagtgtcgca tctgacaacc cttgccacaa tctccacgag tcctcaaccc cccacaacca 1140
aaccaggtcc ggacaacagc acccacaata cacccgtgta taaacttgac atctctgagg 1200
caactcaagt tgaacaacat caccgcagaa cagacaacga cagcacagcc tccgacactc 1260
cccccgccac gaccgcagcc ggacccctaa aagcagagaa caccaacacg agcaagggta 1320
ccgacctcct ggaccccgcc accacaacaa gtccccaaaa ccacagcgag accgctggca 1380
acaacaacac tcatcaccaa gataccggag aagagagtgc cagcagcggg aagctaggct 1440
taattaccaa tactattgct ggagtcgcag gactgatcac aggcgggagg agagctcgaa 1500
gagaagcaat tgtcaatgct caacccaaat gcaaccctaa tttacattac tggactactc 1560
aggatgaagg tgctgcaatc ggactggcct ggataccata tttcgggcca gcagccgagg 1620
gaatttacat agaggggctg atgcacaatc aagatggttt aatctgtggg ttgagacagc 1680
tggccaacga gacgactcaa gctcttcaac tgttcctgag agccacaacc gagctacgca 1740
ccttttcaat cctcaaccgt aaggcaattg atttcttgct gcagcgatgg ggcggcacat 1800
gccacatttt gggaccggac tgctgtatcg aaccacatga ttggaccaag aacataacag 1860
acaaaattga tcagattatt catgattttg ttgataaaac ccttccggac caggggggaca 1920
atgacaattg gtggacagga tggagacaat ggataccggc aggtattgga gttacaggcg 1980
ttataattgc agttatcgct ttattctgta tatgcaaatt tgtcttttag 2030

<210> SEQ ID NO 80
<211> LENGTH: 389

<212> TYPE: DNA
<213> ORGANISM: Artificial Sequence
<220> FEATURE:
<223> OTHER INFORMATION: Short WPRE sequence

<400> SEQUENCE: 80
aatcaacctc tggattacaa aatttgtgaa agattgactg atattcttaa ctatgttgct 60
ccttttacgc tgtgtggata tgctgcttta atgcctctgt atcatgctat tgcttcccgt 120
acggctttcg ttttctcctc cttgtataaa tcctggttgc tgtctcttta tgaggagttg 180
tggcccgttg tccgtcaacg tggcgtggtg tgctctgtgt ttgctgacgc aacccccact 240
ggctggggca ttgccaccac ctgtcaactc ctttctggga ctttcgcttt ccccctcccg 300
atcgccacgg cagaactcat cgccgcctgc cttgcccgct gctggacagg ggctaggttg 360
ctgggcactg ataattccgt ggtgttgtc 389

<210> SEQ ID NO 81
<211> LENGTH: 31
<212> TYPE: DNA
<213> ORGANISM: Artificial Sequence
<220> FEATURE:
<223> OTHER INFORMATION: Primer

<400> SEQUENCE: 81
taagcagaat tcatgaattt gccaggaaga t 31

<210> SEQ ID NO 82
<211> LENGTH: 36
<212> TYPE: DNA
<213> ORGANISM: Artificial Sequence
<220> FEATURE:
<223> OTHER INFORMATION: Primer

<400> SEQUENCE: 82
ccatacaatg aatggacact aggcggccgc acgaat 36

<210> SEQ ID NO 83
<211> LENGTH: 2745
<212> TYPE: DNA
<213> ORGANISM: Artificial Sequence
<220> FEATURE:
<223> OTHER INFORMATION: Gag, Pol, Integrase fragment

<400> SEQUENCE: 83
gaattcatga atttgccagg aagatggaaa ccaaaaatga tagggggaat tggaggtttt 60
atcaaagtaa gacagtatga tcagatactc atagaaatct gcggacataa agctataggt 120
acagtattag taggacctac acctgtcaac ataattggaa gaaatctgtt gactcagatt 180
ggctgcactt taaattttcc cattagtcct attgagactg taccagtaaa attaaagcca 240
ggaatggatg gcccaaaagt taaacaatgg ccattgacag aagaaaaaat aaaagcatta 300
gtagaaattt gtacagaaat ggaaaaggaa ggaaaaattt caaaaattgg gcctgaaaat 360
ccatacaata ctccagtatt tgccataaag aaaaaagaca gtactaaatg gagaaaatta 420
gtagatttca gagaacttaa taagagaact caagatttct gggaagttca attaggaata 480
ccacatcctg cagggttaaa acagaaaaaa tcagtaacag tactggatgt gggcgatgca 540
tatttttcag ttcccttaga taaagacttc aggaagtata ctgcatttac catacctagt 600
ataaacaatg agacaccagg gattagatat cagtacaatg tgcttccaca gggatggaaa 660
ggatcaccag caatattcca gtgtagcatg acaaaaatct tagagccttt tagaaaacaa 720

-continued

```
aatccagaca tagtcatcta tcaatacatg gatgatttgt atgtaggatc tgacttagaa    780
atagggcagc atagaacaaa aatagaggaa ctgagacaac atctgttgag gtggggattt    840
accacaccag acaaaaaaca tcagaaagaa cctccattcc tttggatggg ttatgaactc    900
catcctgata aatggacagt acagcctata gtgctgccag aaaaggacag ctggactgtc    960
aatgacatac agaaattagt gggaaaattg aattgggcaa gtcagattta tgcagggatt   1020
aaagtaaggc aattatgtaa acttcttagg ggaaccaaag cactaacaga agtagtacca   1080
ctaacagaag aagcagagct agaactggca gaaaacaggg agattctaaa agaaccggta   1140
catggagtgt attatgaccc atcaaaagac ttaatagcag aaatacagaa gcaggggcaa   1200
ggccaatgga catatcaaat ttatcaagag ccatttaaaa atctgaaaac aggaaagtat   1260
gcaagaatga agggtgccca cactaatgat gtgaaacaat taacagaggc agtacaaaaa   1320
atagccacag aaagcatagt aatatgggga aagactccta aatttaaatt acccatacaa   1380
aaggaaacat gggaagcatg gtggacagag tattggcaag ccacctggat tcctgagtgg   1440
gagtttgtca atacccctcc cttagtgaag ttatggtacc agttagagaa agaacccata   1500
ataggagcag aaactttcta tgtagatggg gcagccaata gggaaactaa attaggaaaa   1560
gcaggatatg taactgacag aggaagacaa aaagttgtcc ccctaacgga cacaacaaat   1620
cagaagactg agttacaagc aattcatcta gctttgcagg attcgggatt agaagtaaac   1680
atagtgacag actcacaata tgcattggga atcattcaag cacaaccaga taagagtgaa   1740
tcagagttag tcagtcaaat aatagagcag ttaataaaaa aggaaaaagt ctacctggca   1800
tgggtaccag cacacaaagg aattggagga aatgaacaag tagataaatt ggtcagtgct   1860
ggaatcagga aagtactatt tttagatgga atagataagg cccaagaaga acatgagaaa   1920
tatcacagta attggagagc aatggctagt gattttaacc taccacctgt agtagcaaaa   1980
gaaatagtag ccagctgtga taaatgtcag ctaaaagggg aagccatgca tggacaagta   2040
gactgtagcc caggaatatg gcagctagat tgtacacatt tagaaggaaa agttatcttg   2100
gtagcagttc atgtagccag tggatatata gaagcagaag taattccagc agagacaggg   2160
caagaaacag catacttcct cttaaaatta gcaggaagat ggccagtaaa aacagtacat   2220
acagacaatg gcagcaattt caccagtact acagttaagg ccgcctgttg gtgggcgggg   2280
atcaagcagg aatttggcat tccctacaat ccccaaagtc aaggagtaat agaatctatg   2340
aataaagaat taaagaaaat tataggacag gtaagagatc aggctgaaca tcttaagaca   2400
gcagtacaaa tggcagtatt catccacaat tttaaaagaa aaggggggat tggggggtac   2460
agtgcagggg aaagaatagt agacataata gcaacagaca tacaaactaa agaattacaa   2520
aaacaaatta caaaaattca aaattttcgg gtttattaca gggacagcag agatccagtt   2580
tggaaaggac cagcaaagct cctctggaaa ggtgaagggg cagtagtaat acaagataat   2640
agtgacataa aagtagtgcc aagaagaaaa gcaaagatca tcagggatta tggaaaacag   2700
atggcaggtg atgattgtgt ggcaagtaga caggatgagg attaa                   2745
```

<210> SEQ ID NO 84
<211> LENGTH: 1586
<212> TYPE: DNA
<213> ORGANISM: Artificial Sequence
<220> FEATURE:
<223> OTHER INFORMATION: DNA Fragment containing Rev, RRE and rabbit
      beta globin poly A

<400> SEQUENCE: 84

```
tctagaatgg caggaagaag cggagacagc gacgaagagc tcatcagaac agtcagactc     60

atcaagcttc tctatcaaag caacccacct cccaatcccg aggggacccg acaggcccga    120

aggaatagaa gaagaaggtg gagagagaga cagagacaga tccattcgat tagtgaacgg    180

atccttggca cttatctggg acgatctgcg gagcctgtgc ctcttcagct accaccgctt    240

gagagactta ctcttgattg taacgaggat tgtggaactt ctgggacgca gggggtggga    300

agccctcaaa tattggtgga atctcctaca atattggagt caggagctaa agaatagagg    360

agctttgttc cttgggttct tgggagcagc aggaagcact atgggcgcag cgtcaatgac    420

gctgacggta caggccagac aattattgtc tggtatagtg cagcagcaga acaatttgct    480

gagggctatt gaggcgcaac agcatctgtt gcaactcaca gtctggggca tcaagcagct    540

ccaggcaaga atcctggctg tggaaagata cctaaaggat caacagctcc tagatctttt    600

tccctctgcc aaaaattatg gggacatcat gaagcccctt gagcatctga cttctggcta    660

ataaaggaaa tttattttca ttgcaatagt gtgttggaat tttttgtgtc tctcactcgg    720

aaggacatat gggagggcaa atcatttaaa acatcagaat gagtatttgg tttagagttt    780

ggcaacatat gccatatgct ggctgccatg aacaaaggtg gctataaaga ggtcatcagt    840

atatgaaaca gccccctgct gtccattcct tattccatag aaaagccttg acttgaggtt    900

agattttttt tatattttgt tttgtgttat ttttttcttt aacatcccta aaattttcct    960

tacatgtttt actagccaga tttttcctcc tctcctgact actcccagtc atagctgtcc   1020

ctcttctctt atgaagatcc ctcgacctgc agcccaagct tggcgtaatc atggtcatag   1080

ctgtttcctg tgtgaaattg ttatccgctc acaattccac acaacatacg agccggaagc   1140

ataaagtgta aagcctgggg tgcctaatga gtgagctaac tcacattaat tgcgttgcgc   1200

tcactgcccg ctttccagtc gggaaacctg tcgtgccagc ggatccgcat ctcaattagt   1260

cagcaaccat agtcccgccc ctaactccgc ccatcccgcc cctaactccg cccagttccg   1320

cccattctcc gccccatggc tgactaattt tttttattta tgcagaggcc gaggccgcct   1380

cggcctctga gctattccag aagtagtgag gaggcttttt tggaggccta ggcttttgca   1440

aaaagctaac ttgtttattg cagcttataa tggttacaaa taaagcaata gcatcacaaa   1500

tttcacaaat aaagcatttt tttcactgca ttctagttgt ggtttgtcca aactcatcaa   1560

tgtatcttat cagcggccgc cccggg                                        1586
```

<210> SEQ ID NO 85
<211> LENGTH: 1614
<212> TYPE: DNA
<213> ORGANISM: Artificial Sequence
<220> FEATURE:
<223> OTHER INFORMATION: DNA fragment containing the CAG enhancer/promoter/intron sequence

<400> SEQUENCE: 85

```
acgcgttagt tattaatagt aatcaattac ggggtcatta gttcatagcc catatatgga     60

gttccgcgtt acataactta cggtaaatgg cccgcctggc tgaccgccca acgacccccg    120

cccattgacg tcaataatga cgtatgttcc catagtaacg ccaataggga ctttccattg    180

acgtcaatgg gtggactatt tacggtaaac tgcccacttg gcagtacatc aagtgtatca    240

tatgccaagt acgcccccta ttgacgtcaa tgacggtaaa tggcccgcct ggcattatgc    300

ccagtacatg accttatggg actttcctac ttggcagtac atctacgtat tagtcatcgc    360

tattaccatg gtcgaggtg agccccacgt tctgcttcac tctccccatc tcccccccct    420
```

```
ccccaccccc aattttgtat ttatttattt tttaattatt ttgtgcagcg atgggggcgg    480
gggggggggg ggcgcgcgcc aggcggggcg gggcggggcg aggggcgggg cggggcgagg    540
cggagaggtg cggcggcagc caatcagagc ggcgcgctcc gaaagtttcc ttttatggcg    600
aggcggcggc ggcggcggcc ctataaaaag cgaagcgcgc ggcgggcggg agtcgctgcg    660
ttgccttcgc cccgtgcccc gctccgcgcc gcctcgcgcc gcccgccccg gctctgactg    720
accgcgttac tcccacaggt gagcgggcgg gacggccctt ctcctccggg ctgtaattag    780
cgcttggttt aatgacggct cgtttctttt ctgtggctgc gtgaaagcct taaagggctc    840
cgggagggcc ctttgtgcgg gggggagcgg ctcggggggt gcgtgcgtgt gtgtgtgcgt    900
ggggagcgcc gcgtgcggcc cgcgctgccc ggcggctgtg agcgctgcgg gcgcggcgcg    960
gggctttgtg cgctccgcgt gtgcgcgagg ggagcgcggc cgggggcggt gccccgcggt   1020
gcgggggggc tgcgagggga acaaaggctg cgtgcggggt gtgtgcgtgg gggggtgagc   1080
agggggtgtg ggcgcggcgg tcgggctgta accccccct gcaccccct ccccgagttg   1140
ctgagcacgg cccggcttcg ggtgcggggc tccgtgcggg gcgtggcgcg gggctcgccg   1200
tgccgggcgg ggggtggcgg caggtggggg tgccgggcgg ggcggggccg cctcgggccg   1260
gggagggctc gggggagggg cgcggcggcc ccggagcgcc ggcggctgtc gaggcgcggc   1320
gagccgcagc cattgccttt tatggtaatc gtgcgagagg gcgcagggac ttcctttgtc   1380
ccaaatctgg cggagccgaa atctgggagg cgccgccgca cccccctctag cgggcgcggg   1440
cgaagcggtg cggcgccggc aggaaggaaa tgggcgggga gggccttcgt gcgtcgccgc   1500
gccgccgtcc ccttctccat ctccagcctc ggggctgccg caggggacg gctgccttcg   1560
gggggacgg ggcagggcgg ggttcggctt ctggcgtgtg accggcggga attc           1614
```

<210> SEQ ID NO 86
<211> LENGTH: 1531
<212> TYPE: DNA
<213> ORGANISM: Artificial Sequence
<220> FEATURE:
<223> OTHER INFORMATION: DNA fragment containing VSV-G

<400> SEQUENCE: 86

```
gaattcatga agtgcctttt gtacttagcc tttttattca ttggggtgaa ttgcaagttc     60
accatagttt ttccacacaa ccaaaaagga aactggaaaa atgttccttc taattaccat    120
tattgcccgt caagctcaga tttaaattgg cataatgact taataggcac agccttacaa    180
gtcaaaatgc ccaagagtca caaggctatt caagcagacg gttggatgtg tcatgcttcc    240
aaatgggtca ctacttgtga tttccgctgg tatggaccga agtatataac acattccatc    300
cgatccttca ctccatctgt agaacaatgc aaggaaagca ttgaacaaac gaaacaagga    360
acttggctga atccaggctt ccctcctcaa agttgtggat atgcaactgt gacggatgcc    420
gaagcagtga ttgtccaggt gactcctcac catgtgctgg ttgatgaata cacaggagaa    480
tgggttgatt cacagttcat caacggaaaa tgcagcaatt acatatgccc cactgtccat    540
aactctacaa cctggcattc tgactataag gtcaaagggc tatgtgattc taacctcatt    600
tccatggaca tcaccttctt ctcagaggac ggagagctat catccctggg aaaggagggc    660
acagggttca gaagtaacta ctttgcttat gaaactggag gcaaggcctg caaaatgcaa    720
tactgcaagc attggggagt cagactccca tcaggtgtct ggttcgagat ggctgataag    780
gatctctttg ctgcagccag attccctgaa tgcccagaag ggtcaagtat ctctgctcca    840
tctcagacct cagtggatgt aagtctaatt caggacgttg agaggatctt ggattattcc    900
```

```
ctctgccaag aaacctggag caaaatcaga gcgggtcttc caatctctcc agtggatctc     960

agctatcttg ctcctaaaaa cccaggaacc ggtcctgctt tcaccataat caatggtacc    1020

ctaaaatact ttgagaccag atacatcaga gtcgatattg ctgctccaat cctctcaaga    1080

atggtcggaa tgatcagtgg aactaccaca gaaagggaac tgtgggatga ctgggcacca    1140

tatgaagacg tggaaattgg acccaatgga gttctgagga ccagttcagg atataagttt    1200

cctttataca tgattggaca tggtatgttg gactccgatc ttcatcttag ctcaaaggct    1260

caggtgttcg aacatcctca cattcaagac gctgcttcgc aacttcctga tgatgagagt    1320

ttattttttg gtgatactgg gctatccaaa aatccaatcg agcttgtaga aggttggttc    1380

agtagttgga aaagctctat tgcctctttt ttctttatca tagggttaat cattggacta    1440

ttcttggttc tccgagttgg tatccatctt tgcattaaat taaagcacac caagaaaaga    1500

cagatttata cagacataga gatgagaatt c                                   1531
```

<210> SEQ ID NO 87
<211> LENGTH: 1227
<212> TYPE: DNA
<213> ORGANISM: Artificial Sequence
<220> FEATURE:
<223> OTHER INFORMATION: Helper plasmid containing RRE and rabbit beta globin poly A

<400> SEQUENCE: 87

```
tctagaagga gctttgttcc ttgggttctt gggagcagca ggaagcacta tgggcgcagc      60

gtcaatgacg ctgacggtac aggccagaca attattgtct ggtatagtgc agcagcagaa     120

caatttgctg agggctattg aggcgcaaca gcatctgttg caactcacag tctggggcat     180

caagcagctc caggcaagaa tcctggctgt ggaaagatac ctaaaggatc aacagctcct     240

agatcttttt ccctctgcca aaaattatgg ggacatcatg aagccccttg agcatctgac     300

ttctggctaa taaaggaaat ttattttcat tgcaatagtg tgttggaatt ttttgtgtct     360

ctcactcgga aggacatatg ggagggcaaa tcatttaaaa catcagaatg agtatttggt     420

ttagagtttg gcaacatatg ccatatgctg gctgccatga acaaaggtgg ctataaagag     480

gtcatcagta tatgaaacag ccccctgctg tccattcctt attccataga aaagccttga     540

cttgaggtta gatttttttt atattttgtt ttgtgttatt tttttcttta acatccctaa     600

aattttcctt acatgtttta ctagccagat ttttcctcct ctcctgacta ctcccagtca     660

tagctgtccc tcttctctta tgaagatccc tcgacctgca gcccaagctt ggcgtaatca     720

tggtcatagc tgtttcctgt gtgaaattgt tatccgctca caattccaca caacatacga     780

gccggaagca taaagtgtaa agcctggggt gcctaatgag tgagctaact cacattaatt     840

gcgttgcgct cactgcccgc tttccagtcg ggaaacctgt cgtgccagcg gatccgcatc     900

tcaattagtc agcaaccata gtcccgcccc taactccgcc catcccgccc ctaactccgc     960

ccagttccgc ccattctccg ccccatggct gactaatttt ttttatttat gcagaggccg    1020

aggccgcctc ggcctctgag ctattccaga agtagtgagg aggctttttt ggaggcctag    1080

gcttttgcaa aaagctaact tgtttattgc agcttataat ggttacaaat aaagcaatag    1140

catcacaaat ttcacaaata aagcattttt ttcactgcat tctagttgtg gtttgtccaa    1200

actcatcaat gtatcttatc acccggg                                        1227
```

<210> SEQ ID NO 88
<211> LENGTH: 884

<212> TYPE: DNA
<213> ORGANISM: Artificial Sequence
<220> FEATURE:
<223> OTHER INFORMATION: RSV promoter and HIV Rev

<400> SEQUENCE: 88
caattgcgat gtacgggcca gatatacgcg tatctgaggg gactagggtg tgtttaggcg 60
aaaagcgggg cttcggttgt acgcggttag gagtcccctc aggatatagt agtttcgctt 120
ttgcataggg agggggaaat gtagtcttat gcaatacact tgtagtcttg caacatggta 180
acgatgagtt agcaacatgc cttacaagga gagaaaaagc accgtgcatg ccgattggtg 240
gaagtaaggt ggtacgatcg tgccttatta ggaaggcaac agacaggtct gacatggatt 300
ggacgaacca ctgaattccg cattgcagag ataattgtat ttaagtgcct agctcgatac 360
aataaacgcc atttgaccat tcaccacatt ggtgtgcacc tccaagctcg agctcgttta 420
gtgaaccgtc agatcgcctg gagacgccat ccacgctgtt ttgacctcca tagaagacac 480
cgggaccgat ccagcctccc ctcgaagcta gcgattaggc atctcctatg gcaggaagaa 540
gcggagacag cgacgaagaa ctcctcaagg cagtcagact catcaagttt ctctatcaaa 600
gcaacccacc tcccaatccc gaggggaccc gacaggcccg aaggaataga agaagaaggt 660
ggagagagag acagagacag atccattcga ttagtgaacg gatccttagc acttatctgg 720
gacgatctgc ggagcctgtg cctcttcagc taccaccgct tgagagactt actcttgatt 780
gtaacgagga ttgtggaact tctgggacgc agggggtggg aagccctcaa atattggtgg 840
aatctcctac aatattggag tcaggagcta aagaatagtc taga 884

<210> SEQ ID NO 89
<211> LENGTH: 19
<212> TYPE: DNA
<213> ORGANISM: Artificial Sequence
<220> FEATURE:
<223> OTHER INFORMATION: Target sequence

<400> SEQUENCE: 89
atggcaggaa gaagcggag 19

<210> SEQ ID NO 90
<211> LENGTH: 52
<212> TYPE: DNA
<213> ORGANISM: Artificial Sequence
<220> FEATURE:
<223> OTHER INFORMATION: shRNA sequence

<400> SEQUENCE: 90
atggcaggaa gaagcggagt tcaagagact ccgcttcttc ctgccatttt tt 52

<210> SEQ ID NO 91
<211> LENGTH: 279
<212> TYPE: DNA
<213> ORGANISM: Artificial Sequence
<220> FEATURE:
<223> OTHER INFORMATION: H1 promoter and shRT sequence

<400> SEQUENCE: 91
gaacgctgac gtcatcaacc cgctccaagg aatcgcgggc ccagtgtcac taggcgggaa 60
cacccagcgc gcgtgcgccc tggcaggaag atggctgtga gggacagggg agtggcgccc 120
tgcaatattt gcatgtcgct atgtgttctg ggaaatcacc ataaacgtga aatgtctttg 180
gatttgggaa tcttataagt tctgtatgag accacttgga tccgcggaga cagcgacgaa 240

-continued gagcttcaag agagctcttc gtcgctgtct ccgctttttt 279

<210> SEQ ID NO 92
<211> LENGTH: 275
<212> TYPE: DNA
<213> ORGANISM: Artificial Sequence
<220> FEATURE:
<223> OTHER INFORMATION: H1 CCR5 sequence

<400> SEQUENCE: 92
gaacgctgac gtcatcaacc cgctccaagg aatcgcgggc ccagtgtcac taggcgggaa 60
cacccagcgc gcgtgcgccc tggcaggaag atggctgtga gggacagggg agtggcgccc 120
tgcaatattt gcatgtcgct atgtgttctg ggaaatcacc ataaacgtga aatgtctttg 180
gatttgggaa tcttataagt tctgtatgag accacttgga tccgtgtcaa gtccaatcta 240
tgttcaagag acatagattg gacttgacac ttttt 275

<210> SEQ ID NO 93
<211> LENGTH: 20
<212> TYPE: DNA
<213> ORGANISM: Artificial Sequence
<220> FEATURE:
<223> OTHER INFORMATION: CCR5 Forward Primer

<400> SEQUENCE: 93
aggaattgat ggcgagaagg 20

<210> SEQ ID NO 94
<211> LENGTH: 24
<212> TYPE: DNA
<213> ORGANISM: Artificial Sequence
<220> FEATURE:
<223> OTHER INFORMATION: CCR5 Reverse Primer

<400> SEQUENCE: 94
ccccaaagaa ggtcaaggta atca 24

<210> SEQ ID NO 95
<211> LENGTH: 18
<212> TYPE: DNA
<213> ORGANISM: Artificial Sequence
<220> FEATURE:
<223> OTHER INFORMATION: Actin Forward Primer

<400> SEQUENCE: 95
agcgcggcta cagcttca 18

<210> SEQ ID NO 96
<211> LENGTH: 20
<212> TYPE: DNA
<213> ORGANISM: Artificial Sequence
<220> FEATURE:
<223> OTHER INFORMATION: Actin Reverse Primer

<400> SEQUENCE: 96
ggcgacgtag cacagcttct 20

<210> SEQ ID NO 97
<211> LENGTH: 20
<212> TYPE: DNA
<213> ORGANISM: Artificial Sequence
<220> FEATURE:
<223> OTHER INFORMATION: AGT103 CCR5 miR30

<400> SEQUENCE: 97
tgtaaactga gcttgctcta 20

<210> SEQ ID NO 98
<211> LENGTH: 20
<212> TYPE: DNA
<213> ORGANISM: Artificial Sequence
<220> FEATURE:
<223> OTHER INFORMATION: AGT103-R5-1

<400> SEQUENCE: 98
tgtaaactga gcttgctcgc 20

<210> SEQ ID NO 99
<211> LENGTH: 19
<212> TYPE: DNA
<213> ORGANISM: Artificial Sequence
<220> FEATURE:
<223> OTHER INFORMATION: AGT103-R5-2

<400> SEQUENCE: 99
catagattgg acttgacac 19

<210> SEQ ID NO 100
<211> LENGTH: 642
<212> TYPE: DNA
<213> ORGANISM: Artificial Sequence
<220> FEATURE:
<223> OTHER INFORMATION: CAG promoter

<400> SEQUENCE: 100
tagttattaa tagtaatcaa ttacggggtc attagttcat agcccatata tggagttccg 60
cgttacataa cttacggtaa atggcccgcc tggctgaccg cccaacgacc cccgcccatt 120
gacgtcaata atgacgtatg ttcccatagt aacgccaata gggactttcc attgacgtca 180
atgggtggac tatttacggt aaactgccca cttggcagta catcaagtgt atcatatgcc 240
aagtacgccc cctattgacg tcaatgacgg taaatggccc gcctggcatt atgcccagta 300
catgacctta tgggactttc ctacttggca gtacatctac gtattagtca tcgctattac 360
catgggtcga ggtgagcccc acgttctgct tcactctccc catctccccc ccctccccac 420
ccccaatttt gtatttattt atttttttaat tattttgtgc agcgatgggg gcgggggggg 480 gggggcgcg cgccaggcgg ggcggggcgg ggcgaggggc ggggcggggc gaggcggaga 540
ggtgcggcgg cagccaatca gagcggcgcg ctccgaaagt ttccttttat ggcgaggcgg 600
cggcggcggc ggccctataa aaagcgaagc gcgcggcggg cg 642

<210> SEQ ID NO 101
<211> LENGTH: 217
<212> TYPE: DNA
<213> ORGANISM: Artificial Sequence
<220> FEATURE:
<223> OTHER INFORMATION: H1 element

<400> SEQUENCE: 101
gaacgctgac gtcatcaacc cgctccaagg aatcgcgggc ccagtgtcac taggcgggaa 60
cacccagcgc gcgtgcgccc tggcaggaag atggctgtga gggacagggg agtggcgccc 120
tgcaatattt gcatgtcgct atgtgttctg ggaaatcacc ataaacgtga aatgtctttg 180
gatttgggaa tcttataagt tctgtatgag accactt 217

<210> SEQ ID NO 102

<211> LENGTH: 250
<212> TYPE: DNA
<213> ORGANISM: Artificial Sequence
<220> FEATURE:
<223> OTHER INFORMATION: 3' delta LTR

<400> SEQUENCE: 102
tggaagggct aattcactcc caacgaagat aagatctgct ttttgcttgt actgggtctc 60
tctggttaga ccagatctga gcctgggagc tctctggcta actagggaac ccactgctta 120
agcctcaata aagcttgcct tgagtgcttc aagtagtgtg tgcccgtctg ttgtgtgact 180
ctggtaacta gagatccctc agaccctttt agtcagtgtg gaaaatctct agcagtagta 240
gttcatgtca 250

<210> SEQ ID NO 103
<211> LENGTH: 243
<212> TYPE: DNA
<213> ORGANISM: Artificial Sequence
<220> FEATURE:
<223> OTHER INFORMATION: 7SK promoter

<400> SEQUENCE: 103
ctgcagtatt tagcatgccc cacccatctg caaggcattc tggatagtgt caaaacagcc 60
ggaaatcaag tccgtttatc tcaaacttta gcattttggg aataaatgat atttgctatg 120
ctggttaaat tagattttag ttaaatttcc tgctgaagct ctagtacgat aagcaacttg 180
acctaagtgt aaagttgaga tttccttcag gtttatatag cttgtgcgcc gcctggctac 240
ctc 243

<210> SEQ ID NO 104
<211> LENGTH: 132
<212> TYPE: DNA
<213> ORGANISM: Artificial Sequence
<220> FEATURE:
<223> OTHER INFORMATION: miR155 Tat

<400> SEQUENCE: 104
ctggaggctt gctgaaggct gtatgctgtc cgcttcttcc tgccataggg ttttggccac 60
tgactgaccc tatggggaag aagcggacag gacacaaggc ctgttactag cactcacatg 120
gaacaaatgg cc 132

<210> SEQ ID NO 105
<211> LENGTH: 1110
<212> TYPE: DNA
<213> ORGANISM: Artificial Sequence
<220> FEATURE:
<223> OTHER INFORMATION: Elongation Factor-1 alpha (EF1-alpha) promoter

<400> SEQUENCE: 105
ccggtgccta gagaaggtgg cgcggggtaa actgggaaag tgatgtcgtg tactggctcc 60
gcctttttcc cgagggtggg ggagaaccgt atataagtgc agtagtcgcc gtgaacgttc 120
tttttcgcaa cgggtttgcc gccagaacac aggtaagtgc cgtgtgtggt tcccgcgggc 180
ctggcctctt tacgggttat ggcccttgcg tgccttgaat tacttccacg cccctggctg 240
cagtacgtga ttcttgatcc cgagcttcgg gttggaagtg ggtgggagag ttcgaggcct 300
tgcgcttaag gagccccttc gcctcgtgct tgagttgagg cctggcctgg gcgctggggc 360
cgccgcgtgc gaatctggtg gcaccttcgc gcctgtctcg ctgctttcga taagtctcta 420
gccatttaaa atttttgatg acctgctgcg acgctttttt tctggcaaga tagtcttgta 480

-continued

```
aatgcgggcc aagatctgca cactggtatt tcggtttttg gggccgcggg cggcgacggg    540

gcccgtgcgt cccagcgcac atgttcggcg aggcggggcc tgcgagcgcg gccaccgaga    600

atcggacggg ggtagtctca agctggccgg cctgctctgg tgcctggcct cgcgccgccg    660

tgtatcgccc cgccctgggc ggcaaggctg gcccggtcgg caccagttgc gtgagcggaa    720

agatggccgc ttcccggccc tgctgcaggg agctcaaaat ggaggacgcg gcgctcggga    780

gagcgggcgg gtgagtcacc cacacaaagg aaaagggcct ttccgtcctc agccgtcgct    840

tcatgtgact ccacggagta ccgggcgccg tccaggcacc tcgattagtt ctcgagcttt    900

tggagtacgt cgtctttagg ttggggggag gggttttatg cgatggagtt tccccacact    960

gagtgggtgg agactgaagt taggccagct tggcacttga tgtaattctc cttggaattt   1020

gccctttttg agtttggatc ttggttcatt ctcaagcctc agacagtggt tcaaagtttt   1080

tttcttccat ttcaggtgtc gtgatgtaca                                    1110


<210> SEQ ID NO 106
<211> LENGTH: 122
<212> TYPE: DNA
<213> ORGANISM: Artificial Sequence
<220> FEATURE:
<223> OTHER INFORMATION: miR21 Vif

<400> SEQUENCE: 106

cccgggcatc tccatggctg taccaccttg tcgggggatg tgtacttctg aacttgtgtt     60

gaatctcatg gagttcagaa gaacacatcc gcactgacat tttggtatct ttcatctgac    120

ca                                                                   122


<210> SEQ ID NO 107
<211> LENGTH: 119
<212> TYPE: DNA
<213> ORGANISM: Artificial Sequence
<220> FEATURE:
<223> OTHER INFORMATION: miR185 Tat

<400> SEQUENCE: 107

gctagcgggc ctggctcgag cagggggcga gggattccgc ttcttcctgc catagcgtgg     60

tcccctcccc tatggcaggc agaagcggca ccttccctcc caatgaccgc gtcttcgtc     119


<210> SEQ ID NO 108
<211> LENGTH: 113
<212> TYPE: DNA
<213> ORGANISM: Artificial Sequence
<220> FEATURE:
<223> OTHER INFORMATION: miR185 Tat

<400> SEQUENCE: 108

gggcctggct cgagcagggg gcgagggatt ccgcttcttc ctgccatagc gtggtcccct     60

cccctatggc aggcagaagc ggcaccttcc ctcccaatga ccgcgtcttc gtc           113
```

HIV IMMUNOTHERAPY WITH NO PRE-IMMUNIZATION STEP

CROSS-REFERENCE TO RELATED APPLICATION

This application claims priority to U.S. Patent Application No. 62/444,147 filed on Jan. 9, 2017, entitled "HIV Immunotherapy With No Pre-Immunization Step," the disclosure of which is incorporated herein by reference.

FIELD OF THE INVENTION

The present invention relates generally to the field of immunotherapy for the treatment and prevention of HIV. In particular, the disclosed methods of treatment and prevention relate to the administration of viral vectors and systems for the delivery of genes and other therapeutic, diagnostic, or research uses without a pre-immunization step.

BACKGROUND OF THE INVENTION

Combination antiretroviral therapy (cART) (also known as Highly Active Antiretroviral Therapy or HAART) limits HIV-1 replication and retards disease progression, but drug toxicities and the emergence of drug-resistant viruses are challenges for long-term control in HIV-infected persons. Additionally, traditional anti-retroviral therapy, while successful at delaying the onset of AIDS or death, has yet to provide a functional cure. Alternative treatment strategies are needed.

Intense interest in immunotherapy for HIV infection has been precipitated by emerging data indicating that the immune system has a major, albeit usually insufficient, role in limiting HIV replication. Virus-specific T-helper cells, which are critical to maintenance of cytolytic T cell (CTL) function, likely play a role. Viremia is also influenced by neutralizing antibodies, but they are generally low in magnitude in HIV infection and do not keep up with evolving viral variants in vivo.

Together these data indicate that increasing the strength and breadth of HIV-specific cellular immune responses might have a clinical benefit through so-called HIV immunotherapy. Some studies have tested vaccines against HIV, but success has been limited to date. Additionally, there has been interest in augmenting HIV immunotherapy by utilizing gene therapy techniques, but as with other immunotherapy approaches, success has been limited.

Viral vectors can be used to transduce genes into target cells owing to specific virus envelope-host cell receptor interactions and viral mechanisms for gene expression. As a result, viral vectors have been used as vehicles for the transfer of genes into many different cell types including whole T cells or other immune cells as well as embryos, fertilized eggs, isolated tissue samples, tissue targets in situ and cultured cells. The ability to introduce and express foreign or altered genes in a cell is useful for therapeutic interventions such as gene therapy, somatic cell reprogramming of induced pluripotent stem cells, and various types of immunotherapy.

Gene therapy is one of the ripest areas of biomedical research with the potential to create new therapeutics that may involve the use of viral vectors. In view of the wide variety of potential genes available for therapy, an efficient means of delivering these genes is needed to fulfill the promise of gene therapy as a means of treating infectious and non-infectious diseases. Several viral systems including murine retrovirus, adenovirus, parvovirus (adeno-associated virus), vaccinia virus, and herpes virus have been developed as therapeutic gene transfer vectors.

There are many factors that must be considered when developing viral vectors, including tissue tropism, stability of virus preparations, stability and control of expression, genome packaging capacity, and construct-dependent vector stability. In addition, in vivo application of viral vectors is often limited by host immune responses against viral structural proteins and/or transduced gene products.

Thus, toxicity and safety are key hurdles that must be overcome for viral vectors to be used in vivo for the treatment of subjects. There are numerous historical examples of gene therapy applications in humans that have met with problems associated with the host immune responses against the gene delivery vehicles or the therapeutic gene products. Viral vectors (e.g., adenovirus) which co-transduce several viral genes together with one or more therapeutic gene(s) are particularly problematic.

Although lentiviral vectors do not generally induce cytotoxicity and do not elicit strong host immune responses, some lentiviral vectors such as HIV-1, which carry several immunostimulatory gene products, have the potential to cause cytotoxicity and induce strong immune responses in vivo. However, this may not be a concern for lentiviral derived transducing vectors that do not encode multiple viral genes after transduction. Of course, this may not always be the case, as sometimes the purpose of the vector is to encode a protein that will provoke a clinically useful immune response.

Another important issue related to the use of lentiviral vectors is that of possible cytopathogenicity upon exposure to some cytotoxic viral proteins. Exposure to certain HIV-1 proteins may induce cell death or functional unresponsiveness in T cells. Likewise, the possibility of generating replication-competent, virulent virus by recombination is often a concern. Accordingly, there remains a need for improved treatments of HIV.

SUMMARY OF THE INVENTION

In one aspect of the disclosure, a method of treating HIV infection in a subject is disclosed. The method includes removing leukocytes from the subject and purifying peripheral blood mononuclear cells (PBMC). The method further includes contacting the PBMC ex vivo with a therapeutically effective amount of a stimulatory agent; transducing the PBMC ex vivo with a viral delivery system encoding at least one genetic element; and culturing the transduced PBMC for at least 1 day. The transduced PBMC may be cultured from about 1 to about 35 days. The method may further involve infusing the transduced PBMC into a subject. The subject may be a human. The stimulatory agent may include a peptide or mixture of peptides. In a preferred embodiment, the stimulatory agents include a gag peptide. The stimulatory agent may include a vaccine. The vaccine may be a HIV vaccine, and in a preferred embodiment, the HIV vaccine is a MVA/HIV62B vaccine or a variant thereof. In a preferred embodiment, the viral delivery system includes a lentiviral particle. In one embodiment, the at least one genetic element may include a small RNA capable of inhibiting production of chemokine receptor CCR5 or at least one small RNA capable of targeting an HIV RNA sequence. In another embodiment, the at least one genetic element may include a small RNA capable of inhibiting production of chemokine receptor CCR5 and at least one small RNA capable of targeting an HIV RNA sequence. The HIV RNA sequence may include a HIV Vif sequence, a HIV Tat sequence, or a variant thereof. The at least one genetic element may include a microRNA or a shRNA. In a preferred embodiment, the at least one genetic element comprises a microRNA cluster.

In another aspect, the at least one genetic element includes a microRNA having at least 80%, or at least 85%, or at least 90%, or at least 95% percent identity with AGGTATATTGCTGTGACAGTGAGCGACTGTAAACTGAGCTTGCTCTACTGTGAAG CCACAGATGGGTAGAGCAAGCACAGTTTACCGCTGCCTAC TGCCTCGGACTCAA GGGGCTT (SEQ ID NO: 1). In a preferred embodiment, the at least one genetic element comprises:

(SEQ ID NO: 1)
AGGTATATTGCTGTTGACAGTGAGCGACTGTAAACTGAGCTTGCTCTACT
GTGAAGCCACAGATGGGTAGAGCAAGCACAGTTTACCGCTGCCTACTGCC
TCGGACTTCAAGGGGCTT.

In another aspect, the at least one genetic element includes a microRNA having at least 80%, or at least 85%, or at least 90%, or at least 95% percent identity with CATCTCCATGGCTGTACCACCTGTCGGGGGATGTGTACTTCTGAACTTGTGTGA ATCTCATGGAGTCAGAAGAACACATCCGCACTGACATTTTGG TATCTTTCATCTG ACCA (SEQ ID NO: 2); or at least 80%, or at least 85%, or at least 90%, or at least 95% percent identity with GGGCCTGGCTCGAGCAGGGGGCGAGGGATTCCGCTTCTTCCTGCCATAGCGTGG TCCCCTCCCCTATGGCAGGCAGAAGCGGCACCTTCCCTCCCAATGACCGCGTCTTC GTCG (SEQ ID NO: 3). In a preferred embodiment, the at least one genetic element includes (SEQ ID NO: 2)
CATCTCCATGGCTGTACCACCTTGTCGGGGGATGTGTACTTCTGAACTTG
TGTTGAATCTCATGGAGTTCAGAAGAACACATCCGCACTGACATTTTGGT
ATCTTTCATCTGACCA;
or (SEQ ID NO: 3)
GGGCCTGGCTCGAGCAGGGGGCGAGGGATTCCGCTTCTTC
CTGCCATAGCGTGGTCCCCTCCCCTATGGCAGGCAGAAGCGGCACCTTCC
CTCCCAATGACCGCGTCTTCGTCG.

In another aspect, the microRNA cluster includes a sequence having at least 80%, or at least 85%, or at least 90%, or at least 95% percent identity with AGGTATATTGCTGTTGACAGTGAGCGACTGTAAACTGAGCTTGCTCTACTGTGAAG CCACAGATGGGTAGAGCAAGCACAGTTTACCGCTGCCTA CTGCCTCGGACTTCAA GGGGCTTCCCGGGCATCTCCATGGCTGTACCACCTTGTCGGGGGATGTGTACTTCT GAACTTGTGTTGAATCTCATGGAGTTCAGAAGAACACATCCGCACTGACATTTTGG TATCTTCATCTGACCAGCTAGCGGGCCTGGCTCGAGCAGGGGGCGAGGGATTCC GCTTCTTCCTGCCATAGCGTGGTCCCCTCCCCTATGGCAGGCAGAAGCGGCACCTT CCCTCCCAATGACCGCGTCTTCGTC (SEQ ID NO: 31). In a preferred embodiment, the microRNA cluster includes:

(SEQ ID NO: 31)
AGGTATATTGCTGTTGACAGTGAGCGACTGTAAACTGAGCTTGCTCT

-continued
ACTGTGAAGCCACAGATGGGTAGAGCAAGCACAGTTTACCGCTGCCTACT
GCCTCGGACTTCAAGGGGCTTCCCGGGCATCTCCATGGCTGTACCACCTT
GTCGGGGGATGTGTACTTCTGAACTTGTGTTGAATCTCATGGAGTTCAGA
AGAACACATCCGCACTGACATTTTGGTATCTTTCATCTGACCAGCTAGCG
GGCCTGGCTCGAGCAGGGGGCGAGGGATTCCGCTTCTTCCTGCCATAGCG
TGGTCCCCTCCCCTATGGCAGGCAGAAGCGGCACCTTCCCTCCCAATGAC
CGCGTCTTCGTC.

In another aspect, a method of treating cells infected with HIV is provided. The method includes contacting peripheral blood mononuclear cells (PBMC) isolated from a subject infected with HIV with a therapeutically effective amount of a stimulatory agent, wherein the contacting is carried out ex vivo; transducing the PBMC ex vivo with a viral delivery system encoding at least one genetic element; and culturing the transduced PBMC for at least 1 day. The transduced PBMC may be cultured from about 1 to about 35 days. The method may further involve infusing the transduced PBMC into a subject. The subject may be a human. The stimulatory agent may include a peptide or mixture of peptides, and in a preferred embodiment includes a gag peptide. The stimulatory agent may include a vaccine. The vaccine may be a HIV vaccine, and in a preferred embodiment, the HIV vaccine is a MVA/HIV62B vaccine or a variant thereof. In a preferred embodiment, the viral delivery system includes a lentiviral particle. In one embodiment, the at least one genetic element may include a small RNA capable of inhibiting production of chemokine receptor CCR5 or at least one small RNA capable of targeting an HIV RNA sequence. In another embodiment, the at least one genetic element may include a small RNA capable of inhibiting production of chemokine receptor CCR5 and at least one small RNA capable of targeting an HIV RNA sequence. The HIV RNA sequence may include a HIV Vif sequence, a HIV Tat sequence, or a variant thereof. The at least one genetic element may include a microRNA or a shRNA. In a preferred embodiment, the at least one genetic element comprises a microRNA cluster.

In another aspect, the at least one genetic element includes a microRNA having at least 80%, or at least 85%, or at least 90%, or at least 95% percent identity with AGGTATATTGCTGTTGACAGTGAGCGACTGTAAACTGAGCTTGCTCTACTGTGAAG CCACAGATGGGTAGAGCAAGCACAGTTTACCGCTGCCTA CTGCCTCGGACTTCAA GGGGCTT (SEQ ID NO: 1). In a preferred embodiment, the at least one genetic element comprises:

(SEQ ID NO: 1)
AGGTATATTGCTGTTGACAGTGAGCGACTGTAAACTGAGCTTGCTCTACT
GTGAAGCCACAGATGGGTAGAGCAAGCACAGTTTACCGCTGCCTACTGCC
TCGGACTTCAAGGGGCTT.

In another aspect, the at least one genetic element includes a microRNA having at least 80%, or at least 85%, or at least 90%, or at least 95% percent identity with CATCTCCATGGCTGTACCACCTGTCGGGGGATGTGTACTTCTGAACTTGTGTGA ATCTCATGGAGTTCAGAAGAACACATCCGCACTGACATTTGGT ATCTTTCATCTG ACCA (SEQ ID NO: 2); or at least 80%, or at least 85%, or at least 90%, or at least 95% percent identity with GGGCCTGGCTCGAGCAGGGGGCGAGGGATTCCGCTTCTTCCTGCCATAGCGTGG TCCCCTCCCC-TATGGCAGGCAGAAGCGGCACCTTCCCTCC-CAATGACCGCGTCTTC GTCG (SEQ ID NO: 3). In a preferred embodiment, the at least one genetic element includes

```
                                          (SEQ ID NO: 2)
CATCTCCATGGCTGTACCACCTTGTCGGGGGATGTGTACTTCTGAACTTG
TGTTGAATCTCATGGAGTTCAGAAGAACACATCCGCACTGACATTTTGGT
ATCTTTCATCTGACCA;
or

                                          (SEQ ID NO: 3)
GGGCCTGGCTCGAGCAGGGGGCGAGGGATTCCGCTTCTTC
CTGCCATAGCGTGGTCCCCTCCCCTATGGCAGGCAGAAGCGGCACCTTCC
CTCCCAATGACCGCGTCTTCGTCG.
```

In another aspect, the microRNA cluster includes a sequence having at least 80%, or at least 85%, or at least 90%, or at least 95% percent identity with AGGTATATTGCTGTTGACAGTGAGCGACTGTAAACT-GAGCTTGCTCTACTGTGAAG CCACA-GATGGGTAGAGCAAGCACAGTTTACCGCTGCCTAC TGCCTCGGACTTCAA GGGGCTTCCCGGGCATCTC-CATGGCTGTACCACCTTGTCGGGG-GATGTGTACTTCT GAACTTGTGTTGAATCTCATG-GAGTTCAGAAGAACACATCCGCACTGACATTTTGG TATCTTT-CATCTGACCAGCTAGCGGGCCTGGCTCGAGCAGG GGGCGAGGGATTCC GCTTCTTCCTGCCAT-AGCGTGGTCCCCTCCCC-TATGGCAGGCAGAAGCGGCACCTT CCCTCC-CAATGACCGCGTCTTCGTC (SEQ ID NO: 31). In a preferred embodiment, the microRNA cluster includes:

```
                                          (SEQ ID NO: 31)
AGGTATATTGCTGTTGACAGTGAGCGACTGTAAACTGAGCTTGCTCT

ACTGTGAAGCCACAGATGGGTAGAGCAAGCACAGTTTACCGCTGCCTACT

GCCTCGGACTTCAAGGGGCTTCCCGGGCATCTCCATGGCTGTACCACCTT

GTCGGGGGATGTGTACTTCTGAACTTGTGTTGAATCTCATGGAGTTCAGA

AGAACACATCCGCACTGACATTTTGGTATCTTTCATCTGACCAGCTAGCG

GGCCTGGCTCGAGCAGGGGGCGAGGGATTCCGCTTCTTCCTGCCATAGCG

TGGTCCCCTCCCCTATGGCAGGCAGAAGCGGCACCTTCCCTCCCAATGAC

CGCGTCTTCGTC.
```

In another aspect, a lentiviral vector is disabled. The lentiviral vector includes at least one encoded genetic element, wherein the at least one encoded genetic element comprises a small RNA capable of inhibiting production of chemokine receptor CCR5 or at least one small RNA capable of targeting an HIV RNA sequence. In another aspect, the at least one encoded genetic element comprises a small RNA capable of inhibiting production of chemokine receptor CCR5 and at least one small RNA capable of targeting an HIV RNA sequence. The HIV RNA sequence may include a HIV Vif sequence, a HIV Tat sequence, or a variant thereof. The at least one encoded genetic element may include a microRNA or a shRNA. The at least one encoded genetic element may include a microRNA cluster.

In another aspect, the at least one genetic element includes a microRNA having at least 80%, or at least 85%, or at least 90%, or at least 95% percent identity with AGGTATATGCTGTGACAGTGAGCGACTGTAAACT-GAGCTTGCTCTACTGTGAAG CCACA-GATGGGTAGAGCAAGCACAGTTTACCGCTGCC-TACTGCCTCGGACTCAA GGGGCTT (SEQ ID NO: 1). In a preferred embodiment, the at least one genetic element comprises:

```
                                          (SEQ ID NO: 1)
AGGTATATTGCTGTTGACAGTGAGCGACTGTAAACTGAGCTTGCTCTACT
GTGAAGCCACAGATGGGTAGAGCAAGCACAGTTTACCGCTGCCTACTGCC
TCGGACTTCAAGGGGCTT.
```

In another aspect, the at least one genetic element includes a microRNA having at least 80%, or at least 85%, or at least 90%, or at least 95% percent identity with CATCTC-CATGGCTGTACCACCTGTCGGGG-GATGTGTACTTCTGAACTTGTGTTGA ATCTCATG-GAGTCAGAAGAACACATCCGCACTGACATTTGGT ATCTTTCATCTG ACCA (SEQ ID NO: 2); or at least 80%, or at least 85%, or at least 90%, or at least 95% percent identity with GGGCCTGGCTCGAGCAGGGGGCGAGG-GATTCCGCTTCTTCCTGCCATAGCGTGG TCCCCTCCCC-TATGGCAGGCAGAAGCGGCACCTTCCCTCC-CAATGACCGCGTCTTC GTCG (SEQ ID NO: 3). In a preferred embodiment, the at least one genetic element includes

```
                                          (SEQ ID NO: 2)
CATCTCCATGGCTGTACCACCTTGTCGGGGGATGTGTACTTCTGAACTTG
TGTTGAATCTCATGGAGTTCAGAAGAACACATCCGCACTGACATTTTGGT
ATCTTTCATCTGACCA;
or

                                          (SEQ ID NO: 3)
GGGCCTGGCTCGAGCAGGGGGCGAGGGATTCCGCTTCTTC
CTGCCATAGCGTGGTCCCCTCCCCTATGGCAGGCAGAAGCGGCACCTTCC
CTCCCAATGACCGCGTCTTCGTCG.
```

In another aspect, the microRNA cluster includes a sequence having at least 80%, or at least 85%, or at least 90%, or at least 95% percent identity with AGGTATATGCTGTGACAGTGAGCGACTGTAAACT-GAGCTTGCTCTACTGTGAAG CCACA-GATGGGTAGAGCAAGCACAGTTTACCGCTGCC-TACTGCCTCGGACTCAA GGGGCTTCCCGGGCATCTCCATGGCTGTAC-CACCTGTCGGGGGATGTGTACTCT GAACTTGTGTT-GAATCTCATGGAGTTCAGAAGAACA-CATCCGCACTGACATTTGG TATCTTT-CATCTGACCAGCTAGCGGGCCTGGCTCGAGCAGG GGGCGAGGGATTCC GCTTCTTCCTGCCAT-AGCGTGGTCCCCTCCCC-TATGGCAGGCAGAAGCGGCACCTT CCCTCC-CAATGACCGCGTCTTCGTC (SEQ ID NO: 31). In a preferred embodiment, the microRNA cluster includes:

```
                                          (SEQ ID NO: 31)
AGGTATATTGCTGTTGACAGTGAGCGACTGTAAACTGAGCTTGCTCT

ACTGTGAAGCCACAGATGGGTAGAGCAAGCACAGTTTACCGCTGCCTACT

GCCTCGGACTTCAAGGGGCTTCCCGGGCATCTCCATGGCTGTACCACCTT

GTCGGGGGATGTGTACTTCTGAACTTGTGTTGAATCTCATGGAGTTCAGA

AGAACACATCCGCACTGACATTTTGGTATCTTTCATCTGACCAGCTAGCG

GGCCTGGCTCGAGCAGGGGGCGAGGGATTCCGCTTCTTCCTGCCATAGCG
```

-continued

TGGTCCCCTCCCCTATGGCAGGCAGAAGCGGCACCTTCCCTCCCAATGAC

CGCGTCTTCGTC.

In another aspect, a lentiviral vector system for expressing a lentiviral particle is disclosed. The system includes a lentiviral vector as described herein; an envelope plasmid for expressing an envelope protein optimized for infecting a cell; and at least one helper plasmid for expressing gag, pol, and rev genes, wherein when the lentiviral vector, the envelope plasmid, and the at least one helper plasmid are transfected into a packaging cell line, a lentiviral particle is produced by the packaging cell line, wherein the lentiviral particle is capable of inhibiting production of chemokine receptor CCR5 or targeting an HIV RNA sequence. The system may further include a first helper plasmid for expressing the gag and pol genes, and a second plasmid for expressing the rev gene.

In another aspect, a lentiviral particle capable of infecting a cell is disclosed. The lentiviral particle includes an envelope protein optimized for infecting a cell, and a lentiviral vector as described herein. The envelope protein may be optimized for infecting a T cell. In a preferred embodiment, the envelope protein is optimized for infecting a CD4+ T cell.

In another aspect, a modified cell is disclosed. The modified cell includes a CD4+ T cell, wherein the CD4+ T cell has been infected with a lentiviral particle as described herein. In a preferred embodiment, the CD4+ T cell also recognizes an HIV antigen. In a further preferred embodiment, the HIV antigen includes a gag antigen. In a further preferred embodiment, the CD4+ T cell expresses a decreased level of CCR5 following infection with the lentiviral particle.

In another aspect, a method of selecting a subject for a therapeutic treatment regimen is disclosed. The method includes removing leukocytes from the subject and purifying peripheral blood mononuclear cells (PBMC) and determining a first quantifiable measurement associated with at least one factor associated with the PBMC; contacting the PBMC ex vivo with a therapeutically effective amount of a second stimulatory agent, and determining a second measurement associated with the at least one factor associated with the PBMC, whereby when the second quantifiable measurement is higher than the first quantifiable measurement, the subject is selected for the treatment regimen. The at least one factor may be T cell proliferation or IFN gamma production.

In another aspect, the methods disclosed herein include depleting at least one subset of cells from the PBMC. The method includes depleting at least one subset of cells from the PBMC, wherein the at least one subset of cells comprises any one or more of CD8+ T cells, γδ cells, NK cells, B cells, neutrophils, basophils, eosinophils, T regulatory cells, NKT cells, and erythrocytes. In embodiments, the depleting occurs after removing the leukocytes. In embodiments, the depleting occurs at the same time as removing the leukocytes.

The foregoing general description and following brief description of the drawings and detailed description are exemplary and explanatory and are intended to provide further explanation of the invention as claimed. Other objects, advantages, and novel features will be readily apparent to those skilled in the art from the following brief description of the drawings and detailed description of the invention.

BRIEF DESCRIPTION OF THE DRAWINGS

FIG. 6 depicts exemplary vector sequences. Positive (genomic) strand sequence of the promoter and miR cluster were developed for inhibiting the spread of CCR5-tropic HIV strains. Sequences that are not underlined comprise the EF-1alpha promoter of transcription (SEQ ID NO: 105) that was selected as best for this miR cluster. Sequences that are underlined show the miR cluster consisting of miR30 CCR5 (SEQ ID NO: 1), (a modification of the natural human miR30 that redirects to CCR5 mRNA), miR21 Vif (SEQ ID NO: 2), (redirects to Vif RNA sequence) and miR185 Tat (redirects to Tat RNA sequence) (SEQ ID NO: 108) (as shown collectively in SEQ ID NO: 33).

FIG. 29 depicts a relationship between the percentage of transduced cells and the vector copy number. (A) depicts a table that shows that as the percentage of transduced cells increase, the vector copy number also increases (n=4). (B) shows regression analysis of the same samples depicted in the table, which shows a positive correlation between the percentage of transduced cells and the vector copy number (n=4).

DETAILED DESCRIPTION

Overview

Disclosed herein are methods and compositions for treating and/or preventing human immunodeficiency virus (HIV) disease to achieve a functional cure. A functional cure is defined as a condition resulting from the disclosed treatments and methods that reduces or eliminates the need for cART and may or may not require supporting adjuvant therapy. The methods of the invention include gene delivery by integrating lentivirus, non-integrating lentivirus, and related viral vector technology as described below.

Figure 1:
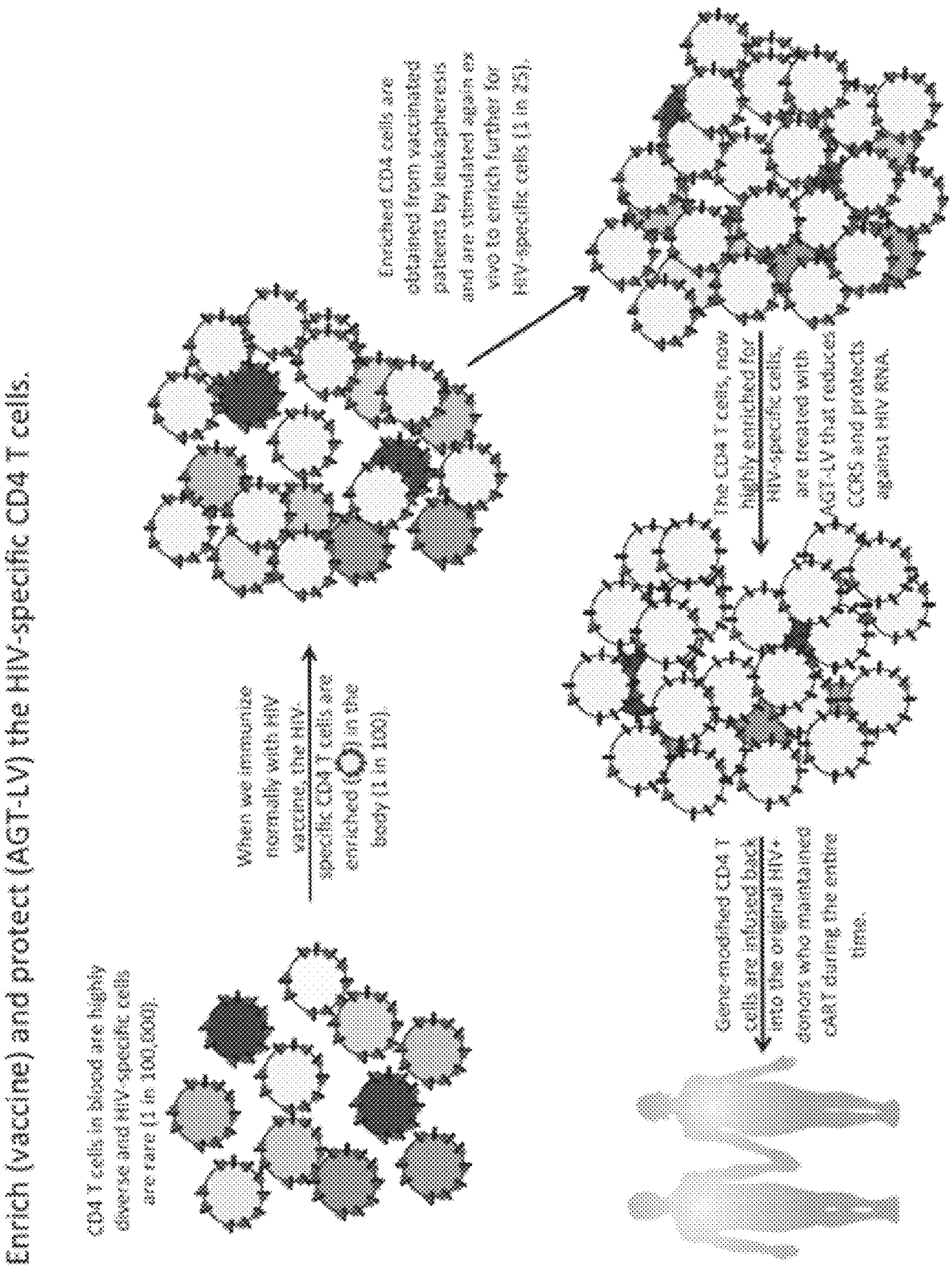
FIG. 1 depicts a flow chart diagram of a particular clinical therapy strategy.

Disclosed herein are therapeutic viral vectors (e.g., lentiviral vectors), immunotherapies, and methods for their use in a strategy to achieve a functional cure for HIV infection. As depicted in FIG. 1 herein, a strategy for treating HIV includes a first therapeutic immunization with vaccines intended to produce strong immune responses against HIV in HIV-infected patients with stable suppression of viremia due to daily administration of HAART, for the purpose of enriching the fraction of HIV-specific CD4 T cells. However, as detailed herein, the first therapeutic immunization may not be necessary. This is then followed by (1) isolating peripheral leukocytes by leukapheresis or purifying PBMC from venous blood, (2) re-stimulating CD4 T cells ex vivo with HIV vaccine proteins, (3) performing therapeutic lentivirus transduction, ex vivo T cell culture, and (4) re-infusion back into the original donor.

Figure 2:
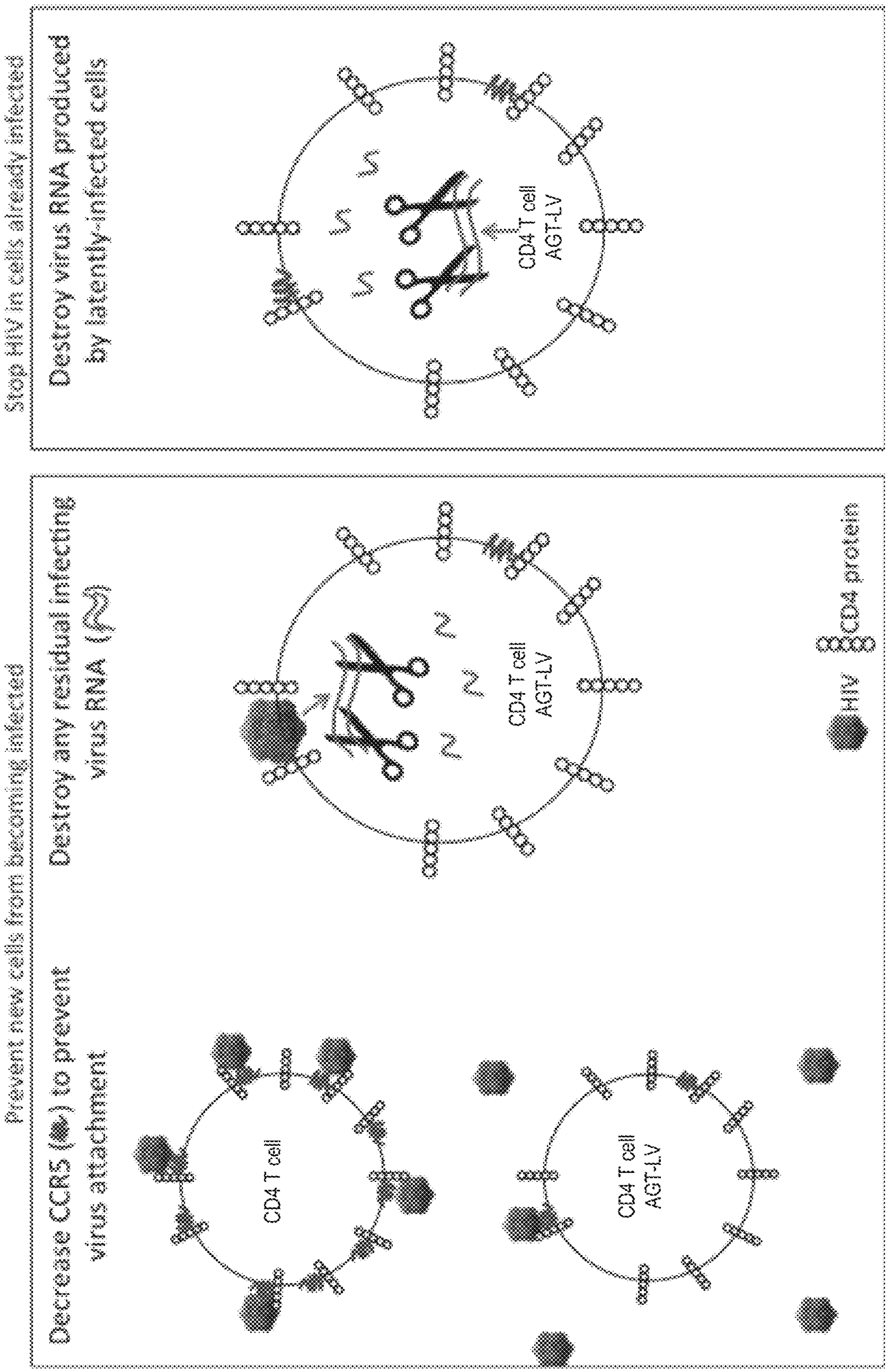
FIG. 2 depicts diagrammatically how CD4+ T cells may be altered using gene therapy to prevent other cells from becoming infected and/or to prevent viral replication.

In respect of the foregoing, and in reference to FIG. 2 herein, the methods can be used to prevent new cells, such as CD4+ T cells, from becoming infected with HIV. To prevent new cells from becoming infected, CCR5 expression can be targeted to prevent virus attachment. Further, destruction of any residual infecting viral RNA can also be targeted. In respect of the foregoing, and in reference to FIG. 2 herein, the methods can also be used to stop the HIV viral cycle in cells that have already become infected with HIV. To stop the HIV viral cycle, viral RNA produced by latently-infected cells, such as latently-infected CD4+ T cells, can be targeted.

By providing highly effective therapeutic lentiviruses capable of inhibiting HIV, a new strategy for achieving a functional cure of HIV has been developed.

Definitions and Interpretation

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well-known and commonly used in the art. The methods and techniques of the present disclosure are generally performed according to conventional methods well-known in the art and as described in various general and more specific references that are cited and discussed throughout the present specification unless otherwise indicated. See, e.g.: Sambrook J. & Russell D. Molecular Cloning: A Laboratory Manual, 3rd ed., Cold Spring Harbor Laboratory Press, Cold Spring Harbor, N.Y. (2000); Ausubel et al., Short Protocols in Molecular Biology: A Compendium of Methods from Current Protocols in Molecular Biology, Wiley, John & Sons, Inc. (2002); Harlow and Lane Using Antibodies: A Laboratory Manual; Cold Spring Harbor Laboratory Press, Cold Spring Harbor, N.Y. (1998); and Coligan et al., Short Protocols in Protein Science, Wiley, John & Sons, Inc. (2003). Any enzymatic reactions or purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

As used herein, the terms "administration of" or "administering" an active agent means providing an active agent of the invention to the subject in need of treatment in a form that can be introduced into that individual's body in a therapeutically useful form and therapeutically effective amount.

As used herein, the term "AGT103" refers to a particular embodiment of a lentiviral vector that contains a miR30-CCR5/miR21-Vif/miR185-Tat microRNA cluster sequence, as detailed herein.

As used herein, the term "AGT103T" refers to a cell that has been transduced with a lentivirus or lentiviral particle that contains the AGT103 lentiviral vector.

Throughout this specification and claims, the word "comprise," or variations such as "comprises" or "comprising," will be understood to imply the inclusion of a stated integer or group of integers but not the exclusion of any other integer or group of integers. Further, as used herein, the term "includes" means includes without limitation.

The term "engraftment" refers to the ability for one skilled in the art to determine a quantitative level of sustained engraftment in a subject following infusion of a cellular source (see for e.g.: Rosenberg et al., *N. Engl. J. Med.* 323:570-578 (1990); Dudley et al., *J. Immunother.* 24:363-373 (2001); Yee et al., *Curr. Opin. Immunol.* 13:141-146 (2001); Rooney et al., *Blood* 92:1549-1555 (1998)).

The terms, "expression," "expressed," or "encodes" refer to the process by which polynucleotides are transcribed into mRNA and/or the process by which the transcribed mRNA is subsequently being translated into peptides, polypeptides, or proteins. Expression may include splicing of the mRNA in a eukaryotic cell or other forms of post-transcriptional modification or post-translational modification.

The term "functional cure" refers to a state or condition wherein HIV+ individuals who previously required cART or HAART, may survive with low or undetectable virus replication using lower doses, intermittent doses, or discontinued dosing of cART or HAART. An individual may be said to have been "functionally cured" while still requiring adjunct therapy to maintain low level virus replication and slow or eliminate disease progression. A possible outcome of a functional cure is the eventual eradication of HIV to prevent all possibility of recurrence.

The term "HIV vaccine" encompasses immunogens plus vehicle plus adjuvant intended to elicit HIV-specific immune responses. A "HIV vaccine" may include purified or whole inactivated virus particles that may be HIV or a recombinant virus vectors capable of expressing HIV proteins, protein fragments or peptides, glycoprotein fragments or glycopeptides, in addition to recombinant bacterial vectors, plasmid DNA or RNA capable of directing cells to producing HIV proteins, glycoproteins or protein fragments able to elicit specific immunity. Alternately, specific methods for immune stimulation including anti-CD3/CD28 beads, T cell receptor-specific antibodies, mitogens, superantigens and other chemical or biological stimuli may be used to activate dendritic, T or B cells for the purposes of enriching HIV-specific CD4 T cells prior to transduction or for in vitro assay of lentivirus-transduced CD4 T cells. Activating substances may be soluble, polymeric assemblies, liposome or endosome-based or linked to beads. Cytokines including interleukin-2, 6, 7, 12, 15, 23 or others may be added to improve cellular responses to stimuli and/or improve the survival of CD4 T cells throughout the culture and transduction intervals. Alternately, and without limiting any of the foregoing, the term "HIV vaccine" encompasses the MVA/HIV62B vaccine and variants thereof. The MVA/HIV62B vaccine is a known highly attenuated double recombinant MVA vaccine. The MVA/HIV62B vaccine was constructed through the insertion of HIV-1 gag-pol and env sequences into the known MVA vector (see: for e.g.: Goepfert et al. (2014) J. Infect. Dis. 210(1): 99-110, and see WO2006026667, both of which are incorporated herein by reference). The term "HIV vaccine" also includes any one or more vaccines provided in Table 1, below.

TABLE 1

| IAVI Clinical Trial ID* | Prime** |
|---|---|
| HVTN 704 AMP | VRC-HIVMAB060-00-AB |
| VAC89220HPX2004 | Ad26.Mos.HIV Trivalent |
| 01-I-0079 | VRC4302 |
| 04/400-003-04 | APL 400-003 GENEVAX-HIV |
| 10-1074 | 10-1074 |
| 87 I-114 | gp160 Vaccine (Immuno-AG) |
| 96-I-0050 | APL 400-003 GENEVAX-HIV |
| ACTG 326; PACTG 326 | ALVAC vCP1452 |
| Ad26.ENVA.01 | Ad26.EnvA-01 |
| Ad26.ENVA.01 Mucosal/IPCAVD003 | Ad26.EnvA-01 |
| Ad5HVR48.ENVA.01 | Ad5HVR48.ENVA.01 |
| ANRS VAC 01 | ALVAC vCP125 |
| ANRS VAC 02 | rgp 160 + peptide V3 ANRS VAC 02 |
| ANRS VAC 03 | ALVAC-HIV MN120TMG strain (vCP205) |
| ANRS VAC 04 | LIPO-6 |
| ANRS VAC 04 bis | LIPO-6 |
| ANRS VAC 05 | ALVAC vCP125 |

TABLE 1-continued

| IAVI Clinical Trial ID* | Prime** |
|---|---|
| ANRS VAC 06 | ALVAC vCP125 |
| ANRS VAC 07 | ALVAC vCP300 |
| ANRS VAC 08 | ALVAC-HIV MN120TMG strain (vCP205) |
| ANRS VAC 09 | ALVAC-HIV MN120TMG strain (vCP205) |
| ANRS VAC 09 bis | LIPO-6 |
| ANRS VAC 10 | ALVAC vCP1452 |
| ANRS VAC 12 | LPHIV1 |
| ANRS VAC 14 | gp160 MN/LAI |
| ANRS VAC 16 | LPHIV1 |
| ANRS VAC 17 | LIPO-6 |
| ANRS VAC 18 | LIPO-5 |
| APL 400-003RX101 | APL 400-003 GENEVAX-HIV |
| AVEG 002 | HIVAC-1e |
| AVEG 002A | HIVAC-1e |
| AVEG 002B | HIVAC-1e |
| AVEG 003 | VaxSyn gp160 Vaccine (MicroGeneSys) |
| AVEG 003A | VaxSyn gp160 Vaccine (MicroGeneSys) |
| AVEG 003B | VaxSyn gp160 Vaccine (MicroGeneSys) |
| AVEG 004 | gp160 Vaccine (Immuno-AG) |
| AVEG 004A | gp160 Vaccine (Immuno-AG) |
| AVEG 004B | gp160 Vaccine (Immuno-AG) |
| AVEG 005A/B | Env 2-3 |
| AVEG 005C | Env 2-3 |
| AVEG 006X; VEU 006 | MN rgp120 |
| AVEG 007A/B | rgp120/HIV-1 SF-2 |
| AVEG 007C | rgp120/HIV-1 SF-2 |
| AVEG 008 | HIVAC-1e |
| AVEG 009 | MN rgp120 |
| AVEG 010 | HIVAC-1e |
| AVEG 011 | UBI HIV-1 Peptide Immunogen, Multivalent |
| AVEG 012A/B | ALVAC vCP125 |
| AVEG 013A | gp160 Vaccine (Immuno-AG) |
| AVEG 013B | gp160 Vaccine (Immuno-AG) |
| AVEG 014A/B | TBC-3B |
| AVEG 014C | TBC-3B |
| AVEG 015 | rgp120/HIV-1 SF-2 |
| AVEG 016 | MN rgp120 |
| AVEG 016A | MN rgp120 |
| AVEG 016B | MN rgp120 |
| AVEG 017 | UBI HIV-1 Peptide Vaccine, Microparticulate Monovalent |
| AVEG 018 | UBI HIV-1 Peptide Vaccine, Microparticulate Monovalent |
| AVEG 019 | p17/p24:Ty- VLP |
| AVEG 020 | gp120 C4-V3 |
| AVEG 021 | P3C541b Lipopeptide |
| AVEG 022 | ALVAC-HIV MN120TMG strain (vCP205) |
| AVEG 022A | ALVAC-HIV MN120TMG strain (vCP205) |
| AVEG 023 | UBI HIV-1 Peptide Immunogen, Multivalent |
| AVEG 024 | rgp120/HIV-1 SF-2 |
| AVEG 026 | ALVAC vCP300 |
| AVEG 027 | ALVAC-HIV MN120TMG strain (vCP205) |
| AVEG 028 | *Salmonella typhi* CVD 908-HIV-1 LAI gp 120 |
| AVEG 029 | ALVAC-HIV MN120TMG strain (vCP205) |
| AVEG 031 | APL 400-047 |
| AVEG 032 | ALVAC-HIV MN120TMG strain (vCP205) |
| AVEG 033 | ALVAC-HIV MN120TMG strain (vCP205) |
| AVEG 034/034A | ALVAC vCP1433 |
| AVEG 036 | MN rgp120 |
| AVEG 038 | ALVAC-HIV MN120TMG strain (vCP205) |
| AVEG 201 | rgp120/HIV-1 SF-2 |
| AVEG 202/HIVNET 014 | ALVAC-HIV MN120TMG strain (vCP205) |
| C060301 | GTU-MultiHIV |
| C86P1 | HIV gp140 ZM96 |
| Cervico-vaginal CN54gp140-hsp70 Conjugate Vaccine (TL01) | CN54gp140 |
| CM235 and SF2gp120 | CM235 (ThaiE) gp120 plus SF2(B) gp120 |
| CM235gp120 and SF2gp120 | CM235 (ThaiE) gp120 plus SF2(B) gp120 |
| CombiHIVvac (KombiVIChvak) | CombiHIVvac |
| CRC282 | P2G12 |
| CRO2049/CUT*HIVAC001 | GTU-MultiHIV |
| CUTHIVAC002 | DNA-C CN54ENV |
| DCVax-001 | DCVax-001 |
| DNA-4 | DNA-4 |
| DP6?001 | DP6?001 DNA |
| DVP-1 | EnvDNA |
| EN41-UGR7C | EN41-UGR7C |
| EnvDNA | EnvDNA |

TABLE 1-continued

| IAVI Clinical Trial ID* | Prime** |
|---|---|
| EnvPro | EnvPro |
| EuroNeut41 | EN41-FPA2 |
| EV01 | NYVAC-C |
| EV02 (EuroVacc 02) | DNA-C |
| EV03/ANRSVAC20 | DNA-C |
| Extention HVTN 073E/SAAVI 102 | Sub C gp140 |
| F4/AS01 | F4/AS01 |
| FIT Biotech | GTU-Nef |
| Guangxi CDC DNA vaccine | Chinese DNA |
| HGP-30 memory responses | HGP-30 |
| HIV-CORE002 | ChAdV63.HIVconsv |
| HIV-POL-001 | MVA-mBN32 |
| HIVIS 01 | HIVIS-DNA |
| HIVIS 02 | MVA-CMDR |
| HIVIS 03 | HIVIS-DNA |
| HIVIS 05 | HIVIS-DNA |
| HIVIS06 | HIVIS-DNA |
| HIVIS07 | HIVIS-DNA |
| HIVNET 007 | ALVAC-HIV MN120TMG strain (vCP205) |
| HIVNET 026 | ALVAC vCP1452 |
| HPTN 027 | ALVAC-HIV vCP1521 |
| HVRF-380-131004 | Vichrepol |
| HVTN 039 | ALVAC vCP1452 |
| HVTN 040 | AVX101 |
| HVTN 041 | rgp120w61d |
| HVTN 042/ANRS VAC 19 | ALVAC vCP1452 |
| HVTN 044 | VRC-HIVDNA009-00-VP |
| HVTN 045 | pGA2/JS7 DNA |
| HVTN 048 | EP HIV-1090 |
| HVTN 049 | Gag and Env DNA/PLG microparticles |
| HVTN 050/Merck 018 | MRKAd5 HIV-1 gag |
| HVTN 052 | VRC-HIVDNA009-00-VP |
| HVTN 054 | VRC-HIVADV014-00-VP |
| HVTN 055 | TBC-M335 |
| HVTN 056 | MEP |
| HVTN 057 | VRC-HIVDNA009-00-VP |
| HVTN 059 | AVX101 |
| HVTN 060 | HIV-1 gag DNA |
| HVTN 063 | HIV-1 gag DNA |
| HVTN 064 | EP HIV-1043 |
| HVTN 065 | pGA2/JS7 DNA |
| HVTN 067 | EP-1233 |
| HVTN 068 | VRC-HIVADV014-00-VP |
| HVTN 069 | VRC-HIVDNA009-00-VP |
| HVTN 070 | PENNVAX-B |
| HVTN 071 | MRKAd5 HIV-1 gag |
| HVTN 072 | VRC-HIVDNA044-00-VP |
| HVTN 073 | SAAVI DNA-C2 |
| HVTN 076 | VRC-HIVDNA016-00-VP |
| HVTN 077 | VRC-HIVADV027-00-VP |
| HVTN 078 | NYVAC-B |
| HVTN 080 | PENNVAX-B |
| HVTN 082 | VRC-HIVDNA016-00-VP |
| HVTN 083 | VRC-HIVADV038-00-VP |
| HVTN 084 | VRC-HIVADV054-00-VP |
| HVTN 085 | VRC-HIVADV014-00-VP |
| HVTN 086, SAAVI 103 | SAAVI MVA-C |
| HVTN 087 | HIV-MAG |
| HVTN 088 | Oligomeric gp140/MF59 |
| HVTN 090 | VSV-Indiana HIV gag vaccine |
| HVTN 092 | DNA-HIV-PT123 |
| HVTN 094 | GEO-D03 |
| HVTN 096 | DNA-HIV-PT123 |
| HVTN 097 | ALVAC-HIV vCP1521 |
| HVTN 098 | PENNVAX-GP |
| HVTN 100 | ALVAC-HIV-C (vCP2438) |
| HVTN 101 | DNA-HIV-PT123 |
| HVTN 102 | DNA-HIV-PT123 |
| HVTN 104 | VRC-HIVMAB060-00-AB |
| HVTN 105 | AIDSVAX B/E |
| HVTN 106 | DNA Nat-B env |
| HVTN 110 | Ad4-mgag |
| HVTN 112 | HIV-1 nef/tat/vif, env pDNA vaccine |
| HVTN 114; GOVX-B11 | AIDSVAX B/E |
| HVTN 116 | VRC-HIVMAB060-00-AB |
| HVTN 203 | ALVAC vCP1452 |
| HVTN 204 | VRC-HIVDNA016-00-VP |
| HVTN 205 | pGA2/JS7 DNA |

TABLE 1-continued

| IAVI Clinical Trial ID* | Prime** |
|---|---|
| HVTN 502/Merck 023 (Step Study) | MRKAd5 HIV-1 gag/pol/nef |
| HVTN 503 (Phambili) | MRKAd5 HIV-1 gag/pol/nef |
| HVTN 505 | VRC-HIVDNA016-00-VP |
| HVTN 702 | ALVAC-HIV-C (vCP2438) |
| HVTN 703 AMP | VRC-HIVMAB060-00-AB |
| HVTN 908 | pGA2/JS7 DNA |
| IAVI 001 | DNA.HIVA |
| IAVI 002 | DNA.HIVA |
| IAVI 003 | MVA.HIVA |
| IAVI 004 | MVA.HIVA |
| IAVI 005 | DNA.HIVA |
| IAVI 006 | DNA.HIVA |
| IAVI 008 | MVA.HIVA |
| IAVI 009 | DNA.HIVA |
| IAVI 010 | DNA.HIVA |
| IAVI 011 | MVA.HIVA |
| IAVI 016 | MVA.HIVA |
| IAVI A001 | tgAAC09 |
| IAVI A002 | tgAAC09 |
| IAVI A003 | AAV1-PG9 |
| IAVI B001 | Ad35-GRIN/ENV |
| IAVI B002 | Adjuvanted GSK investigational HIV vaccine formulation 1 |
| IAVI B003 | Ad26.EnvA-01 |
| IAVI B004 | HIV-MAG |
| IAVI C001 | ADVAX |
| IAVI C002 | ADMVA |
| IAVI C003 | ADMVA |
| IAVI C004/DHO-614 | ADVAX |
| IAVI D001 | TBC-M4 |
| IAVI N004 HIV-CORE 004 | Ad35-GRIN |
| IAVI P001 | ADVAX |
| IAVI P002 | ADVAX |
| IAVI R001 | rcAd26.MOS1.HIVEnv |
| IAVI S001 | SeV-G |
| IAVI V001 | VRC-HIVDNA016-00-VP |
| IAVI V002 | VRC-HIVDNA016-00-VP |
| IDEA EV06 | DNA-HIV-PT123 |
| IHV01 | Full-Length Single Chain (FLSC) |
| IMPAACT P1112 | VRC-HIVMAB060-00-AB |
| IPCAVD006 | MVA mosaic |
| IPCAVD008 | Trimeric gp140 |
| IPCAVD009 | Ad26.Mos.HIV Trivalent |
| IPCAVD010 | Ad26.Mos.HIV Trivalent |
| ISS P-001 | Tat vaccine |
| ISS P-002 | Tat vaccine |
| LFn-p24 vaccine | LFn-p24 |
| MCA-0835 | 3BNC117 |
| Merck V520-007 | Ad-5 HIV-1 gag (Merck) |
| MRC V001 | rgp120w61d |
| MRK Ad5 | Ad-5 HIV-1 gag (Merck) |
| MRKAd5 + ALVAC | MRKAd5 HIV-1 gag |
| Mucovac2 | CN54gp140 |
| MV1-F4 | Measles Vector - GSK |
| MYM-V101 | Virosome-Gp41 |
| NCHECR-AE1 | pHIS-HIV-AE |
| PACTG 230 | AIDSVAX B/E |
| PAVE100 | VRC-HIVDNA016-00-VP |
| PEACHI-04 | ChAdV63.HIVconsv |
| PedVacc001 & PedVacc002 | MVA.HIVA |
| PolyEnv1 | PolyEnv1 |
| PXVX-HIV-100-001 | Ad4-mgag |
| RISVAC02 | MVA-B |
| RisVac02 boost | MVA-B |
| RV 124 | ALVAC-HIV MN120TMG strain (vCP205) |
| RV 132 | ALVAC-HIV vCP1521 |
| RV 135 | ALVAC-HIV vCP1521 |
| RV 138; B011 | ALVAC-HIV MN120TMG strain (vCP205) |
| RV 144 | ALVAC-HIV vCP1521 |
| RV 151/WRAIR 984 | LFn-p24 |
| RV 156 | VRC-HIVDNA009-00-VP |
| RV 156A | VRC-HIVDNA009-00-VP |
| RV 158 | MVA-CMDR |
| RV 172 | VRC-HIVDNA016-00-VP |
| RV 305 | ALVAC-HIV vCP1521 |
| RV 306 | ALVAC-HIV vCP1521 |
| RV 328 | AIDSVAX B/E |
| RV 365 | MVA-CMDR |

TABLE 1-continued

| IAVI Clinical Trial ID* | Prime** |
|---|---|
| RV262 | Pennvax-G |
| SG06RS02 | HIV gp140 ZM96 |
| TAB9 | TAB9 |
| TaMoVac II | HIVIS-DNA |
| TAMOVAC-01-MZ | HIVIS-DNA |
| Tiantan vaccinia HIV Vaccine | Chinese DNA |
| Tiantan vaccinia HIV Vaccine and DNA | Chinese DNA |
| TMB-108 | Ibalizumab |
| UBI HIV-1 MN China | UBI HIV-1 Peptide Immunogen, Multivalent |
| UBI HIV-1MN octameric - Australia study | UBI HIV-1 Peptide Immunogen, Multivalent |
| UBI V106 | UBI HIV-1 Peptide Vaccine, Microparticulate Monovalent |
| UCLA MIG-001 | TBC-3B |
| UCLA MIG-003 | ALVAC-HIV MN120TMG strain (vCP205) |
| UKHVCSpoke003 | DNA - CN54ENV and ZM96GPN |
| V24P1 | HIV p24/MF59 Vaccine |
| V3-MAPS | V3-MAPS |
| V520-016 | MRKAd5 HIV-1 gag/pol/nef |
| V520-027 | MRKAd5 HIV-1 gag/pol/nef |
| V526-001 MRKAd5 and MRKAd6 HIV-1 Trigene Vaccines | MRKAd5 HIV-1 gag/pol/nef |
| VAX 002 | AIDSVAX B/B |
| VAX 003 | AIDSVAX B/E |
| VAX 004 | AIDSVAX B/B |
| VRC 004 (03-I-0022) | VRC-HIVDNA009-00-VP |
| VRC 006 (04-I-0172) | VRC-HIVADV014-00-VP |
| VRC 007 (04-I-0254) | VRC-HIVDNA016-00-VP |
| VRC 008 (05-I-0148) | VRC-HIVDNA016-00-VP |
| VRC 009 (05-I-0081) | VRC-HIVDNA009-00-VP |
| VRC 010 (05-I-0140) | VRC-HIVADV014-00-VP |
| VRC 011(06-I-0149) | VRC-HIVDNA016-00-VP |
| VRC 012 (07-I-0167) | VRC-HIVADV027-00-VP |
| VRC 015 (08-I-0171) | VRC-HIVADV014-00-VP |
| VRC 016 | VRC-HIVDNA016-00-VP |
| VRC 602 | VRC-HIVMAB060-00-AB |
| VRC 607 | VRCHIVMAB080-00-AB |
| VRC01LS | VRCHIVMAB080-00-AB |
| VRI01 | MVA-B |
| X001 | CN54gp140 |

*IAVI is the International AIDS Vaccine Initiative, whose clinical trials database is publicly available at http://www.iavi.org/trials-database/trials.
**As used herein, the term "Prime" refers to the composition initially used as an immunological inoculant in a given clinical trial as referenced in Table 1 herein.

The term "in vivo" refers to processes that occur in a living organism. The term "ex vivo" refers to processes that occur outside of a living organism.

The term "miRNA" refers to a microRNA and also maybe referred to as "miR".

The term "packaging cell line" refers to any cell line that can be used to express a lentiviral particle.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present disclosure can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

As used herein, "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see, e.g., Berge et al. (1977) *J Pharm Sci* 66:1-19).

As used herein, the term "SEQ ID NO" is synonymous with the term "Sequence ID No."

As used herein, "small RNA" refers to non-coding RNA that are generally less than about 200 nucleotides or less in length and possess a silencing or interference function. In other embodiments, the small RNA is about 175 nucleotides or less, about 150 nucleotides or less, about 125 nucleotides or less, about 100 nucleotides or less, or about 75 nucleotides or less in length. Such RNAs include microRNA (miRNA), small interfering RNA (siRNA), double stranded RNA (dsRNA), and short hairpin RNA (shRNA). "Small RNA" of the disclosure should be capable of inhibiting or knocking-down gene expression of a target gene, generally through pathways that result in the destruction of the target gene mRNA.

As used herein, the term "stimulatory agent" refers to any exogenous agent that can stimulate a leukocyte.

As used herein, the term "subject" includes a human patient but also includes other mammals. The terms "subject," "individual," "host," and "patient" may be used interchangeably herein.

As used herein, the term "target cell" generally refers to a CD4+ T cell that responds to stimulation with protein or peptide fragments representing HIV gene sequences, and includes a CD4+ T cell that has been transduced with the lentivirus vectors detailed herein rendering it less sensitive to HIV.

The term "therapeutically effective amount" refers to a sufficient quantity of the active agents of the present invention, in a suitable composition, and in a suitable dosage form to treat or prevent the symptoms, progression, or onset of the complications seen in patients suffering from a given ailment, injury, disease, or condition. The therapeutically effective amount will vary depending on the state of the patient's condition or its severity, and the age, weight, etc., of the subject to be treated. A therapeutically effective amount can vary, depending on any of a number of factors, including, e.g., the route of administration, the condition of the subject, as well as other factors understood by those in the art.

As used herein, the term "therapeutic vector" is synonymous with a lentiviral vector such as the AGT103 vector.

The term "treatment" or "treating" generally refers to an intervention in an attempt to alter the natural course of the subject being treated, and can be performed either for prophylaxis or during the course of clinical pathology. Desirable effects include, but are not limited to, preventing occurrence or recurrence of disease, alleviating symptoms, suppressing, diminishing or inhibiting any direct or indirect pathological consequences of the disease, ameliorating or palliating the disease state, and causing remission or improved prognosis.

DESCRIPTION OF ASPECTS OF THE DISCLOSURE

As detailed herein, in one aspect, a method of treating HIV infection in a subject is disclosed. The method includes removing leukocytes from the subject and purifying peripheral blood mononuclear cells (PBMC). The method further includes contacting the PBMC ex vivo with a therapeutically effective amount of a stimulatory agent; transducing the PBMC ex vivo with a viral delivery system encoding at least one genetic element; and culturing the transduced PBMC for at least 1 day. The method may further include further enrichment of the PBMC, for example, by preferably enriching the PBMC for CD4+ T cells. The transduced PBMC may be cultured from about 1 to about 35 days. The method may further involve infusing the transduced PBMC into a subject. The subject may be a human. The stimulatory agent may include a peptide or mixture of peptides. In a preferred embodiment, the stimulatory agent includes a gag peptide. The stimulatory agent may include a vaccine. The vaccine may be a HIV vaccine, and in a preferred embodiment, the HIV vaccine is a MVA/HIV62B vaccine or a variant thereof. In a preferred embodiment, the viral delivery system includes a lentiviral particle. In one embodiment, the at least one genetic element may include a small RNA capable of inhibiting production of chemokine receptor CCR5 or at least one small RNA capable of targeting an HIV RNA sequence. In another embodiment, the at least one genetic element may include a small RNA capable of inhibiting production of chemokine receptor CCR5 and at least one small RNA capable of targeting an HIV RNA sequence. The HIV RNA sequence may include a HIV Vif sequence, a HIV Tat sequence, or a variant thereof. The at least one genetic element may include a microRNA or a shRNA. In a preferred embodiment, the at least one genetic element comprises a microRNA cluster.

In another aspect, the at least one genetic element includes a microRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with AGGTATATGCTGTGACAGTGAGCGACTGTAAACTGAGCTTGCTCTACTGTGAAG CCACAGATGGGTAGAGCAAGCACAGTTTACCGCTGCCTACTGCCTCGGACTCAA GGGGCTT (SEQ ID NO: 1). In a preferred embodiment, the at least one genetic element comprises:

```
                                                (SEQ ID NO: 1)
AGGTATATTGCTGTTGACAGTGAGCGACTGTAAACTGAGCTTGCTCTACT
GTGAAGCCACAGATGGGTAGAGCAAGCACAGTTTACCGCTGCCTACTGCC
TCGGACTTCAAGGGGCTT.
```

In another aspect, the at least one genetic element includes a microRNA having at least 80%, or at least 85%, or at least 90%, or at least 95% percent identity with CATCTCCATGGCTGTACCACCTTGTCGGGGGATGTGTACTTCTGAACTGTGTTGA ATCTCATGGAGTCAGAAGAACACATCCGCACTGACATTTGGTATCTTTCATCTG ACCA (SEQ ID NO: 2); or at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with GGGCCTGGCTCGAGCAGGGGGCGAGGGATTCCGCTTCTTCCTGCCATAGCGTGG TCCCCTCCCCTATGGCAGGCAGAAGCGGCACCTTCCCTCCCAATGACCGCGTCTTC GTCG (SEQ ID NO: 3). In a preferred embodiment, the at least one genetic element includes

```
                                                (SEQ ID NO: 2)
CATCTCCATGGCTGTACCACCTTGTCGGGGGATGTGTACTTCTGAACTTG
TGTTGAATCTCATGGAGTTCAGAAGAACACATCCGCACTGACATTTTGGT
ATCTTTCATCTGACCA;
or
                                                (SEQ ID NO: 3)
GGGCCTGGCTCGAGCAGGGGGCGAGGGATTCCGCTTCTTC
CTGCCATAGCGTGGTCCCCTCCCCTATGGCAGGCAGAAGCGGCACCTTCC
CTCCCAATGACCGCGTCTTCGTCG.
```

In another aspect, the microRNA cluster includes a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with AGGTATATGCTGTGACAGTGAGCGACTGTAAACTGAGCTTGCTCTACTGTGAAG CCACAGATGGGTAGAGCAAGCACAGTTTACCGCTGCCTACTGCCTCGGACTCAA GGGGCTTCCCGGGCATCTCCATGGCTGTACCACCTGTCGGGGGATGTGTACTCT GAACTTGTGTTGAATCTCATGGAGTTCAGAAGAACACATCCGCACTGACATTTTGG TATCTTTCATCTGACCAGCTAGCGGGCCTGGCTCGAGCAGG GGGCGAGGGATTCC GCTTCTTCCTGCCATAGCGTGGTCCCCTCCCCTATGGCAGGCAGAAGCGGCACCTT CCCTCCCAATGACCGCGTCTTCGTC (SEQ ID NO: 31). In a preferred embodiment, the microRNA cluster includes:

```
                                                (SEQ ID NO: 31)
AGGTATATTGCTGTTGACAGTGAGCGACTGTAAACTGAGCTTGCTCT
```

-continued

```
ACTGTGAAGCCACAGATGGGTAGAGCAAGCACAGTTTACCGCTGCCTACT
GCCTCGGACTTCAAGGGGCTTCCCGGGCATCTCCATGGCTGTACCACCTT
GTCGGGGGATGTGTACTTCTGAACTTGTGTTGAATCTCATGGAGTTCAGA
AGAACACATCCGCACTGACATTTTGGTATCTTTCATCTGACCAGCTAGCG
GGCCTGGCTCGAGCAGGGGGCGAGGGATTCCGCTTCTTCCTGCCATAGCG
TGGTCCCCTCCCCTATGGCAGGCAGAAGCGGCACCTTCCCTCCCAATGAC
CGCGTCTTCGTC.
```

In another aspect, a method of treating cells infected with HIV is provided. The method includes contacting peripheral blood mononuclear cells (PBMC) isolated from a subject infected with HIV with a therapeutically effective amount of a stimulatory agent, wherein the contacting is carried out ex vivo; transducing the PBMC ex vivo with a viral delivery system encoding at least one genetic element; and culturing the transduced PBMC for at least 1 day. The transduced PBMC may be cultured from about 1 to about 35 days. The method may further involve infusing the transduced PBMC into a subject. The subject may be a human. The stimulatory agent may include a peptide or mixture of peptides, and in a preferred embodiment includes a gag peptide. The stimulatory agent may include a vaccine. The vaccine may be a HIV vaccine, and in a preferred embodiment, the HIV vaccine is a MVA/HIV62B vaccine or a variant thereof. In a preferred embodiment, the viral delivery system includes a lentiviral particle. In one embodiment, the at least one genetic element may include a small RNA capable of inhibiting production of chemokine receptor CCR5 or at least one small RNA capable of targeting an HIV RNA sequence. In another embodiment, the at least one genetic element may include a small RNA capable of inhibiting production of chemokine receptor CCR5 and at least one small RNA capable of targeting an HIV RNA sequence. The HIV RNA sequence may include a HIV Vif sequence, a HIV Tat sequence, or a variant thereof. The at least one genetic element may include a microRNA or a shRNA. In a preferred embodiment, the at least one genetic element comprises a microRNA cluster.

In another aspect, the at least one genetic element includes a microRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with AGGTATATGCTGTGACAGTGAGCGACTGTAAACTGAGCTTGCTCTACTGTGAAG CCACAGATGGGTAGAGCAAGCACAGTTTACCGCTGCCTACTGCCTCGGACTCAA GGGGCTT (SEQ ID NO: 1). In a preferred embodiment, the at least one genetic element

```
                                                (SEQ ID NO: 1)
AGGTATATTGCTGTTGACAGTGAGCGACTGTAAACTGAGCTTGCTCTACT
GTGAAGCCACAGATGGGTAGAGCAAGCACAGTTTACCGCTGCCTACTGCC
TCGGACTTCAAGGGGCTT.
```

In another aspect, the at least one genetic element includes a microRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with CATCTCCATGGCTGTACCACCTTGTCGGGGGATGTGTACTTCTGAACTTGTGTTGA ATCTCATG- GAGTTCAGAAGAACACATCCGCACTGACATTTGGT ATCTTTCATCTG ACCA (SEQ ID NO: 2); or at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with GGGCCTGGCTCGAGCAGGGGGCGAGGGAT-TCCGCTTCTTCCTGCCATAGCGTGG TCCCCTCCCC-TATGGCAGGCAGAAGCGGCACCTTCCCTCC-CAATGACCGCGTCTTC GTCG (SEQ ID NO: 3). In a preferred embodiment, the at least one genetic element includes

```
(SEQ ID NO: 2)
CATCTCCATGGCTGTACCACCTTGTCGGGGGATGTGTACTTCTGAACTTG
TGTTGAATCTCATGGAGTTCAGAAGAACACATCCGCACTGACATTTTGGT
ATCTTTCATCTGACCA;
or

(SEQ ID NO: 3)
GGGCCTGGCTCGAGCAGGGGGCGAGGGATTCCGCTTCTTC
CTGCCATAGCGTGGTCCCCTCCCCTATGGCAGGCAGAAGCGGCACCTTCC
CTCCCAATGACCGCGTCTTCGTCG.
```

In another aspect, the microRNA cluster includes a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with AGGTATATTGCTGTTGACAGT-GAGCGACTGTAAACTGAGCTTGCTCTACTGTGAAG CCACAGATGGGTAGAGCAAGCACAGTT-TACCGCTGCCTACTGCCTCGGACTTCAA GGGGCTTCCCGGGCATCTCCATGGCTGTAC-CACCTTGTCGGGGGATGTGTACTTCT GAACTTGTGTTGAATCTCATG-GAGTTCAGAAGAACACATCCGCACTGACATTTTGG TATCTTT-CATCTGACCAGCTAGCGGGCCTGGCTCGAGCAGG GGGCGAGGGATTCC GCTTCTTCCTGCCAT-AGCGTGGTCCCCTCCCC-TATGGCAGGCAGAAGCGGCACCTT CCCTCC-CAATGACCGCGTCTTCGTC (SEQ ID NO: 31). In a preferred embodiment, the microRNA cluster includes:

```
(SEQ ID NO: 31)
AGGTATATTGCTGTTGACAGTGAGCGACTGTAAACTGAGCTTGCTCT

ACTGTGAAGCCACAGATGGGTAGAGCAAGCACAGTTTACCGCTGCCTACT

GCCTCGGACTTCAAGGGGCTTCCCGGGCATCTCCATGGCTGTACCACCTT

GTCGGGGGATGTGTACTTCTGAACTTGTGTTGAATCTCATGGAGTTCAGA

AGAACACATCCGCACTGACATTTTGGTATCTTTCATCTGACCAGCTAGCG

GGCCTGGCTCGAGCAGGGGGCGAGGGATTCCGCTTCTTCCTGCCATAGCG

TGGTCCCCTCCCCTATGGCAGGCAGAAGCGGCACCTTCCCTCCCAATGAC

CGCGTCTTCGTC.
```

In another aspect, a lentiviral vector is disclosed. The lentiviral vector includes at least one encoded genetic element, wherein the at least one encoded genetic element comprises a small RNA capable of inhibiting production of chemokine receptor CCR5 or at least one small RNA capable of targeting an HIV RNA sequence. In another aspect a lentiviral vector is disclosed in the at least one encoded genetic element comprises a small RNA capable of inhibiting production of chemokine receptor CCR5 and at least one small RNA capable of targeting an HIV RNA sequence. The HIV RNA sequence may include a HIV Vif sequence, a HIV Tat sequence, or a variant thereof. The at least one encoded genetic element may include a microRNA or a shRNA. The at least one encoded genetic element may include a microRNA cluster.

In another aspect, the at least one genetic element includes a microRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with AGGTATATGCTGTGACAGT-GAGCGACTGTAAACTGAGCTTGCTCTACTGTGAAG CCACAGATGGGTAGAGCAAGCACAGTT-TACCGCTGCCTACTGCCTCGGACTCAA GGGGCTT (SEQ ID NO: 1). In a preferred embodiment, the at least one genetic element comprises:

```
(SEQ ID NO: 1)
AGGTATATTGCTGTTGACAGTGAGCGACTGTAAACTGAGCTTGCTCTACT
GTGAAGCCACAGATGGGTAGAGCAAGCACAGTTTACCGCTGCCTACTGCC
TCGGACTTCAAGGGGCTT.
```

In another aspect, the at least one genetic element includes a microRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with CATCTCCATGGCTGTAC-CACCTGTCGGGGGATGTGTACTTCT-GAACTTGTGTGA ATCTCATGGAGTCAGAAGAACA-CATCCGCACTGACATTTTGGTATCTTTCATCTG ACCA (SEQ ID NO: 2); or at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with GGGCCTGGCTCGAGCAGGGGGCGAGGGAT-TCCGCTTCTTCCTGCCATAGCGTGG TCCCCTCCCC-TATGGCAGGCAGAAGCGGCACCTTCCCTCC-CAATGACCGCGTCTTC GTCG (SEQ ID NO: 3). In a preferred embodiment, the at least one genetic element includes

```
(SEQ ID NO: 2)
CATCTCCATGGCTGTACCACCTTGTCGGGGGATGTGTACTTCTGAACTTG
TGTTGAATCTCATGGAGTTCAGAAGAACACATCCGCACTGACATTTTGGT
ATCTTTCATCTGACCA;
or

(SEQ ID NO: 3)
GGGCCTGGCTCGAGCAGGGGGCGAGGGATTCCGCTTCTTC
CTGCCATAGCGTGGTCCCCTCCCCTATGGCAGGCAGAAGCGGCACCTTCC
CTCCCAATGACCGCGTCTTCGTCG.
```

In another aspect, the microRNA cluster includes a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with AGGTATATGCTGTGACAGT-GAGCGACTGTAAACTGAGCTTGCTCTACTGTGAAG CCACAGATGGGTAGAGCAAGCACAGTT-TACCGCTGCCTACTGCCTCGGACTCAA GGGGCTTCCCGGGCATCTCCATGGCTGTAC-CACCTGTCGGGGGATGTGTACTCT GAACTTGTGTT-GAATCTCATGGAGTTCAGAAGAACA-CATCCGCACTGACATTTTGG TATCTTT- CATCTGACCAGCTAGCGGGCCTGGCTCGAGCAGG GGGCGAGGGATTCC GCTTCTTCCTGCCAT-AGCGTGGTCCCCTCCCC-TATGGCAGGCAGAAGCGGCACCTT CCCTCC-CAATGACCGCGTCTTCGTC (SEQ ID NO: 31). In a preferred embodiment, the microRNA cluster includes:

```
                                        (SEQ ID NO: 31)
AGGTATATTGCTGTTGACAGTGAGCGACTGTAAACTGAGCTTGCTCT

ACTGTGAAGCCACAGATGGGTAGAGCAAGCACAGTTTACCGCTGCCTACT

GCCTCGGACTTCAAGGGGCTTCCCGGGCATCTCCATGGCTGTACCACCTT

GTCGGGGGATGTGTACTTCTGAACTTGTGTTGAATCTCATGGAGTTCAGA

AGAACACATCCGCACTGACATTTTGGTATCTTTCATCTGACCAGCTAGCG

GGCCTGGCTCGAGCAGGGGGCGAGGGATTCCGCTTCTTCCTGCCATAGCG

TGGTCCCCTCCCCTATGGCAGGCAGAAGCGGCACCTTCCCTCCCAATGAC

CGCGTCTTCGTC.
```

In another aspect, a lentiviral vector system for expressing a lentiviral particle is disclosed. The system includes a lentiviral vector as described herein; an envelope plasmid for expressing an envelope protein optimized for infecting a cell; and at least one helper plasmid for expressing gag, pol, and rev genes, wherein when the lentiviral vector, the envelope plasmid, and the at least one helper plasmid are transfected into a packaging cell line, a lentiviral particle is produced by the packaging cell line, wherein the lentiviral particle is capable of inhibiting production of chemokine receptor CCR5 or targeting an HIV RNA sequence.

In another aspect, a lentiviral particle capable of infecting a cell is disclosed. The lentiviral particle includes an envelope protein optimized for infecting a cell, and a lentiviral vector as described herein. The envelope protein may be optimized for infecting a T cell. In a preferred embodiment, the envelope protein is optimized for infecting a CD4+ T cell.

In another aspect, a modified cell is disclosed. The modified cell includes a CD4+ T cell, wherein the CD4+ T cell has been infected with a lentiviral particle as described herein. In a preferred embodiment, the CD4+ T cell also recognizes an HIV antigen. In a further preferred embodiment, the HIV antigen includes a gag antigen. In a further preferred embodiment, the CD4+ T cell expresses a decreased level of CCR5 following infection with the lentiviral particle.

In another aspect, a method of selecting a subject for a therapeutic treatment regimen is disclosed. The method includes removing leukocytes from the subject and purifying peripheral blood mononuclear cells (PBMC) and determining a first quantifiable measurement associated with at least one factor associated with the PBMC; contacting the PBMC ex vivo with a therapeutically effective amount of a second stimulatory agent, and determining a second measurement associated with the at least one factor associated with the PBMC, whereby when the second quantifiable measurement is higher than the first quantifiable measurement, the subject is selected for the treatment regimen. The at least one factor may be T cell proliferation or IFN gamma production.

In another aspect, any of the methods comprising treating cells infected with HIV described herein further comprise depleting at least one subset of cells from the PBMC. In embodiments, the method includes depleting at least one subset of cells from the PBMC, wherein the at least one subset of cells comprises any one or more of CD8+ T cells, γδ cells, NK cells, B cells, neutrophils, basophils, eosinophils, T regulatory cells, NKT cells, and erythrocytes. In embodiments, the depleting occurs after removing the leukocytes. In embodiments, the depleting occurs at the same time as removing the leukocytes.

In other aspect, any of the methods comprising treating HIV in a subject described herein further comprise depleting at least one subset of cells from the PBMC. In embodiments, the method includes depleting at least one subset of cells from the PBMC, wherein the at least one subset of cells comprises any one or more of CD8+ T cells, γδ cells, NK cells, B cells, neutrophils, basophils, eosinophils, T regulatory cells, NKT cells, and erythrocytes. In embodiments, the depleting occurs after removing the leukocytes. In embodiments, the depleting occurs at the same time as removing the leukocytes.

In another aspect, any of the methods comprising selected a subject for a therapeutic regimen described herein further comprise depleting at least one subset of cells from the PBMC. In embodiments, the method includes depleting at least one subset of cells from the PBMC, wherein the at least one subset of cells comprises any one or more of CD8+ T cells, γδ cells, NK cells, B cells, neutrophils, basophils, eosinophils, T regulatory cells, NKT cells, and erythrocytes. In embodiments, the depleting occurs after removing the leukocytes. In embodiments, the depleting occurs at the same time as removing the leukocytes.

In another aspect, any of the methods described herein further comprise depleting at least one subset of immune cells from the PBMC, wherein the at least one subset of cells comprises any one or more of CD8+ T cells, γδ cells, NK cells, B cells, neutrophils, basophils, eosinophils, T regulatory cells, NKT cells, and erythrocytes. In embodiments, the cells depleted from the PBMC are CD8+ T cells. In embodiments, the cells depleted from the PBMC are γδ cells. In embodiments, the cells depleted from the PBMC are NK cells. In embodiments, the cells depleted from the PBMC are B cells. In embodiments, the cells depleted from the PBMC are T regulatory cells. In embodiments, the cells depleted from the PBMC are NKT cells. In embodiments, the cells depleted from the PBMC are erythrocytes. In embodiments, the cells depleted from the PBMC are CD8+ T cells and γδ cells. In embodiments, the cells depleted from the PBMC are CD8+ T cells, γδ cells, and NK cells. In embodiments, the cells depleted from the PBMC are CD8+ T cells, γδ cells, NK cells, and B cells. In embodiments, the cells depleted from the PBMC are CD8+ T cells, γδ cells, NK cells, B cells, and T regulatory cells. In embodiments, the cells depleted from the PBMC are CD8+ T cells, γδ cells, NK cells, B cells, T regulatory cells, and NKT cells. In embodiments, the cells depleted from the PBMC are CD8+ T cells, γδ cells, NK cells, B cells, T regulatory cells, NKT cells, and erythrocytes. In embodiments, the cells depleted from the PBMC are γδ cells and NK cells. In embodiments, the cells depleted from the PBMC are γδ cells, NK cells, and B cells. In embodiments, the cells depleted from the PBMC are γδ cells, NK cells, B cells, and T regulatory cells. In embodiments, the cells depleted from the PBMC are γδ cells, NK cells, B cells, T regulatory cells, and NKT cells. In embodiments, the cells depleted from the PBMC are γδ cells, NK cells, B cells, T regulatory cells, NKT cells, and erythrocytes. In embodiments, the cells depleted from the PBMC are NK cells and B cells. In embodiments, the cells depleted from the PBMC are NK cells, B cells, and T regulatory cells. In embodiments, the cells depleted from the PBMC are NK cells, B cells, T regulatory cells, and NKT cells. In embodiments, the cells depleted from the PBMC are NK cells, B cells, T regulatory cells, NKT cells, and erythrocytes. In embodiments, the cells depleted from the PBMC are B cells and T regulatory cells. In embodiments, the cells depleted from the PBMC are B cells, T regulatory cells, and NKT cells. In embodiments, the cells depleted from the PBMC are B cells, T regulatory cells, NKT cells, and erythrocytes. In embodiments, the cells depleted from the PBMC are T regulatory cells and NKT cells. In embodiments, the cells depleted from the PBMC are T regulatory cells, NKT cells, and erythrocytes. In embodiments, the cells depleted from the PBMC are NKT cells and erythrocytes. In embodiments, the cells depleted from the PBMC are CD8+ T cells and NK cells. In embodiments, the cells depleted from the PBMC are CD8+ T cells, NK cells, and B cells. In embodiments, the cells depleted from the PBMC are CD8+ T cells, NK Cells, B cells, and T regulatory cells. In embodiments, the cells depleted from the PBMC are CD8+ T cells, NK Cells, B cells, T regulatory cells, and NKT cells. In embodiments, the cells depleted from the PBMC are CD8+ T cells, NK Cells, B cells, T regulatory cells, NKT cells, and erythrocytes. In embodiments, the cells depleted from the PBMC are γδ and B cells. In embodiments, the cells depleted from the PBMC are γδ, B cells, and T regulatory cells. In embodiments, the cells depleted from the PBMC are γδ, B cells, T regulatory cells, and NKT cells. In embodiments, the cells depleted from the PBMC are γδ, B cells, T regulatory cells, NKT cells, and erythrocytes. In embodiments, the cells depleted from the PBMC are NK cells and T regulatory cells. In embodiments, the cells depleted from the PBMC are NK cells, T regulatory cells, and NKT cells. In embodiments, the cells depleted from the PBMC are NK cells, T regulatory cells, NKT cells, and erythrocytes. In embodiments, the cells depleted from the PBMC are B cells and NKT cells. In embodiments, the cells depleted from the PBMC are B cells, NKT cells, and erythrocytes. In embodiments, the cells depleted from the PBMC are T regulatory cells and erythrocytes. In embodiments, the cells depleted from the PBMC, as described herein, include any one or any combination of neutrophils, basophils, and eosinophils.

In another aspect, CD8+ T cells are depleted at the beginning of cell expansion to improve CD4+ T cell expansion. In embodiments, the cell depletion is performed after peptide stimulation and before lentivirus transduction, when cells are better able to withstand mechanical stress. In embodiments, after CD8+ T cell depletion, the cells are placed in culture medium for approximately 24 hours. In embodiments, after CD8+ cell depletion, the cells are placed in culture for less than 24 hours, for example, less than 20 hours, less than 16 hours, less than 8 hours, or less than 4 hours. In embodiments, after CD8+ T cell depletion, the cells are placed in culture for greater than 24 hours, for example, greater than 30 hours, greater than 36 hours, greater than 42 hours, or greater than 48 hours. In embodiments, the culture medium comprises IL-7. In embodiments, the culture medium comprises IL-15. In embodiments, the culture medium comprises IL-7 and IL-15. In embodiments, the cell depletion is performed before peptide stimulation. In embodiments, a gag protein is used to cause peptide stimulation. In embodiments, a HIV vaccine is used to cause peptide stimulation. In embodiments, the vaccine is a MVA/HIV62B vaccine, which is used to cause peptide stimulation. In embodiments, CD8+ T cells are depleted with a PE anti-human CD8 antibody and anti-PE microbeads. In embodiments, the CD8 antibody is an anti-rat antibody. In embodiments, the CD8 antibody is an anti-mouse antibody. In embodiments, the CD8 antibody is an anti-rabbit antibody. In embodiments, the CD8 antibody is an anti-goat antibody. In embodiments, after cell depletion and peptide stimulation, the cells are transduced. In embodiments, the cells are transduced with a lentivirus. In embodiments, the lentivirus carries GFP. In embodiments, the lentivirus carries RFP. In embodiments, the lentivirus carries EGFP. In embodiments, the cells are placed in culture after transduction. In embodiments, the culture medium comprises IL-7. In embodiments, the culture medium comprises IL-15. In embodiments, the culture medium comprises IL-7 and IL-15. In embodiments, the cells are cultured for approximately 2 days to allow for CD4+ T cell expansion. In embodiments, the cells are cultured approximately 3 days to allow for CD4+ T cell expansion. In embodiments, the cells are cultured for less than 2 days, for example, less than 42 hours, less than 36 hours, less than 30 hours, less than 24 hours, less than 18 hours, less than 12 hours, or less than 6 hours. In embodiments, the cells are cultured for greater than 3 days, for example, greater than 4 days, greater than 5 days, greater than 6 days, greater than 7 days, greater than 8 days, greater than 9 days, or greater than 10 days. In embodiments, the cells are cultured between 2 and 3 days, for example, approximately 30 hours, approximately 36 hours, or approximately 42 hours.

In another aspect, CD8+, γδ, NK, or B cells are depleted to improve CD4+ T cell expansion. In embodiments, any two or more of CD8+, γδ, NK, and B cells are depleted to improve CD4+ T cell expansion. In embodiments, CD8+, γδ, NK, B, T regulatory, NKT, or erythrocyte cells are depleted to improve CD4+ T cell expansion. In embodiments any two or more of CD8+, γδ, NK, B, T regulatory, NKT, and erythrocyte cells are depleted to improve CD4+ T cell expansion. In embodiments, cell depletion is performed after peptide stimulation and before lentivirus transduction. In embodiments, after cell depletion, the cells are placed in culture medium for ~24 hours. In embodiments, after cell depletion, the cells are placed in culture for less than 24 hours, for example, less than 20 hours, less than 16 hours, less than 8 hours, or less than 4 hours. In embodiments, after CD8+ T cell depletion, the cells are placed in culture for greater than 24 hours, for example, greater than 30 hours, greater than 36 hours, greater than 42 hours, or greater than 48 hours. In embodiments, the culture medium comprises IL-7. In embodiments, the culture medium comprises IL-15. In embodiments, the culture medium comprises IL-7 and IL-15. In embodiments, cell depletion is performed before peptide stimulation. In embodiments, a gag protein is used to cause peptide stimulation. In embodiments, a HIV vaccine is used to cause peptide stimulation. In embodiments, the MVA/HIV62B vaccine is used to cause peptide stimulation. In embodiments, CD8+ T, γδ, NK, and/or B cells are depleted with PE labeled specific antibodies and anti-PE microbeads. In embodiments, the antibody used is an anti-human antibody. In embodiments, the antibody used was an anti-rat antibody. In embodiments, the antibody used is an anti-mouse antibody. In embodiments, the antibody used is an anti-goat antibody. In embodiments, after cell depletion and peptide stimulation, the cells are transduced. In embodiments, the cells are transduced with a lentivirus. In embodiments, the lentivirus carries GFP. In embodiments, the lentivirus carries RFP. In embodiments, the lentivirus carries EGFP. In embodiments, the cells are placed in culture after transduction. In embodiments, the culture medium comprises IL-7. In embodiments, the culture medium comprises IL-15. In embodiments, the culture medium comprises IL-7 and IL-15. In embodiments, the cells are cultured for approximately 2 days to allow for CD4+ T cell expansion. In embodiments, the cells are cultured ~3 days to allow for CD4+ T cell expansion. In embodiments, the cells are cultured for less than 2 days, for example, less than 42 hours, less than 36 hours, less than 30 hours, less than 24 hours, less than 18 hours, less than 12 hours, or less than 6 hours. In embodiments, the cells are cultured for greater than 3 days, for example, greater than 4 days, greater than 5 days, greater than 6 days, greater than 7 days, greater than 8 days, greater than 9 days, or greater than 10 days. In embodiments, the cells are cultured between 2 and 3 days, for example, ~30 hours, ~36 hours, or ~42 hours.

In another aspect, a lentivirus includes GFP, which is used to measure transduction efficiency. In embodiments, the lentivirus includes RFP. In embodiments, the lentivirus is carrying EGFP. In embodiments, a cytokine capture system is used to identify antigen-specific CD4+ T cells with GFP positive cells. In embodiments, GFP is used to identify the transduced cell subsets. In embodiments, RFP is used to identify the transduced cell subsets. In embodiments, EGFP is used to identify the transduced cell subsets. In embodiments, any of the transduction methods described herein can be used to measure transduction efficiency. In embodiments, prior to lentiviral transduction, any of the depletion methods described herein can be used to deplete any one or more of CD8+ T, γδ, NK, B, neutrophils, basophils, eosinophils, T regulatory, NKT, and erythrocyte cells.

In other aspect, transduction efficiency is measured by detecting vector copy number (VCN) by qPCR. In embodiments, the percentage of transduced cells based on VCN in the final cell product can be estimated by establishing the relationship between transduced cells and VCN. In embodiments, a lentivirus carrying GFP is used to determine the percentage of the cells transduced. In embodiments, a lentivirus carrying RFP is used to determine the percentage of cells transduced. In embodiments, a lentivirus carrying EGFP is used to determine the percentage of cells transduced. In embodiments, any of the transduction methods described herein can be used to measure transduction efficiency. In embodiments, prior to lentiviral transduction, any of the depletion methods described herein can be used to deplete any one or more of CD8+ T, γδ, NK, B cells.

Human Immunodeficiency Virus (HIV)

Human Immunodeficiency Virus, which is also commonly referred to as "HIV", is a retrovirus that causes acquired immunodeficiency syndrome (AIDS) in humans. AIDS is a condition in which progressive failure of the immune system allows life-threatening opportunistic infections and cancers to thrive. Without treatment, average survival time after infection with HIV is estimated to be 9 to 11 years, depending upon the HIV subtype. Infection with HIV occurs by the transfer of bodily fluids, including but not limited to blood, semen, vaginal fluid, pre-ejaculate, saliva, tears, lymph or cerebro-spinal fluid, or breast milk. HIV may be present in an infected individual as both free virus particles and within infected immune cells.

HIV infects vital cells in the human immune system such as helper T cells, although tropism can vary among HIV subtypes. Immune cells that may be specifically susceptible to HIV infection include but are not limited to CD4+ T cells, macrophages, and dendritic cells. HIV infection leads to low levels of CD4+ T cells through a number of mechanisms, including but not limited to apoptosis of uninfected bystander cells, direct viral killing of infected cells, and killing of infected CD4+ T cells by CD8 cytotoxic lymphocytes that recognize infected cells. When CD4+ T cell numbers decline below a critical level, cell-mediated immunity is lost, and the body becomes progressively more susceptible to opportunistic infections and cancer.

Structurally, HIV is distinct from many other retroviruses. The RNA genome consists of at least seven structural landmarks (LTR, TAR, RRE, PE, SLIP, CRS, and INS), and at least nine genes (gag, pol, env, tat, rev, nef, vif, vpr, vpu, and sometimes a tenth tev, which is a fusion of tat, env and rev), encoding 19 proteins. Three of these genes, gag, pol, and env, contain information needed to make the structural proteins for new virus particles.

HIV replicates primarily in CD4 T cells, and causes cellular destruction or dysregulation to reduce host immunity. Because HIV establishes infection as an integrated provirus and may enter a state of latency wherein virus expression in a particular cell decreases below the level for cytopathology affecting that cell or detection by the host immune system, HIV is difficult to treat and has not been eradicated even after prolonged intervals of highly active antiretroviral therapy (HAART). In the vast majority of cases, HIV infection causes fatal disease although survival may be prolonged by HAART.

A major goal in the fight against HIV is to develop strategies for curing disease. Prolonged HAART has not accomplished this goal, so investigators have turned to alternative procedures. Early efforts to improve host immunity by therapeutic immunization (using a vaccine after infection has occurred) had marginal or no impact. Likewise, treatment intensification had moderate or no impact.

Some progress has been made using genetic therapy, but positive results are sporadic and found only among rare human beings carrying defects in one or both alleles of the gene encoding CCR5 (chemokine receptor), which plays a critical role in viral penetration of host cells. However, many investigators are optimistic that genetic therapy holds the best promise for eventually achieving an HIV cure.

As disclosed herein, the methods and compositions of the invention are able to achieve a functional cure that may or may not include complete eradication of all HIV from the body. As mentioned above, a functional cure is defined as a state or condition wherein HIV+ individuals who previously required HAART, may survive with low or undetectable virus replication and using lower or intermittent doses of HAART, or are potentially able to discontinue HAART altogether. As used herein, a functional cure may still possibly require adjunct therapy to maintain low level virus replication and slow or eliminate disease progression. A possible outcome of a functional cure is the eventual eradication of HIV to prevent all possibility of recurrence.

The primary obstacles to achieving a functional cure lie in the basic biology of HIV itself. Virus infection deletes CD4 T cells that are critical for nearly all immune functions. Most importantly, HIV infection and depletion of CD4 T cells requires activation of individual cells. Activation is a specific mechanism for individual CD4 T cell clones that recognize pathogens or other molecules, using a rearranged T cell receptor.

In the case of HIV, infection activates a population of HIV-specific T cells that become infected and are consequently depleted before other T cells that are less specific for the virus, which effectively cripples the immune system's defense against the virus. The capacity for HIV-specific T cell responses is rebuilt during prolonged HAART; however, when HAART is interrupted the rebounding virus infection repeats the process and again deletes the virus-specific cells, resetting the clock on disease progression.

Clearly, a functional cure is only possible if enough HIV-specific CD4 T cells are protected to allow for a host's native immunity to confront and control HIV once HAART is interrupted. In one embodiment, aspects of the disclosure provide methods and compositions for enhancing host immunity against HIV to provide a functional cure without the need for prior immunization.

Gene Therapy

Viral vectors are used to deliver genetic constructs to host cells for the purposes of disease therapy or prevention.

Genetic constructs can include, but are not limited to, functional genes or portions of genes to correct or complement existing defects, DNA sequences encoding regulatory proteins, DNA sequences encoding regulatory RNA molecules including antisense, short homology RNA, long noncoding RNA, small interfering RNA or others, and decoy sequences encoding either RNA or proteins designed to compete for critical cellular factors to alter a disease state. Gene therapy involves delivering these therapeutic genetic constructs to target cells to provide treatment or alleviation of a particular disease.

There are multiple ongoing efforts to utilize genetic therapy in the treatment of HIV disease, but thus far, the results have been poor. A small number of treatment successes were obtained in rare HIV patients carrying a spontaneous deletion of the CCR5 gene (an allele known as CCR5delta32).

Lentivirus-delivered nucleases or other mechanisms for gene deletion/modification may be used to lower the overall expression of CCR5 and/or help to lower HIV replication. At least one study has reported having success in treating the disease when lentivirus was administered in patients with a genetic background of CCR5delta32. However, this was only one example of success, and many other patients without the CCR5delta32 genotype have not been treated as successfully. Consequently, there is a substantial need to improve the performance of viral genetic therapy against HIV, both in terms of performance for the individual viral vector construct and for improved use of the vector through a strategy for achieving functional HIV cure.

For example, some existing therapies rely on zinc finger nucleases to delete a portion of CCR5 in an attempt to render cells resistant to HIV infection. However, even after optimal treatment, only 30% of T cells had been modified by the nuclease at all, and of those that were modified, only 10% of the total CD4 T cell population had been modified in a way that would prevent HIV infection. In contrast, the disclosed methods result in virtually every cell carrying a lentivirus transgene having a reduction in CCR5 expression below the level needed to allow HIV infection. This can result in successful treatment of HIV even without a prior immunization step to increase the number of the initial CD4+ T cell pool.

For the purposes of the disclosed methods, gene therapy can include, but is not limited to, affinity-enhanced T cell receptors, chimeric antigen receptors on CD4 T cells (or alternatively on CD8 T cells), modification of signal transduction pathways to avoid cell death cause by viral proteins, increased expression of HIV restriction elements including TREX, SAMHD1, MxA or MxB proteins, APOBEC complexes, TRIM5-alpha complexes, tetherin (BST2), and similar proteins identified as being capable of reducing HIV replication in mammalian cells.

Immunotherapy

Historically, vaccines have been a go-to weapon against deadly infectious diseases, including smallpox, polio, measles, and yellow fever. Unfortunately, there is no currently approved vaccine for HIV. The HIV virus has unique ways of evading the immune system, and the human body seems incapable of mounting an effective immune response against it. As a result, scientists do not have a clear picture of what is needed to provide protection against HIV.

However, immunotherapy may provide a solution that was previously unaddressed by conventional vaccine approaches. Immunotherapy, also called biologic therapy, is a type of treatment designed to boost the body's natural defenses to fight infections or cancer. It uses materials either made by the body or in a laboratory to improve, target, or restore immune system function.

In certain aspects of the present disclosure, immunotherapeutic approaches may be used to enrich a population of HIV-specific CD4 T cells for the purpose of increasing the host's anti-HIV immunity. In other aspects of the disclosed invention, integrating or non-integrating lentivirus vectors may be used to transduce a host's immune cells for the purposes of increasing the host's anti-HIV immunity. In other aspects of the disclosure, a vaccine comprising HIV proteins including but not limited to a killed particle, a virus-like particle, HIV peptides or peptide fragments, a recombinant viral vector, a recombinant bacterial vector, a purified subunit or plasmid DNA combined with a suitable vehicle and/or biological or chemical adjuvants to increase a host's immune responses may be used to enrich the population of virus-specific T cells or antibodies, and these methods may be further enhanced through the use of HIV-targeted genetic therapy using lentivirus or other viral vector.

Methods

In one aspect, the disclosure provides methods for using viral vectors to achieve a functional cure for HIV disease. The methods may include immunotherapy to enrich the proportion of HIV-specific CD4 T cells, followed by lentivirus transduction to deliver inhibitors of HIV and CCR5 and CXCR4 as required. Importantly, enrichment for HIV-specific CD4 T cells and lentiviral transduction can be effective even without a prior immunization step.

In embodiments, the methods include therapeutic immunization as a method for enriching the proportion of HIV-specific CD4 T cells, wherein the immunization occurs simultaneously with or after infusion of stimulated cells into a subject. Therapeutic immunization can include purified proteins, inactivated viruses, virally vectored proteins, bacterially vectored proteins, peptides or peptide fragments, virus-like particles (VLPs), biological or chemical adjuvants including cytokines and/or chemokines, vehicles, and methods for immunization.

Therapeutic vaccines can include one or more HIV protein with protein sequences representing the predominant viral types of the geographic region where treatment is occurring. Therapeutic vaccines will include purified proteins, inactivated viruses, virally vectored proteins, bacterially vectored proteins, peptides or peptide fragments, virus-like particles (VLPs), biological or chemical adjuvants including cytokines and/or chemokines, vehicles, and methods for immunization. Vaccinations may be administered according to standard methods known in the art and HIV patients may continue antiretroviral therapy during the interval of immunization and subsequent ex vivo lymphocyte culture including lentivirus transduction.

In certain embodiments, HIV+ patients can be immunized with an HIV vaccine, increasing the frequency of HIV-specific CD4 T cells by about 2, about 25, about 250, about 500, about 750, about 1000, about 1250, or about 1500-fold (or any amount in between these values). The vaccine may be any clinically utilized or experimental HIV vaccine, including the disclosed lentiviral, other viral vectors or other bacterial vectors used as vaccine delivery systems. In another embodiment, the vectors can encode virus-like particles (VLPs) to induce higher titers of neutralizing antibodies and stronger HIV-specific T cell responses. In another embodiment, the vectors can encode peptides or peptide fragments associated with HIV including but not limited to gag, pol, and env, tat, rev, nef, vif, vpr, vpu, and tev, as well as LTR, TAR, RRE, PE, SLIP, CRS, and INS. Alternatively, the HIV vaccine used in the disclosed methods may comprise purified proteins, inactivated viruses, virally vectored proteins, bacterially vectored proteins, peptides or peptide fragments, virus-like particles (VLPs), or biological or chemical adjuvants including cytokines and/or chemokines.

For example, peripheral blood mononuclear cells (PBMCs) can be obtained by leukapheresis and treated ex vivo to obtain about $1\times10^{10}$ CD4 T cells of which about 0.1%, about 1%, about 5% or about 10% or about 30% are both HIV-specific in terms of antigen responses, and HIV-resistant by virtue of carrying the therapeutic transgene delivered by the disclosed lentivirus vector. Alternatively, about $1\times10^{7}$, about $1\times10^{8}$, about $1\times10^{9}$, about $1\times10^{10}$, about $1\times10^{11}$, or about $1\times10^{12}$ CD4 T cells may be isolated for re-stimulation. Importantly, any suitable amount of CD4 T cells can be isolated for ex vivo re-stimulation.

The isolated CD4 T cells can be cultured in appropriate medium throughout re-stimulation with HIV vaccine antigens, which may or may not include antigens present in the prior therapeutic vaccination. Antiretroviral therapeutic drugs including inhibitors of reverse transcriptase, protease or integrase may be added to prevent virus re-emergence during prolonged ex vivo culture. CD4 T cell re-stimulation can be used to enrich the proportion of HIV-specific CD4 T cells in culture. The same procedure may also be used for analytical objectives wherein smaller blood volumes with peripheral blood mononuclear cells obtained by purification, are used to identify HIV-specific T cells and measure the frequency of this sub-population.

The PBMC fraction may be enriched for HIV-specific CD4 T cells by contacting the cells with HIV proteins matching or complementary to the components of the vaccine previously used for in vivo immunization. Ex vivo re-stimulation can increase the relative frequency of HIV-specific CD4 T cells by about 5, about 10, about 25, about 50, about 75, about 100, about 125, about 150, about 175, or about 200-fold. Er vivo re-stimulation can increase the relative frequency of HIV-specific CD4 T cells regardless of whether there has been a pre-immunization step.

The methods detailed herein can include ex vivo re-stimulation of CD4 T cells with ex vivo lentiviral transduction and culturing. The methods detailed herein can also include ex vivo re-stimulation of CD4 T cells with ex vivo lentiviral transduction and culturing without a pre-immunization step.

Thus, in one embodiment, the re-stimulated PBMC fraction that has been enriched for HIV-specific CD4 T cells can be transduced with therapeutic anti-HIV lentivirus or other vectors and maintained in culture about 1 to about 21 days or up to about 35 days. Alternatively, the cells may be cultured for about 1-about 18 days, about 1-about 15 days, about 1-about 12 days, about 1-about 9 days, or about 3-about 7 days. Thus, the transduced cells may be cultured for about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, or about 35 days.

Once the transduced cells have been sufficiently cultured, transduced CD4 T cells are infused back into the original patient. Infusion can be performed using various machines and methods known in the art. In some embodiments, infusion may be accompanied by pre-treatment with cyclophosphamide or similar compounds to increase the efficiency of re-engraftment.

In some embodiments, a CCR5-targeted therapy may be added to a subject's antiretroviral therapy regimen, which was continued throughout the treatment process. Examples of CCR5-targeted therapies include but are not limited to Maraviroc (a CCR5 antagonist) or Rapamycin (immunosuppressive agent that lowers CCR5). In some embodiments, the antiretroviral therapy may be ceased and the subject can be tested for virus rebound. If no rebound occurs, adjuvant therapy can also be removed and the subject can be tested again for virus rebound.

Continued virus suppression with reduced or no antiretroviral therapy including cART or HAART, and reduced or no adjuvant therapy for about 26 weeks can be considered a functional cure for HIV. Other definitions of a functional cure are described herein.

The lentiviral and other vectors used in the disclosed methods may encode at least one, at least two, at least three, at least four, or at least five genes, or at least six genes, or at least seven genes, or at least eight genes, or at least nine genes, or at least ten genes, or at least eleven genes, or at least twelve genes of interest. Given the versatility and therapeutic potential of HIV-targeted gene therapy, a viral vector of the invention may encode genes or nucleic acid sequences that include but are not limited to (i) an antibody directed to an antigen associated with an infectious disease or a toxin produced by the infectious pathogen, (ii) cytokines including interleukins that are required for immune cell growth or function and may be therapeutic for immune dysregulation encountered in HIV and other chronic or acute human viral or bacterial pathogens, (iii) factors that suppress the growth of HIV in vivo including CD8 suppressor factors, (iv) mutations or deletions of chemokine receptor CCR5, mutations or deletions of chemokine receptor CXCR4, or mutations or deletions of chemokine receptor CXCR5, (v) antisense DNA or RNA against specific receptors or peptides associated with HIV or host protein associated with HIV, (vi) small interfering RNA against specific receptors or peptides associated with HIV or host protein associated with HIV, or (vii) a variety of other therapeutically useful sequences that may be used to treat HIV or AIDS.

Additional examples of HIV-targeted gene therapy that can be used in the disclosed methods include, but are not limited to, affinity-enhanced T cell receptors, chimeric antigen receptors on CD4 T cells (or alternatively on CD8 T cells), modification of signal transduction pathways to avoid cell death cause by viral proteins, increased expression of HIV restriction elements including TREX, SAMHD1, MxA or MxB proteins, APOBEC complexes, TRIM5-alpha complexes, tetherin (BST2), and similar proteins identified as being capable of reducing HIV replication in mammalian cells.

In some embodiments, a patient may be undergoing cART or HAART concurrently while being treated according to the methods of the invention. In other embodiments, a patient may undergo cART or HAART before or after being treated according to the methods of the invention. In some embodiments, cART or HAART is maintained throughout treatment according to the methods of the invention and the patient may be monitored for HIV viral burden in blood and frequency of lentivirus-transduced CD4 T cells in blood.

Preferably, a patient receiving cART or HAART prior to being treated according to the methods of the invention is able to discontinue or reduce cART or HAART following treatment according to the methods of the invention.

For the purpose of assessing efficacy, the frequency of transduced, HIV-specific CD4 T cells, which is a novel surrogate marker for gene therapy effects, may be determined, as discussed in more detail herein.

Compositions

In one aspect, the disclosed invention provides lentiviral vectors capable of delivering genetic constructs to inhibit HIV penetration of susceptible cells. For instance, one mechanism of action is to reduce mRNA levels for CCR5 and/or CXCR4 chemokine receptors and thus reduce the rates for viral entry into susceptible cells.

Alternatively, the disclosed lentiviral vectors may be capable of inhibiting the formation of HIV-infected cells by reducing the stability of incoming HIV genomic RNA. And in yet another embodiment, the disclosed lentivirus vectors are capable of preventing HIV production from a latently infected cell, wherein the mechanism of action is to cause instability of viral RNA sequences through the action of inhibitory RNA including short-homology, small-interfering or other regulatory RNA species.

The therapeutic lentiviruses disclosed in this application generally comprise at least one of two types of genetic cargo. First, the lentiviruses may encode genetic elements that direct expression of small RNA capable of inhibiting the production of chemokine receptors CCR5 and/or CXCR4 that are important for HIV penetration of susceptible cells. The second type of genetic cargo includes constructs capable of expressing small RNA molecules targeting HIV RNA sequences for the purpose of preventing reverse transcription, RNA splicing, RNA translation to produce proteins, or packaging of viral genomic RNA for particle production and spreading infection. An exemplary structure is diagrammed in FIG. 3.

Figure 3:
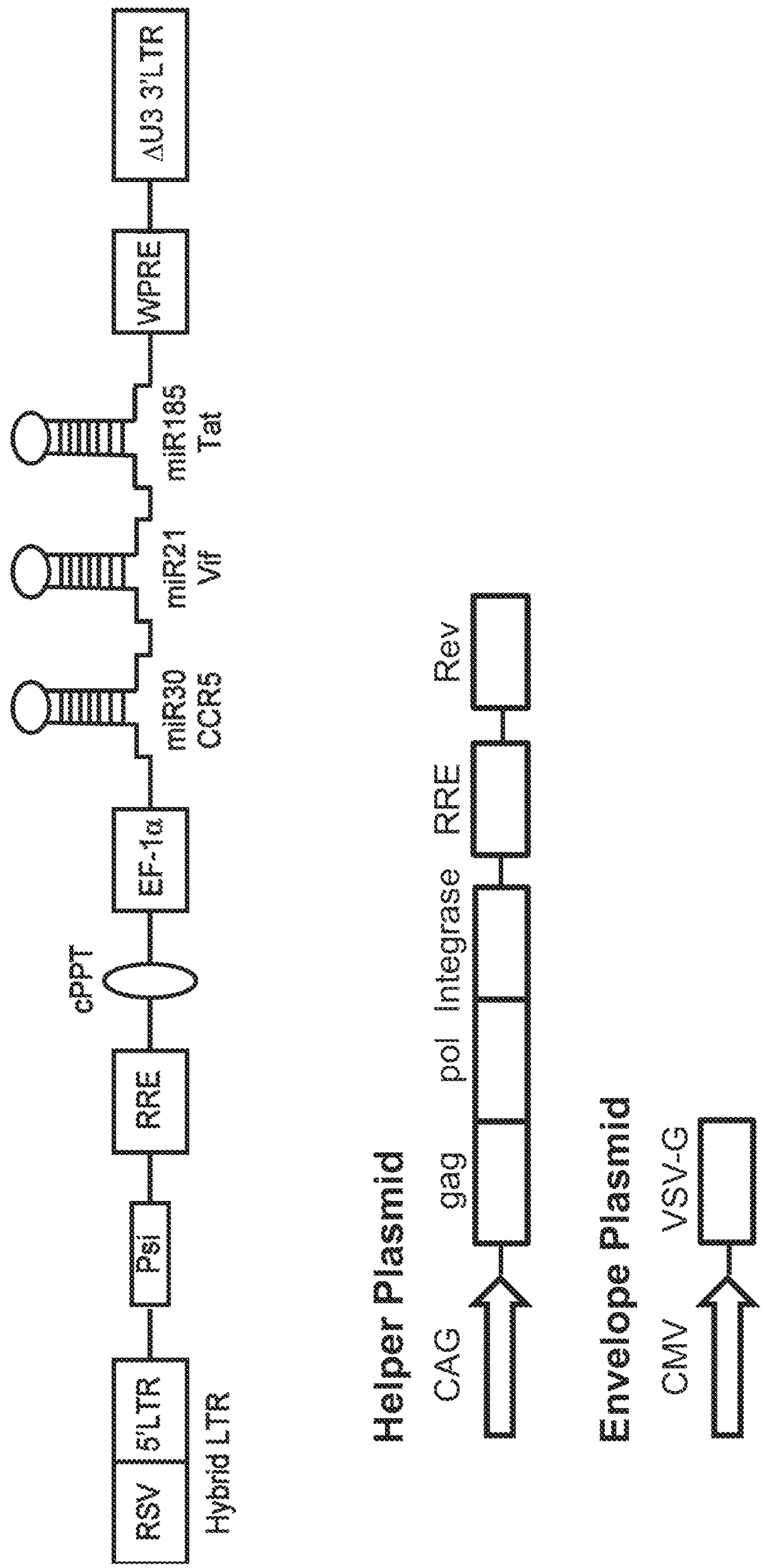
FIG. 3 depicts an exemplary lentiviral vector system comprised of a therapeutic vector, a helper plasmid, and an envelope plasmid. The therapeutic vector shown here is a preferred therapeutic vector, which is also referred to herein as AGT103, and contains miR30CCR5-miR21Vif-miR185-Tat.

As shown in FIG. 3 (top panel), an exemplary construct may comprise numerous sections or components. For example, in one embodiment, an exemplary LV construct may comprise the following sections or components:

- RSV—a Rous Sarcoma virus long terminal repeat;
- 5'LTR—a portion of an HIV long terminal repeat that can be truncated to prevent replication of the vector after chromosomal integration;
- Psi—a packaging signal that allows for incorporation of the vector RNA genome into viral particles during packaging;
- RRE—a Rev Responsive element can be added to improve expression from the transgene by mobilizing RNA out of the nucleus and into the cytoplasm of cells;
- c PPT—a Poly purine tract that facilitates second strand DNA synthesis prior to integration of the transgene into the host cell chromosome;
- Promoter—a promoter initiates RNA transcription from the integrated transgene to express micro-RNA clusters (or other genetic elements of the construct), and in some embodiments, the vectors may use an EF-1 promoter;
- Anti-CCR5—a micro RNA targeting messenger RNA for the host cell factor CCR5 to reduce its expression on the cell surface;
- Anti-Rev/Tat—a micro RNA targeting HIV genomic or messenger RNA at the junction between HIV Rev and Tat coding regions, which is sometimes designated miRNA Tat or given a similar description in this application;
- Anti-Vif—a micro RNA targeting HIV genomic or messenger RNA within the Vif coding region;
- WPRE—a woodchuck hepatitis virus post-transcriptional regulatory element is an additional vector component that can be used to facilitate RNA transport of the nucleus; and
- deltaU3 3'LTR—a modified version of a HIV 3' long terminal repeat where a portion of the U3 region has been deleted to improve safety of the vector.

One of skill in the art will recognize that the above components are merely examples, and that such components may be reorganized, substituted with other elements, or otherwise changed, including but not limited to making nucleotide substitutions, deletions, additions, or mutations, so long as the construct is able to prevent expression of HIV genes and decrease the spread of infection.

Vectors of the invention may include either or both of the types of genetic cargo discussed above (i.e., genetic elements that direct expression of a gene or small RNAs, such as siRNA, shRNA, or miRNA that can prevent translation or transcription), and the vectors of the invention may also encode additionally useful products for the purpose of treatment or diagnosis of HIV. For instance, in some embodiments, these vectors may also encode green fluorescent protein (GFP) for the purpose of tracking the vectors or antibiotic resistance genes for the purposes of selectively maintaining genetically-modified cells in vivo.

The combination of genetic elements incorporated into the disclosed vectors is not particularly limited. For example, a vector may encode a single small RNA, two small RNAs, three small RNA, four small RNAs, five small RNAs, six small RNAs, seven small RNAs, eight small RNAs, nine small RNAs, or ten small RNAs, or eleven small RNAs, or twelve small RNAs. Such vectors may additionally encode other genetic elements to function in concert with the small RNAs to prevent expression and infection of HIV.

Those of skill in the art will understand that the therapeutic lentivirus may substitute alternate sequences for the promoter region, targeting of regulatory RNA, and types of regulatory RNA. Further, the therapeutic lentivirus of the disclosure may comprise changes in the plasmids used for packaging the lentivirus particles; these changes are required to increase levels of production in vitro.

Lentiviral Vector System

A lentiviral virion (particle) is expressed by a vector system encoding the necessary viral proteins to produce a virion (viral particle). There is at least one vector containing a nucleic acid sequence encoding the lentiviral pol proteins necessary for reverse transcription and integration, operably linked to a promoter. In another embodiment, the pol proteins are expressed by multiple vectors. There is also a vector containing a nucleic acid sequence encoding the lentiviral gag proteins necessary for forming a viral capsid operably linked to a promoter. In an embodiment, this gag nucleic acid sequence is on a separate vector than at least some of the pol nucleic acid sequence. In another embodiment, the gag nucleic acid is on a separate vector from all the pol nucleic acid sequences that encode pol proteins.

Numerous modifications can be made to the vectors, which are used to create the particles to further minimize the chance of obtaining wild type revertants. These include, but are not limited to deletions of the U3 region of the LTR, tat deletions and matrix (MA) deletions.

The gag, pol and env vector(s) do not contain nucleotides from the lentiviral genome that package lentiviral RNA, referred to as the lentiviral packaging sequence.

The vector(s) forming the particle preferably do not contain a nucleic acid sequence from the lentiviral genome that expresses an envelope protein. Preferably, a separate vector that contains a nucleic acid sequence encoding an envelope protein operably linked to a promoter is used. This env vector also does not contain a lentiviral packaging sequence. In one embodiment the env nucleic acid sequence encodes a lentiviral envelope protein.

In another embodiment the envelope protein is not from the lentivirus, but from a different virus. The resultant particle is referred to as a pseudotyped particle. By appropriate selection of envelopes one can "infect" virtually any cell. For example, one can use an env gene that encodes an envelope protein that targets an endocytic compartment such as that of the influenza virus, VSV-G, alpha viruses (Semliki forest virus, Sindbis virus), arenaviruses (lymphocytic choriomeningitis virus), flaviviruses (tick-borne encephalitis virus, Dengue virus, hepatitis C virus, GB virus), rhabdoviruses (vesicular stomatitis virus, rabies virus), paramyxoviruses (mumps or measles) and orthomyxoviruses (influenza virus). Other envelopes that can preferably be used include those from Moloney Leukemia Virus such as MLV-E, MLV-A and GALV. These latter envelopes are particularly preferred where the host cell is a primary cell. Other envelope proteins can be selected depending upon the desired host cell. For example, targeting specific receptors such as a dopamine receptor can be used for brain delivery. Another target can be vascular endothelium. These cells can be targeted using a filovirus envelope. For example, the GP of Ebola, which by post-transcriptional modification become the GP, and $GP_2$ glycoproteins. In another embodiment, one can use different lentiviral capsids with a pseudotyped envelope. For example, FIV or SHIV [U.S. Pat. No. 5,654, 195]. A SHIV pseudotyped vector can readily be used in animal models such as monkeys.

As detailed herein, a lentiviral vector system typically includes at least one helper plasmid comprising at least one of a gag, pol, or rev gene. Each of the gag, pol and rev genes may be provided on individual plasmids, or one or more genes may be provided together on the same plasmid. In one embodiment, the gag, pol, and rev genes are provided on the same plasmid (e.g., FIG. 4). In another embodiment, the gag and pol genes are provided on a first plasmid and the rev gene is provided on a second plasmid (e.g., FIG. 5). Accordingly, both 3-vector and 4-vector systems can be used to produce a lentivirus as described in the Examples section and elsewhere herein. The therapeutic vector, the envelope plasmid and at least one helper plasmid are transfected into a packaging cell line. A non-limiting example of a packaging cell line is the 293T/17 HEK cell line. When the therapeutic vector, the envelope plasmid, and at least one helper plasmid are transfected into the packaging cell line, a lentiviral particle is ultimately produced.

In another aspect, a lentiviral vector system for expressing a lentiviral particle is disclosed. The system includes a lentiviral vector as described herein; an envelope plasmid for expressing an envelope protein optimized for infecting a cell; and at least one helper plasmid for expressing gag, pol, and rev genes, wherein when the lentiviral vector, the envelope plasmid, and the at least one helper plasmid are transfected into a packaging cell line, a lentiviral particle is produced by the packaging cell line, wherein the lentiviral particle is capable of inhibiting production of chemokine receptor CCR5 or targeting an HIV RNA sequence.

In another aspect, and as detailed herein, the lentiviral vector, which is also referred to herein as a therapeutic vector, can include the following elements: hybrid 5' long terminal repeat (RSV/5' LTR) (SEQ ID NOS: 34-35), Psi sequence (RNA packaging site) (SEQ ID NO: 36), RRE (Rev-response element) (SEQ ID NO: 37), cPPT (polypurine tract) (SEQ ID NO: 38), EF-Ia promoter (SEQ ID NO: 4), miR30CCR5 (SEQ ID NO: 1), miR21Vif (SEQ ID NO: 2), miR185Tat (SEQ ID NO: 3), Woodchuck Post-Transcriptional Regulatory Element (WPRE) (SEQ ID NOS: 32 or 80), and ΔU3 3' LTR (SEQ ID NO: 39). In another aspect, sequence variation, by way of substitution, deletion, or addition can be used to modify the above-referenced sequences.

In another aspect, and as detailed herein, a helper plasmid has been designed to include the following elements: CAG promoter (SEQ ID NO: 41); HIV component gag (SEQ ID NO: 43); HIV component pol (SEQ ID NO: 44); HIV Int (SEQ ID NO: 45); HIV RRE (SEQ ID NO: 46); and HIV Rev (SEQ ID NO: 47). In another aspect, the helper plasmid may be modified to include a first helper plasmid for expressing the gag and pol genes, and a second and separate plasmid for expressing the rev gene. In another aspect, sequence variation, by way of substitution, deletion, or addition can be used to modify the above-referenced sequences.

In another aspect, and as detailed herein, an envelope plasmid has been designed to include the following elements being from left to right: RNA polymerase II promoter (CMV) (SEQ ID NO: 60) and vesicular stomatitis virus G glycoprotein (VSV-G) (SEQ ID NO: 62). In another aspect, sequence variation, by way of substitution, deletion, or addition can be used to modify the above-referenced sequences.

In another aspect, the plasmids used for lentiviral packaging can be modified with similar elements and the intron sequences could potentially be removed without loss of vector function. For example, the following elements can replace similar elements in the plasmids that comprise the packaging system: Elongation Factor-1 (EF-1), phosphoglycerate kinase (PGK), and ubiquitin C (UbC) promoters can replace the CMV or CAG promoter. SV40 poly A and bGH poly A can replace the rabbit beta globin poly A. The HIV sequences in the helper plasmid can be constructed from different HIV strains or clades. The VSV-G glycoprotein can be substituted with membrane glycoproteins from feline endogenous virus (RD114), gibbon ape leukemia virus (GALV), Rabies (FUG), lymphocytic choriomeningitis virus (LCMV), influenza A fowl plague virus (FPV), Ross River alphavirus (RRV), murine leukemia virus 10A1 (MLV), or Ebola virus (EboV).

Of note, lentiviral packaging systems can be acquired commercially (e.g., Lenti-vpak packaging kit from OriGene Technologies, Inc., Rockville, MD), and can also be designed as described herein. Moreover, it is within the skill of a person skilled in the art to substitute or modify aspects of a lentiviral packaging system to improve any number of relevant factors, including the production efficiency of a lentiviral particle.

Bioassays

In one aspect, the present invention includes bioassays for determining the success of HIV treatment for achieving a functional cure. These assays will provide a method for measuring the efficacy of the disclosed methods by measuring the frequency of transduced, HIV specific CD4 T cells in a patient. HIV-specific CD4 T cells are recognizable because they proliferate, change the composition of cell surface markers, induce signaling pathways including phosphorylation, or express specific marker proteins that may be cytokines, chemokines, caspases, phosphorylated signaling molecules or other cytoplasmic and/or nuclear components. Specific responding CD4 T cells are recognized for example, using labeled monoclonal antibodies or specific in situ amplification of mRNA sequences, that allow sorting of HIV-specific cells using flow cytometry sorting, magnetic bead separation or other recognized methods for antigen-specific CD4 T cell isolation. The isolated CD4 T cells are tested to determine the frequency of cells carrying integrated therapeutic lentivirus. Single cell testing methods may also be used including microfluidic separation of individual cells that are coupled with mass spectrometry, PCR, ELISA or antibody staining to confirm responsiveness to HIV and presence of integrated therapeutic lentivirus.

Thus, in certain embodiments, following application of a treatment according to the invention (e.g., (a) no immunization, (b) ex vivo lymphocyte culture; (c) re-stimulation with purified proteins, inactivated viruses, virally vectored proteins, bacterially vectored proteins, biological or chemical adjuvants including cytokines and/or chemokines, vehicles; and (d) infusion of the enriched, transduced T cells), a patient may be subsequently assayed to determine the efficacy of the treatment. A threshold value of target T cells in the cell product for infusion may be established to measure a functional cure at, for instance, about $1\times10^8$ HIV-specific CD4 T cells bearing genetic modification from therapeutic lentivirus. Alternatively, the threshold value may be about $1\times10^5$, about $1\times10^6$, about $1\times10^7$, about $1\times10^8$, about $1\times10^9$, or about $1\times10^{10}$ CD4 T cells in the body of the patient.

HIV-specific CD4 T cells bearing genetic modification from therapeutic lentivirus can be determined using any suitable method, such as but not limited to flow cytometry, cell sorting, FACS analysis, DNA cloning, PCR, RT-PCR or Q-PCR, ELISA, FISH, western blotting, southern blotting, high throughput sequencing, RNA sequencing, oligonucleotide primer extension, or other methods known in the art.

Methods for defining antigen specific T cells with genetic modifications are known in the art. However, utilizing such methods to combine identifying HIV-specific T cells with integrated or non-integrated gene therapy constructs as a standard measure for efficacy is a new concept in the field of HIV treatment.

Doses and Dosage Forms

The disclosed methods and compositions can be used for treating HIV+ patients during various stages of their disease. Accordingly, dosing regimens may vary based upon the condition of the patient and the method of administration.

In one aspect, HIV-specific vaccines may be administered simultaneously with infusion or after infusion of stimulated cells into a subject. In one embodiment, HIV-specific vaccines may be administered to a subject in need in varying doses. In general, vaccines delivered by intramuscular injection include about 10 μg to about 300 μg, about 25 μg to about 275 μg, about 50 μg to about 250 μg, about 75 μg to about 225, or about 100 μg to about 200 μg of HIV protein, either total virus protein prepared from inactivated virus particles, virus-like particles or purified virus protein from recombinant systems or purified from virus preparations. Recombinant viral or bacterial vectors may be administered by any and all of the routes described. Intramuscular vaccines will include about 1 μg to about 100 μg, about 10 μg to about 90 μg, about 20 μg to about 80 μg, about 30 μg to about 70 μg, about 40 μg to about 60 μg, or about 50 μg of suitable adjuvant molecules and be suspended in oil, saline, buffer or water in volumes of 0.1 to 5 ml per injection dose, and may be soluble or emulsion preparations. Vaccines delivered orally, rectally, buccally, at genital mucosal or intranasally, including some virally-vectored or bacterially-vectored vaccines, fusion proteins, liposome formulations or similar preparations, may contain higher amounts of virus protein and adjuvant. Dermal, sub-dermal or subcutaneous vaccines utilize protein and adjuvant amounts more similar to oral, rectal or intranasal-delivered vaccines. Depending on responses to the initial immunization, vaccination may be repeated 1-5 times using the same or alternate routes for delivery. Intervals may be of 2-24 weeks between immunizations. Immune responses to vaccination are measured by testing HIV-specific antibodies in serum, plasma, vaginal secretions, rectal secretions, saliva or bronchoalveolar lavage fluids, using ELISA or similar methodology. Cellular immune responses are tested by in vitro stimulation with vaccine antigens followed by staining for intracellular cytokine accumulation followed by flow cytometry or similar methods including lymphoproliferation, expression of phosphorylated signaling proteins or changes in cell surface activation markers. Upper limits of dosing may be determined based on the individual patient and will depend on toxicity/safety profiles for each individual product or product lot.

Immunization may occur once, twice, three times, or repeatedly. For instance, an agent for HIV immunization may be administered to a subject in need once a week, once every other week, once every three weeks, once a month, every other month, every three months, every six months, every nine months, once a year, every eighteen months, every two years, every 36 months, or every three years.

After ex vivo expansion and enrichment of CD4 T cells, immunization may occur once, twice, three times, or more after ex vivo lymphocyte culture/re-stimulation and infusion.

In one embodiment, HIV-vaccines for immunization are administered as a pharmaceutical composition. In one embodiment, the pharmaceutical composition comprising an HIV vaccine can be formulated in a wide variety of nasal, pulmonary, oral, topical, or parenteral dosage forms for clinical application. Each of the dosage forms can comprise various disintegrating agents, surfactants, fillers, thickeners, binders, diluents such as wetting agents or other pharmaceutically acceptable excipients. The pharmaceutical composition comprising an HIV vaccine can also be formulated for injection.

HIV vaccine compositions for the purpose of immunization can be administered using any pharmaceutically acceptable method, such as intranasal, buccal, sublingual, oral, rectal, ocular, parenteral (intravenously, intradermally, intramuscularly, subcutaneously, intracistemally, intraperitoneally), pulmonary, intravaginal, locally administered, topically administered, topically administered after scarification, mucosally administered, via an aerosol, or via a buccal or nasal spray formulation.

Further, the HIV vaccine compositions can be formulated into any pharmaceutically acceptable dosage form, such as a solid dosage form, tablet, pill, lozenge, capsule, liquid dispersion, gel, aerosol, pulmonary aerosol, nasal aerosol, ointment, cream, semi-solid dosage form, and a suspension. Further, the composition may be a controlled release formulation, sustained release formulation, immediate release formulation, or any combination thereof. Further, the composition may be a transdermal delivery system.

In another embodiment, the pharmaceutical composition comprising an HIV vaccine can be formulated in a solid dosage form for oral administration, and the solid dosage form can be powders, granules, capsules, tablets or pills. In yet another embodiment, the solid dosage form can include one or more excipients such as calcium carbonate, starch, sucrose, lactose, microcrystalline cellulose or gelatin. In addition, the solid dosage form can include, in addition to the excipients, a lubricant such as talc or magnesium stearate. In some embodiments, the oral dosage form can be immediate release or a modified release form. Modified release dosage forms include controlled or extended release, enteric release, and the like. The excipients used in the modified release dosage forms are commonly known to a person of ordinary skill in the art.

In a further embodiment, the pharmaceutical composition comprising a HIV vaccine can be formulated as a sublingual or buccal dosage form. Such dosage forms comprise sublingual tablets or solution compositions that are administered under the tongue and buccal tablets that are placed between the cheek and gum.

In yet a further embodiment, the pharmaceutical composition comprising an HIV vaccine can be formulated as a nasal dosage form. Such dosage forms of the present invention comprise solution, suspension, and gel compositions for nasal delivery.

In one embodiment, the pharmaceutical composition can be formulated in a liquid dosage form for oral administration, such as suspensions, emulsions or syrups. In other embodiments, the liquid dosage form can include, in addition to commonly used simple diluents such as water and liquid paraffin, various excipients such as humectants, sweeteners, aromatics or preservatives. In particular embodiments, the composition comprising HIV vaccine or a pharmaceutically acceptable salt thereof can be formulated to be suitable for administration to a pediatric patient.

In one embodiment, the pharmaceutical composition can be formulated in a dosage form for parenteral administration, such as sterile aqueous solutions, suspensions, emulsions, non-aqueous solutions or suppositories. In other embodiments, the non-aqueous solutions or suspensions can include propyleneglycol, polyethyleneglycol, vegetable oils such as olive oil or injectable esters such as ethyl oleate. As a base for suppositories, witepsol, macrogol, tween 61, cacao oil, laurin oil or glycerinated gelatin can be used.

The dosage of the pharmaceutical composition can vary depending on the patient's weight, age, gender, administration time and mode, excretion rate, and the severity of disease.

For the purposes of re-stimulation, lymphocytes, PBMC, and/or CD4 T cells are removed from a patient and isolated for stimulation and culturing. The isolated cells may be contacted with the same HIV vaccine or activating agent used for immunization or a different HIV vaccine or activating agent. In one embodiment, the isolated cells are contacted with about 10 ng to 5 μg of an HIV vaccine or activating agent per about 106 cells in culture (or any other suitable amount). More specifically, the isolated cells may be contacted with about 50 ng, about 100 ng, about 200 ng, about 300 ng, about 400 ng, about 500 ng, about 600 ng, about 700 ng, about 800 ng, about 900 ng, about 1 μg, about 1.5 μg, about 2 μg, about 2.5 μg, about 3 μg, about 3.5 μg, about 4 μg, about 4.5 μg, or about 5 μg of an HIV vaccine or activating agent per about 106 cells in culture.

Activating agents or vaccines are generally used once for each in vitro cell culture but may be repeated after intervals of about 15 to about 35 days. For example, a repeat dosing could occur at about 15, about 16, about 17, about 18, about 19, about 20, about 21, about 22, about 23, about 24, about 25, about 26, about 27, about 28, about 29, about 30, about 31, about 32, about 33, about 34, or about 35 days.

For transduction of the enriched, re-stimulated cells, the cells may be transduced with lentiviral vectors or with other known vector systems as disclosed herein. The cells being transduced may be contacted with about 1-1,000 viral genomes (measured by RT-PCR assay of culture fluids containing lentivirus vector) per target cell in culture (or any other suitable amount). Lentivirus transduction may be repeated 1-5 times using the same range of 1-1,000 viral genomes per target cell in culture.

Cellular Enrichment

In one approach, cells such as T cells may be obtained from an HIV infected patient and cultured in multi-well plates in a culture medium comprising conditioned media ("CM"). The levels of supernatant $p24^{gag}$ ("p24") and viral RNA levels may be assessed by standard means. Those patients whose CM-cultured cells have peak p24 supernatant levels of less than 1 ng/ml may be suitable patients for large-scale T-cell expansion in CM with or without the use of additional anti-viral agents. Additionally, different drugs or drug combinations of interest may be added to different wells and the impact on virus levels in the sample may be assessed by standard means. Those drug combinations providing adequate viral suppression are therapeutically useful combinations. It is within the capacity of a competent technician to determine what constitutes adequate viral suppression in relation to a particular subject. In order to test the effectiveness of drugs of interest in limiting viral expansion, additional factors such as anti-CD3 antibodies may be added to the culture to stimulate viral production. Unlike culture methods for HIV infected cell samples known in the art, CM allows the culture of T cells for periods of over two months, thereby providing an effective system in which to assay long term drug effectiveness.

This approach allows the inhibition of gene expression driven by the HIV LTR promoter region in a cell population by the culture of cells in a medium comprising the CM. Culture in CM4 likely inhibits HIV LTR driven gene expression by altering one or more interactions between transcription mediating proteins and HIV gene expression regulatory elements. Transcription-mediating proteins of interest include host cell encoded proteins such as AP-1, NFkappaB, NF-AT, IRF, LEF-1 and Sp1, and the HIV encoded protein Tat. HIV gene expression regulatory elements of interest include binding sites for AP-1, NFkappaB, NF-AT, IRF, LEF-1 and Sp1, as well as the transacting responsive element ("TAR") which interacts with Tat.

In a preferred embodiment, the HIV infected cells are obtained from a subject with susceptible transcription mediating protein sequences and susceptible HIV regulatory element sequences. In a more preferred embodiment, the HIV infected cells are obtained from a subject having wild-type transcription-mediating protein sequences and wild-type HIV regulatory sequences.

Another method of enriching T cells utilizes immunoaffinity-based selection. This approach may involve the simultaneous enrichment or selection of a first and second population of cells, such as a CD4+ and CD8+ cell population. Cells containing primary human T cells are contacted with a first immunoaffinity reagent that specifically binds to CD4 and a second immunoaffinity reagent that specifically binds to CD8 in an incubation composition, under conditions whereby the immunoaffinity reagents specifically bind to CD4 and CD8 molecules, respectively, on the surface of cells in the sample. Cells bound to the first and/or the second immunoaffinity reagent are recovered, thereby generating an enriched composition comprising CD4+ cells and CD8+ cells. This approach may include incubation of the composition with a concentration of the first and/or second immunoaffinity reagent that is at a sub-optimal yield concentration. Notably, in some embodiments, transduced cells are a mixed T cell population, and in other embodiments transduced cells are not a mixed T cell population.

In some embodiments, immunoaffinity-based selection is used where the solid support is a sphere, such as a bead, such as a microbead or nanobead. In other embodiments, the bead can be a magnetic bead. In another embodiment, the antibody contains one or more binding partners capable of forming a reversible bond with a binding reagent immobilized on the solid surface, such as a sphere or chromatography matrix, wherein the antibody is reversibly mobilized to the solid surface. In some embodiments, cells expressing a cell surface marker bound by the antibody on said solid surface are capable of being recovered from the matrix by disruption of the reversible binding between the binding reagent and binding partner. In some embodiments, the binding reagent is streptavidin or is a streptavidin analog or mutant.

Stable transduction of primary cells of the hematopoietic system and/or hematopoietic stem cells may be obtained by contacting, in vitro or ex vivo, the surface of the cells with both a lentiviral vector and at least one molecule which binds the cell surface. The cells may be cultured in a ventilated vessel comprising two or more layers under conditions conducive to growth and/or proliferation. In some embodiments, this approach may be used in conjunction with non-CD4+ T cell depletion and/or broad polyclonal expansion.

In another approach to T cell enrichment, PBMC are stimulated with a peptide and enriched for cells secreting a cytokine, such as interferon-gamma. This approach generally involves stimulating a mixture of cells containing T cells with antigen, and effecting a separation of antigen-stimulated cells according to the degree to which they are labeled with the product. Antigen stimulation is achieved by exposing the cells to at least one antigen under conditions effective to elicit antigen-specific stimulation of at least one T cell. Labeling with the product is achieved by modifying the surface of the cells to contain at least one capture moiety, culturing the cells under conditions in which the product is secreted, released and specifically bound ("captured" or "entrapped") to said capture moiety; and labeling the captured product with a label moiety, where the labeled cells are not lysed as part of the labeling procedure or as part of the separation procedure. The capture moiety may incorporate detection of cell surface glycoproteins CD3 or CD4 to refine the enrichment step and increase the proportion of antigen-specific T cells in general, of CD4+ T cells in specific.

The following examples are given to illustrate aspects of the present invention. It should be understood, however, that the invention is not to be limited to the specific conditions or details described in these examples. All printed publications referenced herein are specifically incorporated by reference.

EXAMPLES

Example 1: Development of a Lentiviral Vector System

Figure 4A:
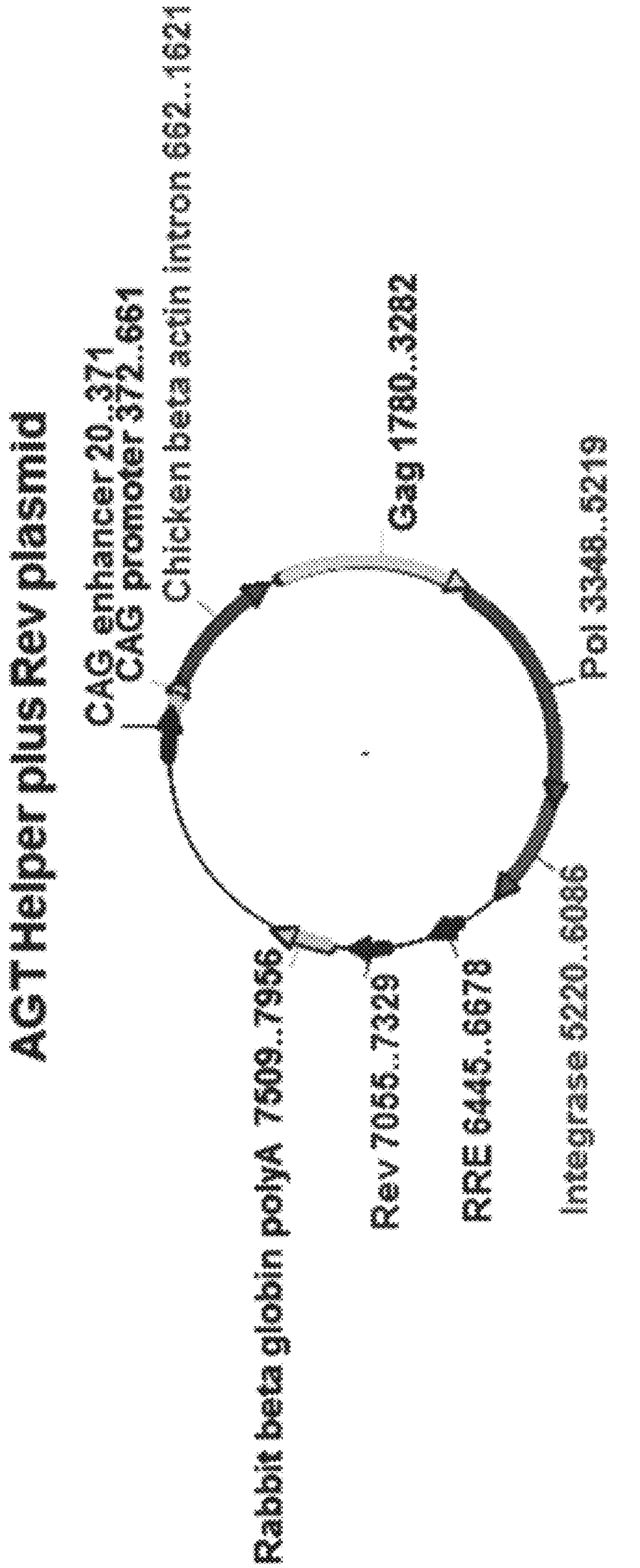
FIG. 4 depicts an exemplary 3-vector lentiviral vector system in a circularized form.
Figure 4B:
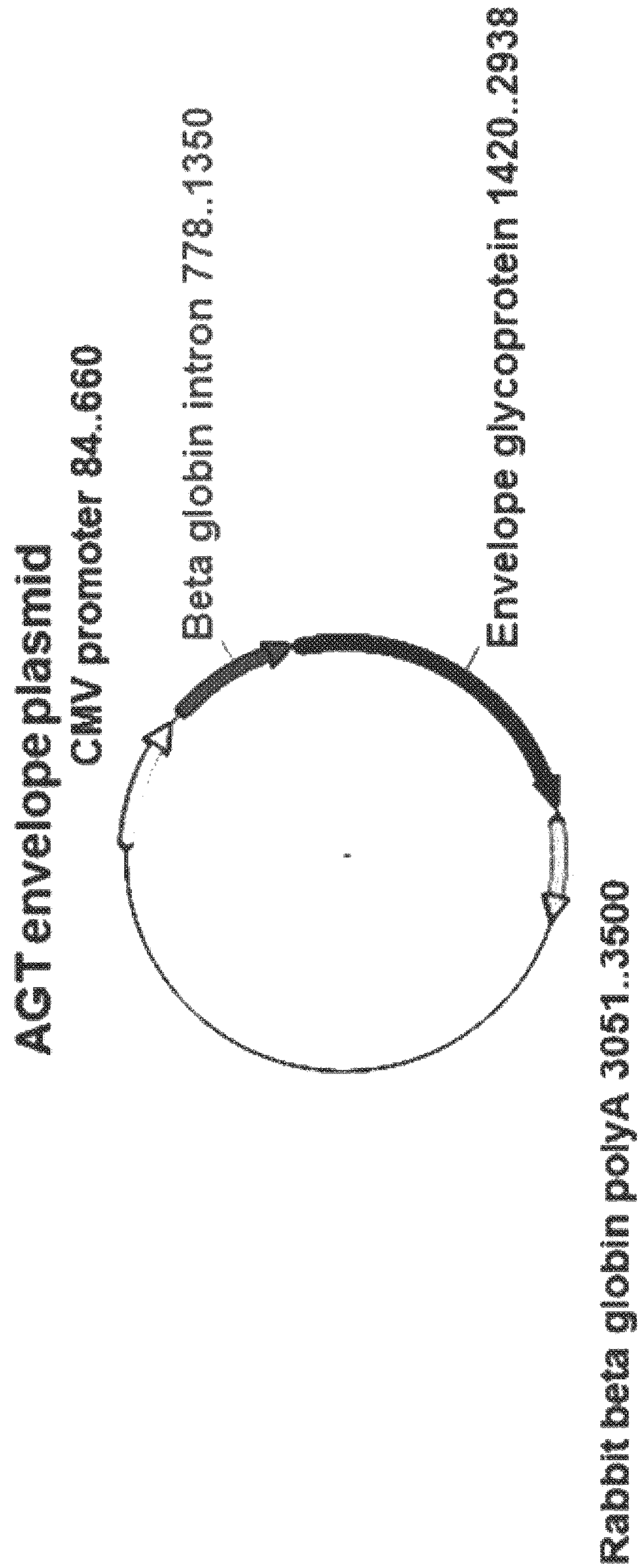
Figure 4C:
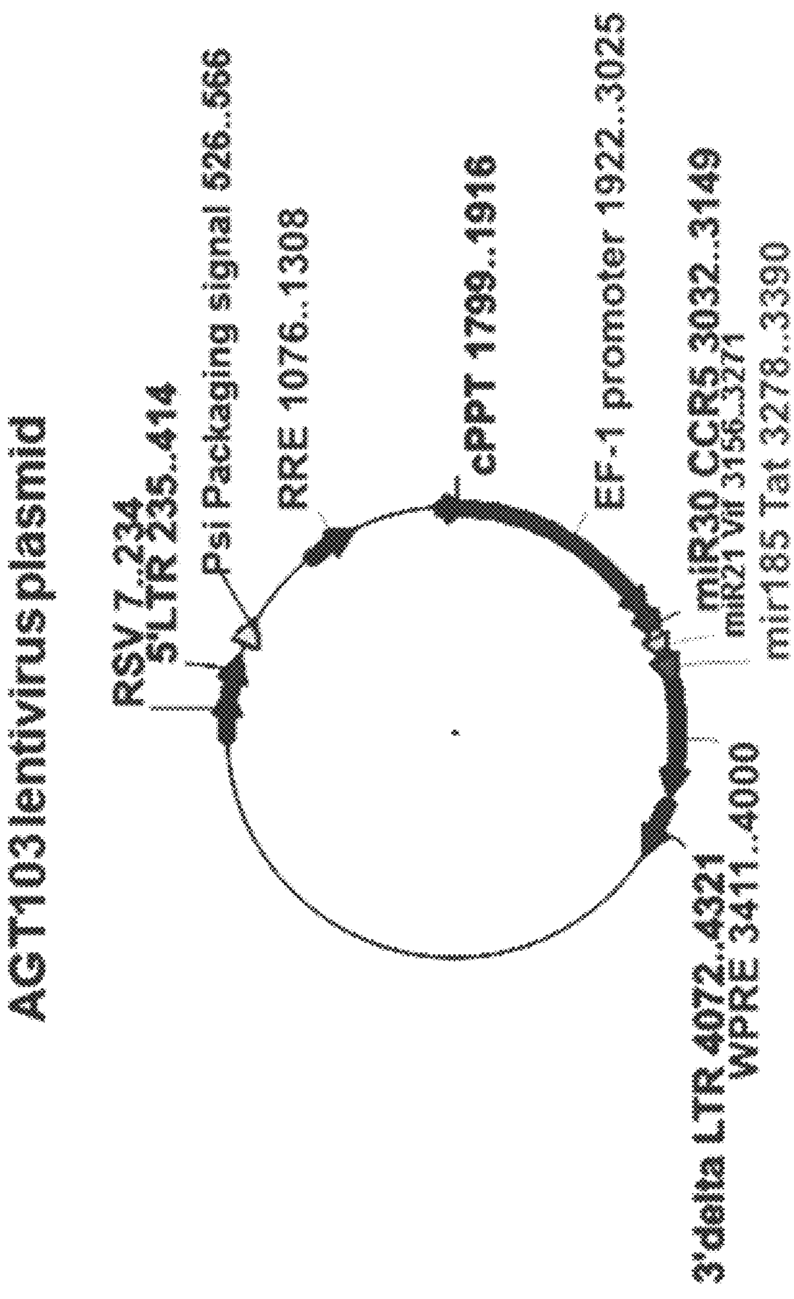
Figure 5A:
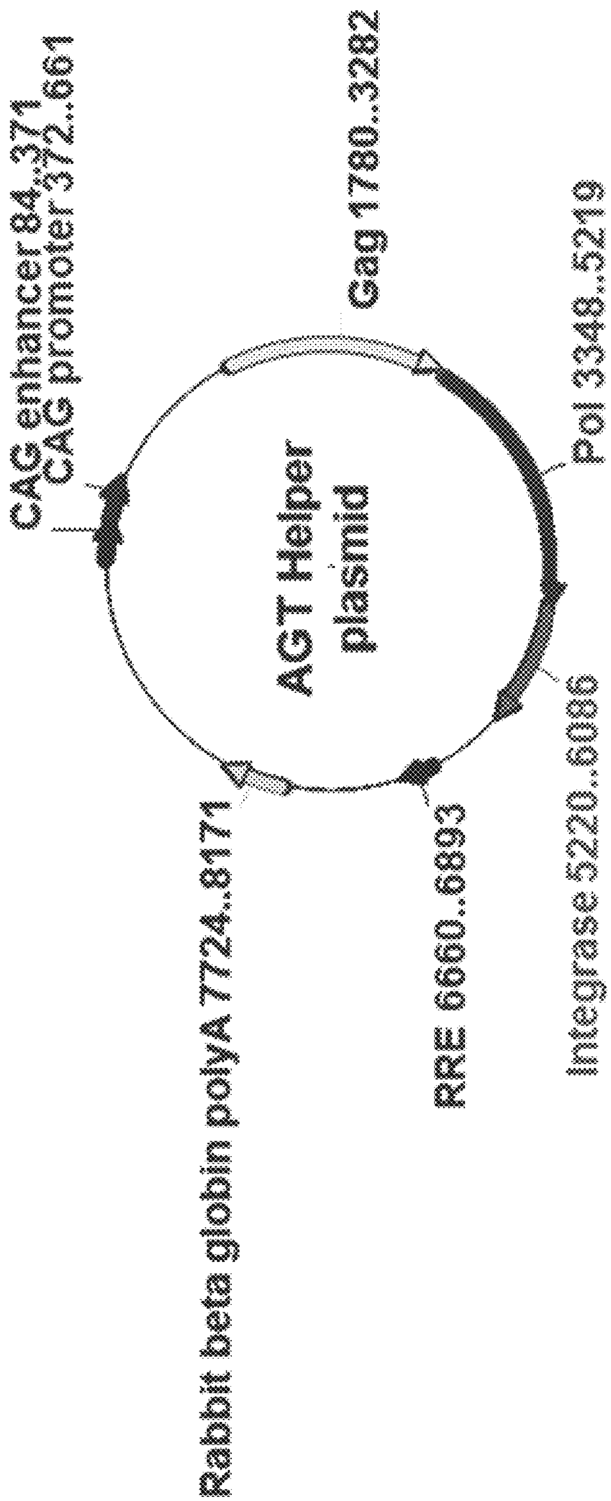
FIG. 5 depicts an exemplary 4-vector lentiviral vector system in a circularized form.
Figure 5B:
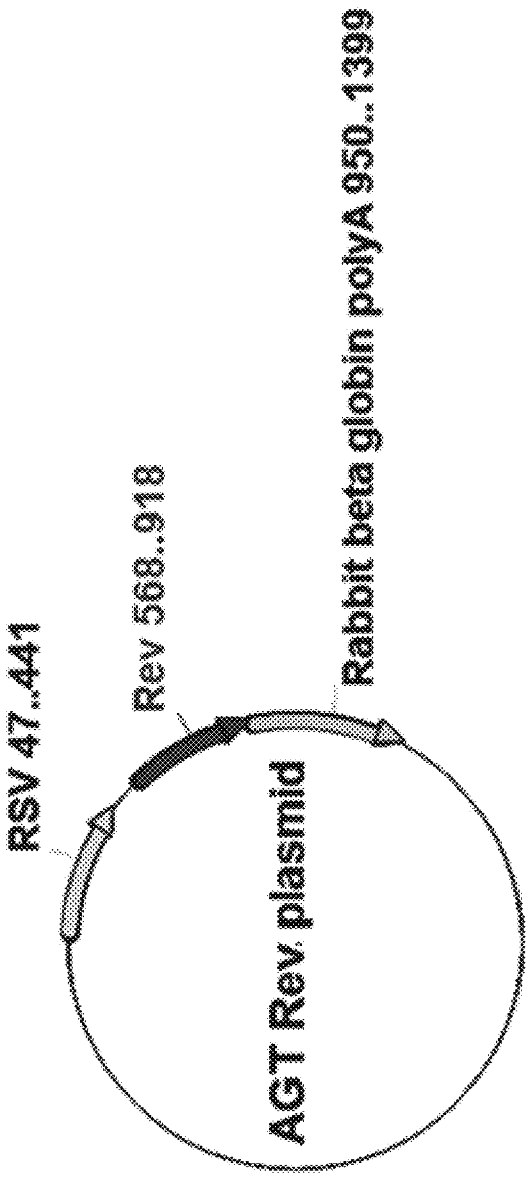
Figure 5C:
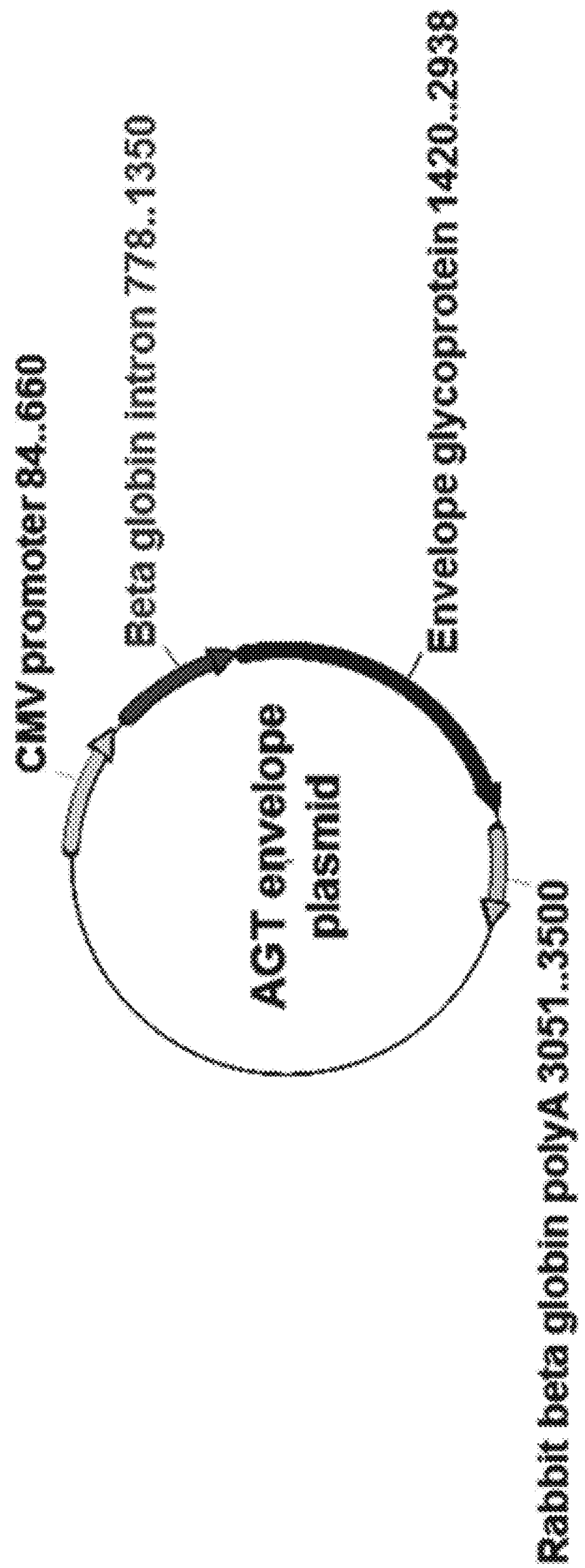
Figure 5D:
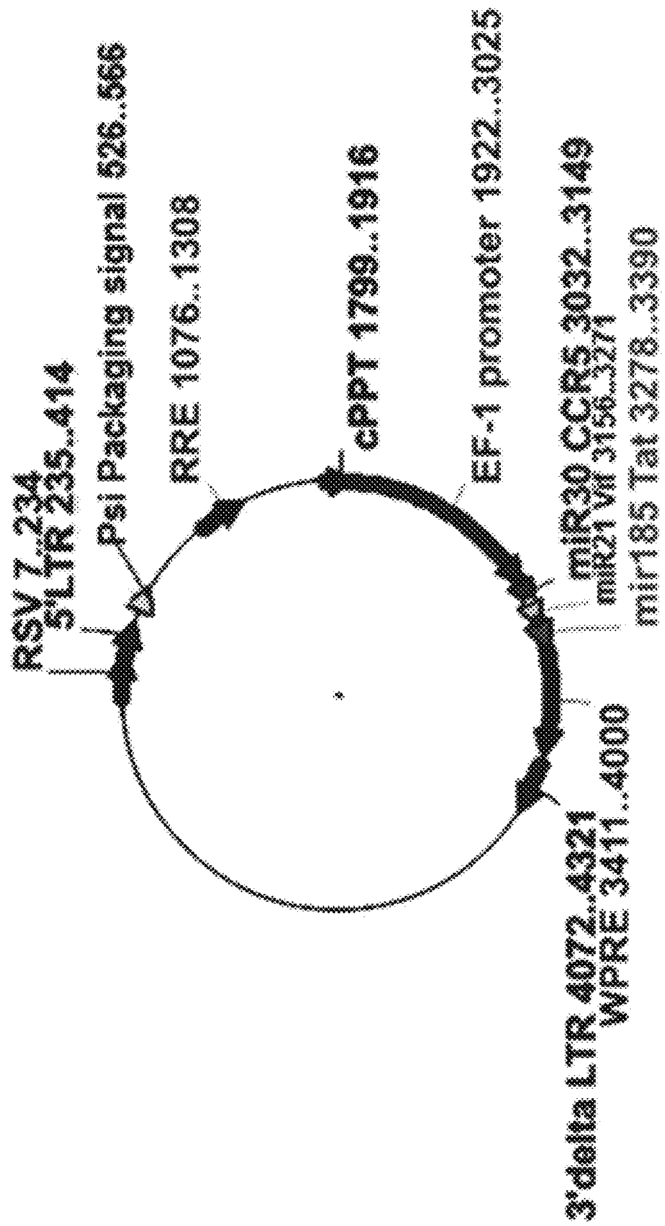

A lentiviral vector system was developed as summarized in FIG. 3 (linear form) and FIG. 4 (circularized form). Referring first to the top portion of FIG. 3, a representative therapeutic vector has been designed and produced with the following elements being from left to right: hybrid 5' long terminal repeat (RSV/5' LTR) (SEQ ID NOS: 34-35), Psi sequence (RNA packaging site) (SEQ ID NO: 36), RRE (Rev-response element) (SEQ ID NO: 37), cPPT (polypurine tract) (SEQ ID NO: 38), EF-la promoter (SEQ ID NO: 4), miR30CCR5 (SEQ ID NO: 1), miR21Vif (SEQ ID NO: 2), miR185Tat (SEQ ID NO: 3), Woodchuck Post-Transcriptional Regulatory Element (WPRE) (SEQ ID NOS: 32 or 80), and ΔU3 3' LTR (SEQ ID NO: 39). The therapeutic vector detailed in FIG. 3 is also referred to herein as AGT103.

Referring next to the middle portion of FIG. 3, a helper plasmid has been designed and produced with the following elements being from left to right: CAG promoter (SEQ ID NO: 41); HIV component gag (SEQ ID NO: 43); HIV component pol (SEQ ID NO: 44); HIV Int (SEQ ID NO: 45); HIV RRE (SEQ ID NO: 46); and HIV Rev (SEQ ID NO: 47).

Referring next to the lower portion of FIG. 3, an envelope plasmid has been designed and produced with the following elements being from left to right: RNA polymerase II promoter (CMV) (SEQ ID NO: 60) and vesicular stomatitis virus G glycoprotein (VSV-G) (SEQ ID NO: 62).

Lentiviral particles were produced in 293T/17 HEK cells (purchased from American Type Culture Collection, Manassas, VA) following transfection with the therapeutic vector, the envelope plasmid, and the helper plasmid (as shown in FIG. 3). The transfection of 293T/17 HEK cells, which produced functional viral particles, employed the reagent Poly (ethylenimine) (PEI) to increase the efficiency of plasmid DNA uptake. The plasmids and DNA were initially added separately in culture medium without serum in a ratio of 3:1 (mass ratio of PEI to DNA). After 2-3 days, cell medium was collected and lentiviral particles were purified by high-speed centrifugation and/or filtration followed by anion-exchange chromatography. The concentration of lentiviral particles can be expressed in terms of transducing units/ml (TU/ml). The determination of TU was accomplished by measuring HIV p24 levels in culture fluids (p24 protein is incorporated into lentiviral particles), measuring the number of viral DNA copies per cell by quantitative PCR, or by infecting cells and using light (if the vectors encode luciferase or fluorescent protein markers).

As mentioned above, a 3-vector system (i.e., a 2-vector lentiviral packaging system) was designed for the production of lentiviral particles. A schematic of the 3-vector system is shown in FIG. 4. The schematic of FIG. 4 is a circularized version of the linear system previously described in FIG. 3. Briefly, and with reference to FIG. 4, the top-most vector is a helper plasmid, which, in this case, includes Rev. The vector appearing in the middle of FIG. 4 is the envelope plasmid. The bottom-most vector is the previously described therapeutic vector.

Referring more specifically to FIG. 4, the Helper plus Rev plasmid includes a CAG enhancer (SEQ ID NO: 40); a CAG promoter (SEQ ID NO: 41); a chicken beta actin intron (SEQ ID NO: 42); a HIV gag (SEQ ID NO: 43); a HIV Pol (SEQ ID NO: 44); a HIV Int (SEQ ID NO: 45); a HIV RRE (SEQ ID NO: 46); a HIV Rev (SEQ ID NO: 47); and a rabbit beta globin poly A (SEQ ID NO: 48).

The Envelope plasmid includes a CMV promoter (SEQ ID NO: 60); a beta globin intron (SEQ ID NO: 61); a VSV-G (SEQ ID NO: 62); and a rabbit beta globin poly A (SEQ ID NO: 63).

Synthesis of a 2-Vector Lentiviral Packaging System Including Helper (Plus Rev) and Envelope Plasmids.

Materials and Methods:

Construction of the helper plasmid: The helper plasmid was constructed by initial PCR amplification of a DNA fragment from the pNL4-3 HIV plasmid (NIH Aids Reagent Program) containing Gag, Pol, and Integrase genes. Primers were designed to amplify the fragment with EcoRI and NotI restriction sites which could be used to insert at the same sites in the pCDNA3 plasmid (Invitrogen). The forward primer was (5'-TAAGCAGAATTC ATGAATTTGCCAG-GAAGAT-3') (SEQ ID NO: 81) and reverse primer was (5'-CCATACAAT-GAATGGACACTAGGCGGCCGCACGAAT-3') (SEQ ID NO: 82). The sequence for the Gag, Pol, Integrase fragment was as follows:

(SEQ ID NO: 83)
GAATTCATGAATTTGCCAGGAAGATGGAAACCAAAAATGATAGGGGGAAT
TGGAGGTTTTATCAAAGTAAGACAGTATGATCAGATACTCATAGAAATCT
GCGGACATAAAGCTATAGGTACAGTATTAGTAGGACCTACACCTGTCAAC
ATAATTGGAAGAAATCTGTTGACTCAGATTGGCTGCACTTTAAATTTTCC
CATTAGTCCTATTGAGACTGTACCAGTAAAATTAAAGCCAGGAATGGATG
GCCCAAAAGTTAAACAATGGCCATTGACAGAAGAAAAAATAAAAGCATTA
GTAGAAATTTGTACAGAAATGGAAAAGGAAGGAAAAATTTCAAAAATTGG
GCCTGAAAATCCATACAATACTCCAGTATTTGCCATAAAGAAAAAAGACA
GTACTAAATGGAGAAAATTAGTAGATTTCAGAGAACTTAATAAGAGAACT
CAAGATTTCTGGGAAGTTCAATTAGGAATACCACATCCTGCAGGGTTAAA
ACAGAAAAAATCAGTAACAGTACTGGATGTGGGCGATGCATATTTTTCAG
TTCCCTTAGATAAAGACTTCAGGAAGTATACTGCATTTACCATACCTAGT
ATAAACAATGAGACACCAGGGATTAGATATCAGTACAATGTGCTTCCACA
GGGATGGAAAGGATCACCAGCAATATTCCAGTGTAGCATGACAAAAATCT
TAGAGCCTTTTAGAAAACAAAATCCAGACATAGTCATCTATCAATACATG
GATGATTTGTATGTAGGATCTGACTTAGAAATAGGGCAGCATAGAACAAA
AATAGAGGAACTGAGACAACATCTGTTGAGGTGGGGATTTACCACACCAG
ACAAAAAACATCAGAAAGAACCTCCATTCCTTTGGATGGGTTATGAACTC
CATCCTGATAAATGGACAGTACAGCCTATAGTGCTGCCAGAAAAGGACAG
CTGGACTGTCAATGACATACAGAAATTAGTGGGAAAATTGAATTGGGCAA
GTCAGATTTATGCAGGGATTAAAGTAAGGCAATTATGTAAACTTCTTAGG
GGAACCAAAGCACTAACAGAAGTAGTACCACTAACAGAAGAAGCAGAGCT
AGAACTGGCAGAAAACAGGGAGATTCTAAAAGAACCGGTACATGGAGTGT
ATTATGACCCATCAAAAGACTTAATAGCAGAAATACAGAAGCAGGGGCAA
GGCCAATGGACATATCAAATTTATCAAGAGCCATTTAAAAATCTGAAAAC
AGGAAAGTATGCAAGAATGAAGGGTGCCCACACTAATGATGTGAAACAAT
TAACAGAGGCAGTACAAAAAATAGCCACAGAAAGCATAGTAATATGGGGA
AAGACTCCTAAATTTAAATTACCCATACAAAAGGAAACATGGGAAGCATG
GTGGACAGAGTATTGGCAAGCCACCTGGATTCCTGAGTGGGAGTTTGTCA
ATACCCCTCCCTTAGTGAAGTTATGGTACCAGTTAGAGAAAGAACCCATA
ATAGGAGCAGAAACTTTCTATGTAGATGGGGCAGCCAATAGGGAAACTAA

-continued

ATTAGGAAAAGCAGGATATGTAACTGACAGAGGAAGACAAAAAGTTGTCC
CCCTAACGGACACAACAAATCAGAAGACTGAGTTACAAGCAATTCATCTA
GCTTTGCAGGATTCGGGATTAGAAGTAAACATAGTGACAGACTCACAATA
TGCATTGGGAATCATTCAAGCACAACCAGATAAGAGTGAATCAGAGTTAG
TCAGTCAAATAATAGAGCAGTTAATAAAAAAGGAAAAAGTCTACCTGGCA
TGGGTACCAGCACACAAAGGAATTGGAGGAAATGAACAAGTAGATAAATT
GGTCAGTGCTGGAATCAGGAAAGTACTATTTTTAGATGGAATAGATAAGG
CCCAAGAAGAACATGAGAAATATCACAGTAATTGGAGAGCAATGGCTAGT
GATTTTAACCTACCACCTGTAGTAGCAAAAGAAATAGTAGCCAGCTGTGA
TAAATGTCAGCTAAAAGGGGAAGCCATGCATGGACAAGTAGACTGTAGCC
CAGGAATATGGCAGCTAGATTGTACACATTTAGAAGGAAAAGTTATCTTG
GTAGCAGTTCATGTAGCCAGTGGATATATAGAAGCAGAAGTAATTCCAGC
AGAGACAGGGCAAGAAACAGCATACTTCCTCTTAAAATTAGCAGGAAGAT
GGCCAGTAAAAACAGTACATACAGACAATGGCAGCAATTTCACCAGTACT
ACAGTTAAGGCCGCCTGTTGGTGGGCGGGGATCAAGCAGGAATTTGGCAT
TCCCTACAATCCCCAAAGTCAAGGAGTAATAGAATCTATGAATAAAGAAT
TAAAGAAAATTATAGGACAGGTAAGAGATCAGGCTGAACATCTTAAGACA
GCAGTACAAATGGCAGTATTCATCCACAATTTTAAAAGAAAAGGGGGGAT
TGGGGGGTACAGTGCAGGGGAAAGAATAGTAGACATAATAGCAACAGACA
TACAAACTAAAGAATTACAAAAACAAATTACAAAAATTCAAAATTTTCGG
GTTTATTACAGGGACAGCAGAGATCCAGTTTGGAAAGGACCAGCAAAGCT
CCTCTGGAAAGGTGAAGGGGCAGTAGTAATACAAGATAATAGTGACATAA
AAGTAGTGCCAAGAAGAAAAGCAAAGATCATCAGGGATTATGGAAAACAG
ATGGCAGGTGATGATTGTGTGGCAAGTAGACAGGATGAGGATTAA.

Next, a DNA fragment containing the Rev, RRE, and rabbit beta globin poly A sequence with XbaI and XmaI flanking restriction sites was synthesized by MWG Operon. The DNA fragment was then inserted into the plasmid at the XbaI and XmaI restriction sites The DNA sequence was as follows:

(SEQ ID NO: 84)
TCTAGAATGGCAGGAAGAAGCGGAGACAGCGACGAAGAGCTCATCAGAAC
AGTCAGACTCATCAAGCTTCTCTATCAAAGCAACCCACCTCCCAATCCCG
AGGGGACCCGACAGGCCCGAAGGAATAGAAGAAGAAGGTGGAGAGAGAGA
CAGAGACAGATCCATTCGATTAGTGAACGGATCCTTGGCACTTATCTGGG
ACGATCTGCGGAGCCTGTGCCTCTTCAGCTACCACCGCTTGAGAGACTTA
CTCTTGATTGTAACGAGGATTGTGGAACTTCTGGGACGCAGGGGGTGGGA
AGCCCTCAAATATTGGTGGAATCTCCTACAATATTGGAGTCAGGAGCTAA
AGAATAGAGGAGCTTTGTTCCTTGGGTTCTTGGGAGCAGCAGGAAGCACT
ATGGGCGCAGCGTCAATGACGCTGACGGTACAGGCCAGACAATTATTGTC
TGGTATAGTGCAGCAGCAGAACAATTTGCTGAGGGCTATTGAGGCGCAAC
AGCATCTGTTGCAACTCACAGTCTGGGGCATCAAGCAGCTCCAGGCAAGA

-continued

ATCCTGGCTGTGGAAAGATACCTAAAGGATCAACAGCTCCTAGATCTTTT
TCCCTCTGCCAAAAATTATGGGGACATCATGAAGCCCCTTGAGCATCTGA
CTTCTGGCTAATAAAGGAAATTTATTTTCATTGCAATAGTGTGTTGGAAT
TTTTTGTGTCTCTCACTCGGAAGGACATATGGGAGGGCAAATCATTTAAA
ACATCAGAATGAGTATTTGGTTTAGAGTTTGGCAACATATGCCATATGCT
GGCTGCCATGAACAAAGGTGGCTATAAAGAGGTCATCAGTATATGAAACA
GCCCCCTGCTGTCCATTCCTTATTCCATAGAAAAGCCTTGACTTGAGGTT
AGATTTTTTTTATATTTTGTTTTGTGTTATTTTTTTCTTTAACATCCCTA
AAATTTTCCTTACATGTTTTACTAGCCAGATTTTTCCTCCTCTCCTGACT
ACTCCCAGTCATAGCTGTCCCTCTTCTCTTATGAAGATCCCTCGACCTGC
AGCCCAAGCTTGGCGTAATCATGGTCATAGCTGTTTCCTGTGTGAAATTG
TTATCCGCTCACAATTCCACACAACATACGAGCCGGAAGCATAAAGTGTA
AAGCCTGGGGTGCCTAATGAGTGAGCTAACTCACATTAATTGCGTTGCGC
TCACTGCCCGCTTTCCAGTCGGGAAACCTGTCGTGCCAGCGGATCCGCAT
CTCAATTAGTCAGCAACCATAGTCCCGCCCCTAACTCCGCCCATCCCGCC
CCTAACTCCGCCCAGTTCCGCCCATTCTCCGCCCCATGGCTGACTAATTT
TTTTTATTTATGCAGAGGCCGAGGCCGCCTCGGCCTCTGAGCTATTCCAG
AAGTAGTGAGGAGGCTTTTTTGGAGGCCTAGGCTTTTGCAAAAAGCTAAC
TTGTTTATTGCAGCTTATAATGGTTACAAATAAAGCAATAGCATCACAAA
TTTCACAAATAAAGCATTTTTTTCACTGCATTCTAGTTGTGGTTTGTCCA
AACTCATCAATGTATCTTATCAGCGGCCGCCCCGGG

Finally, the CMV promoter of pCDNA3.1 was replaced with the CAG enhancer/promoter plus a chicken beta actin intron sequence. A DNA fragment containing the CAG enhancer/promoter/intron sequence with MluI and EcoRI flanking restriction sites was synthesized by MWG Operon. The DNA fragment was then inserted into the plasmid at the MluI and EcoRI restriction sites. The DNA sequence was as follows:

(SEQ ID NO: 85)
ACGCGTTAGTTATTAATAGTAATCAATTACGGGGTCATTAGTTCATAGCC
CATATATGGAGTTCCGCGTTACATAACTTACGGTAAATGGCCCGCCTGGC
TGACCGCCCAACGACCCCCGCCCATTGACGTCAATAATGACGTATGTTCC
CATAGTAACGCCAATAGGGACTTTCCATTGACGTCAATGGGTGGACTATT
TACGGTAAACTGCCCACTTGGCAGTACATCAAGTGTATCATATGCCAAGT
ACGCCCCCTATTGACGTCAATGACGGTAAATGGCCCGCCTGGCATTATGC
CCAGTACATGACCTTATGGGACTTTCCTACTTGGCAGTACATCTACGTAT
TAGTCATCGCTATTACCATGGGTCGAGGTGAGCCCCACGTTCTGCTTCAC
TCTCCCCATCTCCCCCCCCTCCCCACCCCCAATTTTGTATTTATTTATTT
TTTAATTATTTTGTGCAGCGATGGGGGCGGGGGGGGGGGGGGCGCGCGCC
AGGCGGGGCGGGGCGGGGCGAGGGGCGGGGCGGGGCGAGGCGGAGAGGTG
CGGCGGCAGCCAATCAGAGCGGCGCGCTCCGAAAGTTTCCTTTTATGGCG
AGGCGGCGGCGGCGGCGGCCCTATAAAAAGCGAAGCGCGCGGCGGGCGGG

-continued

AGTCGCTGCGTTGCCTTCGCCCCGTGCCCCGCTCCGCGCCGCCTCGCGCC
GCCCGCCCCGGCTCTGACTGACCGCGTTACTCCCACAGGTGAGCGGGCGG
GACGGCCCTTCTCCTCCGGGCTGTAATTAGCGCTTGGTTTAATGACGGCT
CGTTTCTTTTCTGTGGCTGCGTGAAAGCCTTAAAGGGCTCCGGGAGGGCC
CTTTGTGCGGGGGGGAGCGGCTCGGGGGGTGCGTGCGTGTGTGTGTGCGT
GGGGAGCGCCGCGTGCGGCCCGCGCTGCCCGGCGGCTGTGAGCGCTGCGG
GCGCGGCGCGGGGCTTTGTGCGCTCCGCGTGTGCGCGAGGGGAGCGCGGC
CGGGGGCGGTGCCCCGCGGTGCGGGGGGGCTGCGAGGGGAACAAAGGCTG
CGTGCGGGGTGTGTGCGTGGGGGGGTGAGCAGGGGGTGTGGGCGCGGCGG
TCGGGCTGTAACCCCCCCCTGCACCCCCCTCCCCGAGTTGCTGAGCACGG
CCCGGCTTCGGGTGCGGGGCTCCGTGCGGGGCGTGGCGCGGGGCTCGCCG
TGCCGGGCGGGGGGTGGCGGCAGGTGGGGGTGCCGGGCGGGGCGGGGCCG
CCTCGGGCCGGGGAGGGCTCGGGGGAGGGGCGCGGCGGCCCCGGAGCGCC
GGCGGCTGTCGAGGCGCGGCGAGCCGCAGCCATTGCCTTTTATGGTAATC
GTGCGAGAGGGCGCAGGGACTTCCTTTGTCCCAAATCTGGCGGAGCCGAA
ATCTGGGAGGCGCCGCCGCACCCCCTCTAGCGGGCGCGGGCGAAGCGGTG
CGGCGCCGGCAGGAAGGAAATGGGCGGGGAGGGCCTTCGTGCGTCGCCGC
GCCGCCGTCCCCTTCTCCATCTCCAGCCTCGGGGCTGCCGCAGGGGGACG
GCTGCCTTCGGGGGGGACGGGGCAGGGCGGGGTTCGGCTTCTGGCGTGTG
ACCGGCGGGAATTC

Construction of the VSV-G Envelop Plasmid:

The vesicular stomatitis Indiana virus glycoprotein (VSV-G) sequence was synthesized by MWG Operon with flanking EcoRI restriction sites. The DNA fragment was then inserted into the pCDNA3.1 plasmid (Invitrogen) at the EcoRI restriction site and the correct orientation was determined by sequencing using a CMV specific primer. The DNA sequence was as follows:

(SEQ ID NO: 86)
GAATTCATGAAGTGCCTTTTGTACTTAGCCTTTTTATTCATTGGGGTGAA
TTGCAAGTTCACCATAGTTTTTCCACACAACCAAAAAGGAAACTGGAAAA
ATGTTCCTTCTAATTACCATTATTGCCCGTCAAGCTCAGATTTAAATTGG
CATAATGACTTAATAGGCACAGCCTTACAAGTCAAAATGCCCAAGAGTCA
CAAGGCTATTCAAGCAGACGGTTGGATGTGTCATGCTTCCAAATGGGTCA
CTACTTGTGATTTCCGCTGGTATGGACCGAAGTATATAACACATTCCATC
CGATCCTTCACTCCATCTGTAGAACAATGCAAGGAAAGCATTGAACAAAC
GAAACAAGGAACTTGGCTGAATCCAGGCTTCCCTCCTCAAAGTTGTGGAT
ATGCAACTGTGACGGATGCCGAAGCAGTGATTGTCCAGGTGACTCCTCAC
CATGTGCTGGTTGATGAATACACAGGAGAATGGGTTGATTCACAGTTCAT
CAACGGAAAATGCAGCAATTACATATGCCCCACTGTCCATAACTCTACAA
CCTGGCATTCTGACTATAAGGTCAAAGGGCTATGTGATTCTAACCTCATT
TCCATGGACATCACCTTCTTCTCAGAGGACGGAGAGCTATCATCCCTGGG
AAAGGAGGGCACAGGGTTCAGAAGTAACTACTTTGCTTATGAAACTGGAG

-continued

```
GCAAGGCCTGCAAAATGCAATACTGCAAGCATTGGGGAGTCAGACTCCCA
TCAGGTGTCTGGTTCGAGATGGCTGATAAGGATCTCTTTGCTGCAGCCAG
ATTCCCTGAATGCCCAGAAGGGTCAAGTATCTCTGCTCCATCTCAGACCT
CAGTGGATGTAAGTCTAATTCAGGACGTTGAGAGGATCTTGGATTATTCC
CTCTGCCAAGAAACCTGGAGCAAAATCAGAGCGGGTCTTCCAATCTCTCC
AGTGGATCTCAGCTATCTTGCTCCTAAAAACCCAGGAACCGGTCCTGCTT
TCACCATAATCAATGGTACCCTAAAATACTTTGAGACCAGATACATCAGA
GTCGATATTGCTGCTCCAATCCTCTCAAGAATGGTCGGAATGATCAGTGG
AACTACCACAGAAAGGGAACTGTGGGATGACTGGGCACCATATGAAGACG
TGGAAATTGGACCCAATGGAGTTCTGAGGACCAGTTCAGGATATAAGTTT
CCTTTATACATGATTGGACATGGTATGTTGGACTCCGATCTTCATCTTAG
CTCAAAGGCTCAGGTGTTCGAACATCCTCACATTCAAGACGCTGCTTCGC
AACTTCCTGATGATGAGAGTTTATTTTTGGTGATACTGGGCTATCCAAA
AATCCAATCGAGCTTGTAGAAGGTTGGTTCAGTAGTTGGAAAAGCTCTAT
TGCCTCTTTTTTCTTTATCATAGGGTTAATCATTGGACTATTCTTGGTTC
TCCGAGTTGGTATCCATCTTTGCATTAAATTAAAGCACACCAAGAAAAGA
CAGATTTATACAGACATAGAGATGAGAATTC
```

A 4-vector system (i.e., a 3-vector lentiviral packaging system) has also been designed and produced using the methods and materials described herein. A schematic of the 4-vector system is shown in FIG. 5. Briefly, and with reference to FIG. 5, the top-most vector is a helper plasmid, which, in this case, does not include Rev. The vector second from the top is a separate Rev plasmid. The vector second from the bottom is the envelope plasmid. The bottom-most vector is the previously described therapeutic vector.

Referring, in part, to FIG. 5, the Helper plasmid includes a CAG enhancer (SEQ ID NO: 49); a CAG promoter (SEQ ID NO: 50); a chicken beta actin intron (SEQ ID NO: 51); a HIV gag (SEQ ID NO: 52); a HIV Pol (SEQ ID NO: 53); a HIV Int (SEQ ID NO: 54); a HIV RRE (SEQ ID NO: 55); and a rabbit beta globin poly A (SEQ ID NO: 56).

The Rev plasmid includes a RSV promoter (SEQ ID NO: 57); a HIV Rev (SEQ ID NO: 58); and a rabbit beta globin poly A (SEQ ID NO: 59).

The Envelope plasmid includes a CMV promoter (SEQ ID NO: 60); a beta globin intron (SEQ ID NO: 61); a VSV-G (SEQ ID NO: 62); and a rabbit beta globin poly A (SEQ ID NO: 63).

Synthesis of a 3-Vector Lentiviral Packaging System Including Helper, Rev, And Envelope Plasmids.

Materials and Methods:

Construction of the Helper Plasmid without Rev:

The Helper plasmid without Rev was constructed by inserting a DNA fragment containing the RRE and rabbit beta globin poly A sequence. This sequence was synthesized by MWG Operon with flanking XbaI and XmaI restriction sites. The RRE/rabbit poly A beta globin sequence was then inserted into the Helper plasmid at the XbaI and XmaI restriction sites. The DNA sequence is as follows

```
                                          (SEQ ID NO: 87)
TCTAGAAGGAGCTTTGTTCCTTGGGTTCTTGGGAGCAGCAGGAAGCACTA
```

-continued

```
TGGGCGCAGCGTCAATGACGCTGACGGTACAGGCCAGACAATTATTGTCT
GGTATAGTGCAGCAGCAGAACAATTTGCTGAGGGCTATTGAGGCGCAACA
GCATCTGTTGCAACTCACAGTCTGGGGCATCAAGCAGCTCCAGGCAAGAA
TCCTGGCTGTGGAAAGATACCTAAAGGATCAACAGCTCCTAGATCTTTTT
CCCTCTGCCAAAAATTATGGGGACATCATGAAGCCCCTTGAGCATCTGAC
TTCTGGCTAATAAAGGAAATTTATTTTCATTGCAATAGTGTGTTGGAATT
TTTTGTGTCTCTCACTCGGAAGGACATATGGGAGGGCAAATCATTTAAAA
CATCAGAATGAGTATTTGGTTTAGAGTTTGGCAACATATGCCATATGCTG
GCTGCCATGAACAAAGGTGGCTATAAAGAGGTCATCAGTATATGAAACAG
CCCCCTGCTGTCCATTCCTTATTCCATAGAAAAGCCTTGACTTGAGGTTA
GATTTTTTTTATATTTTGTTTTGTGTTATTTTTTTCTTTAACATCCCTAA
AATTTTCCTTACATGTTTTACTAGCCAGATTTTTCCTCCTCTCCTGACTA
CTCCCAGTCATAGCTGTCCCTCTTCTCTTATGAAGATCCCTCGACCTGCA
GCCCAAGCTTGGCGTAATCATGGTCATAGCTGTTTCCTGTGTGAAATTGT
TATCCGCTCACAATTCCACACAACATACGAGCCGGAAGCATAAAGTGTAA
AGCCTGGGGTGCCTAATGAGTGAGCTAACTCACATTAATTGCGTTGCGCT
CACTGCCCGCTTTCCAGTCGGGAAACCTGTCGTGCCAGCGGATCCGCATC
TCAATTAGTCAGCAACCATAGTCCCGCCCCTAACTCCGCCCATCCCGCCC
CTAACTCCGCCCAGTTCCGCCCATTCTCCGCCCCATGGCTGACTAATTTT
TTTTATTTATGCAGAGGCCGAGGCCGCCTCGGCCTCTGAGCTATTCCAGA
AGTAGTGAGGAGGCTTTTTTGGAGGCCTAGGCTTTTGCAAAAAGCTAACT
TGTTTATTGCAGCTTATAATGGTTACAAATAAAGCAATAGCATCACAAAT
TTCACAAATAAAGCATTTTTTTCACTGCATTCTAGTTGTGGTTTGTCCAA
ACTCATCAATGTATCTTATCACCCGGG
```

Construction of the Rev Plasmid:

The RSV promoter and HIV Rev sequence was synthesized as a single DNA fragment by MWG Operon with flanking MfeI and XbaI restriction sites. The DNA fragment was then inserted into the pCDNA3.1 plasmid (Invitrogen) at the MfeI and XbaI restriction sites in which the CMV promoter is replaced with the RSV promoter. The DNA sequence was as follows:

```
                                          (SEQ ID NO: 88)
CAATTGCGATGTACGGGCCAGATATACGCGTATCTGAGGGGACTAGGGTG
TGTTTAGGCGAAAAGCGGGGCTTCGGTTGTACGCGGTTAGGAGTCCCCTC
AGGATATAGTAGTTTCGCTTTTGCATAGGGAGGGGGAAATGTAGTCTTAT
GCAATACACTTGTAGTCTTGCAACATGGTAACGATGAGTTAGCAACATGC
CTTACAAGGAGAGAAAAAGCACCGTGCATGCCGATTGGTGGAAGTAAGGT
GGTACGATCGTGCCTTATTAGGAAGGCAACAGACAGGTCTGACATGGATT
GGACGAACCACTGAATTCCGCATTGCAGAGATAATTGTATTTAAGTGCCT
AGCTCGATACAATAAACGCCATTTGACCATTCACCACATTGGTGTGCACC
TCCAAGCTCGAGCTCGTTTAGTGAACCGTCAGATCGCCTGGAGACGCCAT
CCACGCTGTTTTGACCTCCATAGAAGACACCGGGACCGATCCAGCCTCCC
```

-continued

```
CTCGAAGCTAGCGATTAGGCATCTCCTATGGCAGGAAGAAGCGGAGACAG

CGACGAAGAACTCCTCAAGGCAGTCAGACTCATCAAGTTTCTCTATCAAA

GCAACCCACCTCCCAATCCCGAGGGGACCCGACAGGCCCGAAGGAATAGA

AGAAGAAGGTGGAGAGAGAGACAGAGACAGATCCATTCGATTAGTGAACG

GATCCTTAGCACTTATCTGGGACGATCTGCGGAGCCTGTGCCTCTTCAGC

TACCACCGCTTGAGAGACTTACTCTTGATTGTAACGAGGATTGTGGAACT

TCTGGGACGCAGGGGGTGGGAAGCCCTCAAATATTGGTGGAATCTCCTAC

AATATTGGAGTCAGGAGCTAAAGAATAGTCTAGA
```

The plasmids for the 2-vector and 3-vector packaging systems could be modified with similar elements and the intron sequences could potentially be removed without loss of vector function. For example, the following elements could replace similar elements in the 2-vector and 3-vector packaging system:

Promoters: Elongation Factor-1 (EF-1) (SEQ ID NO: 64), phosphoglycerate kinase (PGK) (SEQ ID NO: 65), and ubiquitin C (UbC) (SEQ ID NO: 66) can replace the CMV (SEQ ID NO: 60) or CAG promoter (SEQ ID NO: 100).

Poly A sequences: SV40 poly A (SEQ ID NO: 67) and bGH poly A (SEQ ID NO: 68) can replace the rabbit beta globin poly A (SEQ ID NO: 48).

HIV Gag, Pol, and Integrase sequences: The HIV sequences in the Helper plasmid can be constructed from different HIV strains or clades. For example, HIV Gag (SEQ ID NO: 69); HIV Pol (SEQ ID NO: 70); and HIV Int (SEQ ID NO: 71) from the Bal strain can be interchanged with the gag, pol, and int sequences contained in the helper/helper plus Rev plasmids as outlined herein.

Envelope: The VSV-G glycoprotein can be substituted with membrane glycoproteins from feline endogenous virus (RD114) (SEQ ID NO: 72), gibbon ape leukemia virus (GALV) (SEQ ID NO: 73), Rabies (FUG) (SEQ ID NO: 74), lymphocytic choriomeningitis virus (LCMV) (SEQ ID NO: 75), influenza A fowl plague virus (FPV) (SEQ ID NO: 76), Ross River alphavirus (RRV) (SEQ ID NO: 77), murine leukemia virus 10A1 (MLV) (SEQ ID NO: 78), or Ebola virus (EboV) (SEQ ID NO: 79). Sequences for these envelopes are identified in the sequence portion herein.

In summary, the 3-vector versus 4-vector systems can be compared and contrasted as follows. The 3-vector lentiviral vector system contains: 1. Helper plasmid: HIV Gag, Pol, Integrase, and Rev/Tat; 2. Envelope plasmid: VSV-G/FUG envelope; and 3. Therapeutic vector: RSV 5'LTR, Psi Packaging Signal, Gag fragment, RRE, Env fragment, cPPT, WPRE, and 3'delta LTR. The 4-vector lentiviral vector system contains: 1. Helper plasmid: HIV Gag, Pol, and Integrase; 2. Rev plasmid: Rev; 3. Envelope plasmid: VSV-G/FUG envelope; and 4. Therapeutic vector: RSV 5'LTR, Psi Packaging Signal, Gag fragment, RRE, Env fragment, cPPT, WPRE, and 3'delta LTR. Sequences corresponding with the above elements are identified in the sequence listings portion herein.

Example 2: Development of an Anti-HIV Lentivirus Vector

The purpose of this example was to develop an anti-HIV lentivirus vector.

Inhibitory RNA Designs. The sequence of *Homo sapiens* chemokine C-C motif receptor 5 (CCR5) (GC03P046377) mRNA was used to search for potential siRNA or shRNA candidates to knockdown CCR5 levels in human cells. Potential RNA interference sequences were chosen from candidates selected by siRNA or shRNA design programs such as from the Broad Institute or the BLOCK-iT RNAi Designer from Thermo Scientific. Individual selected shRNA sequences were inserted into lentiviral vectors immediately 3' to a RNA polymerase III promoter such as H1, U6, or 7SK to regulate shRNA expression. These lentivirus-shRNA constructs were used to transduce cells and measure the change in specific mRNA levels. The shRNA most potent for reducing mRNA levels were embedded individually within a microRNA backbone to allow for expression by either the CMV or EF-1alpha RNA polymerase II promoters. The microRNA backbone was selected from mirbase.org. RNA sequences were also synthesized as synthetic siRNA oligonucleotides and introduced directly into cells without using a lentiviral vector.

The genomic sequence of Bal strain of human immunodeficiency virus type 1 (HIV-1 85US_BaL, accession number AY713409) was used to search for potential siRNA or shRNA candidates to knockdown HIV replication levels in human cells. Based on sequence homology and experience, the search focused on regions of the Tat and Vif genes of HIV although an individual of skill in the art will understand that use of these regions is non-limiting and other potential targets might be selected. Importantly, highly conserved regions of Gag or Polymerase genes could not be targeted by shRNA because these same sequences were present in the packaging system complementation plasmids needed for vector manufacturing. As with the CCR5 (NM 000579.3, NM 001100168.1-specific) RNAs, potential HIV-specific RNA interference sequences were chosen from candidates selected by siRNA or shRNA design programs such as from the Gene-E Software Suite hosted by the Broad Institute (broadinstitute.org/mai/public) or the BLOCK-iT RNAi Designer from Thermo Scientific (madesigner.thermofisher.com/maiexpress/setOption.do?designOption=shma&pid=6712627360706061801). Individual selected shRNA sequences were inserted into lentiviral vectors immediately 3' to a RNA polymerase III promoter such as H1, U6, or 7SK to regulate shRNA expression. These lentivirus-shRNA constructs were used to transduce cells and measure the change in specific mRNA levels. The shRNA most potent for reducing mRNA levels were embedded individually within a microRNA backbone to allow for expression by either the CMV or EF-1alpha RNA polymerase II promoters.

Vector Constructions. For CCR5, Tat or Vif shRNA, oligonucleotide sequences containing BamHI and EcoRI restriction sites were synthesized by Eurofins MWG Operon, LLC. Overlapping sense and antisense oligonucleotide sequences were mixed and annealed during cooling from 70 degrees Celsius to room temperature. The lentiviral vector was digested with the restriction enzymes BamHI and EcoRI for one hour at 37 degrees Celsius. The digested lentiviral vector was purified by agarose gel electrophoresis and extracted from the gel using a DNA gel extraction kit from Invitrogen. The DNA concentrations were determined and vector to oligo (3:1 ratio) were mixed, allowed to anneal, and ligated. The ligation reaction was performed with T4 DNA ligase for 30 minutes at room temperature. 2.5 microliters of the ligation mix were added to 25 microliters of STBL3 competent bacterial cells. Transformation was achieved after heat-shock at 42 degrees Celsius. Bacterial cells were spread on agar plates containing ampicillin and drug-resistant colonies (indicating the presence of ampicillin-resistance plasmids) were recovered, purified and expanded in LB broth. To check for insertion of the oligo sequences, plasmid DNA were extracted from harvested bacteria cultures with the Invitrogen DNA mini prep kit. Insertion of the shRNA sequence in the lentiviral vector was verified by DNA sequencing using a specific primer for the promoter used to regulate shRNA expression. Exemplary vector sequences that were determined to restrict HIV replication can be found in FIG. 6. For example, the shRNA sequences with the highest activity against CCR5, Tat or Vif gene expression were then assembled into a microRNA (miR) cluster under control of the EF-1alpha promoter. The promoter and miR sequences are depicted in FIG. 6.

Figure 7:
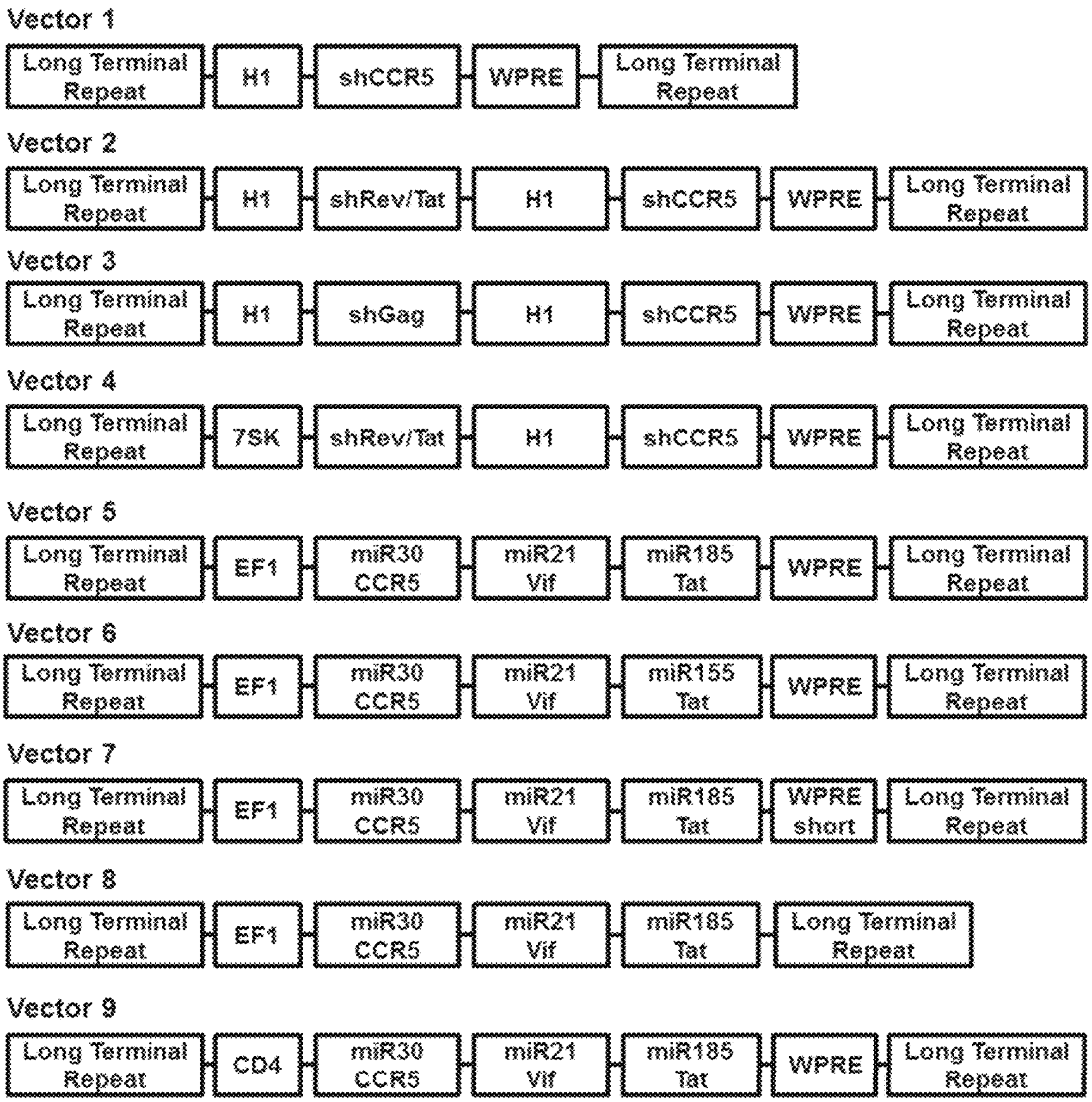
FIG. 7 depicts exemplary lentiviral vector constructs according to aspects of the disclosure.

Further, and using standard molecular biology techniques (e.g., Sambrook; Molecular Cloning: A Laboratory Manual, $4^{th}$ Ed.) as well as the techniques described herein, a series of lentiviral vectors have been developed as depicted in FIG. 7 herein.

Vector 1 was developed and contains, from left to right: a long terminal repeat (LTR) portion (SEQ ID NO: 35); a H1 element (SEQ ID NO: 101); a shCCR5 (SEQ ID NOS: 16, 18, 20, 22, or 24); a posttranscriptional regulatory element of woodchuck hepatitis virus (WPRE) (SEQ ID NOS: 32, 80); and a long terminal repeat portion (SEQ ID NO: 102).

Vector 2 was developed and contains, from left to right: a long terminal repeat (LTR) portion (SEQ ID NO: 35); a H1 element (SEQ ID NO: 101); a shRev/Tat (SEQ ID NO: 10); a H1 element (SEQ ID NO: 101); a shCCR5 (SEQ ID NOS: 16, 18, 20, 22, or 24); a posttranscriptional regulatory element of woodchuck hepatitis virus (WPRE) (SEQ ID NOS: 32, 80); and a long terminal repeat portion (SEQ ID NO: 102).

Vector 3 was developed and contains, from left to right: a long terminal repeat (LTR) portion (SEQ ID NO: 35); a H1 element (SEQ ID NO: 101); a shGag (SEQ ID NO: 12); a H1 element (SEQ ID NO: 101); a shCCR5 (SEQ ID NOS: 16, 18, 20, 22, or 24); a posttranscriptional regulatory element of woodchuck hepatitis virus (WPRE) (SEQ ID NOS: 32, 80); and a long terminal repeat portion (SEQ ID NO: 102).

Vector 4 was developed and contains, from left to right: a long terminal repeat (LTR) portion (SEQ ID NO: 35); a 7SK element (SEQ ID NO: 103); a shRev/Tat (SEQ ID NO: 10); a H1 element (SEQ ID NO: 101); a shCCR5 (SEQ ID NOS: 16, 18, 20, 22, or 24); a posttranscriptional regulatory element of woodchuck hepatitis virus (WPRE) (SEQ ID NOS: 32, 80); and a long terminal repeat portion (SEQ ID NO: 102).

Vector 5 was developed and contains, from left to right: a long terminal repeat (LTR) portion (SEQ ID NO: 35); a EF1 element (SEQ ID NO: 4); miR30CCR5 (SEQ ID NO: 1); MiR21Vif (SEQ ID NO: 2); miR185Tat (SEQ ID NO: 3); a posttranscriptional regulatory element of woodchuck hepatitis virus (WPRE) (SEQ ID NOS: 32, 80); and a long terminal repeat portion (SEQ ID NO: 102).

Vector 6 was developed and contains, from left to right: a long terminal repeat (LTR) portion (SEQ ID NO: 35); a EF1 element (SEQ ID NO: 4); miR30CCR5 (SEQ ID NO: 1); MiR21Vif (SEQ ID NO: 2); miR155Tat (SEQ ID NO: 104); a posttranscriptional regulatory element of woodchuck hepatitis virus (WPRE) (SEQ ID NOS: 32, 80); and a long terminal repeat portion (SEQ ID NO: 102).

Vector 7 was developed and contains, from left to right: a long terminal repeat (LTR) portion (SEQ ID NO: 35); a EF1 element (SEQ ID NO: 4); miR30CCR5 (SEQ ID NO: 1); MiR21Vif (SEQ ID NO: 2); miR185Tat (SEQ ID NO: 3); a posttranscriptional regulatory element of woodchuck hepatitis virus (WPRE) (SEQ ID NOS: 32, 80); and a long terminal repeat portion (SEQ ID NO: 102).

Vector 8 was developed and contains, from left to right: a long terminal repeat (LTR) portion (SEQ ID NO: 35); a EF1 element (SEQ ID NO: 4); miR30CCR5 (SEQ ID NO: 1); MiR21Vif (SEQ ID NO: 2); miR185Tat (SEQ ID NO: 3); and a long terminal repeat portion (SEQ ID NO: 102).

Vector 9 was developed and contains, from left to right: a long terminal repeat (LTR) portion (SEQ ID NO: 35); a CD4 element (SEQ ID NO: 30); miR30CCR5 (SEQ ID NO: 1); MiR21Vif (SEQ ID NO: 2); miR185Tat (SEQ ID NO: 3); a posttranscriptional regulatory element of woodchuck hepatitis virus (WPRE) (SEQ ID NOS: 32, 80); and a long terminal repeat portion (SEQ ID NO: 102).

Development of Vectors

It should be noted that not all vectors developed for these experiments necessarily worked as planned. More specifically, a lentivirus vector against HIV might include three main components: 1) inhibitory RNA to reduce the level of HIV binding proteins (receptors) on the target cell surface to block initial virus attachment and penetration; 2) overexpression of the HIV TAR sequence that will sequester viral Tat protein and decrease its ability to transactivate viral gene expression; and 3) inhibitory RNA that attack important and conserved sequences within the HIV genome.

With respect to the first point above, a key cell surface HIV binding protein is the chemokine receptor CCR5. HIV particles attach to susceptible T cells by binding to the CD4 and CCR5 cell surface proteins. Because CD4 is an essential glycoprotein on the cell surface that is important for the immunological function of T cells, this was not chosen as a target to manipulate its expression levels. However, people born homozygous for null mutations in the CCR5 gene and completely lacking receptor expression, live normal lives save for enhanced susceptibility to a few infectious diseases and the possibility of developing rare autoimmunity. Safety is enhanced in this example, because relatively few of total body CD4+ T cells are genetically modified to reduce CCR5 expression, and CD4+ T cells needed for pathogen immunity or control of autoimmunity are unlikely to be among the modified cells. Thus, modulating CCR5 was determined to be a relatively safe approach and was a primary target in the development of anti-HIV lentivirus vectors.

With respect to the second point above, the viral TAR sequence is a highly structured region of HIV genomic RNA that binds tightly to viral Tat protein. The Tat:TAR complex is important for efficient generation of viral RNA. Overexpression of the TAR region was envisioned as a decoy molecule that would sequester Tat protein and decrease the levels of viral RNA. However, TAR proved toxic to most mammalian cells including cells used for manufacturing lentivirus particles. Further, TAR was inefficient for inhibiting viral gene expression in other laboratories and has been discarded as a viable component in HIV gene therapy.

With respect to the third point above, viral gene sequences have been identified that meet 3 criteria: i) Sequences are reasonably conserved across a range of HIV isolates representative of the epidemic in a geographic region of interest; ii) reduction in RNA levels due to the activity of an inhibitory RNA in a viral vector will reduce the corresponding protein levels by an amount sufficient to meaningfully reduce HIV replication; and iii) the viral gene sequence(s) targeted by inhibitory RNA are not present in the genes required for packaging and assembling viral vector particles during manufacturing. The lattermost point is important as it would be completely disadvantageous to have an inhibitory RNA that targets genes necessary for effective functioning of the viral particles themselves. In the present embodiment, a sequence at the junction of HIV Tat and Rev genes and a second sequence within the HIV Vif gene have been targeted by inhibitory RNA. The Tat/Rev targeting has an additional benefit of reducing HIV envelope glycoprotein expression because this region overlaps with the envelope gene in the HIV genome.

The strategy for vector development and testing relies first on identifying suitable targets (as described herein) followed by constructing plasmid DNAs expressing individual or multiple inhibitory RNA species for testing in cell models, and finally constructing lentivirus vectors containing inhibitory RNA with proven anti-HIV function. The lentivirus vectors are tested for toxicity, yield during in vitro production, and effectiveness against HIV in terms of reducing CCR5 expression levels or lowering viral gene products to inhibit virus replication.

Table 2 below demonstrates progression through multiple versions of inhibitory constructs until arriving at a clinical candidate. Initially, shRNA (short homology RNA) molecules were designed and expressed from plasmid DNA constructs.

Plasmids 1-4, as detailed in Table 2 below, tested shRNA sequences against Gag, Pol and RT genes of HIV. While each shRNA was active for suppressing viral protein expression in a cell model, there were two important problems that prevented further development. First, the sequences were targeted to a laboratory isolate of HIV that was not representative of Clade B HIV strains currently circulating in North America and Europe. Second, these shRNA targeted critical components in the lentivirus vector packaging system and would severely reduce vector yield during manufacturing. Plasmid 5, as detailed in Table 2, was selected to target CCR5 and provided a lead candidate sequence. Plasmids 6, 7, 8, 9, 10, and 11, as detailed in Table 2, incorporated the TAR sequence and it was found they produced unacceptable toxicity for mammalian cells including cells used for lentivirus vector manufacturing. Plasmid 2, as detailed in Table 2, identified a lead shRNA sequence capable of reducing Tat RNA expression. Plasmid 12, as detailed in Table 2, demonstrated the effectiveness of shCCR5 expressed as a microRNA (miR) in a lentiviral vector and confirmed it should be in the final product. Plasmid 13, as detailed in Table 2, demonstrated the effectiveness of a shVif expressed as a microRNA (miR) in a lentiviral vector and confirmed it should be in the final product. Plasmid 14, as detailed in Table 2, demonstrated the effectiveness of shTat expressed as a microRNA (miR) in a lentiviral vector and confirmed it should be in the final product. Plasmid 15, as detailed in Table 2, contained the miR CCR5, miR Tat and miR Vif in the form of a miR cluster expressed from a single promoter. These miR do not target critical components in the lentivirus vector packaging system and proved to have negligible toxicity for mammalian cells. The miR within the cluster was equally effective to individual miR that were tested previously, and the overall impact was a substantial reduction in replication of a CCR5-tropic HIV BaL strain.

TABLE 2

Development of HIV Vectors

| | Internal Code | Material | Description | Remarks | Decision |
|---|---|---|---|---|---|
| 1 | SIH-H1-shRT-1,3 | Lentiviral vector | shRNA construct for RT of LAI strain | Wrong target, lab virus, no virus test | Abandon |
| 2 | SIH-H1-shRT43 (Tat/Rev NL4-3) | Lentiviral vector | H1 promoter shRNA Tat/Rev overlap | Tat protein knock-down >90% | Lead |

Vector Construction: For Rev/Tat (RT) shRNA, oligonucleotide sequences containing BamHI and EcoRI restriction sites were synthesized by MWG Operon. Two different Rev/Tat target sequences were tested for their ability to decrease Tat mRNA expression. The RT1,3 target sequence is (5'-ATGGCAGGAAGAAGCGGAG-3') (SEQ ID NO: 89) and shRNA sequence is (5'-ATGGCAGGAAGAAGCGGAGTTCAAGAGACTCCGCTTCTTCCTGCCATTTTTT-3') (SEQ ID NO: 90). The RT43 sequence is (5'-GCGGAGACAGCGACGAAGAGC-3') (SEQ ID NO: 9) and shRNA sequence is (5'-GCGGAGACAGCGACGAAGAGCTTCAAGAGAGCTCTTCGTCGCTGTCTCCGCTTTTT-3') (SEQ ID NO: 10). Oligonucleotide sequences were inserted into the pSIH lentiviral vector (System Biosciences).

Functional test for shRNA against Rev/Tat: The ability of the vector to reduce Tat expression was tested using a luciferase reporter plasmid which contained the Rev/Tat target sequences inserted into the 3'-UTR (untranslated region of the mRNA). Either the shRT1,3 or shRT43 plasmid was co-transfected with the plasmid containing luciferase and the Rev/Tar target sequence. There was a 90% reduction in light emission indicating strong function of the shRT43 shRNA sequence but less than 10% with the shRT1,3 plasmid.

Conclusion: The SIH-H1-shRT43 was superior to SIH-H1-shRT-1,3 in terms of reducing mRNA levels in the Luciferase assay system. This indicates potent inhibitory activity of the shRT43 sequence and it was selected as a lead candidate for further development.

| | | | | | |
|---|---|---|---|---|---|
| 3 | SIH-H1-shGag-1 | Lentivital vector | shRNA construct for LAI Gag | Inhibits Gag expression but will inhibit packaging | Abandon |

Vector Construction: For Gag shRNA, oligonucleotide sequences containing BamHI and EcoRI restriction sites were synthesized by MWG Operon. A Gag target sequence was tested for their ability to decrease Gag mRNA expression. The Gag target sequence is (5'-GAAGAAATGATGACAGCAT -3') (SEQ ID NO: 11) and shRNA sequence is (5'-GAAGAAATGATGACAGCATTTCAAGAGAATGCTGTCATCATTTCTTCTTTTT-3')

TABLE 2-continued

Development of HIV Vectors

| | Internal Code | Material | Description | Remarks | Decision |
|---|---|---|---|---|---|
| | (SEQ ID NO: 12). Oligonucleotide sequences were inserted into the pSIH lentiviral vector (System Biosciences).<br>Functional test for shRNA against Gag: The ability of the vector to reduce Gag expression was tested using a luciferase reporter plasmid which contained the Gag target sequences inserted into the 3'-UTR (untranslated region of the mRNA). The Gag plasmid was co-transfected with the plasmid containing luciferase and the Gag target sequence. There was nearly a 90% reduction in light emission indicating a strong effect of the shGag shRNA sequence.<br>Conclusion: This shRNA sequence is potent against HIV Gag expression but was abandoned. The lentivirus packaging system requires production of Gag from the helper plasmid and shRNA inhibition of Gag will reduce lentivirus vector yield. This shRNA sequence could be used as an oligonucleotide inhibitor of HIV or incorporated into an alternate viral vector packaging system that uses a different vector genome or is modified to resist inhibition by this shRNA. | | | | |
| 4 | SIH-H1-shPol-1 | Lentiviral vector | shRNA construct for Pol | Inhibits Pol expression but will inhibit packaging | Abandon |
| | Vector Construction: A Pol shRNA was constructed with oligonucleotide sequences containing BamHI and EcoRI restriction sites that were synthesized by MWG Operon. A Pol target sequence was tested for its ability to decrease Pol mRNA expression. The Pol target sequence is (5'- CAGGAGCAGATGATACAG -3') (SEQ ID NO: 13) and shRNA sequence is (5'-CAGGAGATGATACAGTTCAAGAGACTGTATCATCTGCTCCTGTTTTT-3') (SEQ ID NO: 14). Oligonucleotide sequences were inserted into the pSIH lentiviral vector (System Biosciences).<br>Functional tests for shRNA against HIV Pol: The ability of the vector to reduce Pol expression was tested using a luciferase reporter plasmid which contained the Pol target sequences inserted into the 3'-UTR (untranslated region of the mRNA). The Pol plasmid was co-transfected with the plasmid containing luciferase and the Pol target sequence. There was a 60% reduction in light emission indicating a strong effect of the shPol shRNA sequence.<br>Conclusion: This shRNA sequence is potent against HIV Pol expression but was abandoned. The lentivirus packaging system requires production of Pol from the helper plasmid and shRNA inhibition of Pol will reduce lentivirus vector yield. This shRNA sequence could be used as an oligonucleotide inhibitor of HIV or incorporated into an alternate viral vector packaging system that uses a different vector genome or is modified to resist inhibition by this shRNA. | | | | |
| 5 | SIH-H1-shCCR5-1 | Lentiviral vector | shRNA construct for CCR5 | Best of 5 candidates, Extracellular CCR5 protein reduction | Lead |
| | Vector Construction: A CCR5 shRNA was constructed with oligonucleotide sequences containing BamHI and EcoRI restriction sites that were synthesized by MWG Operon. Oligonucleotide sequences were inserted into the pSIH lentiviral vector (System Biosciences). The CCR5 target sequence #1, which focuses on CCR5 gene sequence 1 (SEQ ID NO: 25), is (5'-GTGTCAAGTCCAATCTATG-3') (SEQ ID NO: 15) and the shRNA sequence is (5'-GTGTCAAGTCCAATCTATGTTCAAGAGACATAGATTGGACTTGACACTTTTT-3') (SEQ ID NO: 16). The CCR5 target sequence #2, which focuses on CCR5 gene sequence 2 (SEQ ID NO: 26), is (5'-GAGCATGACTGACATCTAC-3') (SEQ ID NO: 17) and the shRNA sequence is (5'-GAGCATGACTGACATCTACTTCAAGAGAGTAGATGTCAGTCATGCTCTTTTT-3') (SEQ ID NO: 18). The CCR5 target sequence #3, which focuses on CCR5 gene sequence 3 (SEQ ID NO: 27), is (5'-GTAGCTCTAACAGGTTGGA-3') (SEQ ID NO: 19) and the shRNA sequence is (5'-GTAGCTCTAACAGGTTGGATTCAAGAGATCCAACCTGTTAGAGCTACTTTTT-3') (SEQ ID NO: 20). The CCR5 target sequence #4, which focuses on CCR5 gene sequence 4 (SEQ ID NO: 28, is (5'-GTTCAGAAACTACCTCTTA-3') (SEQ ID NO: 21) and the shRNA sequence is (5'-GTTCAGAAACTACCTCTTATTCAAGAGATAAGAGGTAGTTTCTGAACTTTTT-3') (SEQ ID NO: 22). The CCR5 target sequence #5, which focuses on CCR5 gene sequence 5 (SEQ ID NO: 29), is (5'-GAGCAAGCTCAGTTTACACC-3') (SEQ ID NO: 23) and the shRNA sequence is (5'-GAGCAAGCTCAGTTTACACCTTCAAGAGAGGTGTAAACTGAGCTTGCTCTTTTT-3') (SEQ ID NO: 24).<br>Functional test for shRNA against CCR5: The ability of a CCR5 shRNA sequence to knock-down CCR5 RNA expression was initially tested by co-transfecting each of the lentiviral plasmids, in separate experiments for each plasmid, containing one of the five CCR5 target sequences with a plasmid expressing the human CCR5 gene. CCR5 mRNA expression was then assessed by qPCR analysis using CCR5-specific primers.<br>Conclusion: Based on the reduction in CCR5 mRNA levels the shRNACCR5-1 was most potent for reducing CCR5 gene expression. This shRNA was selected as a lead candidate. | | | | |

TABLE 2-continued

| Development of HIV Vectors | | | | | |
|---|---|---|---|---|---|
| | Internal Code | Material | Description | Remarks | Decision |
| 6 | SIH-U6-TAR | Lentiviral vector | U6 promoter-TAR | Toxic to cells | Abandon |
| 7 | SIH-U6-TAR-H1-shCCR5 | Lentiviral vector | U6 promoter-TAR-H1-shCCR5 | Toxic to cells | Abandon |
| 8 | U6-TAR-H1-shRT | Lentiviral vector | U6 promoter-TAR-H1-RT | Suppress HIV, toxic to cells, poor packaging | Abandon |
| 9 | U6-TAR-7SK-shRT | Lentiviral vector | Change shRNA promoter to 7SK | Toxic, poor packaging | Abandon |
| 10 | U6-TAR-H1-shRT-H1-shCCR5 | Lentiviral vector | U6 promoter-TAR-H1-RT-H1-shCCR5 | Toxic, poor packaging, H1 repeats | Abandon |
| 11 | U6-TAR-7SK-shRT-H1-CCR5 | Lentiviral vector | Change shRNA promoter to 7SK | Toxic, poor packaging | Abandon |

Vector Construction: A TAR decoy sequence containing flanking KpnI restriction sites was synthesized by MWG operon and inserted into the pSIH lentiviral vector (System Biosciences) at the KpnI site. In this vector, TAR expression is regulated by the U6 promoter. The TAR decoy sequence is (5'-CTTGCAATGATGTCGTAATTTGCGTCTTACCTCGTTCTCGACAGCGACCAGATCTGAGCCTGGGAGCTCTCTGGCTGTCAGTAAGCTGGTACAGAAGGTTGACGAAAATTCTTACTGAGCAAGAAA-3') (SEQ ID NO: 8). Expression of the TAR decoy sequence was determined by qPCR analysis using specific primers for the TAR sequence. Additional vectors were constructed also containing the TAR sequence. The H1 promoter and shRT sequence was inserted in this vector in the XhoI site. The H1 shRT sequence is (5'-GAACGCTGACGTCATCAACCCGCTCCAAGGAATCGCGGGCCCAGTGTCACTAGGCGGGAACACCCAGCGCGCGTGCGCCCTGGCAGGAAGATGGCTGTGAGGGACAGGGGAGTGGCGCCCTGCAATATTTGCATGTCGCTATGTGTTCTGGGAAATCACCATAAACGTGAAATGTCTTTGGATTTGGGAATCTTATAAGTTCTGTATGAGACCACTTGGATCCGCGGAGACAGCGACGAAGAGCTTCAAGAGAGCTCTTCGTCGCTGTCTCCGCTTTTT-3') (SEQ ID NO: 91). This vector could express TAR and knockdown RT. The 7SK promoter was also substituted for the HI promoter to regulate shRT expression. Another vector was constructed containing U6 TAR, H1 shRT, and H1 shCCR5. The H1 shCCR5 sequence was inserted into the SpeI site of the plasmid containing U6 TAR and H1 shRT. The H1 CCR5 sequence is (5'-GAACGCTGACGTCATCAACCCGCTCCAAGGAATCGCGGGCCCAGTGTCACTAGGCGGGAACACCCAGCGCGCGTGCGCCCTGGCAGGAAGATGGCTGTGAGGGACAGGGGAGTGGCGCCCTGCAATATTTGCATGTCGCTATGTGTTCTGGGAAATCACCATAAACGTGAAATGTCTTTGGATTTGGGAATCTTATAAGTTCTGTATGAGACCACTTGGATCCGTGTCAAGTCCAATCTATGTTCAAGAGACATAGATTGGACTTGACACTTTTT-3') (SEQ ID NO: 92). The 7SK promoter was also substituted for the HI promoter to regulate shRT expression.

Functional test for TAR decoy activity: We tested the effect of SIH-U6-TAR on packaging efficiency. When TAR sequence was included, the yield of vector in the SIH packaging system was reduced substantially.

Conclusion: Lentivirus vectors expressing the TAR decoy sequence are unsuitable for commercial development due to low vector yields. These constructs were abandoned.

| | | | | | |
|---|---|---|---|---|---|
| 12 | shCCR5 | Lentiviral vector | microRNA sequence | Extracellular CCR5 protein reduction >90% | Lead |

Vector Construction: A CCR5 microRNA was constructed with oligonucleotide sequences containing BsrGI and NotI restriction sites that were synthesized by MWG Operon. Oligonucleotide sequences were inserted into the pCDH lentiviral vector (System Biosciences). The EF-1 promoter was substituted for a CMV promoter that was used in the plasmid construct Test Material 5. The EF-1 promoter was synthesized by MWG Operon containing flanking ClaI and BsrGI restriction sites and inserted into the pCDH vector containing shCCR5-1. The EF-1 promoter sequence is (5'-CCGGTGCCTAGAGAAGGTGGCGCGGGGTAAACTGGGAAAGTGATGTCGTGTACTGGCTCCGCCTTTTTCCCGAGGGTGGGGGAGAACCGTATATAAGTGCAGTAGTCGCCGTGAACGTTCTTTTTCGCAACGGGTTTGCCGCCAGAACACAGGTAAGTGCCGTGTGTGGTTCCCGCGGGCCTGGCCTCTTTACGGGTTATGGCCCTTGCGTGCCTTGAATTACTTCCACGCCCCTGGCTGCAGTACGTGATTCTTGATCCCGAGCTTCGGGTTGGAAGTGGGTGGGAGAGTTCGAGGCCTTGCGCTTAAGGAGCCCCTTCGCCTCGTGCTTGAGTTGAGGCCTGGCCTGGGCGCTGGGGCCGCCGCGTGCGAATCTGGTGGCACCTTCGCGCCTGTCTCGCTGCTTTCGATAAGTCTCTAGCCATTTAAAATTTTTGATGACCTGCTGCGACGCTTTTTTTCTGGCAAGATAGTCTTGTAAATGCGGGCCAAGATCTGCACACTGGTATTTCGGTTTTTGGGGCCGCGGGCGGCGACGGGGCCCGTGCGTCCCAGCGCACATGTTCGGCGAGGCGGGGCCTGCGAGCGCGGCCACCGAGAATCGGACGGGGGTAGTCTCAAGCTGGCCGGCCTGCTCTGGTGCCTGGCCTCGCGCCGCCGTGTATCGCCCCGCCCTGGGCGGCAAGGCTGGCCCGGTCGGCACCAGTTGCGTGAGCGGAAAGA TABLE 2-continued

| Development of HIV Vectors | | | | | |
|---|---|---|---|---|---|
| | Internal Code | Material | Description | Remarks | Decision |

TGGCCGCTTCCCGGCCCTGCTGCAGGGAGCTCAAAATGGAGGACGCGGCGCTCGG GAGAGCGGGCGGGTGAGTCACCCACACAAAGGAAAAGGGCCTTTCCGTCCTCAGC CGTCGCTTCATGTGACTCCACGGAGTACCGGGCGCCGTCCAGGCACCTCGATTAGT TCTCGAGCTTTTGGAGTACGTCGTCTTTAGGTTGGGGGGAGGGGTTTTATGCGATG GAGTTTCCCCACACTGAGTGGGTGGAGACTGAAGTTAGGCCAGCTTGGCACTTGA TGTAATTCTCCTTGGAATTTGCCCTTTTTGAGTTTGGATCTTGGTTCATTCTCAAGC CTCAGACAGTGGTTCAAAGTTTTTTTCTTCCATTTCAGGTGTCGTGA-3') (SEQ ID NO: 4).

Functional test for lentivirus CDH-shCCR5-1: The ability of the miR CCR5 sequences to knock-down CCR5 expression was determined by transducing CEM-CCR5 T cells and measuring cell surface CCR5 expression after staining with a fluorescently-labeled monoclonal antibody against CCR5 and measuring the intensity of staining, that is directly proportional to the number of cell surface CCR5 molecules, by analytical flow cytometry. The most effective shRNA sequence for targeting CCR5 was CCR5 shRNA sequence #1. However, the most effective CCR5 targeting sequence for constructing the synthetic microRNA sequence was overlapping with CCR5 sequence #5; this conclusion was based on sequence alignments and experience with miRNA construction. Finally, the miR30 hairpin sequence was used to construct the synthetic miR30 CCR5 sequence which is (5'-AGGTATATTGCTGTTGACAGTGAGCGACTGTAAACTGAGCTTGCTCTACTGTGAAG CCACAGATGGGTAGAGCAAGCACAGTTTACCGCTGCCTACTGCCTCGGACTTCAA GGGG CTT-3') (SEQ ID NO: 1). The miR CCR5 target sequence is (5'-GAGCAAGCTCAGTTTACA-3') (SEQ ID NO: 5). At multiplicity of infection equal to 5, generating on average 1.25 genome copies of integrated lentivirus per cell, CCR5 expression levels were reduce by ≥90% indicating potent inhibition of CCR5 mRNA by the miR30CCR5 micro RNA construct in a lentivirus vector.

Conclusion: The miR30CCR5 construct is potent for reducing CCR5 cell surface expression and is a lead candidate for a therapeutic lentivirus for HIV.

| 13 | shVif | Lentiviral vector | microRNA sequence | Vif protein reduction >80% | Lead |
|---|---|---|---|---|---|

Vector Construction: A Vif microRNA was constructed with oligonucleotide sequences containing BsrGI and NotI restriction sites that were synthesized by MWG Operon. Oligonucleotide sequences were inserted into the pCDH lentiviral vector (System Biosciences) containing an EF-1 promoter. Based on sequence alignments and experience with constructing synthetic miRNA, the miR21 hairpin sequence was used to construct the synthetic miR21 Vif sequence which is (5'-CATCTCCATGGCTGTACCACCTTGTCGGGGGATGTGTACTTCTGAACTTGTGTTGA ATCTCATGGAGTTCAGAAGAACACATCCGCACTGACATTTGGTATCTTTCATCTG ACCA-3') (SEQ ID NO: 2). The miR Vif target sequence is (5'-GGGATGTGTACTTCTGAACTT-3') (SEQ ID NO: 6).

Functional test for potency of miR21Vif. The ability of the miR Vif sequence to knock-down Vif expression was determined by measuring Vif protein expression by immunoblot analysis using an anti-Vif monoclonal antibody to identify the Vif protein.

Conclusion: the miR21Vif reduced Vif protein expression by ≥10-fold as determined by quantitative image analysis of immunoblot data. This was sufficient to justify miR21 Vif as a lead candidate for our therapeutic lentivirus.

| 14 | shTat | Lentiviral vector | microRNA sequence | Tat RNA reduction >80% | Lead |
|---|---|---|---|---|---|

Vector Construction: A Tat microRNA was constructed with oligonucleotide sequences containing BsrGI and NotI restriction sites that were synthesized by MWG Operon. The microRNA cluster was inserted into the pCDH lentiviral vector (System Biosciences) containing an EF-1 promoter. Based on sequence alignments and experience in the construction of synthetic miRNA, the miR185 hairpin sequence was selected for constructing a synthetic miR185 Tat sequence which is (5'-GGGCCTGGCTCGAGCAGGGGGCGAGGGATTCCGCTTCTTCCTGCCATAGCGTGGT CCCCTCCCCTATGGCAGGCAGAAGCGGCACCTTCCCTCCCAATGACCGCGTCTTCG TCG-3') (SEQ ID NO: 3). The miR Tat target sequence is (5'-TCCGCTTCTTCCTGCCATAG-3') (SEQ ID NO: 7).

Functional test for potency of miR185Tat: The ability of miR Tat to knock-down Tat expression was determined by measuring Tat mRNA expression by RT-PCR analysis using Tat specific primers. We compared the miR185Tat (SEQ ID NO: 108) with a similar miR155Tat on the basis of reducing the relative levels of Tat mRNA.

Conclusion: The miR185Tat (SEQ ID NO: 108) was approximately twice as potent for reducing Tat mRNA compare to miR155Tat, and was selected as the lead candidate for our therapeutic lentivirus.

TABLE 2-continued

| Development of HIV Vectors | | | | | |
|---|---|---|---|---|---|
| | Internal Code | Material | Description | Remarks | Decision |
| 15 | shCCR5-shVif-shTat | Lentiviral vector | microRNA cluster sequence | CCR5 reduction >90%, Vif protein reduction >80%, Tat RNA reduction >80%, >95% inhibition of HIV replication | Candidate |

Vector Construction: A miR30CCR5 miR21 Vif miR185Tat microRNA cluster sequence was constructed with a synthetic DNA fragment containing BsrGI and NotI restriction sites that was synthesized by MWG Operon. The DNA fragment was inserted into the pCDH lentiviral vector (System Biosciences) containing the EF-1 promoter. The miR cluster sequence is (5'-AGGTATATTGCTGTTGACAGTGAGCGACTGTAAACTGAGCTTGCTCTACTGTGAAGCCACAGATGGGTAGAGCAAGCACAGTTTACCGCTGCCTACTGCCTCGGACTTCAAGGGGCTTCCCGGGCATCTCCATGGCTGTACCACCTTGTCGGGGGATGTGTACTTCTGAACTTGTGTTGAATCTCATGGAGTTCAGAAGAACACATCCGCACTGACATTTTGGTATCTTTCATCTGACCAGCTAGCGGGCCTGGCTCGAGCAGGGGGCGAGGGATTCCGCTTCTTCCTGCCATAGCGTGGTCCCCTCCCCTATGGCAGGCAGAAGCGGCACCTTCCCTCCCAATGACCGCGTCTTCGTC-3') (SEQ ID NO: 31) and incorporates Test Material 12, Test Material 13 and Test Material 14 into a single cluster that can be expressed under control of the EF-1 promoter.

Functional test for potency of the Lentivirus Vector AGT103 containing the microRNA cluster of miR30CCR5, miR21Vif and miR185Tat: The AGT103 vector was tested for potency against CCR5 using the assay for reduction in cell surface CCR5 expression (Test Material 12). The AGT103 vector was tested for potency against Vif using the assay for reduction in cell surface Vif expression (Test Material 13). The AGT103 vector was tested for potency against Tat using the assay for reduction in cell surface Tat expression (Test Material 14).

Conclusion: Potency for reducing CCR5 expression by the miRNA cluster was similar to potency observed for the miR30CCR5 alone. Potency for reducing Vif expression by the miRNA cluster was similar to potency observed for the miR21 Vif alone. Potency for reducing Tat expression by the miRNA cluster was similar to potency observed for the miR185Tat alone. The miRNA cluster is potent for reducing cell surface CCR5 levels and for inhibiting two HIV genes. Thus, AGT103 containing this miRNA cluster was selected as the therapeutic vector construct for our HIV functional cure program.

Functional Assays. Individual lentivirus vectors containing CCR5, Tat or Vif shRNA sequences and, for experimental purposes, expressing green fluorescent protein (GFP) under control of the CMV Immediate Early Promoter, and designated AGT103/CMV-GFP were tested for their ability to knockdown CCR5, Tat or Vif expression. Mammalian cells were transduced with lentiviral particles either in the presence or absence of Polybrene. Cells were collected after 2-4 days; protein and RNA were analyzed for CCR5, Tat or Vif expression. Protein levels were tested by Western blot assay or by labeling cells with specific fluorescent antibodies (CCR5 assay), followed by analytical flow cytometry comparing modified and unmodified cell fluorescence using either the CCR5-specific or isotype control antibodies.

Starting Testing of Lentivirus. T cell culture medium was made using RPMI 1640 supplemented with 10% FBS and 1% penicillin-streptomycin. Cytokine stocks of IL2 10,000 units/ml, IL-12 1 μg/ml, IL-7 1 μg/ml, IL-15 1 μg/ml were also prepared in advance.

Prior to transduction with the lentivirus, an infectious viral titer was determined and used to calculate the amount of virus to add for the proper multiplicity of infection (MOI).

Day 0-12: Antigen-specific enrichment. On day 0, cryopreserved PBMC were thawed, washed with 10 ml 37° C. medium at 1200 rpm for 10 minutes and resuspended at a concentration of $2\times10^6$/ml in 37° C. medium. The cells were cultured at 0.5 ml/well in a 24-well plate at 37° C. in 5% CO2. To define the optimal stimulation conditions, cells were stimulated with combinations of reagents as listed in Table 3 below:

TABLE 3

| 1 | 2 | 3 | 4 | 5 | 6 |
|---|---|---|---|---|---|
| IL-2 + IL-12 | IL-7 + IL-15 | Peptides + IL-2 + IL-12 | Peptides + IL-7 + IL-15 | MVA + IL-2 + IL-12 | MVA + IL-7 + IL-15 |

Final concentrations: IL-2=20 units/ml, IL-12=10 ng/ml, IL-7=10 ng/ml, IL-15=10 ng/ml, peptides=5 μg/ml individual peptide, MVA MOI=1.

On days 4 and 8, 0.5 ml fresh medium and cytokine at listed concentrations (all concentrations indicate the final concentration in the culture) were added to the stimulated cells.

Day 12-24: non-specific expansion and lentivirus transduction. On day 12, the stimulated cells were removed from the plate by pipetting and resuspended in fresh T cell culture medium at a concentration of 1×106/ml. The resuspended cells were transferred to T25 culture flasks and stimulated with DYNABEADS® Human T-Activator CD3/CD28 following the manufacturer's instruction plus cytokine as listed above; flasks were incubated in the vertical position.

On day 14, AGT103/CMV-GFP was added at MOI 20 and cultures were returned to the incubator for 2 days. At this time, cells were recovered by pipetting, collected by centrifugation at 1300 rpm for 10 minutes, resuspended in the same volume of fresh medium, and centrifuged again to form a loose cell pellet That cell pellet was resuspended in fresh medium with the same cytokines used in previous steps, with cells at $0.5\times10^6$ viable cells per ml.

From days 14 to 23, the number of the cells was evaluated every 2 days and the cells were diluted to $0.5\times10^6$/ml with fresh media. Cytokines were added every time.

On day 24, the cells were collected and the beads were removed from the cells. To remove the beads, cells were transferred to a suitable tube that was placed in the sorting magnet for 2 minutes. Supernatant containing the cells was transferred to a new tube. Cells were then cultured for 1 day in fresh medium at $1\times10^6$/ml. Assays were performed to determine the frequencies of antigen-specific T cells and lentivirus transduced cells.

To prevent possible viral outgrowth, amprenavir (0.5 ng/ml) or saquinavir (0.5 ng/ml) or another suitable protease or integrase inhibitor was added to the cultures on the first day of stimulation and every other day during the culture.

Examine antigen-specific T cells by intracellular cytokine staining for IFN-gamma. Cultured cells after peptide stimulation or after lentivirus transduction at $1\times10^6$ cells/ml were stimulated with medium alone (negative control), Gag peptides (5 μg/ml individual peptide), or PHA (5 μg/ml, positive control). After 4 hours, BD GolgiPlug™ (1:1000, BD Biosciences) was added to block Golgi transport. After 8 hours, cells were washed and stained with extracellular (CD3, CD4 or CD8; BD Biosciences) and intracellular (IFN-gamma; BD Biosciences) antibodies with BD Cytofix/Cytoperm™ kit following the manufacturer's instruction. Samples were analyzed on a BD FACSCalibur™ Flow Cytometer. Control samples labeled with appropriate isotype-matched antibodies were included in each experiment. Data were analyzed using Flowjo software.

Lentivirus transduction rate was determined by the frequency of GFP+ cells. The transduced antigen-specific T cells are determined by the frequency of CD3+CD4+GFP+ IFN gamma+cells; tests for CD3+CD8+GFP+IFN gamma+ cells are included as a control.

These results indicate that CD4 T cells, the target T cell population, can be transduced with lentiviruses that are designed to specifically knock down the expression of HIV-specific proteins, thus producing an expandable population of T cells that are immune to the virus. This example serves as a proof of concept indicating that the disclosed lentiviral constructs can be used to produce a functional cure in HIV patients.

Example 4: CCR5 Knockdown with Experimental Vectors

AGTc120 is a Hela cell line that stably expresses large amounts of CD4 and CCR5. AGTc120 was transduced with or without LV-CMV-mCherry (the red fluorescent protein mCherry expressed under control of the CMV Immediate Early Promoter) or AGT103/CMV-mCherry. Gene expression of the mCherry fluorescent protein was controlled by a CMV (cytomegalovirus immediate early promoter) expression cassette. The LV-CMV-mCherry vector lacked a microRNA cluster, while AGT103/CMV-mCherry expressed therapeutic miRNA against CCR5, Vif, and Tat.

Figure 8A:
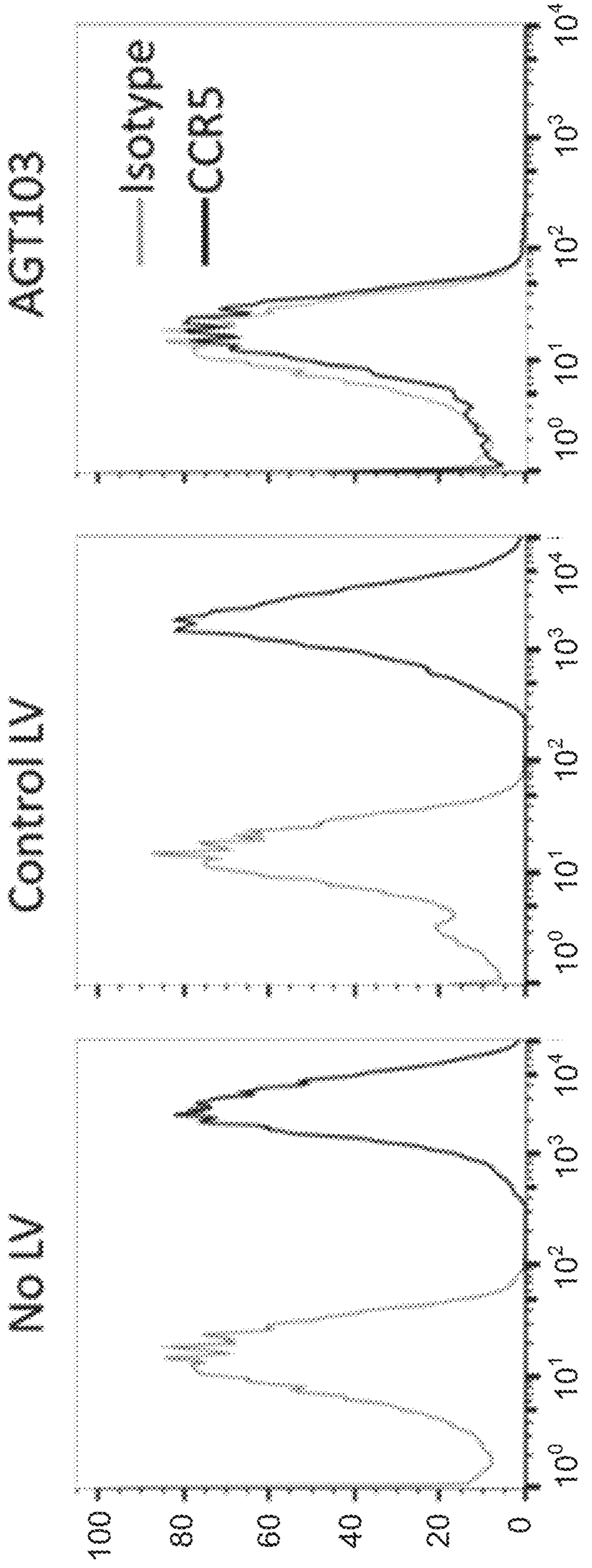
FIG. 8 shows that knockdown of CCR5 by an experimental vector prevents R5-tropic HIV infection in AGTc120 cells. (A) shows CCR5 expression in AGTc120 cells with or without AGT103 lentivirus vector. (B) shows the sensitivity of transduced AGTc120 cells to infection with a HIV BaL virus stock that was expressing green fluorescent protein (GFP) fused to the Nef gene of HIV.

As shown in FIG. 8A, transduction efficiency was >90%. After 7 days, cells were collected and stained with fluorescent monoclonal antibody against CCR5 and subjected to analytical flow cytometry. Isotype controls are shown in gray on these histograms plotting Mean Fluorescence Intensity of CCR5 APC (x axis) versus cell number normalized to mode (y axis). After staining for cell surface CCR5, cells treated with no lentivirus or control lentivirus (expressing only the mCherry marker) showed no changes in CCR5 density while AGT103 (right section) reduced CCR5 staining intensity to nearly the levels of isotype control. After 7 days, cells were infected with or without R5-tropic HIV reporter virus Bal-GFP. 3 days later, cells were collected and analyzed by flow cytometry. More than 90% of cells were transduced. AGT103-CMV/CMVmCherry reduced CCR5 expression in transduced AGTc120 cells and blocked R5-tropic HIV infection compared with cells treated with the Control vector.

Figure 8B:
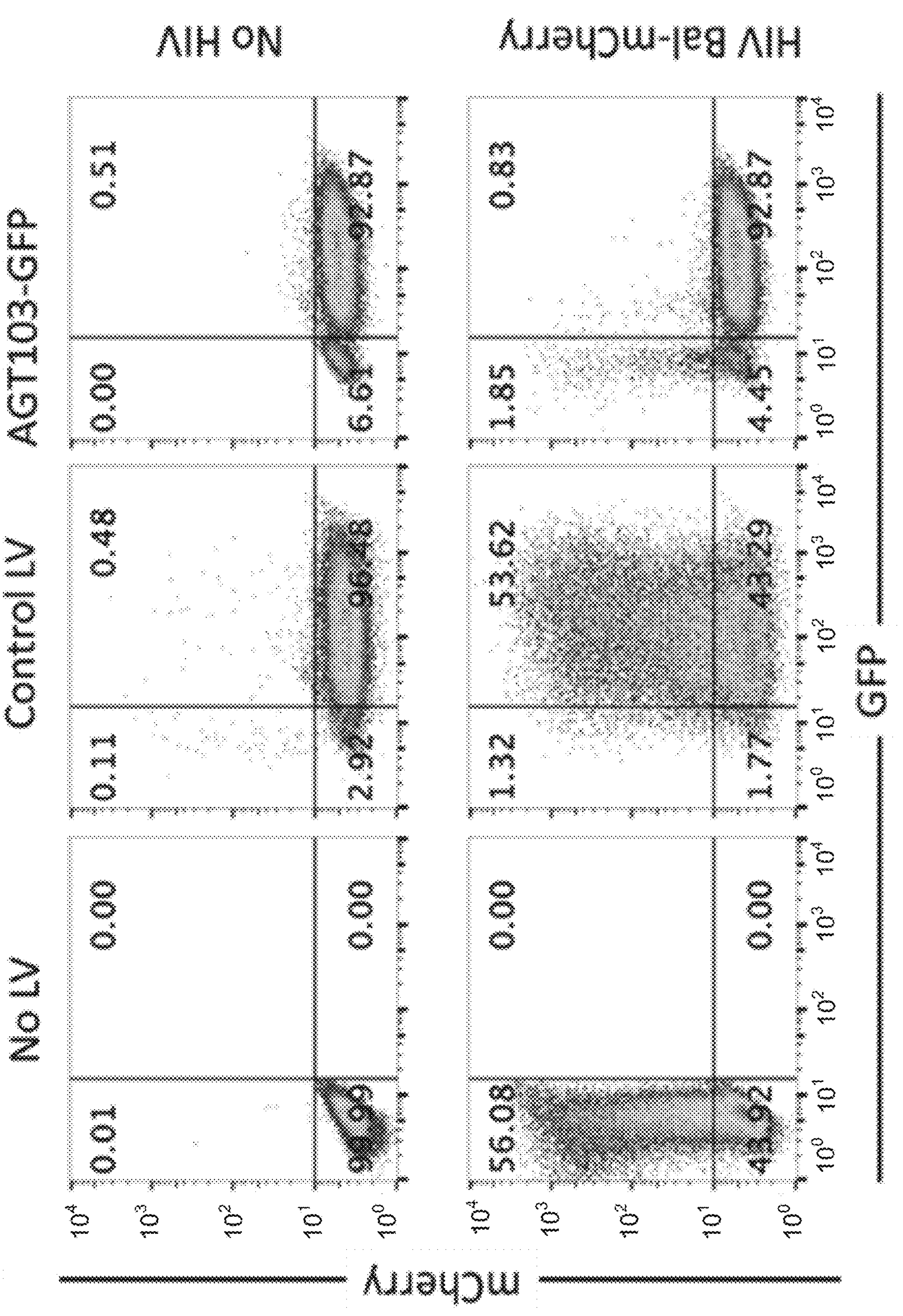

FIG. 8B shows the relative insensitivity of transfected AGTc120 cells to infection with HIV. As above, the lentivirus vectors express mCherry protein and a transduced cell that was also infected with HIV (expressing GFP) would appear as a double positive cell in the upper right quadrant of the false color flow cytometry dot plots. In the absence of HIV (upper panels), there were no GFP+ cells under any condition. After HIV infection (lower panels), 56% of cells were infected in the absence of lentivirus transduction and 53.6% of cells became infected in AGTc120 cells transduced with the LV-CMV-mCherry. When cells were transduced with the therapeutic AGT103/CMV-mCherry vector, only 0.83% of cells appeared in the double positive quadrant indicating they were transduced and infected.

Dividing 53.62 (proportion of double positive cells with control vector) by 0.83 (the proportion of double positive cells with the therapeutic vector) shows that AGT103 provided greater than 65-fold protection against HIV in this experimental system.

Example 5: Regulation of CCR5 Expression by shRNA Inhibitor Sequences in a Lentiviral Vector Inhibitory RNA Design. The sequence of *Homo sapiens* chemokine receptor CCR5 (CCR5, NC 000003.12) was used to search for potential siRNA or shRNA candidates to knockdown CCR5 levels in human cells. Potential RNA interference sequences were chosen from candidates selected by siRNA or shRNA design programs such as from the Broad Institute or the BLOCK-IT RNA iDesigner from Thermo Scientific. A shRNA sequence may be inserted into a plasmid immediately after a RNA polymerase III promoter such as H1, U6, or 7SK to regulate shRNA expression. The shRNA sequence may also be inserted into a lentiviral vector using similar promoters or embedded within a microRNA backbone to allow for expression by an RNA polymerase II promoter such as CMV or EF-1 alpha. The RNA sequence may also be synthesized as a siRNA oligonucleotide and utilized independently of a plasmid or lentiviral vector.

Plasmid Construction. For CCR5 shRNA, oligonucleotide sequences containing BamHI and EcoRI restriction sites were synthesized by MWG Operon. Oligonucleotide sequences were annealed by incubating at 70° C. then cooled to room temperature. Annealed oligonucleotides were digested with the restriction enzymes BamHI and EcoRI for one hour at 37° C., then the enzymes were inactivated at 70° C. for 20 minutes. In parallel, plasmid DNA was digested with the restriction enzymes BamHI and EcoRI for one hour at 37° C. The digested plasmid DNA was purified by agarose gel electrophoresis and extracted from the gel using a DNA gel extraction kit from Invitrogen. The DNA concentration was determined and the plasma to oligonucleotide sequence was ligated in the ratio 3:1 insert to vector. The ligation reaction was done with T4 DNA ligase for 30 minutes at room temperature. 2.5 μL of the ligation mix were added to 25 μL of STBL3 competent bacterial cells. Transformation required heat shock at 42° C. Bacterial cells were spread on agar plates containing ampicillin and colonies were expanded in L broth. To check for insertion of the oligo sequences, plasmid DNA was extracted from harvested bacterial cultures using the Invitrogen DNA Miniprep kit and tested by restriction enzyme digestion. Insertion of the shRNA sequence into the plasmid was verified by DNA sequencing using a primer specific for the promoter used to regulate shRNA expression.

Functional Assay for CCR5 mRNA Reduction: The assay for inhibition of CCR5 expression required co-transfection of two plasmids. The first plasmid contains one of five different shRNA sequences directed against CCR5 mRNA. The second plasmid contains the cDNA sequence for human CCR5 gene. Plasmids were co-transfected into 293T cells. After 48 hours, cells were lysed and RNA was extracted using the RNeasy kit from Qiagen. cDNA was synthesized from RNA using a Super Script Kit from Invitrogen. The samples were then analyzed by quantitative RT-PCR using an Applied Biosystems Step One PCR machine. CCR5 expression was detected with SYBR Green from Invitrogen using the forward primer (5'-AGGAATT-GATGGCGAGAAGG-3') (SEQ ID NO: 93) and reverse primer (5'-CCCCAAAGAAGGTCAAGGTAATCA-3') (SEQ ID NO: 94) with standard conditions for polymerase chain reaction analysis. The samples were normalized to the mRNA for beta actin gene expression using the forward primer (5'-AGCGCGGCTACAGCTTCA-3') (SEQ ID NO: 95) and reverse primer (5'-GGCGACGTAGCACAGCTTCT-3') (SEQ ID NO: 96) with standard conditions for polymerase chain reaction analysis. The relative expression of CCR5 mRNA was determined by its Ct value normalized to the level of actin messenger RNA for each sample. The results are shown in FIG. 9.

Figure 9A:
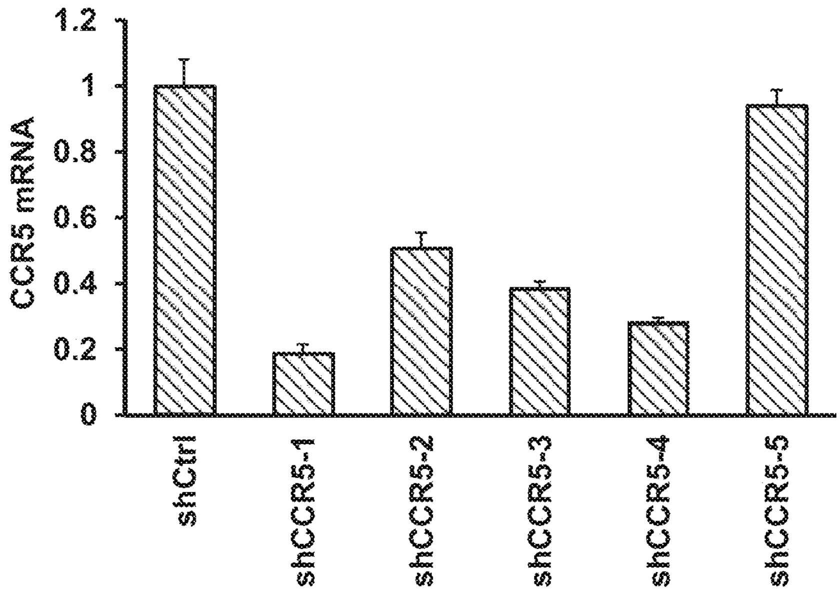
FIG. 9 depicts data demonstrating regulation of CCR5 expression by shRNA inhibitor sequences in a lentiviral vector. (A) Screening data for potential candidates is shown. (B) CCR5 knock-down data following transduction with CCR5 shRNA-1 (SEQ ID NO: 16) is shown.
Figure 9B:
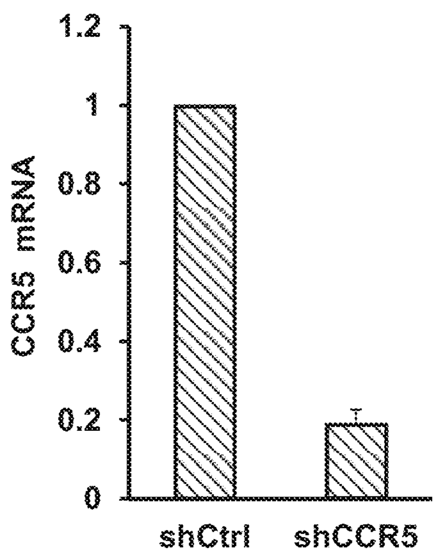

As shown in FIG. 9A, CCR5 knock-down was tested in 293T cells by co-transfection of the CCR5 shRNA construct and a CCR5-expressing plasmid. Control samples were transfected with a scrambled shRNA sequence that did not target any human gene and the CCR5-expressing plasmid. After 60 hours post-transfection, samples were harvested and CCR5 mRNA levels were measured by quantitative PCR. Further, as shown in FIG. 9B, CCR5 knock-down after transduction with lentivirus expressing CCR5 shRNA-1 (SEQ ID NO: 16).

Example 6: Regulation of HIV Components by shRNA Inhibitor Sequences in a Lentiviral Vector Inhibitory RNA Design.

The sequences of HIV type 1 Rev/Tat (5'-GCGGA-GACAGCGACGAAGAGC-3') (SEQ ID NO: 9) and Gag (5'-GAAGAAATGATGACAGCAT-3') (SEQ ID NO: 11) were used to design:

```
Rev/Tat:
                                          (SEQ ID NO: 10)
(5'GCGGAGACAGCGACGAAGAGCTTCAAGAGAGCTCTTCGTCGCTGTC
TCCGCTTTTT-3')
and

Gag:
                                          (SEQ ID NO: 12)
(5'GAAGAAATGATGACAGCATTTCAAGAGAATGCTGTCATCATTTCTT
CTTTTT-3')
```

shRNA that were synthesized and cloned into plasmids as described above.

Plasmid Construction. The Rev/Tat or Gag target sequences were inserted into the 3'UTR (untranslated region) of the firefly luciferase gene used commonly as a reporter of gene expression in cells or tissues. Additionally, one plasmid was constructed to express the Rev/Tat shRNA and a second plasmid was constructed to express the Gag shRNA. Plasmid constructions were as described above.

Functional assay for shRNA targeting of Rev/Tat or Gag mRNA: Using plasmid co-transfection we tested whether a shRNA plasmid was capable of degrading luciferase messenger RNA and decreasing the intensity of light emission in co-transfected cells. A shRNA control (scrambled sequence) was used to establish the maximum yield of light from luciferase transfected cells. When the luciferase construct containing a Rev/Tat target sequence inserted into the 3'-UTR (untranslated region of the mRNA) was co-transfected with the Rev/Tat shRNA sequence there was nearly a 90% reduction in light emission indicating strong function of the shRNA sequence. A similar result was obtained when a luciferase construct containing a Gag target sequence in the 3'-UTR was co-transfected with the Gag shRNA sequence. These results indicate potent activity of the shRNA sequences.

Figure 10A:
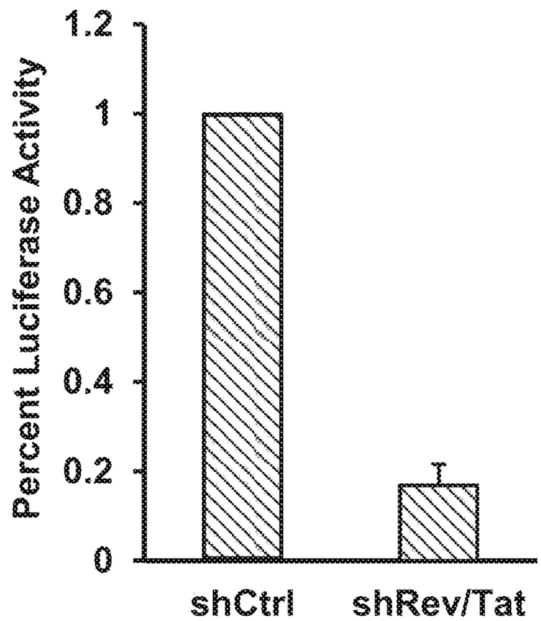
FIG. 10 depicts data demonstrating regulation of HIV components by shRNA inhibitor sequences in a lentiviral vector. (A) Knock-down data for the Rev/Tat target gene is shown. (B) Knock-down data for the Gag target gene is shown.
Figure 10B:
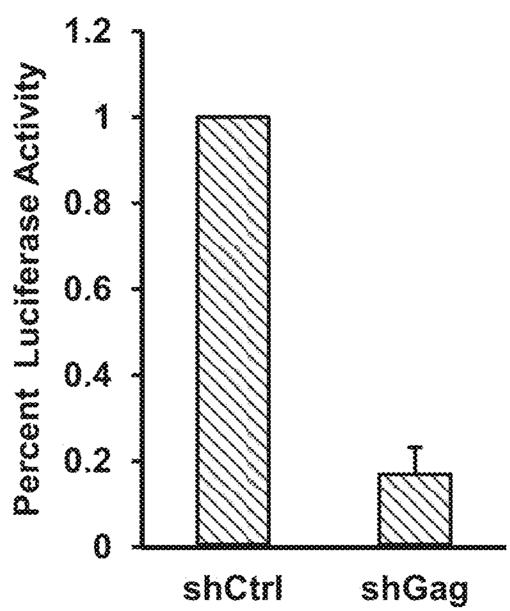

As shown in FIG. 10A, knock-down of the Rev/Tat target gene was measured by a reduction of luciferase activity, which was fused with the target mRNA sequence in the 3'UTR, by transient transfection in 293T cells. As shown in FIG. 10B, knock-down of the Gag target gene sequence fused with the luciferase gene. The results are displayed as the mean f SD of three independent transfection experiments, each in triplicate.

Example 7: AGT103 Decreases Expression of Tat and Vif

Cells were transfected with exemplary vector AGT103/CMV-GFP. AGT103 and other exemplary vectors are defined in Table 3 below.

TABLE 3

| Vector Designation | Composition |
|---|---|
| AGT103 | EF1-miR30CCR5-miR21Vif-miR185-Tat-WPRE |
| Control-mCherry | CMV-mCherry |
| AGT103/CMV-mCherry | CMV-mCherry-EF1-miR30CCR5-miR21Vif-miR185-Tat-WPRE- |
| Control-GFP | CMV-mCherry |
| AGT103/CMV-GFP | CMV-GFP-EF1-miR30CCR5-miR21Vif-miR185-Tat-WPRE- |

Figure 11:
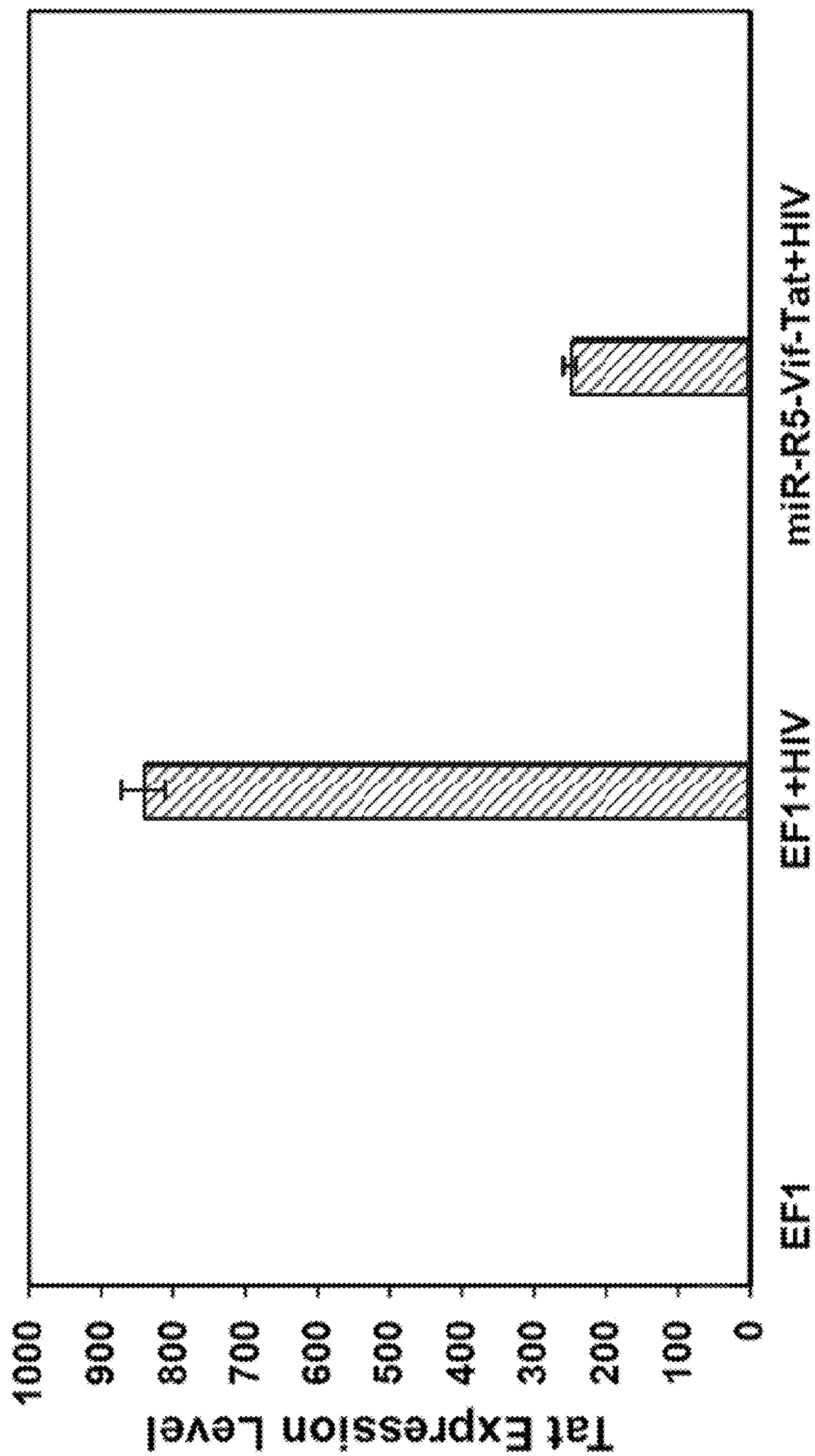
FIG. 11 depicts data demonstrating that AGT103 reduces expression of Tat protein expression in cells transfected with an HIV expression plasmid, as described herein.

Abbreviations:
EF-1: elongation factor 1 transcriptional promoter
miR30CCR5—synthetic microRNA capable of reducing CCR5 protein on cell surfaces
miR21Vif—synthetic microRNA capable of reducing levels of HIV RNA and Vif protein expression
miR185Tat—synthetic micro RNA capable of reducing levels of HIV RNA and Tat protein expression
CMV—Immediate early transcriptional promoter from human cytomegalovirus
mCherry—coding region for the mCherry red fluorescent protein
GFP—coding region for the green fluorescent protein
WPRE—Woodchuck hepatitis virus post transcriptional regulatory element A T lymphoblastoid cell line (CEM; CCRF-CEM; American Type Culture Collection Catalogue number CCL119) was transduced with AGT103/CMV-GFP. 48 hours later the cells were transfected with an HIV expression plasmid encoding the entire viral sequence. After 24 hours, RNA was extracted from cells and tested for levels of intact Tat sequences using reverse transcriptase polymerase chain reaction. Relative expression levels for intact Tat RNA were reduced from approximately 850 in the presence of control lentivirus vector, to approximately 200 in the presence of AGT103/CMV-GFP for a total reduction of >4 fold, as shown in FIG. 11.

Example 8: Regulation of HIV Components by Synthetic MicroRNA Sequences in a Lentiviral Vector Inhibitory RNA Design. The sequence of HIV-1 Tat and Vif genes were used to search for potential siRNA or shRNA candidates to knockdown Tat or Vif levels in human cells. Potential RNA interference sequences were chosen from candidates selected by siRNA or shRNA design programs such as from the Broad Institute or the BLOCK-IT RNA iDesigner from Thermo Scientific. The selected shRNA sequences most potent for Tat or Vif knockdown were embedded within a microRNA backbone to allow for expression by an RNA polymerase II promoter such as CMV or EF-I alpha. The RNA sequence may also be synthesized as a siRNA oligonucleotide and used independently of a plasmid or lentiviral vector.

Plasmid Construction. The Tat target sequence (5'-TCCGCTTCTTCCTGCCATAG-3') (SEQ ID NO: 7) was incorporated into the miR185 backbone to create a Tat miRNA (5'-GGGCCTGGCTCGAGCAGGGGGCGAGG-GATTCCGCTCTTCCTGCCATAGCGTGGT CCCCTCCCC-TATGGCAGGCAGAAGCGGCACCTTCCCTCC-CAATGACCGCGTCTTCG TCG-3') (SEQ ID NO: 3) that was inserted into a lentivirus vector and expressed under control of the EF-1 alpha promoter. Similarly, the Vif target sequence (5'-GGGATGTGTACTTCTGAACTT-3') (SEQ ID NO: 6) was incorporated into the miR21 backbone to create a Vif miRNA (5'-CATCTCCATGGCTGTAC-CACCTGTCGGGGGATGTGTACTTCT-GAACTTGTGTGA ATCTCATGGAGTCAGAAGAACA-CATCCGCACTGACATTTGGTATCTTTCATCTG ACCA-3') (SEQ ID NO: 2) that was inserted into a lentivirus vector and expressed under control of the EF-1 alpha promoter. The resulting Vif/Tat miRNA-expressing lentivirus vectors were produced in 293T cells using a lentiviral vector packaging system. The Vif and Tat miRNA were embedded into a microRNA cluster consisting of miR CCR5, miR Vif, and miR Tat all expressed under control of the EF-1 promoter.

Functional assay for miR185Tat inhibition of Tat mRNA accumulation. A lentivirus vector expressing miR185 Tat (LV-EF1-miR-CCR5-Vif-Tat) was used at a multiplicity of infection equal to 5 for transducing 293T cells. 24 hours after transduction the cells were transfected with a plasmid expressing HIV strain NL4-3 (pNL4-3) using Lipofectamine2000 under standard conditions. 24 hours later RNA was extracted and levels of Tat messenger RNA were tested by RT-PCR using Tat-specific primers and compared to actin mRNA levels for a control.

Functional assay for miR21 Vif inhibition of Vif protein accumulation. A lentivirus vector expressing miR21 Vif (LV-EF1-miR-CCR5-Vif-Tat) was used at a multiplicity of infection equal to 5 for transducing 293T cells. 24 hours after transduction, the cells were transfected with a plasmid expressing HIV strain NL4-3 (pNL4-3) using Lipofectamine2000. 24 hours later cells were lysed and total soluble protein was tested to measure the content of Vif protein. Cell lysates were separated by SDS-PAGE according to established techniques. The separated proteins were transferred to nylon membranes and probed with a Vif-specific monoclonal antibody or actin control antibody.

Figure 12:
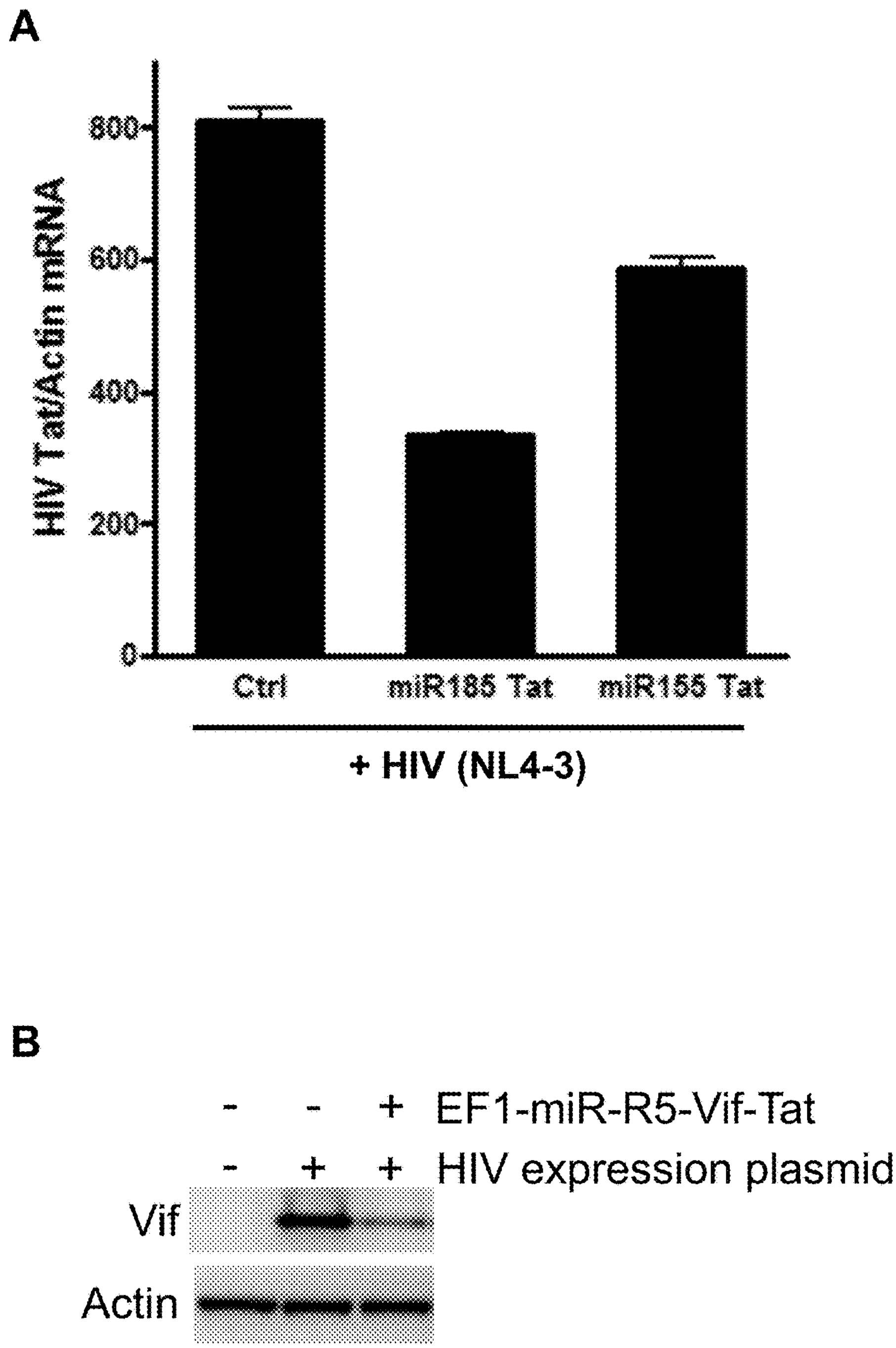
FIG. 12 depicts data demonstrating regulation of HIV components by synthetic microRNA sequences in a lentiviral vector. (A) Tat knock-down data is shown. (B) Vif knock-down data is shown.

As shown in FIG. 12A, Tat knock-down was tested in 293T cells transduced with either a control lentiviral vector or a lentiviral vector expressing either synthetic miR185 Tat or miR155 Tat microRNA. After 24 hours, the HIV vector pNL4-3 was transfected with Lipofectamine2000 for 24 hours and then RNA was extracted for qPCR analysis with primers for Tat. As shown in FIG. 12B, Vif knock-down was tested in 293T cells transduced with either a control lentiviral vector or a lentiviral vector expressing a synthetic miR21 Vif microRNA. After 24 hours, the HIV vector pNL4-3 was transfected with Lipofectamine2000 for 24 hours and then protein was extracted for immunoblot analysis with an antibody for HIV Vif.

Figure 13:
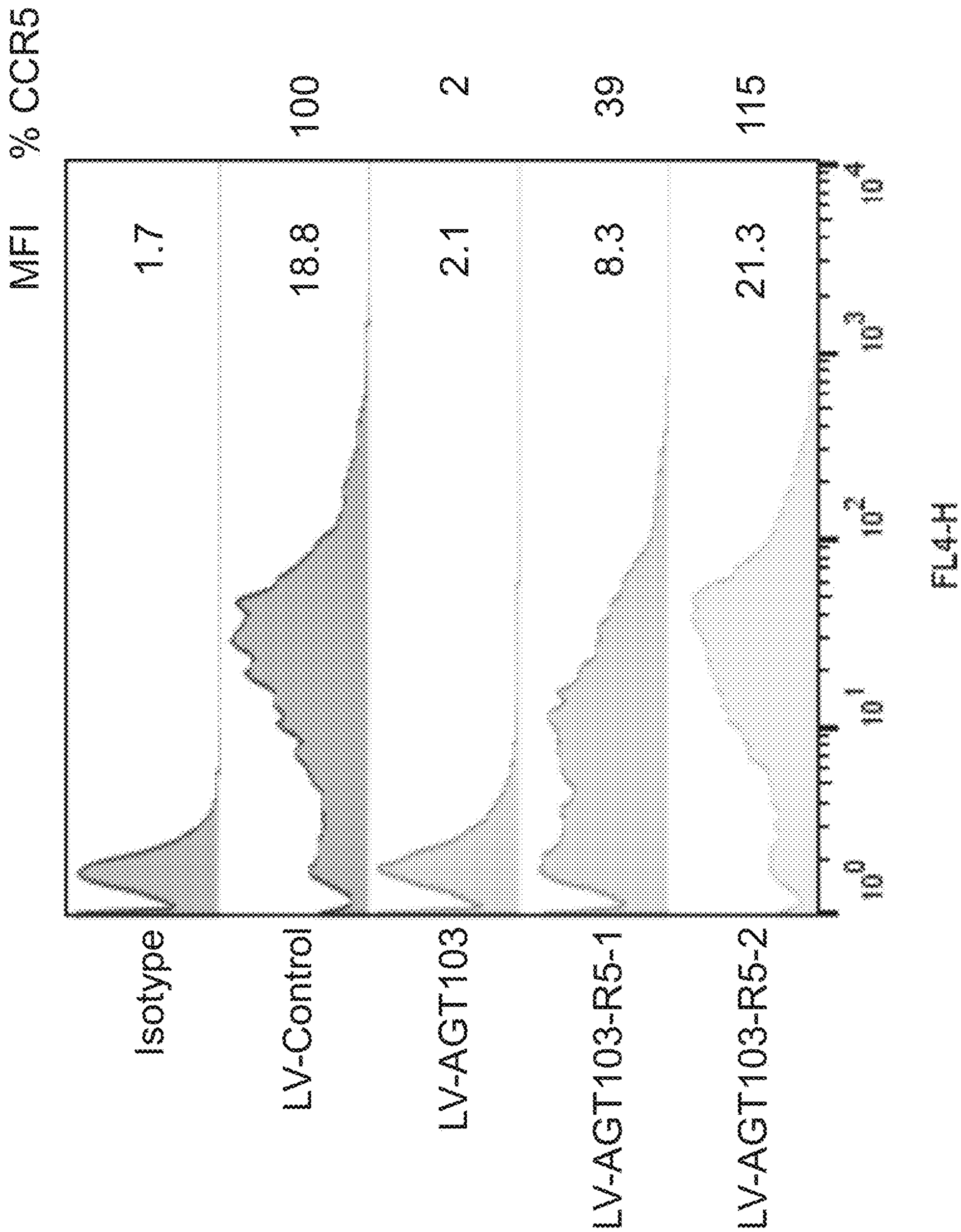
FIG. 13 depicts data demonstrating regulation of CCR5 expression by synthetic microRNA sequences in a lentiviral vector.

Example 9: Regulation of CCR5 Expression by Synthetic microRNA Sequences in a Lentiviral Vector CEM-CCR5 cells were transduced with a lentiviral vector containing a synthetic miR30 sequence for CCR5 (AGT103: TGTAAACTGAGCTTGCTCTA (SEQ ID NO: 97), AGT103-R5-1: TGTAAACTGAGCTTGCTCGC (SEQ ID NO: 98), or AGT103-R5-2: CATAGATTGGACTTGACAC (SEQ ID NO: 99). After 6 days, CCR5 expression was determined by FACS analysis with an APC-conjugated CCR5 antibody and quantified by mean fluorescence intensity (MFI). CCR5 levels were expressed as % CCR5 with LV-Control set at 100%. The target sequence of AGT103 and AGT103-R5-1 is in the same region as CCR5 target sequence #5. The target sequence of AGT103-R5-2 is the same as CCR5 target sequence #1. AGT103 (2% of total CCR5) is most effective at reducing CCR5 levels as compared with AGT103-R5-1 (39% of total CCR5) and AGT103-R5-2 which does not reduce CCR5 levels. The data is demonstrated in FIG. 13 herein.

Example 10: Regulation of CCR5 Expression by Synthetic microRNA Sequences in a Lentiviral Vector Containing Either a Long or Short WPRE Sequence Vector Construction. Lentivirus vectors often require an RNA regulatory element for optimal expression of therapeutic genes or genetic constructs. A common choice is to use the Woodchuck hepatitis virus post transcriptional regulatory element (WPRE). We compared AGT103 that contains a full-length WPRE:

```
                                           (SEQ ID NO: 32)
(5'AATCAACCTCTGATTACAAAATTTGTGAAAGATTGACTGGTATTCTT
AACTATGTTGCTCCTTTTACGCTATGTGGATACGCTGCTTTAATGCCTTT
GTATCATGCTATTGCTTCCCGTATGGCTTTCATTTTCTCCTCCTTGTATA
AATCCTGGTTGCTGTCTCTTTATGAGGAGTTGTGGCCCGTTGTCAGGCAA
CGTGGCGTGGTGTGCACTGTGTTTGCTGACGCAACCCCCACTGGTTGGGG
CATTGCCACCACCTGTCAGCTCCTTTCCGGGACTTTCGCTTTCCCCCTCC
CTATTGCCACGGCGGAACTCATCGCCGCCTGCCTTGCCCGCTGCTGGACA
GGGGCTCGGCTGTTGGGCACTGACAATTCCGTGGTGTTGTCGGGGAAATC
ATCGTCCTTTCCTTGGCTGCTCGCCTGTGTTGCCACCTGGATTCTGCGCG
GGACGTCCTTCTGCTACGTCCCTTCGGCCCTCAATCCAGCGGACCTTCCT
TCCCGCGGCCTGCTGCCGGCTCTGCGGCCTCTTCCGCGTCTTCGCCTTCG
CCCTCAGACGAGTCGGATCTCCCTTTGGGCCGCCTCCCCGCCT-3')
```

with a modified AGT103 vector containing a shortened WPRE element (SEQ ID NO: 80)
(5'AATCAACCTCTGGATTACAAAATTTGTGAAAGATTGACTGATATTCT

TAACTATGTTGCTCCTTTTACGCTGTGTGGATATGCTGCTTTAATGCCTC

TGTATCATGCTATTGCTTCCCGTACGGCTTTCGTTTTCTCCTCCTTGTAT

AAATCCTGGTTGCTGTCTCTTTATGAGGAGTTGTGGCCCGTTGTCCGTCA

ACGTGGCGTGGTGTGCTCTGTGTTTGCTGACGCAACCCCCACTGGCTGGG

GCATTGCCACCACCTGTCAACTCCTTTCTGGGACTTTCGCTTTCCCCCTC

CCGATCGCCACGGCAGAACTCATCGCCGCCTGCCTTGCCCGCTGCTGGAC

AGGGGCTAGGTTGCTGGGCACTGATAATTCCGTGGTGTTGTC-3').

Functional assay for modulating cell surface CCR5 expression as a function of long versus short WPRE element in the vector sequence. AGT103 containing long or short WPRE elements were used for transducing CEM-CCR5 T cells a multiplicity of infection equal to 5. Six days after transduction cells were collected and stained with a monoclonal antibody capable of detecting cell surface CCR5 protein. The antibody was conjugated to a fluorescent marker and the intensity of staining is directly proportional to the level of CCR5 on the cell surface. A control lentivirus had no effect on cell surface CCR5 levels resulting in a single population with a mean fluorescence intensity of 73.6 units. The conventional AGT103 with a long WPRE element reduced CCR5 expression to a mean fluorescence intensity level of 11 units. AGT103 modified to incorporate a short WPRE element resulted in a single population of cells with mean fluorescence intensity of 13 units. Accordingly, substituting a short WPRE element had little or no effect on the capacity for AGT103 to reduce cell surface CCR5 expression.

Figure 14:
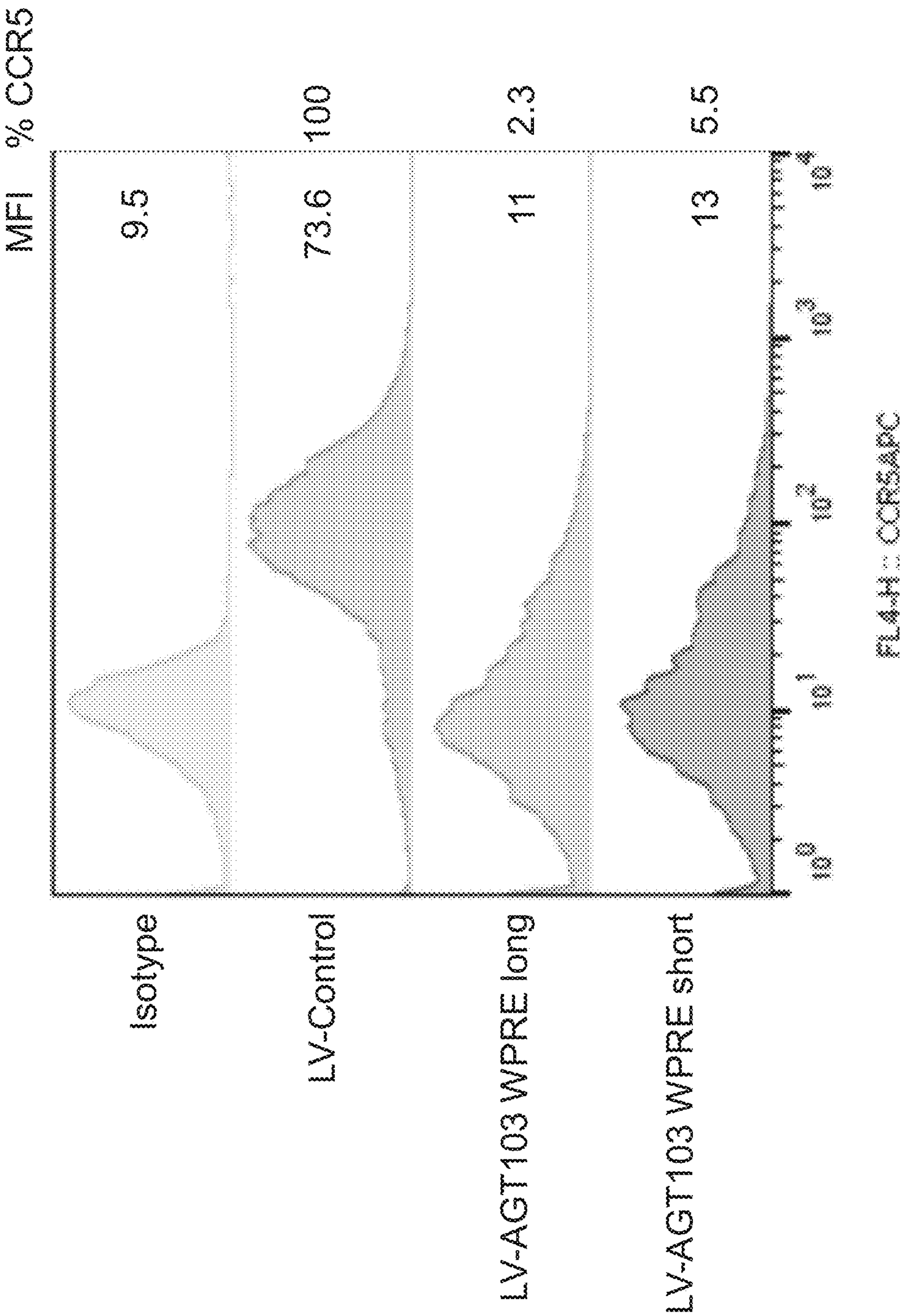
FIG. 14 depicts data demonstrating regulation of CCR5 expression by synthetic microRNA sequences in a lentiviral vector containing either a long or short WPRE sequence.

As shown in FIG. 14, CEM-CCR5 cells were transduced with AGT103 containing either a long or short WPRE sequence. After 6 days, CCR5 expression was determined by FACS analysis with an APC-conjugated CCR5 antibody and quantified as mean fluorescence intensity (MFI). CCR5 levels were expressed as % CCR5 with LV-Control set at 100%. The reduction in CCR5 levels was similar for AGT103 with either the short (5.5% of total CCR5) or long (2.3% of total CCR5) WPRE sequence.

Example 11: Regulation of CCR5 Expression by Synthetic microRNA Sequences in a Lentiviral Vector with or without a WPRE Sequence Vector construction. In order to test whether WPRE was required for AGT103 down regulation of CCR5 expression we constructed a modified vector without WPRE element sequences.

Functional assay for modulating cell surface CCR5 expression as a function of including or not including a long WPRE element in the AGT103 vector. In order to test whether WPRE was required for AGT103 modulation of CCR5 expression levels we transduced CEM-CCR5 T cells with AGT103 or a modified vector lacking WPRE using a multiplicity of infection equal to 5. Six days after transduction cells were collected and stained with a monoclonal antibody capable of recognizing cell surface CCR5 protein. The monoclonal antibody was directly conjugated to a fluorescent marker and the intensity of staining is directly proportional to the number of CCR5 molecules per cell surface. A lentivirus control vector had no effect on cell surface CCR5 levels resulting in a uniform population with mean fluorescence intensity of 164. The lentivirus vector (AGT103 with a long WPRE and also expressing GFP marker protein), AGT103 lacking GFP but containing a long WPRE element, or AGT103 lacking both GFP and WPRE all were similarly effective for modulating cell surface CCR5 expression. After removing GFP, AGT103 with or without WPRE elements were indistinguishable in terms of their capacity for modulating cell surface CCR5 expression.

Figure 15:
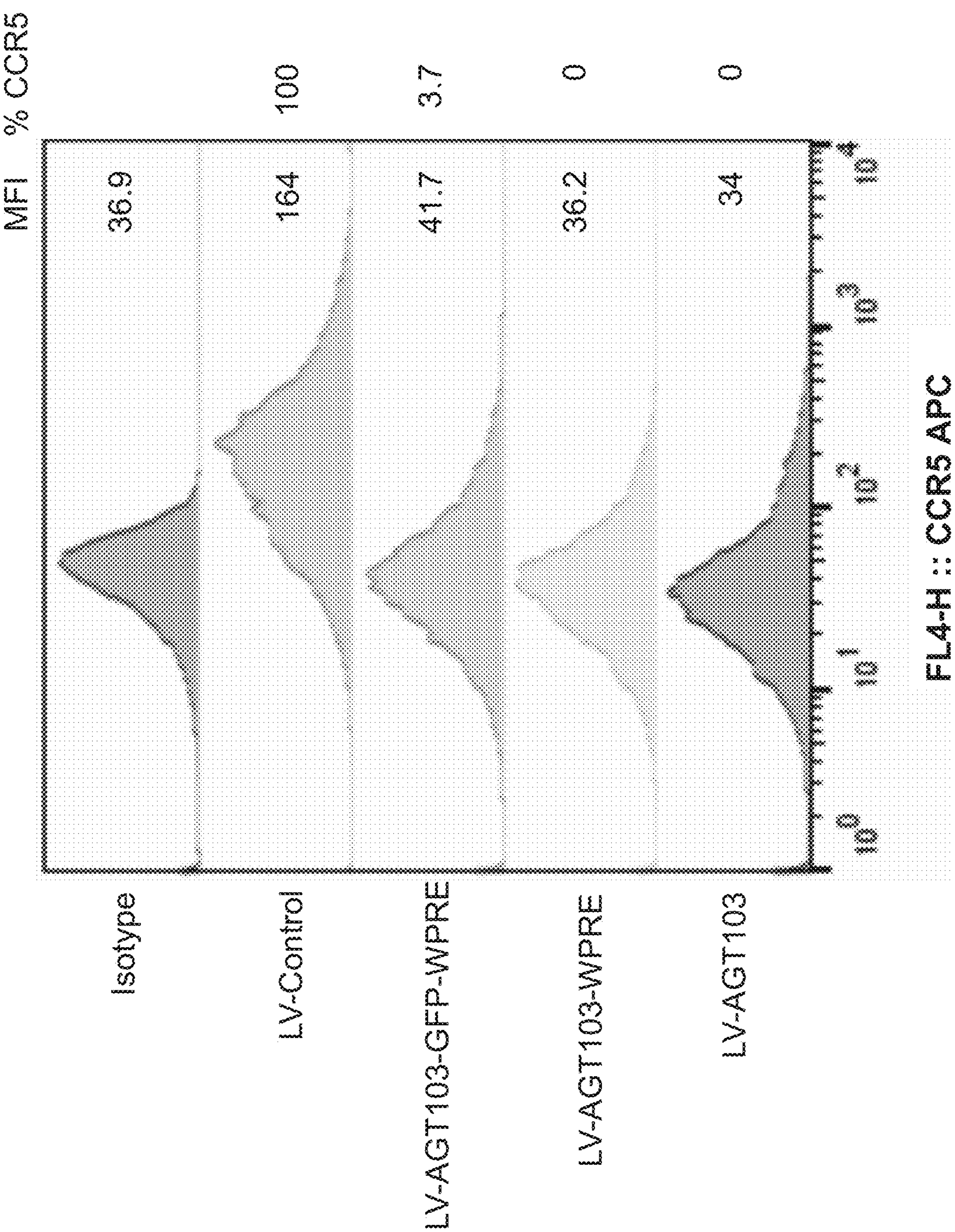
FIG. 15 depicts data demonstrating regulation of CCR5 expression by synthetic microRNA sequences in a lentiviral vector with or without a WPRE sequence.

CEM-CCR5 cells were transduced with AGT103 with or without GFP and WPRE. After 6 days, CCR5 expression was determined by FACS analysis with an APC-conjugated CCR5 antibody and quantified as mean fluorescence intensity (MFI). CCR5 levels were expressed as % CCR5 with LV-Control set at 100%. The reduction in CCR5 levels was similar for AGT103 with (0% of total CCR5) or without (0% of total CCR5) the WPRE sequence. This data is demonstrated in FIG. 15.

Example 12: Regulation of CCR5 Expression by a CD4 Promoter Regulating Synthetic microRNA Sequences in a Lentiviral Vector Vector Construction. A modified version of AGT103 was constructed to test the effect of substituting alternate promoters for expressing the microRNA cluster that suppresses CCR5, Vif and Tat gene expression. In place of the normal EF-1 promoter we substituted the T cell-specific promoter for CD4 glycoprotein expression using the sequence:

(SEQ ID NO: 30)
(5'TGTTGGGGTTCAAATTTGAGCCCCAGCTGTTAGCCCTCTGCAAAGAA

AAAAAAAAAAAAAAAAGAACAAAGGGCCTAGATTTCCCTTCTGAGCCCCA

CCCTAAGATGAAGCCTCTTCTTTCAAGGGAGTGGGGTTGGGGTGGAGGCG

GATCCTGTCAGCTTTGCTCTCTCTGTGGCTGGCAGTTTCTCCAAAGGGTA

ACAGGTGTCAGCTGGCTGAGCCTAGGCTGAACCCTGAGACATGCTACCTC

TGTCTTCTCATGGCTGGAGGCAGCCTTTGTAAGTCACAGAAAGTAGCTGA

GGGGCTCTGGAAAAAAGACAGCCAGGGTGGAGGTAGATTGGTCTTTGACT

CCTGATTTAAGCCTGATTCTGCTTAACTTTTTCCCTTGACTTTGGCATTT

TCACTTTGACATGTTCCCTGAGAGCCTGGGGGGTGGGGAACCCAGCTCCA

GCTGGTGACGTTTGGGGCCGGCCCAGGCCTAGGGTGTGGAGGAGCCTTGC

CATCGGGCTTCCTGTCTCTCTTCATTTAAGCACGACTCTGCAGA-3').

Functional assay comparing EF-1 and CD4 gene promoters in terms of potency for reducing cell surface CCR5 protein expression. AGT103 modified by substituting the CD4 gene promoter for the normal EF-1 promoter was used for transducing CEM-CCR5 T cells. Six days after transduction cells were collected and stained with a monoclonal antibody capable of recognizing cell surface CCR5 protein. The monoclonal antibody was conjugated to a fluorescent marker and staining intensity is directly proportional to the level of cell surface CCR5 protein. A control lentivirus transduction resulted in a population of CEM-CCR5 T cells that were stained with a CCR5-specific monoclonal antibody and produced a mean fluorescence intensity of 81.7 units. The modified AGT103 using a CD4 gene promoter in place of the EF-1 promoter for expressing microRNA showed a broad distribution of staining with a mean fluorescence intensity roughly equal to 17.3 units. Based on this result, the EF-1 promoter is at least similar and likely superior to the CD4 gene promoter for microRNA expression. Depending on the desired target cell population, the EF-1 promoter is universally active in all cell types and the CD4 promoter is only active in T-lymphocytes.

Figure 16:
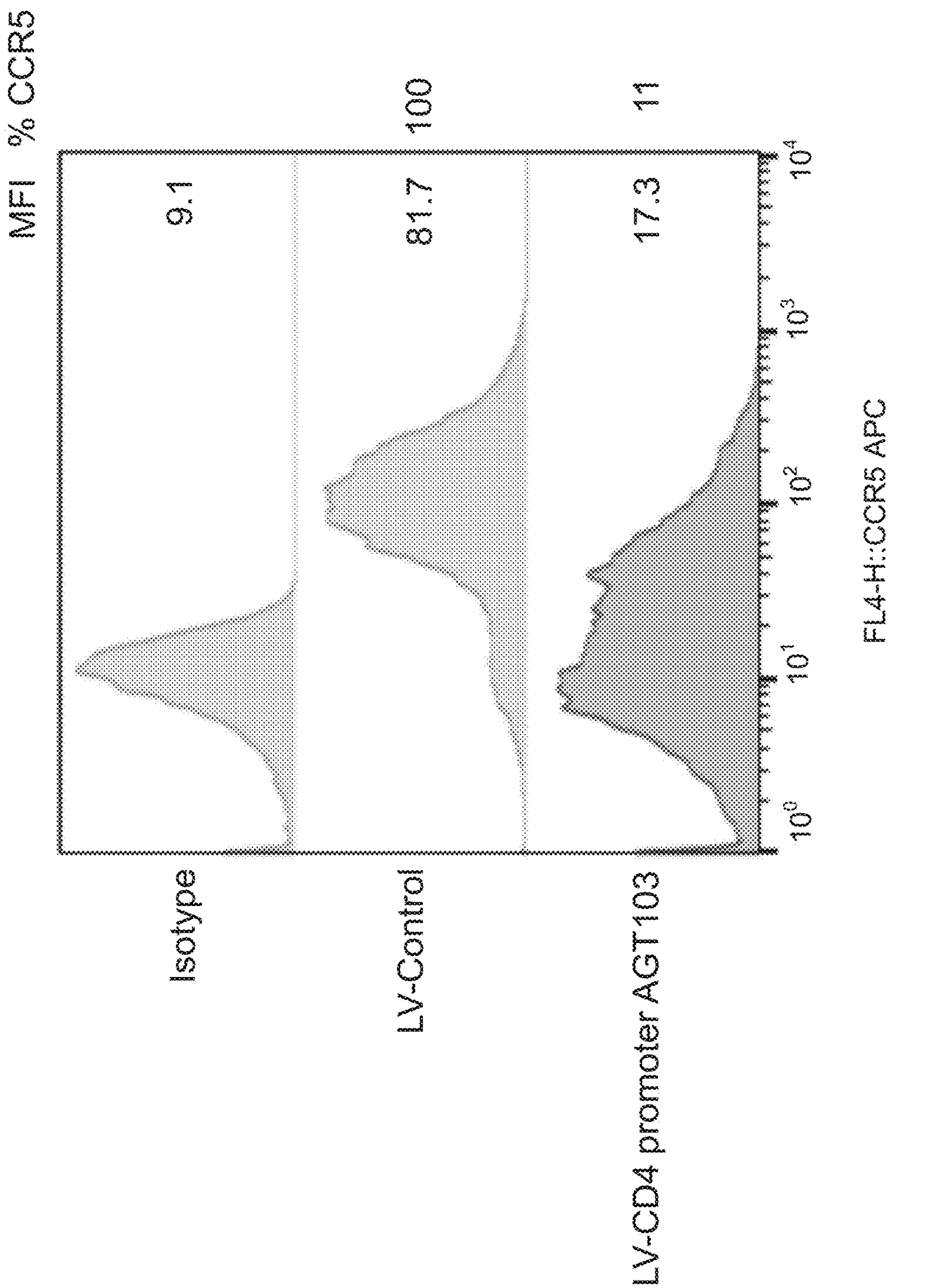
FIG. 16 depicts data demonstrating regulation of CCR5 expression by a CD4 promoter regulating synthetic microRNA sequences in a lentiviral vector.

CEM-CCR5 cells were transduced with a lentiviral vector containing a CD4 promoter regulating a synthetic microRNA sequence for CCR5, Vif, and Tat (AGT103). After 6 days, CCR5 expression was determined by FACS analysis with an APC-conjugated CCR5 antibody and quantified as mean fluorescence intensity (MFI). CCR5 levels were expressed as % CCR5 with LV-Control set at 100%. In cells transduced with LV-CD4-AGT103, CCR5 levels were 11% of total CCR5. This is comparable to that observed for LV-AGT103 which contains the EF1 promoter. This data is demonstrated in FIG. 16.

Example 13: Detecting HIV Gag-Specific CD4 T Cells

Cells and reagents. Viable frozen peripheral blood mononuclear cells (PBMC) were obtained from a vaccine company. Data were obtained with a representative specimen from an HIV+ individual who was enrolled into an early stage clinical trial (TRIAL REGISTRATION: clinicaltrials-.gov NCT01378156) testing a candidate HIV therapeutic vaccine. Two specimens were obtained for the "Before vaccination" and "After vaccination" studies. Cell culture products, supplements and cytokines were from commercial suppliers. Cells were tested for responses to recombinant Modified Vaccinia Ankara 62B from Geovax Corporation as described in Thompson, M., S. L. Heath, B. Sweeton, K. Williams, P. Cunningham, B. F. Keele, S. Sen, B. E. Palmer, N. Chomont, Y. Xu, R. Basu, M. S. Hellerstein, S. Kwa and H. L. Robinson (2016). "DNA/MVA Vaccination of HIV-1 Infected Participants with Viral Suppression on Antiretroviral Therapy, followed by Treatment Interruption: Elicitation of Immune Responses without Control of Re-Emergent Virus." PLoS One 11(10): e0163164. Synthetic peptides representing the entire HIV-1 Gag polyprotein were obtained from GeoVax or the HIV (GAG) Ultra peptide sets were obtained from JPT Peptide Technologies GmbH (www.jpt.com), Berlin, Germany. HIV (GAG) Ultra contains 150 peptides each being 15 amino acids in length and overlapping by 11 amino acids. They were chemically synthesized then purified and analyzed by liquid chromatography-mass spectrometry. Collectively these peptides represent major immunogenic regions of the HIV Gag polyprotein and are designed for average coverage of 57.8% among known HIV strains. Peptide sequences are based on the HIV sequence database from the Los Alamos National Laboratory (http://www.hiv.lanl.gov/content/sequence/NEWALIGN/align.html). Peptides are provided as dried trifluoroacetate salts, 25 micrograms per peptide, and are dissolved in approximately 40 microliters of DMSO then diluted with PBS to final concentration. Monoclonal antibodies for detecting CD4 and cytoplasmic IFN-gamma were obtained from commercial sources and intracellular staining was done with the BD Pharmingen Intracellular Staining Kit for interferon-gamma. Peptides were resuspended in DMSO and we include a DMSO only control condition.

Functional assay for detecting HIV-specific CD4+ T cells. Frozen PBMC were thawed, washed and resuspended in RPMI medium containing 10% fetal bovine serum, supplements and cytokines. Cultured PBMC collected before or after vaccination were treated with DMSO control, MVA GeoVax (multiplicity of infection equal to 1 plaque forming unit per cell), Peptides GeoVax (1 microgram/ml) or HIV (GAG) Ultra peptide mixture (1 microgram/ml) for 20 hours in the presence of Golgi Stop reagent. Cells were collected, washed, fixed, permeabilized and stained with monoclonal antibodies specific for cell surface CD4 or intracellular interferon-gamma. Stained cells were analyzed with a FACSCalibur analytical flow cytometer and data were gated on the CD4+ T cell subset. Cells highlighted within boxed regions are double-positive and designated HIV-specific CD4 T cells on the basis of interferon-gamma expression after MVA or peptide stimulation. Numbers within the boxed regions show the percentage of total CD4 that were identified as HIV-specific. We did not detect strong responses to DMSO or MVA. Peptides from GeoVax elicited fewer responding cells compared to HIV (GAG) Ultra peptide mixture from JPT but differences were small and not significant.

Figure 17:
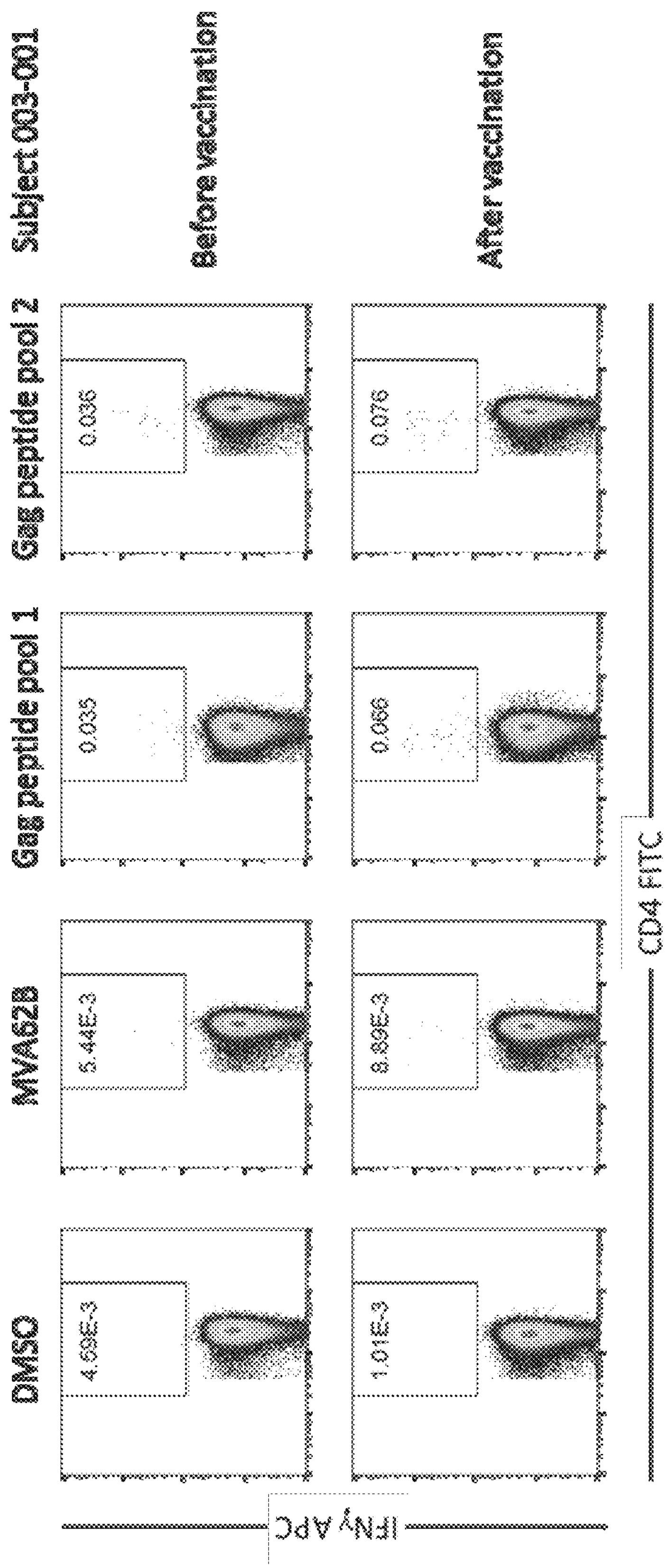
FIG. 17 depicts data demonstrating detection of HIV Gag-specific CD4 T cells.
Figure 18A:
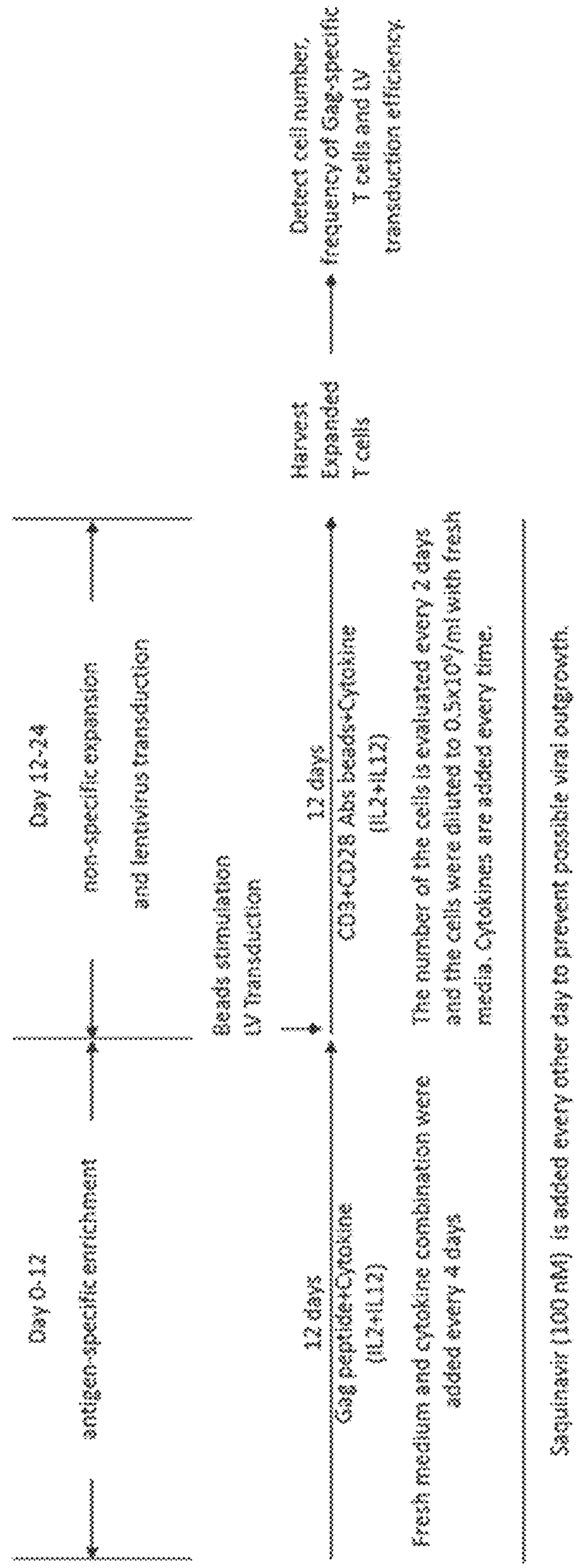
FIG. 18 depicts data demonstrating HIV-specific CD4 T cell expansion and lentivirus transduction. (A) A schedule of treatment is shown. (B) IFN-gamma production in CD4-gated T cells is shown, as described herein. (C) IFN-gamma production and GFP expression in CD4-gated T cells is shown, as described herein. (D) Frequency of HIV-specific CD4+ T cells is shown, as described herein, and importantly, pre- and post-vaccination. (E) IFN-gamma production from PBMCs post-vaccination is shown, as described herein.
Figure 18B:
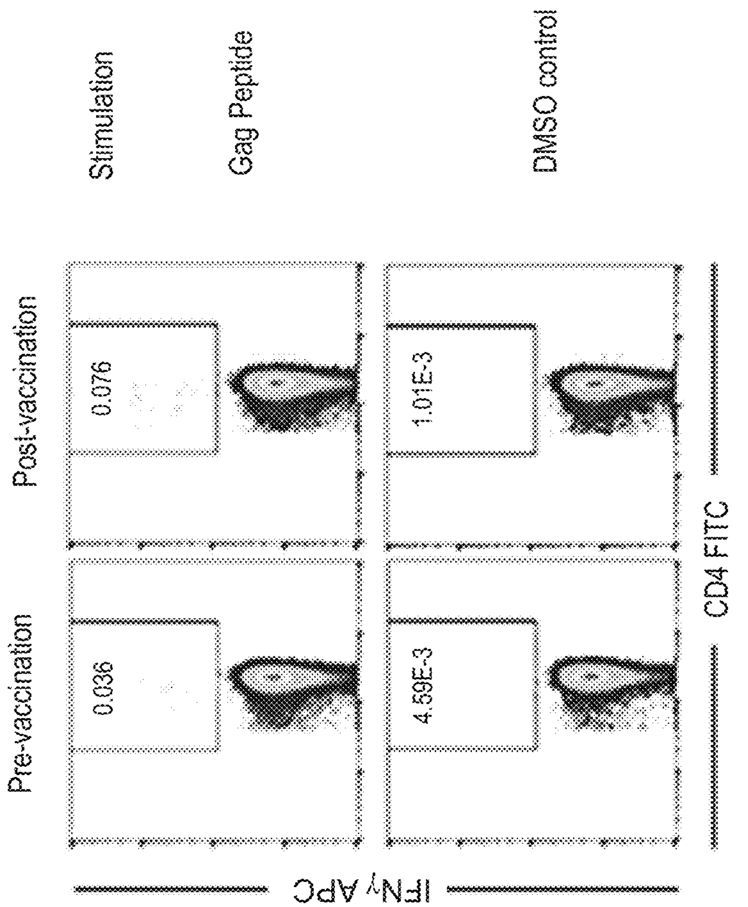
Figure 18C:
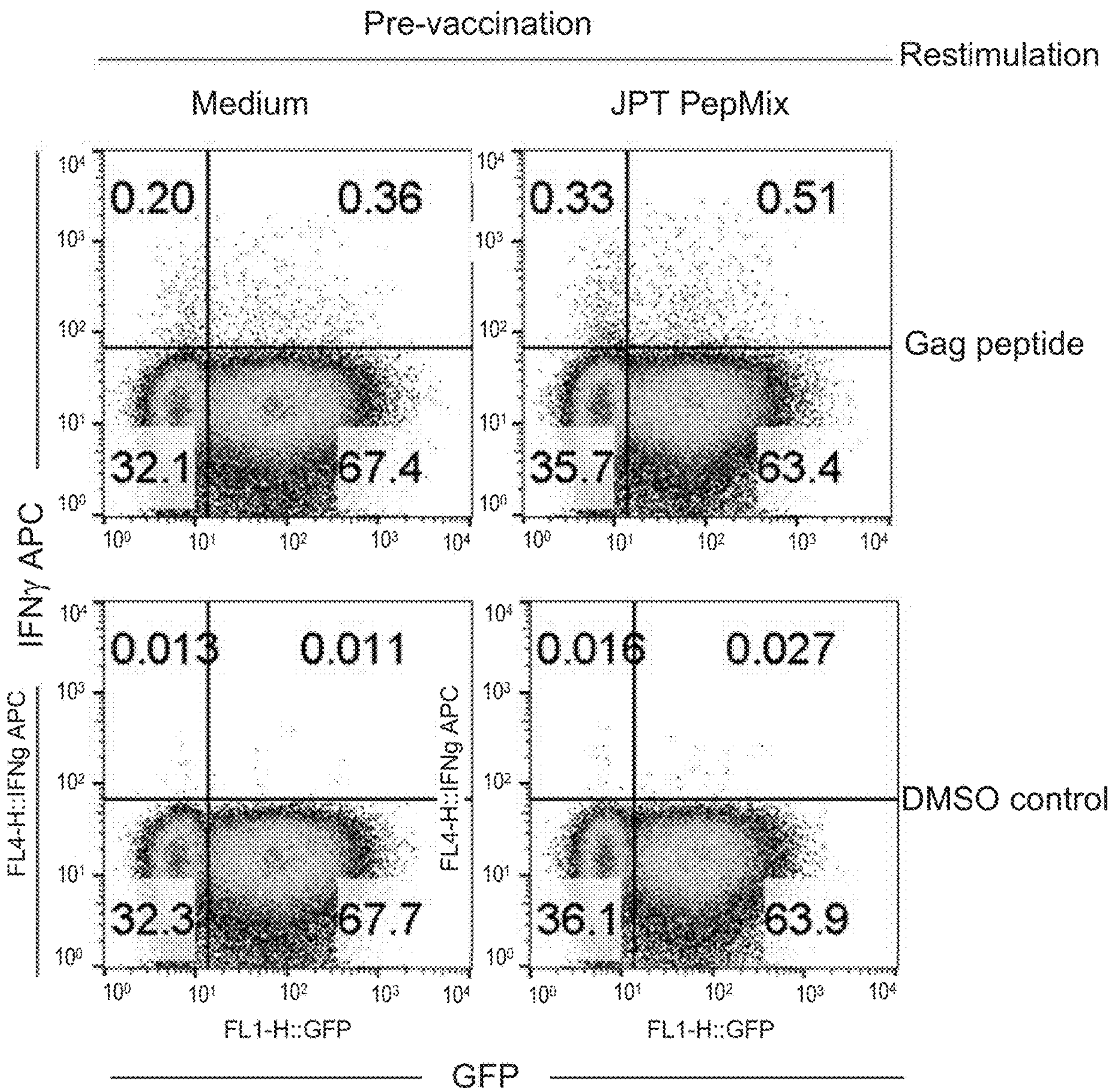
Figure 18C:
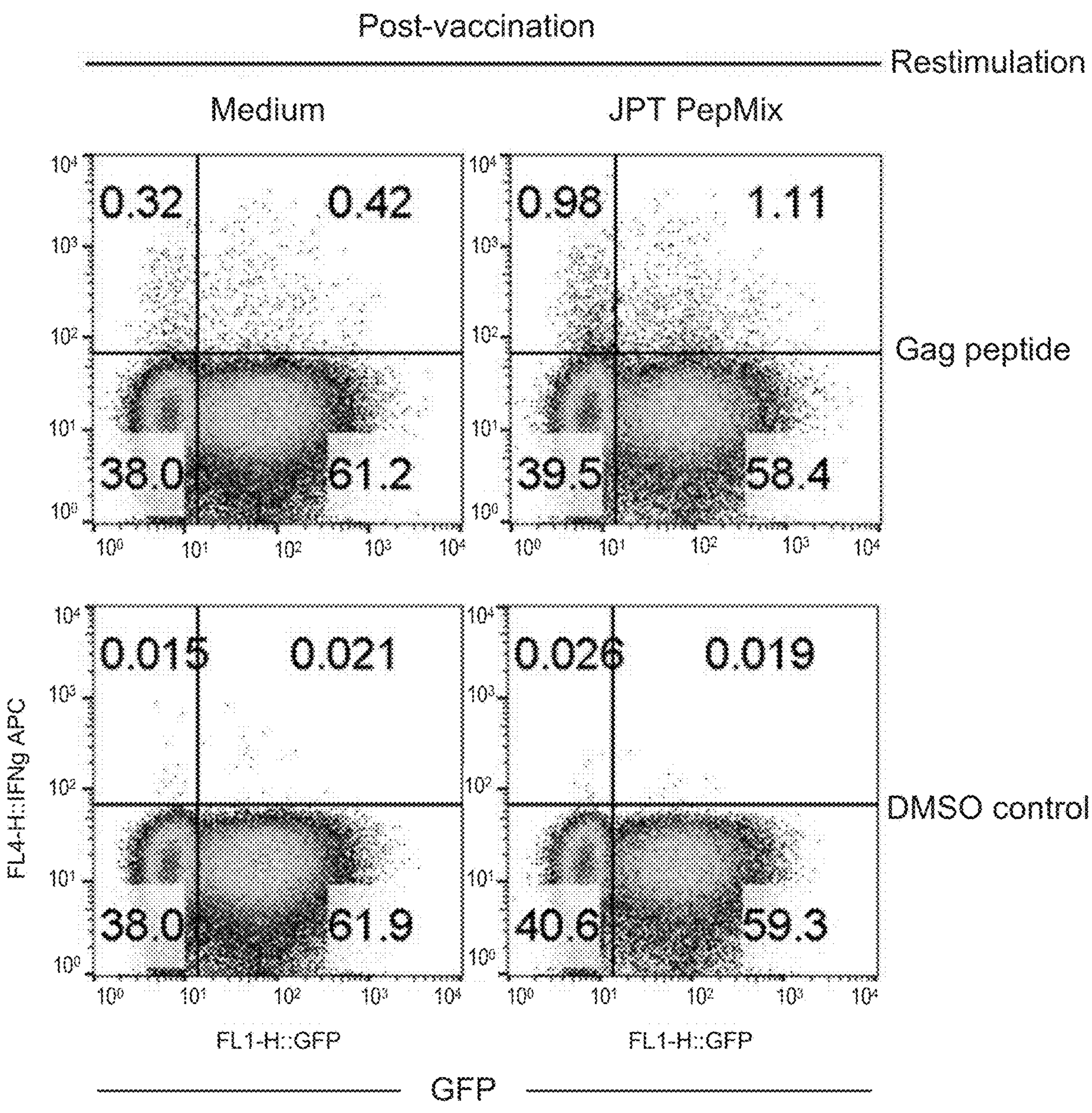
Figure 18D:
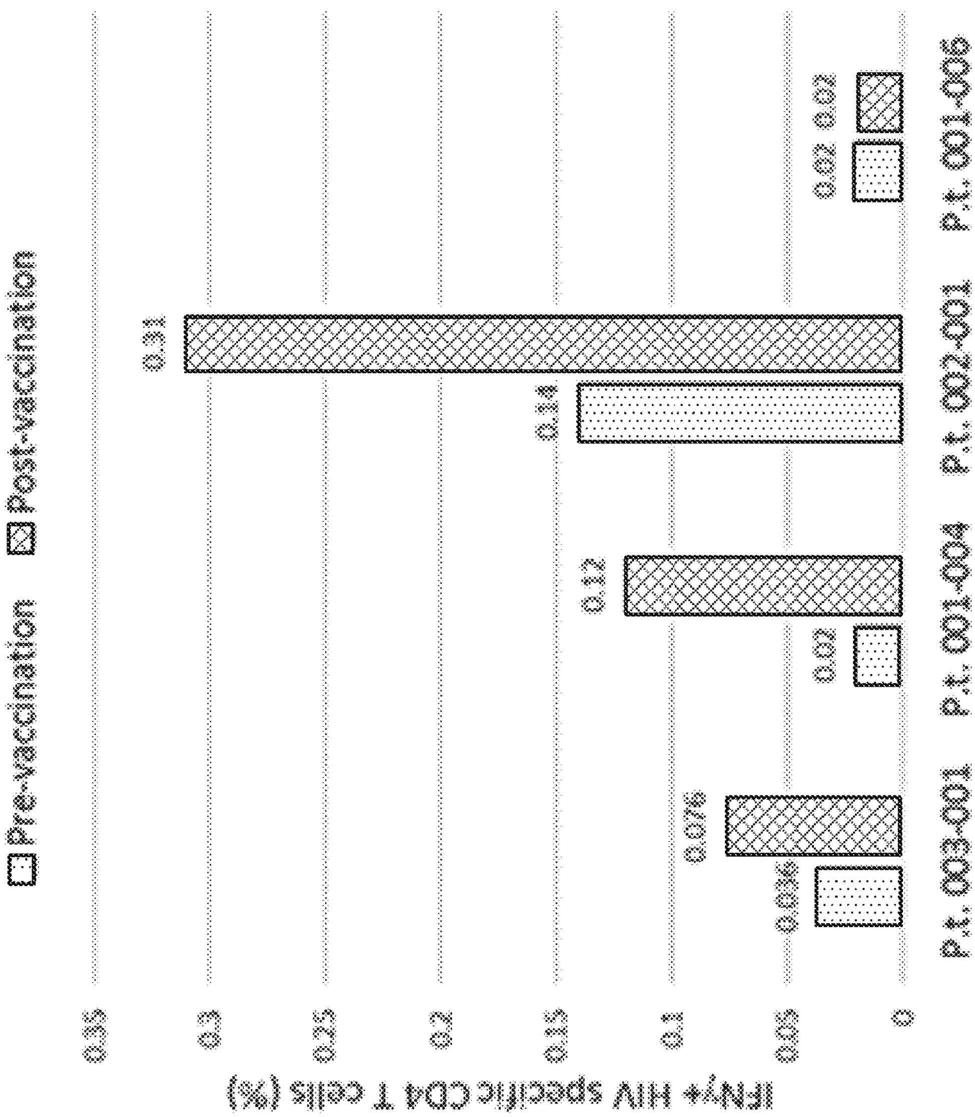
Figure 18E:
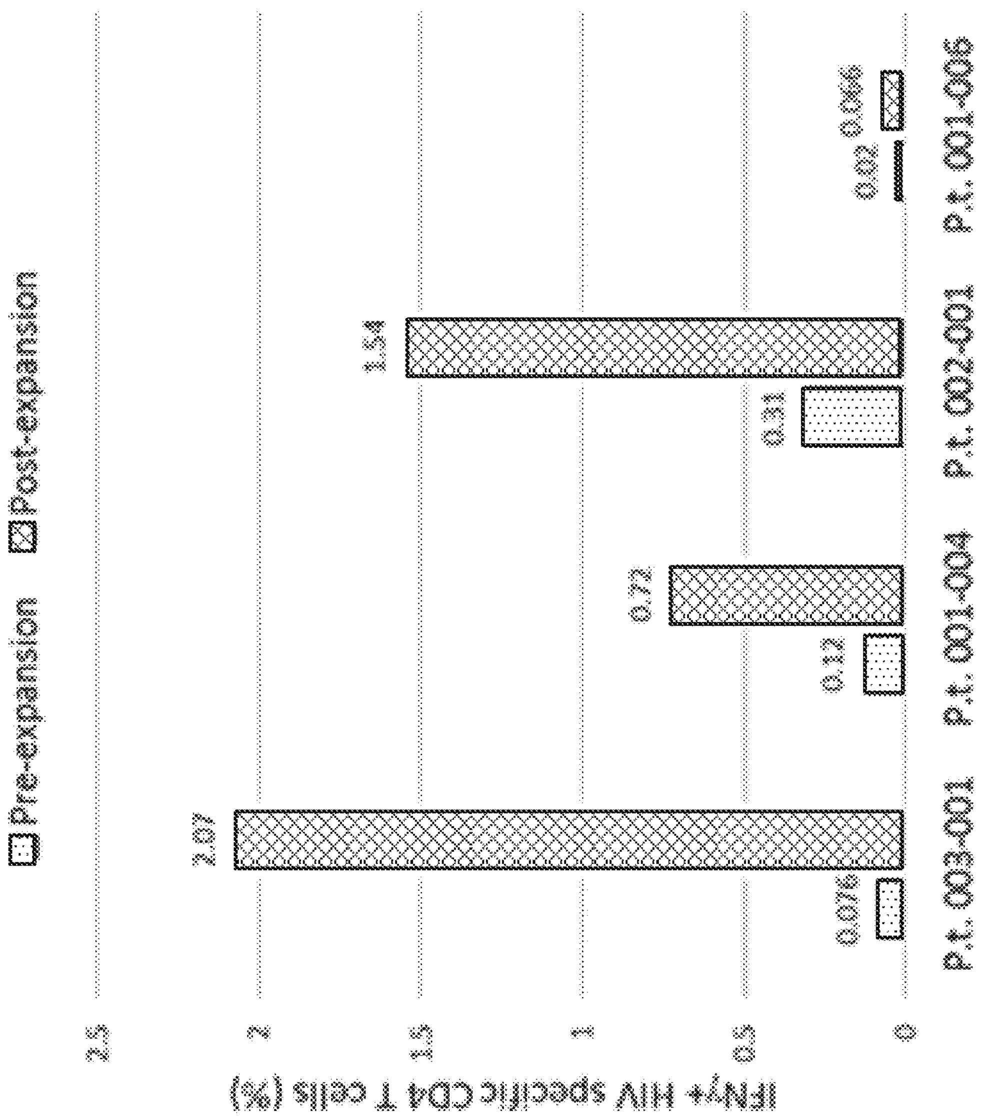

As shown in FIG. 17, PBMCs from a HIV-positive patient before or after vaccination were stimulated with DMSO (control), recombinant MVA expressing HIV Gag from GeoVax (MVA GeoVax), Gag peptide from GeoVax (Pep GeoVax, also referred to herein as Gag peptide pool 1) or Gag peptides from JPT (HIV (GAG) Ultra peptide mixture, also referred to herein as Gag peptide pool 2) for 20 hours. IFNg production was detected by intracellular staining and flow cytometry using standard protocols. Flow cytometry data were gated on CD4 T cells. Numbers captured in boxes are the percentage of total CD4 T cells designated "HIV-specific" on the basis of cytokine response to antigen-specific stimulation.

Example 14: HIV-Specific CD4 T Cell Expansion and Lentivirus Transduction

Designing and testing methods for enriching PBMC to increase the proportion of HIV-specific CD4 T cells and transducing these cells with AGT103 to produce the cellular product AGT103T. The protocol was designed for ex vivo culture of PBMC (peripheral blood mononuclear cells) from HIV-positive patients who had received a therapeutic HIV vaccine. In this example, the therapeutic vaccine consisted of three doses of plasmid DNA expressing HIV Gag, Pol and Env genes followed by two doses of MVA 62-B (modified vaccinia Ankara number 62-B) expressing the same HIV Gag, Pol, and Env genes. The protocol is not specific for a vaccine product and only requires a sufficient level of HIV-specific CD4+ T cells after immunization. Venous blood was collected and PBMC were purified by Ficoll-Paque density gradient centrifugation. Alternately, PBMC or defined cellular tractions can be prepared by positive or negative selection methods using antibody cocktails and fluorescence activated or magnetic bead sorting. The purified PBMC are washed and cultured in standard medium containing supplements, antibiotics and fetal bovine serum. To these cultures, a pool of synthetic peptides was added representing possible T cell epitopes within the HIV Gag polyprotein. Cultures are supplemented by adding cytokines interleukin-2 and interleukin-12 that were selected after testing combinations of interleukin-2 and interleukin-12, interleukin 2 and interleukin-7, interleukin 2 and interleukin-15. Peptide stimulation is followed by a culture interval of approximately 12 days. During the 12 days culture, fresh medium and fresh cytokine supplements were added approximately once every four days.

The peptide stimulation interval is designed to increase the frequency of HIV-specific CD4 T cells in the PBMC culture. These HIV-specific CD4 T cells were activated by prior therapeutic immunization and can be re-stimulated and caused to proliferate by synthetic peptide exposure. Our goal is to achieve greater than or equal to 1% of total CD4 T cells being HIV-specific by end of the peptide stimulation culture period.

On approximately day 12 of culture cells are washed to remove residual materials then stimulated with synthetic beads decorated with antibodies against CD4 T cell surface proteins CD3 and CD28. This well-established method for polyclonal stimulation of T cells will reactivate the cells and make them more susceptible for AGT103 lentivirus transduction. The lentivirus transduction is performed on approximately day 13 of culture and uses a multiplicity of infection between 1 and 5. After transduction cells are washed to remove residual lentivirus vector and cultured in media containing interleukin-2 and interleukin-12 with fresh medium and cytokines added approximately once every four days until approximately day 24 of culture.

Throughout the culture interval the antiretroviral drug Saquinavir is added at a concentration of approximately 100 nM to suppress any possible outgrowth of HIV.

On approximately day 24 of culture cells are harvested, washed, a sample is set aside for potency and release assay, then the remaining cells are suspended in cryopreservation medium before freezing in single aliquots of approximately $1\times10^{10}$ cells per dose that will contain approximately $1\times10^{8}$ HIV-specific CD4 T cells that are transduced with AGT103.

Potency of the cell product (AGT103T) is tested in one of two alternate potency assays. Potency assay 1 tests for the average number of genome copies (integrated AGT103 vector sequences) per CD4 T cell. The minimum potency is approximately 0.5 genome copies per CD4 T cell in order to release the product. The assay is performed by positive selection of CD3 positive/CD4 positive T cells using magnetic bead labeled monoclonal antibodies, extracting total cellular DNA and using a quantitative PCR reaction to detect sequences unique to the AGT103 vector. Potency assay 2 tests for the average number of genome copies of integrated AGT103 within the subpopulation of HIV-specific CD4 T cells. This essay is accomplished by first stimulating the PBMC with the pool of synthetic peptides representing HIV Gag protein. Cells are then stained with a specific antibody reagent capable of binding to the CD4 T cell and also capturing secreted interferon-gamma cytokine. The CD4 positive/interferon-gamma positive cells are captured by magnetic bead selection, total cellular DNA is prepared, and the number of genome copies of AGT103 per cell is determined with a quantitative PCR reaction. Release criterion based on potency using Assay 2 require that greater than or equal to 0.5 genome copies per HIV-specific CD4 T-cell are present in the AGT103 cell product.

Functional test for enriching and transducing HIV-specific CD4 T cells from PBMC of HIV-positive patients that received a therapeutic HIV vaccine. The impact of therapeutic vaccination on the frequency of HIV-specific CD4 T cells was tested by a peptide stimulation assay (FIG. 14 panel B). Before vaccination the frequency of HIV-specific CD4 T cells was 0.036% in this representative individual. After vaccination, the frequency of HIV-specific CD4 T cells was increased approximately 2-fold to the value of 0.076%. Responding cells (HIV-specific) identified by accumulation of cytoplasmic interferon-gamma, were only detected after specific peptide stimulation.

We also tested whether peptide stimulation to enrich for HIV-specific CD4 T cells followed by AGT103 transduction would reach our goal of generating approximately 1% of total CD4 T cells in culture that were both HIV-specific and transduced by AGT103. In this case, we used an experimental version of AGT103 that expresses green fluorescence protein (see GFP). In FIG. 14, panel C the post-vaccination culture after peptide stimulation (HIV (GAG) Ultra) and AGT103 transduction demonstrated that 1.11% of total CD4 T cells were both HIV-specific (based on expressing interferon-gamma in response to peptide stimulation) and AGT103 transduced (based on expression of GFP).

Several patients from a therapeutic HIV vaccine study were tested to assess the range of responses to peptide stimulation and to begin defining eligibility criteria for entering a gene therapy arm in a future human clinical trial. FIG. 18 Panel D shows the frequency of HIV-specific CD4 T cells in 4 vaccine trial participants comparing their pre-and post-vaccination specimens. Importantly, in three cases, the post-vaccination specimens show a value of HIV-specific CD4 T cells that was greater than or equal to 0.076% of total CD4 T cells. The ability to reach this value was not predicted by the pre-vaccination specimens as patient 001-004 and patient 001-006 both started with pre-vaccination values of 0.02% HIV-specific CD4 T cells but one reached an eventual post-vaccination value of 0.12% HIV-specific CD4 T cells while the other individual fail to increase this value after vaccination. The same three patients that responded well to vaccine, in terms of increasing the frequency of HIV-specific CD4 T cells, also showed substantial enrichment of HIV-specific CD4 T cells after peptide stimulation and culture. In the three cases shown in FIG. 18 Panel E, peptide stimulation and subsequent culture generated samples where 2.07%, 0.72% or 1.54% respectively of total CD4 T cells were HIV-specific. These values indicate that a majority of individuals responding to a therapeutic HIV vaccine will have a sufficiently large ex vivo response to peptide stimulation in order to enable our goal of achieving approximately 1% of total CD4 T cells that are HIV-specific and transduced with AGT103 in the final cell product.

As shown in FIG. 18, Panel A describes the schedule of treatment. Panel B demonstrates that PBMCs were stimulated with Gag peptide or DMSO control for 20 hours. IFN gamma production was detected by intracellular staining by FACS. $CD4^+$ T cells were gated for analysis. Panel C demonstrates $CD4^+$ T cells were expanded and transduced with AGT103-GFP using the method as shown in Panel A. Expanded $CD4^+$ T cells were rested in fresh medium without any cytokine for 2 days and re-stimulated with Gag peptide or DMSO control for 20 hours. IFN gamma production and GFP expression was detected by FACS. $CD4^+$ T cells were gated for analysis. Panel D demonstrates frequency of HIV-specific $CD4^+$ T cells (IFN gamma positive, pre- and post-vaccination) were detected from 4 patients as discussed herein. Panel E demonstrates Post-vaccination PBMCs from 4 patients were expanded and HIV-specific $CD4^+$ T cells were examined.

Example 15: Dose Response

Vector Construction. A modified version of AGT103 was constructed to test the dose response for increasing AGT103 and its effects on cell surface CCR5 levels. The AGT103 was modified to include a green fluorescent protein (GFP) expression cassette under control of the CMV promoter. Transduced cells expression the miR30CCR5 miR21Vif miR185Tat micro RNA cluster and emit green light due to expressing GFP.

Functional assay for dose response of increasing AGT103-GFP and inhibition of CCR5 expression. CEM-CCR5 T cells were transduced with AGT103-GFP using multiplicity of infection per cell from 0 to 5. Transduced cells were stained with a fluorescently conjugated (APC) monoclonal antibody specific for cell surface CCR5. The intensity of staining is proportional to the number of CCR5 molecules per cell surface. The intensity of green fluorescence is proportional to the number of integrated AGT103-GFP copies per cell.

Figure 19A:
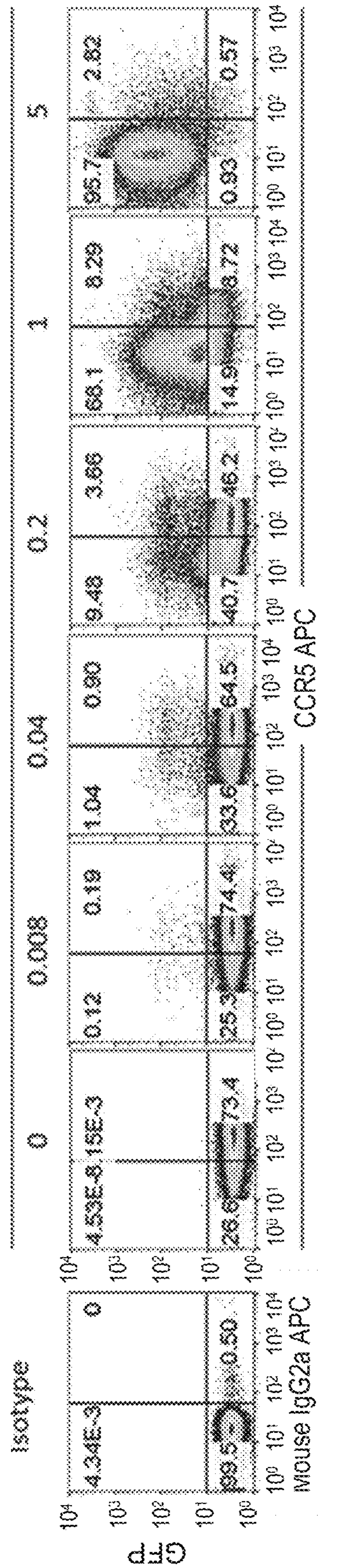
FIG. 19 depicts data demonstrating a functional assay for a dose response of increasing AGT103-GFP and inhibition of CCR5 expression. (A) Dose response data for increasing amounts of AGT103-GFP is shown. (B) Normal distribution populations in terms of CCR5 expression are shown. (C) Percentage inhibition of CCR5 expression with increasing doses of AGT103-GFP is shown.
Figure 19B:
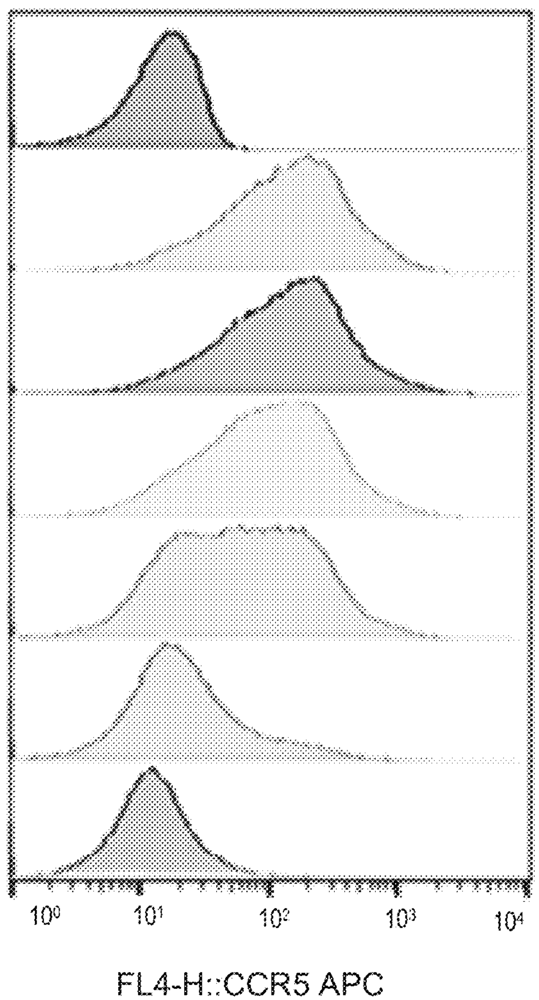
Figure 19C:
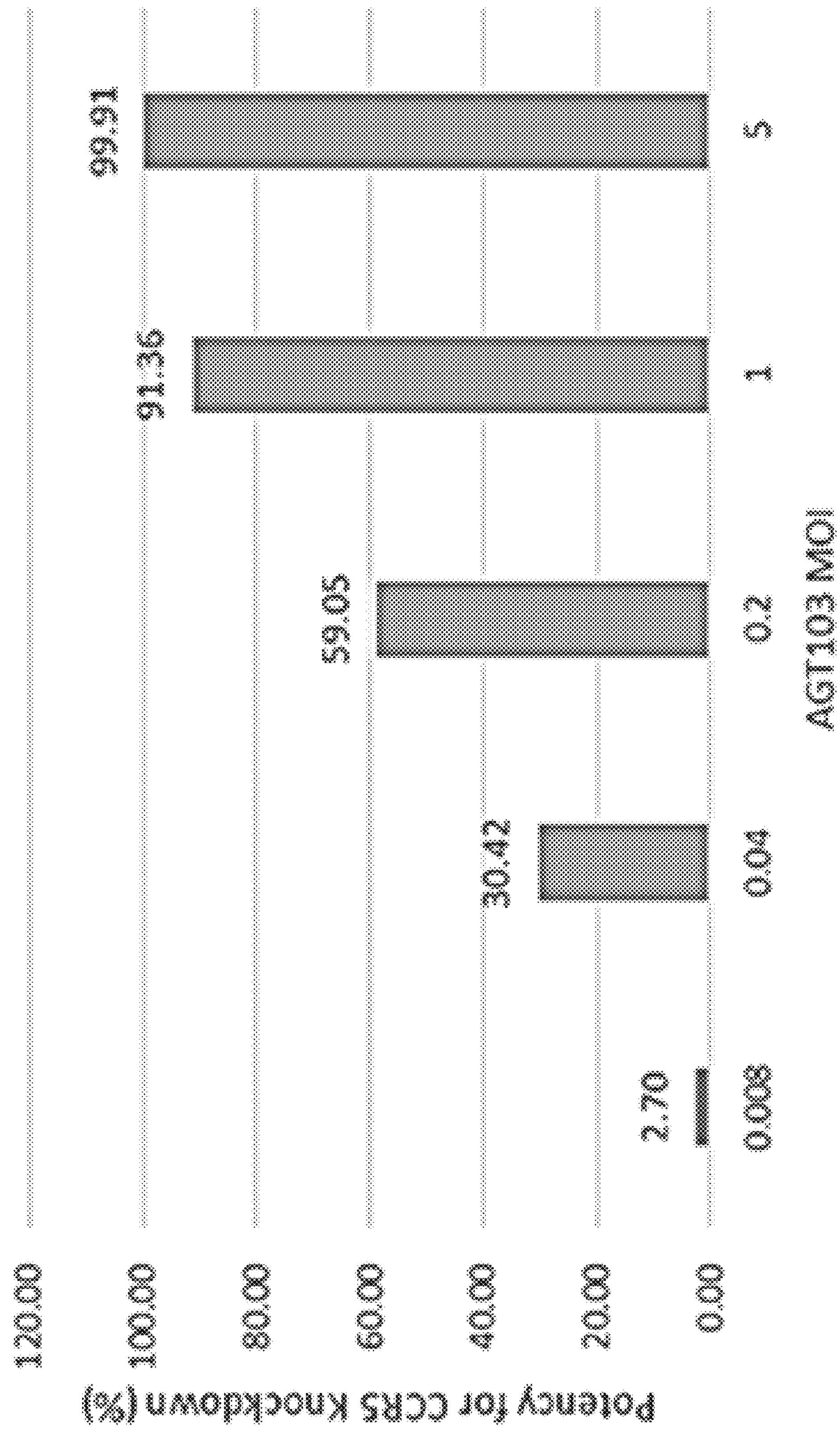

As shown in FIG. 19, Panel A demonstrates the dose response for increasing AGT103-GFP and its effects on cell surface CCR5 expression. At multiplicity of infection equal to 0.4 only 1.04% of cells are both green (indicating transduction) and showing significantly reduced CCR5 expression. At multiplicity of infection equal to 1 the number of CCR5low, GFP+ cells increases to 68.1%/ At multiplicity of infection equal to 5 the number of CCR5low, GFP+ cells increased to 95.7%. These data are presented in histogram form in FIG. 19, Panel B that shows a normally distribution population in terms of CCR5 staining, moving toward lower mean fluorescence intensity with increasing doses of AGT103-GFP. The potency of AGT103-GFP is presented in graphical form in FIG. 19, Panel C showing the percentage inhibition of CCR5 expression with increasing doses of AGT103-GFP. At multiplicity of infection equal to 5, there was greater than 99% reduction in CCR5 expression levels.

Example 16: AGT103 Efficiently Transduces Primary Human CD4+ T Cells

Transducing primary CD4 T cells with AGT103 lentivirus vector. A modified AGT103 vector containing the green fluorescence protein marker (GFP) was used at multiplicities of infection between 0.2 and 5 for transducing purified, primary human CD4 T cells.

Figure 20A:
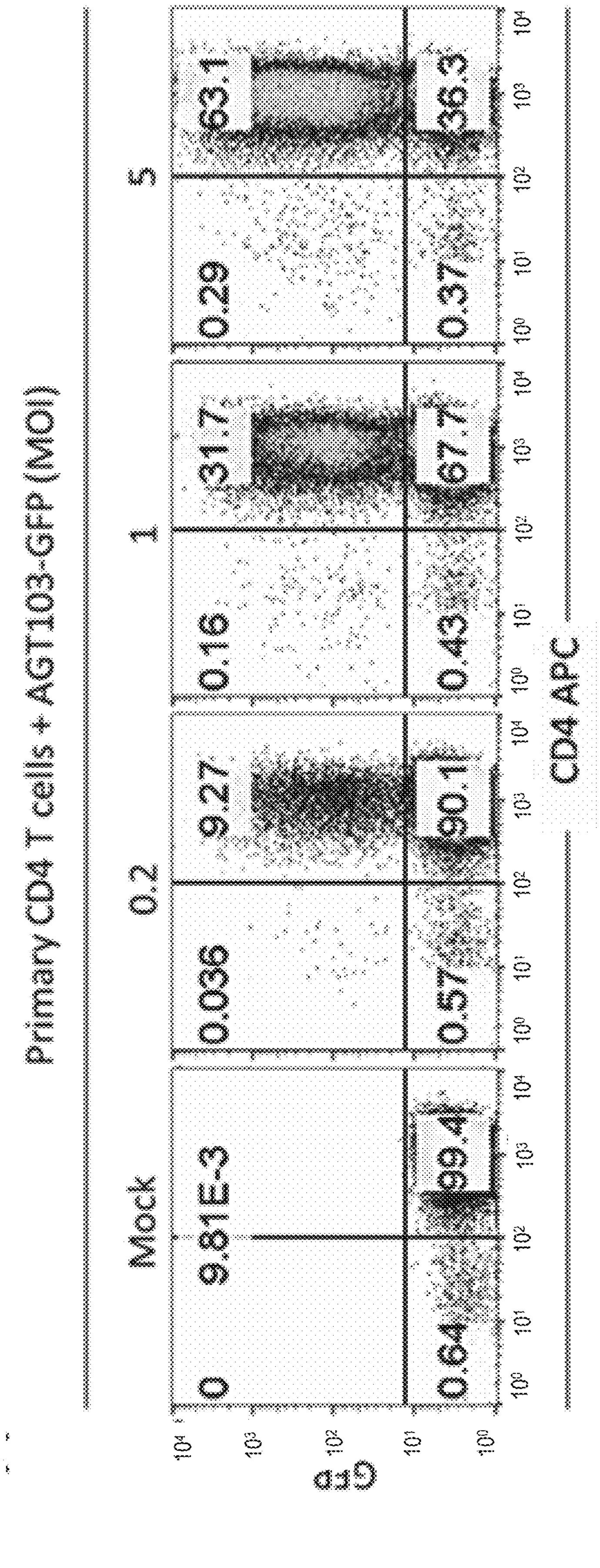
FIG. 20 depicts data demonstrating that that AGT103 efficiently transduces primary human CD4+ T cells. (A) Frequency of transduced cells (GFP-positive) is shown by FACS, as described herein. (B) Number of vector copies per cell is shown, as described herein.
Figure 20B:
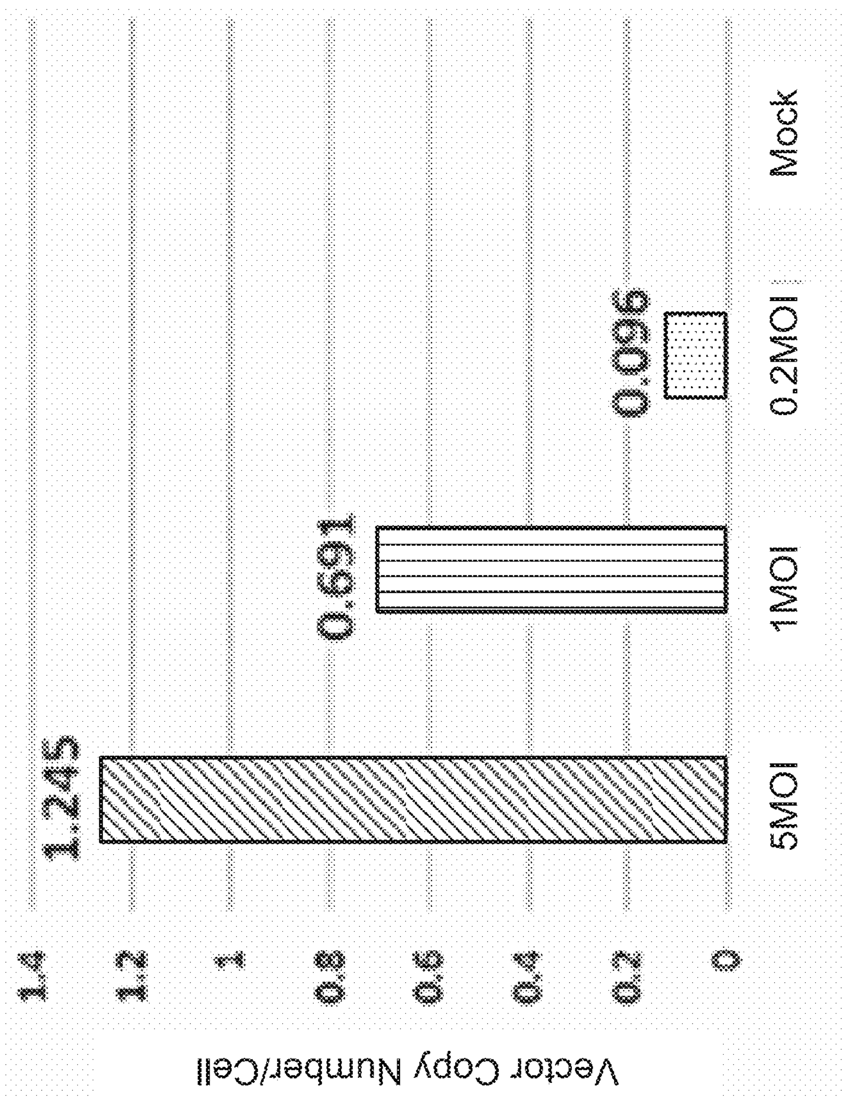

Functional assay for transduction efficiency of AGT103 in primary human CD4 T cells. CD4 T cells were isolated from human PBMC (HIV-negative donor) using magnetic bead labeled antibodies and standard procedures. The purified CD4 T cells were stimulated ex vivo with CD3/CD28 beads and cultured in media containing interleukin-2 for 1 day before AGT103 transduction. The relationship between lentivirus vector dose (the multiplicity of infection) and transduction efficiency is demonstrated in FIG. 20, Panel A showing that multiplicity of infection equal to 0.2 resulted in 9.27% of CD4 positive T cells being transduced by AGT103 and that value was increased to 63.1% of CD4 positive T cells being transduced by AGT103 with a multiplicity of infection equal to 5. In addition to achieving efficient transduction of primary CD4 positive T cells it is also necessary to quantify the number of genome copies per cell. In FIG. 20, Panel B total cellular DNA from primary human CD4 T cells transduced at several multiplicities of infection were tested by quantitative PCR to determine the number of genome copies per cell. In a multiplicity of infection equal to 0.2 we measured 0.096 genome copies per cell that was in good agreement with 9.27% GFP positive CD4 T cells in panel A. Multiplicity of infection equal to 1 generated 0.691 genome copies per cell and multiplicity of infection equal to 5 generated 1.245 genome copies per cell.

As shown in FIG. 20, $CD4^+$ T cells isolated from PBMC were stimulated with CD3/CD28 beads plus IL-2 for 1 day and transduced with AGT103 at various concentrations. After 2 days, beads were removed and $CD4^+$ T cells were collected. As shown in Panel A, frequency of transduced cells (GFP positive) were detected by FACS. As shown in Panel B, the number of vector copies per cell was determined by qPCR. At a multiplicity of infection (MOI) of 5, 63% of $CD4^+$ T cells were transduced with an average of 1 vector copy per cell.

Example 17: AGT103 Inhibits HIV Replication in Primary CD4+ T Cells

Protecting primary human CD4 positive T cells from HIV infection by transducing cells with AGT103. Therapeutic lentivirus AGT103 was used for transducing primary human CD4 positive T cells at multiplicities of infection between 0.2 and 5 per cell. The transduced cells were then challenged with a CXCR4-tropic HIV strain NL4.3 that does not require cell surface CCR5 for penetration. This assay tests the potency of microRNA against Vif and Tat genes of HIV in terms of preventing productive infection in primary CD4 positive T cells, but uses an indirect method to detect the amount of HIV released from infected, primary human CD4 T cells.

Functional assay for AGT103 protection against CXCR4-tropic HIV infection of primary human CD4 positive T cells. CD4 T cells were isolated from human PBMC (HIV-negative donor) using magnetic bead labeled antibodies and standard procedures. The purified CD4 T cells were stimulated ex vivo with CD3/CD28 beads and cultured in media containing interleukin-2 for 1 day before AGT103 transduction using multiplicities of infection between 0.2 and 5. Two days after transduction the CD4 positive T cell cultures were challenged with HIV strain NL4.3 that was engineered to express the green fluorescent protein (GFP). The transduced and HIV-exposed primary CD4 T cell cultures were maintained for 7 days before collecting cell-free culture fluids containing HIV. The cell-free culture fluids were used to infect a highly permissive T cell line C8166 for 2 days. The proportion of HIV-infected C8166 cells was determined by flow cytometry detecting GFP fluorescence. With a mock lentivirus infection, the dose of 0.1 multiplicity of infection for NL4.3 HIV resulted in an amount of HIV being released into culture fluids that was capable of establishing productive infection in 15.4% of C8166 T cells. With the dose 0.2 multiplicity of infection for AGT103, this value for HIV infection of C8166 cells is reduced to 5.3% and multiplicity of infection equal to 1 for AGT103 resulted in only 3.19% of C8166 T cells being infected by HIV. C8166 infection was reduced further to 0.62% after AGT103 transduction using a multiplicity of infection equal to 5. There is a clear dose response relationship between the amount of AGT103 used for transduction and the amount of HIV released into the culture medium.

Figure 21:
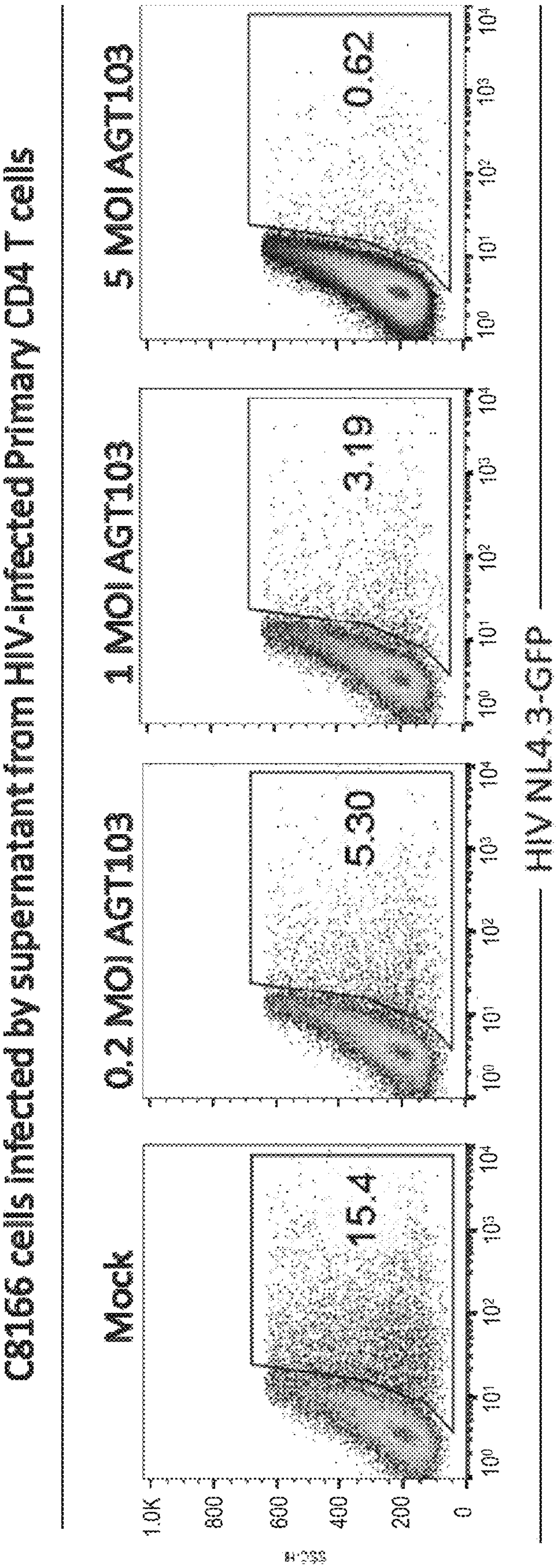
FIG. 21 depicts data demonstrating that AGT103 inhibits HIV replication in primary CD4+ T cells, as described herein.

As shown in FIG. 21, $CD4^+$ T cells isolated from PBMC were stimulated with CD3/CD28 beads plus IL-2 for 1 day and transduced with AGT103 at various concentrations (MOI). After 2 days, beads were removed and $CD4^+$ T cells were infected with 0.1 MOI of HIV NL4.3-GFP. 24 hours later, cells were washed 3 times with PBS and cultured with IL-2 (30U/ml) for 7 days. At the end of the culture, supernatant was collected to infect the HIV permissive cell line C8166 for 2 days. HIV-infected C8166 cells (GFP positive) were detected by FACS. There was a reduction in viable HIV with an increase in the multiplicity of infection of AGT103 as observed by less infection of C8166 cells MOI 0.2=65.6%, MOI 1=79.3%, and MOI 5=96%).

Example 18: AGT103 Protects Primary Human CD4+ T Cells from HIV-Induced Depletion AGT103 transduction of primary human CD4 T cells to protect against HIV-mediated cytopathology and cell depletion. PBMC were obtained from healthy, HIV-negative donors and stimulated with CD3/CD28 beads then cultured for 1 day in medium containing interleukin-2 before AGT103 transduction using multiplicities of infection between 0.2 and 5.

Functional assay for AGT103 protection of primary human CD4 T cells against HIV-mediated cytopathology. AGT103-transduced primary human CD4 T cells were infected with HIV NL 4.3 strain (CXCR4-tropic) that does not require CCR5 for cellular entry. When using the CXCR4-tropic NL 4.3, only the effect of Vif and Tat microRNA on HIV replication is being tested. The dose of HIV NL 4.3 was 0.1 multiplicity of infection. One day after HIV infection, cells were washed to remove residual virus and cultured in medium plus interleukin-2. Cells were collected every three days during a 14-day culture then stained with a monoclonal antibody that was specific for CD4 and directly conjugated to a fluorescent marker to allow measurement of the proportion of CD4 positive T cells in PBMC. Untreated CD4 T cells or CD4 T cells transduced with the control lentivirus vector were highly susceptible to HIV challenge and the proportion of CD4 positive T cells in PBMC fell below 10% by day 14 culture. In contrast, there was a dose-dependent effect of AGT103 on preventing cell depletion by HIV challenge. With a AGT103 dose of 0.2 multiplicity of infection more than 20% of PBMC were CD4 T cells by day 14 of culture and this value increased to more than 50% of PBMC being CD4 positive T cells by day 14 of culture with a AGT103 dose of multiplicity of infection equal to 5. Again, there is a clear dose response effect of AGT103 on HIV cytopathogenicity in human PBMC.

Figure 22:
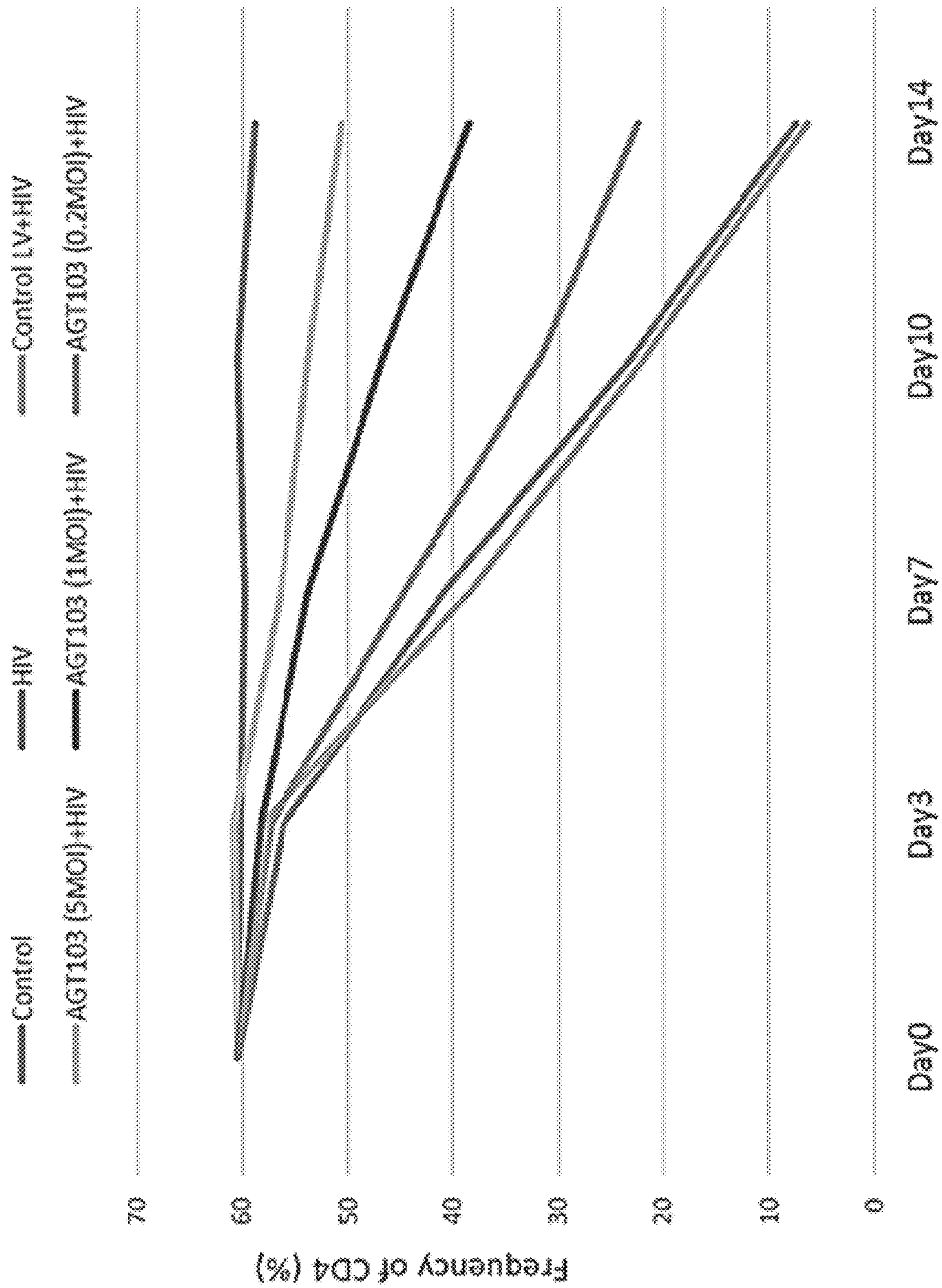
FIG. 22 depicts data demonstrating that AGT103 protects primary human CD4+ T cells from HIV-induced depletion.

As shown in FIG. 22, PBMCs were stimulated with CD3/CD28 beads plus IL-2 for 1 day and transduced with AGT103 at various concentrations (MOI). After 2 days, beads were removed and cells were infected with 0.1 MOI of HIV NL4.3. 24 hours later, cells were washed 3 times with PBS and cultured with IL-2 (30U/ml). Cells were collected every 3 days and the frequency of $CD4^+$ T cells were analyzed by FACS. After 14 days of exposure to HIV, there was an 87% reduction in $CD4^+$ T cells transduced with LV-Control, a 60% reduction with AGT103 MOI 0.2, a 37% reduction with AGT103 MOI 1, and a 17% reduction with AGT103 MOI 5.

Figure 23A:
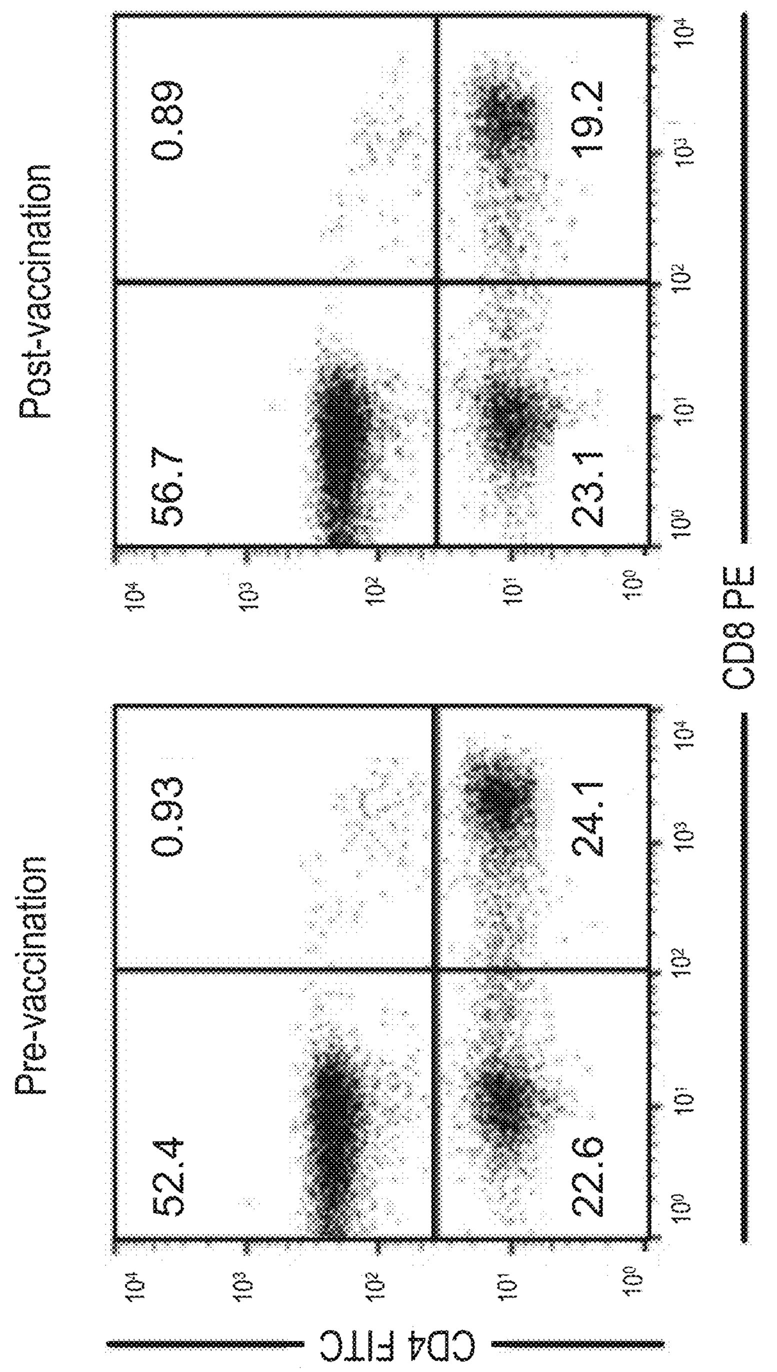
FIG. 23 depicts data demonstrating generation of a CD4+ T cell population that is highly enriched for HIV-specific, AGT103-transduced CD4 T cells. (A) shows CD4 and CD8 expression profiles for cell populations, as described herein. (B) shows CD4 and CD8 expression profiles for cell populations, as described herein. (C) shows IFN-gamma and CD4 expression profiles for cell populations, as described herein. (D) shows IFN-gamma and GFP expression profiles for cell populations, as described herein.

Example 19: Generating a Population of CD4+ T Cells Enriched for HIV-Specificity and Transduced with AGT103/CMV-GFP Therapeutic vaccination against HIV had minimal effect on the distribution of CD4+, CD8+ and CD4+/CD8+ T cells. As shown in FIG. 23A, the CD4 T cell population is shown in the upper left quadrant of the analytical flow cytometry dot plots, and changes from 52% to 57% of total T cells after the vaccination series. These are representative data.

Figure 23B:
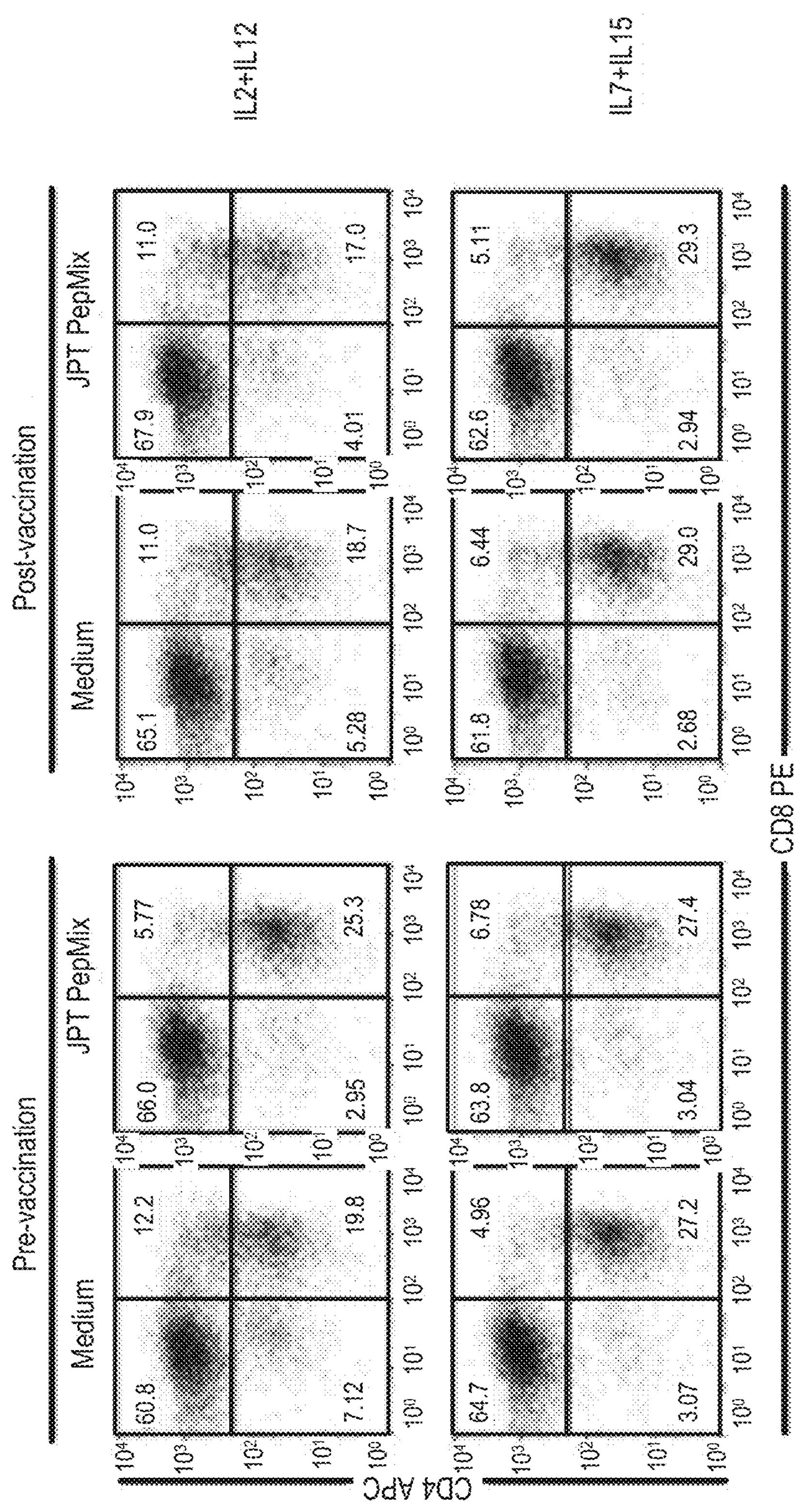

Peripheral blood mononuclear cells from a participant in an HIV therapeutic vaccine trial were cultured for 12 days in medium+/−interleukin-2/interleukin-12 or +/−interleukin-7/interleukin-15. Some cultures were stimulated with overlapping peptides representing the entire p55 Gag protein of HIV-1 (HIV (GAG) Ultra peptide mixture) as a source of epitope peptides for T cell stimulation. These peptides are 10-20 amino acids in length and overlap by 20-50% of their length to represent the entire Gag precursor protein (p55) from HIV-1 BaL strain. The composition and sequence of individual peptides can be adjusted to compensate for regional variations in the predominant circulating HIV sequences or when detailed sequence information is available for an individual patient receiving this therapy. At culture end, cells were recovered and stained with anti-CD4 or anti-CD8 monoclonal antibodies and the CD3+ population was gated and displayed here. The HIV (GAG) Ultra peptide mixture stimulation for either pre- or post-vaccination samples was similar to the medium control indicating that HIV (GAG) Ultra peptide mixture was not toxic to cells and was not acting as a polyclonal mitogen. The results of this analysis can be found in FIG. 23B.

HIV (GAG) Ultra peptide mixture and interleukin-2/interleukin-12 provided for optimal expansion of antigen-specific CD4 T cells. As shown in the upper panels of FIG. 23C, there was an increase in cytokine (interferon-gamma) secreting cells in post-vaccination specimens exposed to HIV (GAG) Ultra peptide mixture. In the pre-vaccination sample, cytokine secreting cells increased from 0.43 to 0.69% as a result of exposure to antigenic peptides. In contrast, the post-vaccination samples showed an increase of cytokine secreting cells from 0.62 to 1.76% of total CD4 T cells as a result of peptide stimulation. These data demonstrate the strong impact of vaccination on the CD4 T cell responses to HIV antigen.

Figure 23C:
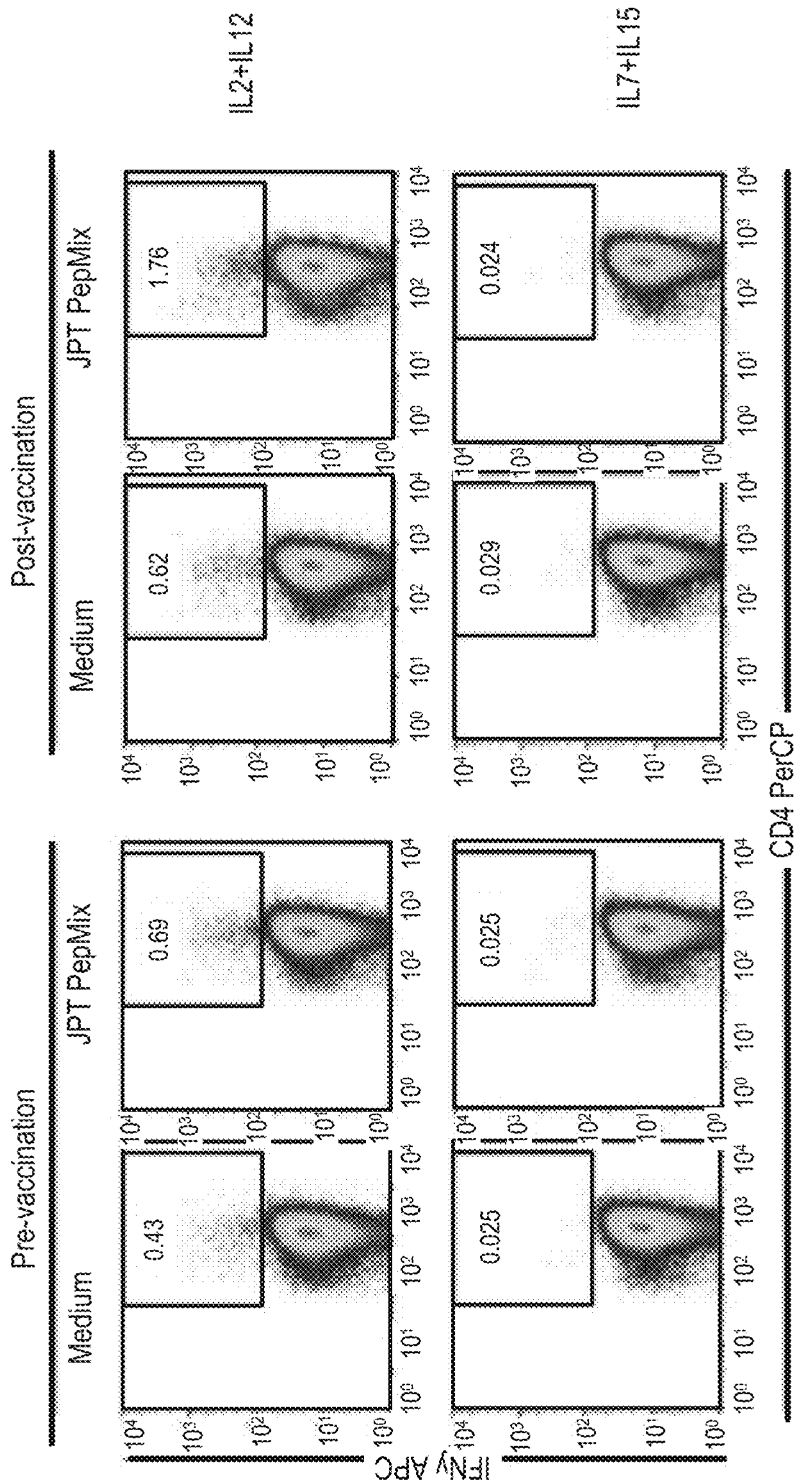
Figure 23D:
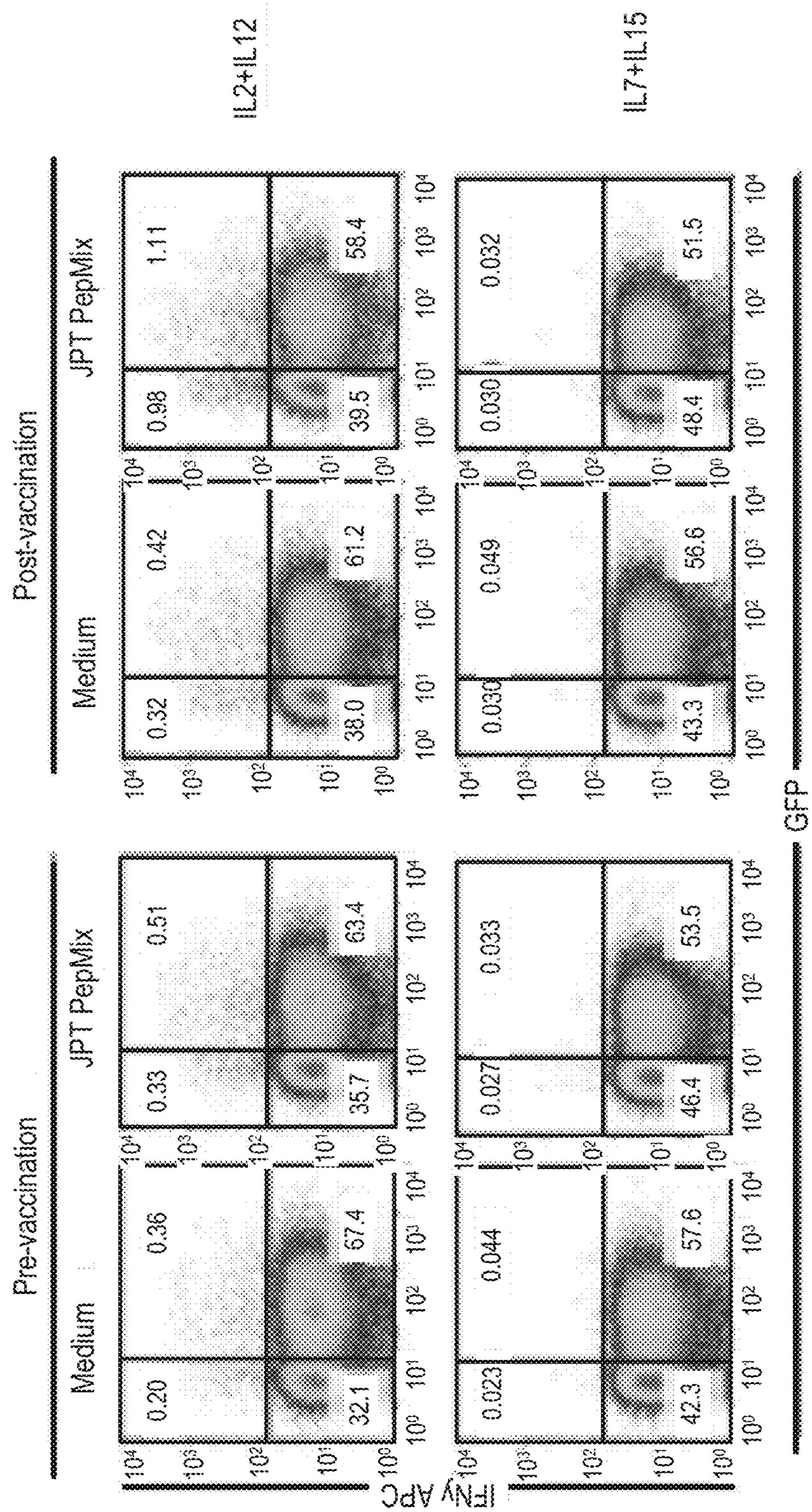

Finally, AGT103/CMV-GFP transduction of antigen-expanded CD4 T cells produced HIV-specific and HIV-resistant helper CD4 T cells that are needed for infusion into patients as part of a functional cure for HIV (in accordance with other various aspects and embodiments, AGT103 alone is used; for example, clinical embodiments may not include the CMV-GFP segment). The upper panels of FIG. 23C show the results of analyzing the CD4+ T cell population in culture. The x axis of FIG. 23C shows Green Fluorescent Protein (GFP) emission indicating that individual cells were transduced with the AGT103/CMV-GFP. In the post-vaccination samples 1.11% of total CD4 T cells that were both cytokine secreting was recovered, indicating that the cells are responding specifically to HIV antigen, and transduced with AGT103/CMV-GFP. This is the target cell population and the clinical product intended for infusion and functional cure of HIV. With the efficiency of cell expansion during the antigen stimulation and subsequent polyclonal expansion phases of ex vivo culture, $4\times10^8$ antigen-specific, lentivirus transduced CD4 T cells can be produced. This exceeds the target for cell production by 4-fold and will allow achievement of a count of antigen-specific and HIV-resistant CD4 T cells of approximately 40 cells/microliter of blood or around 5.7% of total circulating CD4 T cells.

Table 4 below shows the results of the ex vivo production of HIV-specific and HIV-resistant CD4 T cells using the disclosed vectors and methods.

TABLE 4

| Material/manipulation | Total CD4 T cells | Percentage HIV-specific | Percentage HIV-specific and HIV-resistant |
|---|---|---|---|
| Leukapheresis pack from HIV+ patient | $\sim 7\times10^8$ | ~0.12 | N/A |
| Peptide expansion ex vivo | $\sim 8\times10^8$ | ~2.4 | N/A |
| Mitogen expansion | $\sim 1.5\times10^{10}$ | ~2.4 | N/A |
| Lentivirus transduction | $\sim 1.5\times10^{10}$ | ~2.4 | ~1.6 |

Example 20: Clinical Study for Treatment of HIV-Positive Subjects with No Immunization AGT103T is a genetically modified autologous PBMC containing $\geq 5\times10^7$ HIV-specific CD4 T cells that are also transduced with AGT103 lentivirus vector A Phase I clinical trial will test the safety and feasibility of infusing ex vivo modified autologous CD4 T cells (AGT103T) in adult research participants with confirmed HIV infection, CD4+ T-cell counts>600 cells per $mm^3$ of blood and stable virus suppression below 200 copies per ml of plasma while on cART. All study participants will continue receiving their standard antiretroviral medications throughout the Phase I clinical trial. Study participants are screened by submitting a blood for in vitro testing to measure the frequency of CD4+ T-cells that respond to stimulation with a pool of overlapping, synthetic peptides representing the HIV-1 Gag polyprotein. Subjects with ≥0.065% of total CD4 T cells designated as Gag-specific CD4 T cells are enrolled in the gene therapy study and undergo leukapheresis followed by purification of PBMC (using Ficoll density gradient centrifugation or negative selection with antibodies) that are cultured ex vivo and stimulated with HIV Gag peptides plus interleukin-2 and interleukin-12 for 12 days, then stimulated again with beads decorated with CD3/CD28 bispecific antibody. The antiretroviral drug Saquinavir is included at 100 nM to prevent emergence of autologous HIV during ex vivo culture. One day after CD3/CD28 stimulation cells are transduced with AGT103 at multiplicity of infection between 1 and 10. The transduced cells are cultured for an additional 7-14 days during which time they expand by polyclonal proliferation. The culture period is ended by harvesting and washing cells, setting aside aliquots for potency and safety release assays, and resuspending the remaining cells in cryopreservation medium. A single dose is $\leq 1\times10^{10}$ autologous PBMC. The potency assay measures the frequency of CD4 T cells that respond to peptide stimulation by expressing interferon-gamma. Other release criteria include the product must include $\geq 0.5\times10^{7}$ HIV-specific CD4 T cells that are also transduced with AGT103. Another release criterion is that the number of AGT103 genome copies per cell must not exceed 3. Five days before infusion with AGT103T subjects receive one dose of busulfuram (or Cytoxan or fludarabine or suitable drug combinations) conditioning regimen followed by infusion of $\leq 1\times10^{10}$ PBMC containing genetically modified CD4 T cells.

A Phase II study will evaluate efficacy of AGT103T cell therapy. Phase II study participants include individuals enrolled previously in our Phase I study who were judged to have successful and stable engraftment of genetically modified, autologous, HIV-specific CD4 T cells and clinical responses defined as positive changes in parameters monitored as described in efficacy assessments (1.3.). Study participants will be asked to add Maraviroc to their existing regimen of antiretroviral medication. Maraviroc is a CCR5 antagonist that will enhance the effectiveness of genetic therapy directed at reducing CCR5 levels. Once the Maraviroc regimen is in place subjects will be asked to discontinue the previous antiretroviral drug regimen and only maintain Maraviroc monotherapy for 28 days or until plasma viral RNA levels exceed 10,000 per ml on 2 sequential weekly blood draws. Persistently high viremia requires participants to return to their original antiretroviral drug regimen with or without Maraviroc according to recommendations of their HIV care physician.

If participants remain HIV suppressed (below 2,000 vRNA copies per ml of plasma) for >28 days on Maraviroc monotherapy, they will be asked to gradually reduce Maraviroc dosing over a period of 4 weeks followed by intensive monitoring for an additional 28 days. Subjects who maintained HIV suppression with Maraviroc monotherapy are considered to have a functional cure. Subjects who maintain HIV suppression even after Maraviroc withdrawal also have a functional cure. Monthly monitoring for 6 months followed by less intensive monitoring will establish the durability of functional cure.

1.1 Patient Selection

Inclusion Criteria:

- Aged between 18 and 60 years.
- Documented HIV infection prior to study entry.
- Must be willing to comply with study-mandated evaluations; including not changing their antiretroviral regimen (unless medically indicated) during the study period.
- CD4+ T-cell count>600 cell per millimeter cubed (cells/mm3)
- CD4+ T-cell nadir of >400 cells/mm3
- HIV viral load>1,000 copies per milliliter (mL)

Exclusion Criteria:

- Any viral hepatitis
- Acute HIV infection
- HIV viral load>1,000,000 copies/mL
- Active or recent (prior 6 months) AIDS defining complication
- Any change in HIV medications within 12 weeks of entering the study
- Cancer or malignancy that has not been in remission for at least 5 years with the exception of successfully treated basal cell carcinoma of the skin
- Current diagnosis of NYHA grade 3 or 4 congestive heart failure or uncontrolled angina or arrhythmias
- History of bleeding problems
- Use of chronic steroids in past 30 days
- Pregnant or breast feeding
- Active drug or alcohol abuse
- Serious illness in past 30 days
- Currently participating in another clinical trial or any prior gene therapy 1.2 Safety Assessments

- Acute infusion reaction
- Post-infusion safety follow-up 1.3 Efficacy Assessments—Phase I

- Number and frequency of modified CD4 T cells.
- Durability of modified CD4 T cells.
- In vitro response to Gag peptide restimulation (ICS assay) as a measure of memory T cell function.
- Polyfunctional anti-HIV CD8 T cell responses compare to pre- and post-vaccination time points.
- Frequency of CD4 T cells making doubly spliced HIV mRNA after in vitro stimulation.

1.4 Efficacy Assessments—Phase II

- Number and frequency of genetically modified CD4 T cells.
- Maintenance of viral suppression (<2,000 vRNA copies per ml but 2 consecutive weekly draws not exceeding $5\times10^{4}$ vRNA copies per ml are permitted) with Maraviroc monotherapy.
- Continued virus suppression during and after Maraviroc withdrawal.
- Stable CD4 T cell count.

Example 21: Generating a Population of CD4+ T Cells Through Depletion of CD8+ T Cells Prior to Peptide Stimulation Because CD8+ T cell overgrowth significantly impacted the expansion of target CD4+ T cells, CD8+ T cells were depleted at the beginning of cell expansion to determine whether it would improve CD4+ T cell expansion. Current CD8+ T cell depletion methods require that cells are passed through a magnetic column. To avoid possible impacts of that procedure on antigen presenting cells and CD4+ T cells, the cell depletion was performed after peptide stimulation and before lentivirus transduction when cells were better able to withstand the mechanical stresses.

Figure 24:
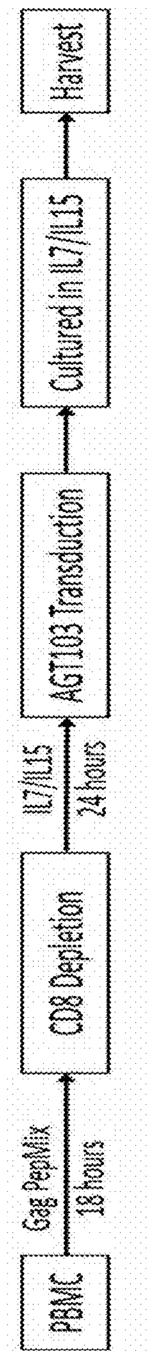
FIG. 24 depicts a schematic of a CD8 depletion protocol.

More specifically, HIV positive human peripheral blood was obtained. PBMCs were separated with Ficoll-Paque PLUS (GE Healthcare, Cat: 17-1440-02). Fresh separated PBMCs ($1\times10^7$) were stimulated with PepMix™ HIV (GAG) Ultra (Cat: PM-HIV-GAG, JPT Peptide Technologies, Berlin, Germany) in 1 mL medium in a 24-well plate for 18 hours. CD8+ T cells were depleted with PE anti-human CD8 antibody and anti-PE microbeads. The negatively selected cells were cultured at $2\times10^6$/mL in Tex-MACS GMP medium (Cat: 170-076-309, Miltenyi Biotech, Bergisch Gladbach, Germany) containing IL-7 (170-076-111, Miltenyi Biotech, Bergisch Gladbach, Germany), IL-15 (170-076-114, Miltenyi Biotech, Bergisch Gladbach, Germany) and Saquinavir (Cat: 4658, NIH AIDS Reagent Program, Germantown, MD). Lentivirus AGT103 was added 24 hours later at MOI 5. Fresh medium containing IL-7, IL-15 and Saquinavir were added every 2-3 days during the expansion. The final concentration of IL-7/IL-15 was 10 ng/mL. The final concentration of Saquinavir was 100 nM. At day 12-16, 2-$3\times10^6$ cells were collected for peptide restimulation and intracellular cytokine staining (ICS) analysis. A schematic of this depletion protocol is shown in FIG. 24.

Figure 25:
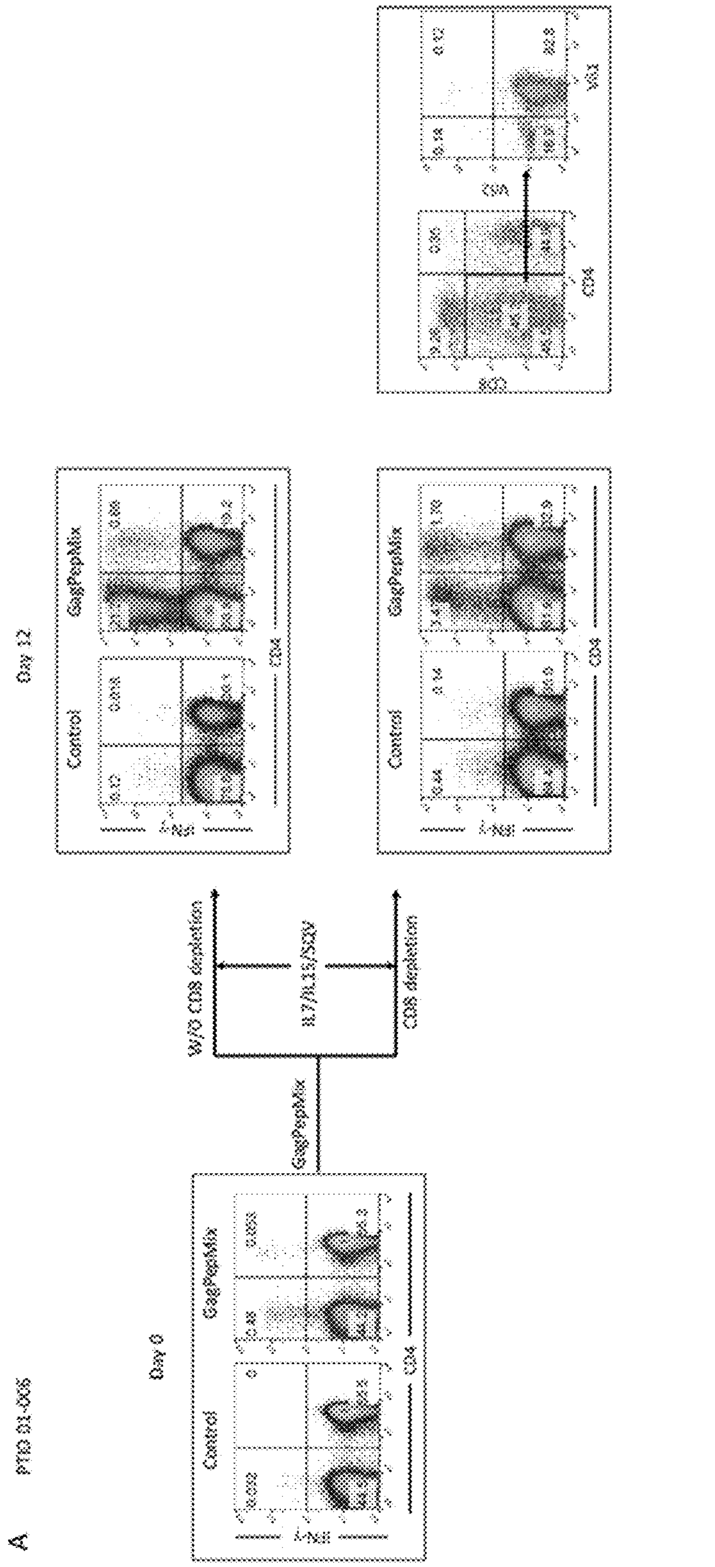
FIG. 25 depicts expansion of Gag-specific T cells by peptide stimulation, CD8 depletion and IL-7/IL-15 incubation. (A), (B), and (C) depict flow cytometry data that shows significantly improved CD4+ T cell expansion after depletion of CD8+ cells. In addition to improved CD4+ T cell expansion, there was also (A) overgrowth of Vδ1 T cells and (C) overgrowth of NK cells.
Figure 25:
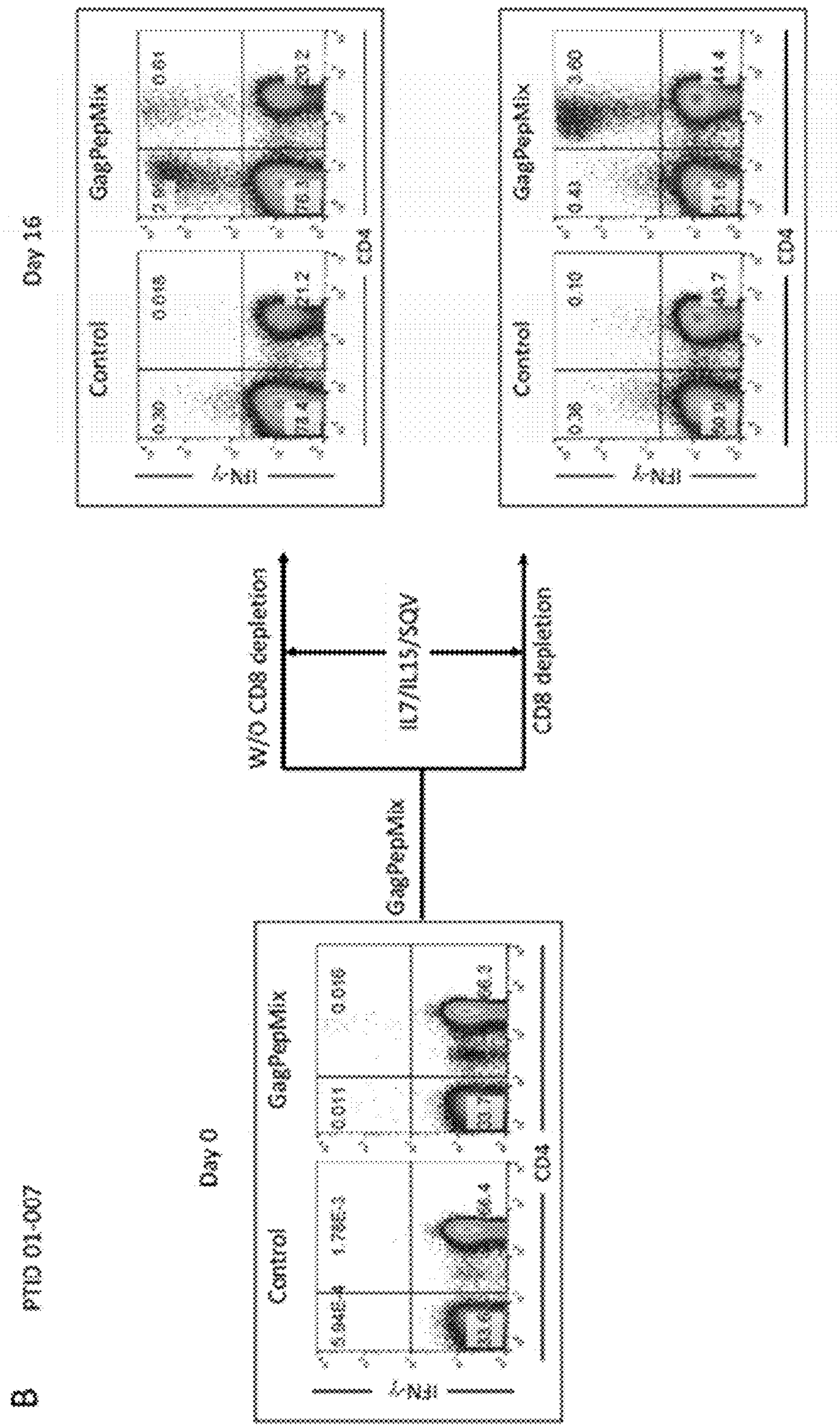
Figure 25:
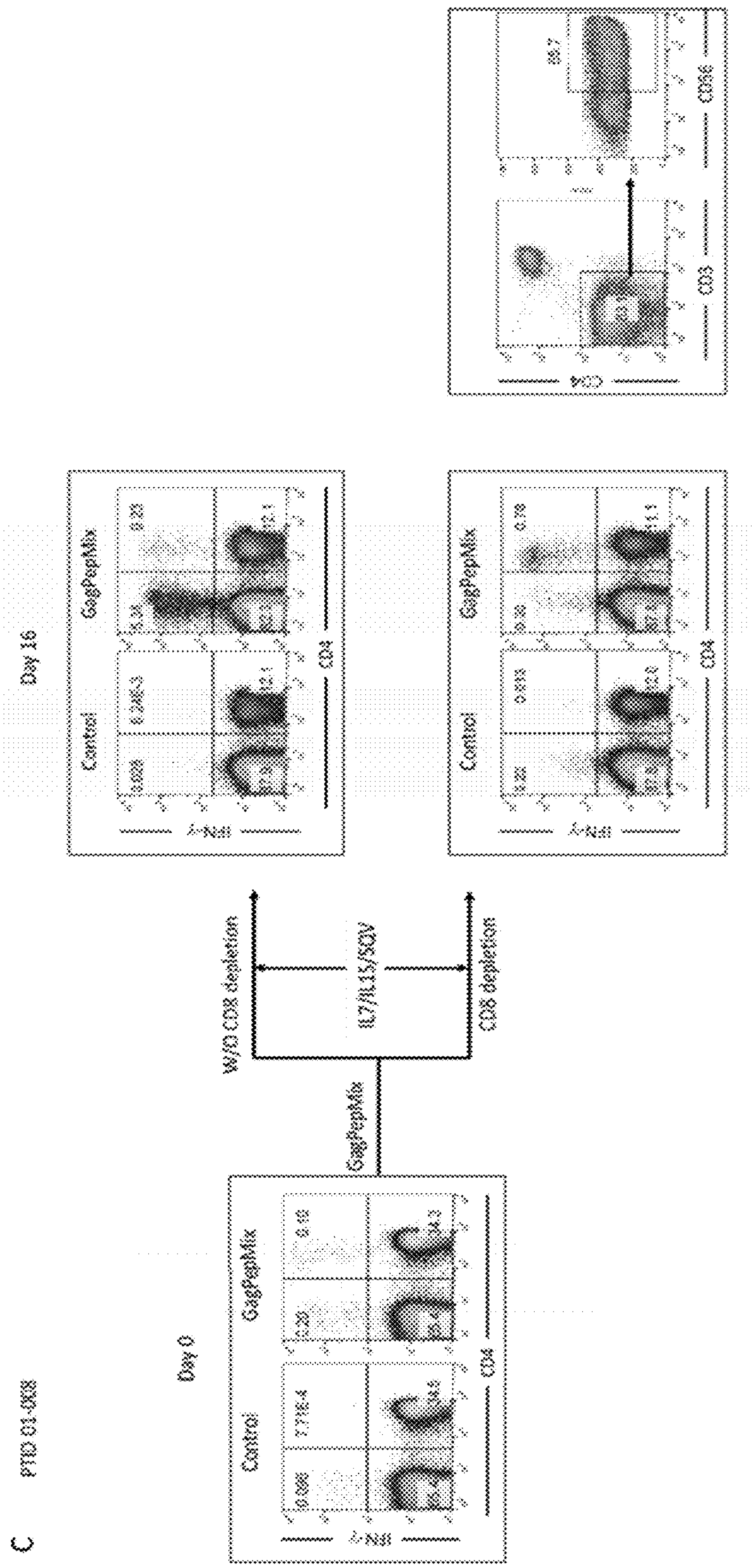

When CD8+ T cells were depleted, HIV-specific CD4 T cell expansion was improved significantly (FIG. 25A-C). However, overgrowth by Vδ1 T cells (PTID 01-006) (FIG. 25A) and NK cells (PTID 01-008) (FIG. 25C) was observed.

Referring to FIG. 25A, on day 0, the lower left quadrant, the lower right quadrant, the upper left quadrant, and the upper right quadrant of the control, had a fluorescence intensity of 44.5%, 55.5%, 0.032%, and 0%, respectively. On day 0, the lower left quadrant, the lower right quadrant, the upper left quadrant, and the upper right quadrant of the GagPepMix, had a fluorescence intensity of 44.2%, 55.3%, 0.48%, and 0.053%, respectively. On day 12, without CD8 depletion, the lower left quadrant, the lower right quadrant, the upper left quadrant, and the upper right quadrant of the control, had a fluorescence intensity of 79.8%, 20.1%, 0.12%, and 0.018%, respectively. On day 12, without CD8 depletion, the lower left quadrant, the lower right quadrant, the upper left quadrant, and the upper right quadrant of the GagPepMix had a fluorescence intensity of 58.9%, 19.2%, 21.2%, and 0.69%, respectively. On day 12, with CD8 depletion, the lower left quadrant, the lower right quadrant, the upper left quadrant, and the upper right quadrant of the control, had a fluorescence intensity of 64.4%, 35.0%, 0.44%, and 0.14%, respectively. On day 12, with CD8 depletion, the lower left quadrant, the lower right quadrant, the upper left quadrant, and the upper right quadrant of the GagPepMix, had a fluorescence intensity of 61.9%, 32.9%, 3.47%, and 1.70%, respectively.

On day 12, with CD8 depletion, gating data was also produced using CD4 and CD8 as variables. The lower left quadrant, the lower right quadrant, the upper left quadrant, and the upper right quadrant had a fluorescence intensity of 45.5%/45.3%, 44.9%, 9.26%, and 0.35%, respectively. In addition, gating data was produced using Vδ1 and Vδ2 as variables. The lower left quadrant, the lower right quadrant, the upper left quadrant, and the upper right quadrant had a fluorescence intensity of 16.9%, 82.8%, 0.14%, and 0.12%, respectively.

Referring to FIG. 25B, on day 0, the lower left quadrant, the lower right quadrant, the upper left quadrant, and the upper right quadrant of the control, had a fluorescence intensity of 33.6%, 66.4%, 5.9E-4%, and 1.78E-3, respectively. On day 0, the lower left quadrant, the lower right quadrant, the upper left quadrant, and the upper right quadrant of the GagPepMix, had a fluorescence intensity of 33.7%, 66.3%, 0.011%, and 0.016%, respectively. On day 16, without CD8 depletion, the lower left quadrant, the lower right quadrant, the upper left quadrant, and the upper right quadrant of the control, had a fluorescence intensity of 78.4%, 21.2%, 0.30%, and 0.018%, respectively. On day 16, without CD8 depletion, the lower left quadrant, the lower right quadrant, the upper left quadrant, and the upper right quadrant of the GagPepMix had a fluorescence intensity of 76.3%, 20.2%, 2.95%, and 0.61%, respectively. On day 16, with CD8 depletion, the lower left quadrant, the lower right quadrant, the upper left quadrant, and the upper right quadrant of the control, had a fluorescence intensity of 50.9%, 48.7%, 0.36%, and 0.10%, respectively. On day 16, with CD8 depletion, the lower left quadrant, the lower right quadrant, the upper left quadrant, and the upper right quadrant of the GagPepMix, had a fluorescence intensity of 51.6%, 44.4%, 0.43%, and 3.60%, respectively.

Referring to FIG. 25C, on day 0, the lower left quadrant, the lower right quadrant, the upper left quadrant, and the upper right quadrant of the control, had a fluorescence intensity of 65.4%, 34.5%, 0.096%, and 7.71E-4, respectively. On day 0, the lower left quadrant, the lower right quadrant, the upper left quadrant, and the upper right quadrant of the GagPepMix, had a fluorescence intensity of 65.4%, 34.3%, 0.20%, and 0.10%, respectively. On day 16, without CD8 depletion, the lower left quadrant, the lower right quadrant, the upper left quadrant, and the upper right quadrant of the control, had a fluorescence intensity of 87.9%, 12.1%, 0.028%, and 6.24E-3%, respectively. On day 16, without CD8 depletion, the lower left quadrant, the lower right quadrant, the upper left quadrant, and the upper right quadrant of the GagPepMix had a fluorescence intensity of 82.3%, 12.1%, 5.38%, and 0.23%, respectively. On day 16, with CD8 depletion, the lower left quadrant, the lower right quadrant, the upper left quadrant, and the upper right quadrant of the control, had a fluorescence intensity of 87.8%, 12.0%, 0.22%, and 0.013%, respectively. On day 16, with CD8 depletion, the lower left quadrant, the lower right quadrant, the upper left quadrant, and the upper right quadrant of the GagPepMix, had a fluorescence intensity of 87.8%, 11.1%, 0.30%, and 0.78%, respectively.

On day 16, with CD8 depletion, gating data was also produced using the variables CD3 and CD4, which showed a fluorescence intensity of 83.1% in the region indicated. In addition, gating data was produced using the variables CD56 and CD4, which showed a fluorescence intensity of 65.7% in the region indicated.

Example 22: Generating a Population of CD4+ T Cells Through Depletion of CD8+, γδ, NK, and B Cells Prior to Peptide Stimulation When CD8+ T cells were depleted, γδ or NK cell overgrowth was observed in multiple patients. Consequently, CD8, γδ, NK or B cells were depleted to test whether it would improve CD4+ T cell expansion. Cell depletion was performed after peptide stimulation and before lentivirus transduction.

Figure 26:
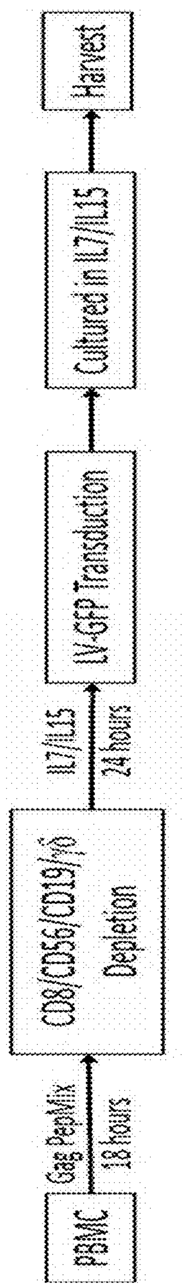
FIG. 26 depicts a schematic of a CD8/CD56/CD19/γδ depletion protocol.

HIV positive human peripheral blood was obtained. PBMCs were separated with Ficoll-Paque PLUS (GE Healthcare, Cat: 17-1440-02). Fresh separated PBMCs ($1\times10^7$) were stimulated with PepMix™ HIV (GAG) Ultra (Cat: PM-HIV-GAG, JPT Peptide Technologies, Berlin, Germany) in 1 mL medium in a 24-well plate for 18 hours. CD8+ T, γδ, NK, or B cells were depleted with PE labeled specific antibodies and anti-PE microbeads. The negative selected cells were cultured at $2\times10^6$/mL in TexMACS GMP medium (Cat: 170-076-309, Miltenyi Biotech, Bergisch Gladbach, Germany) containing IL-7 (170-076-111, Miltenyi Biotech, Bergisch Gladbach, Germany), IL-15 (170-076-114, Miltenyi Biotech, Bergisch Gladbach, Germany) and Saquinavir (Cat: 4658, NIH AIDS Reagent Program, Germantown, MD). Lentivirus AGT103 was added 24 hours later at MOI 5. Fresh medium containing IL-7, IL-15 and Saquinavir were added every 2-3 days during the expansion. The final concentration of IL-7/IL-15 was 10 ng/mL. At day 12-16, $2\text{-}3\times10^6$ cells were collected for peptide restimulation and intracellular cytokine staining (ICS) analysis. A schematic of this depletion protocol is shown in FIG. 26.

Figure 27:
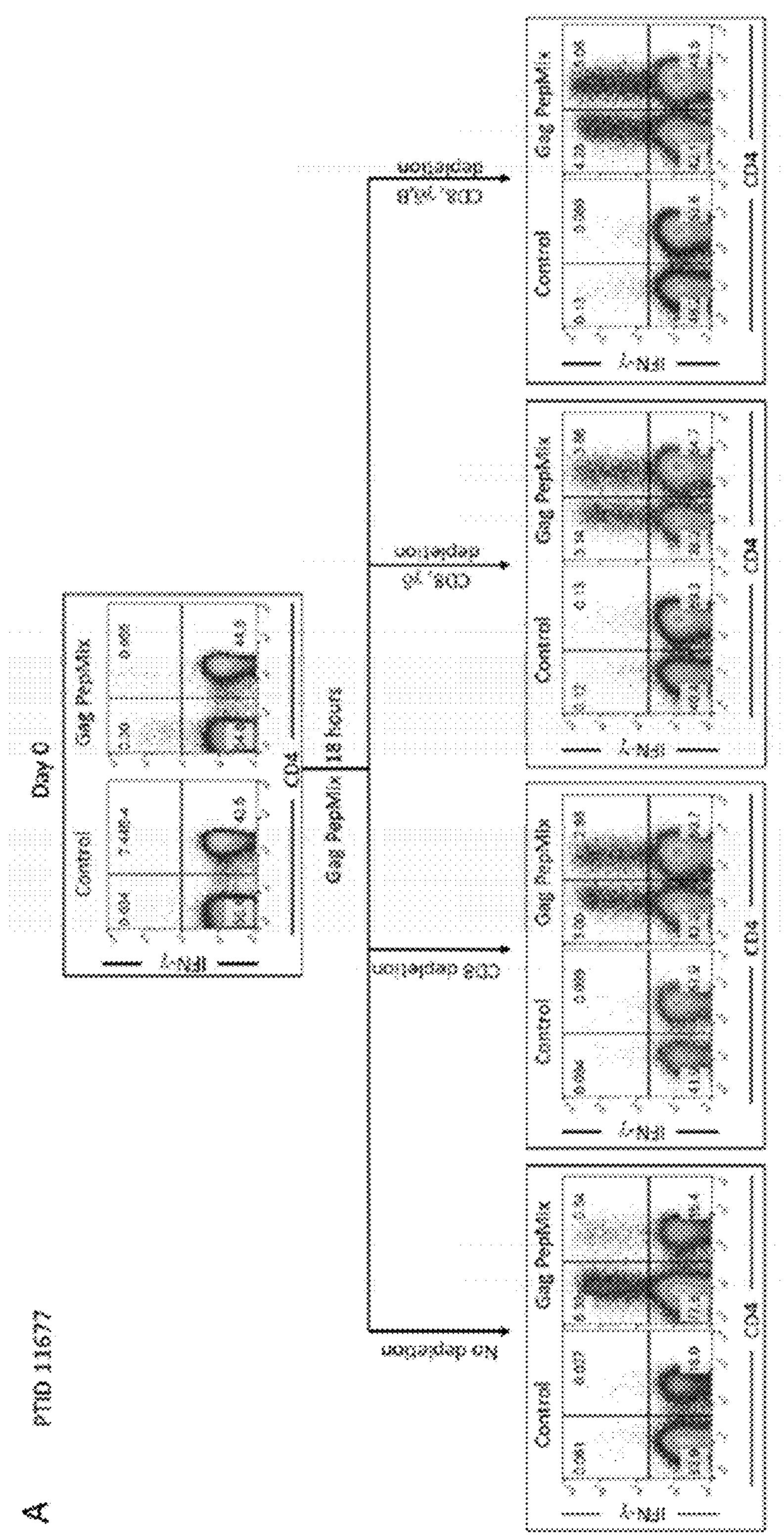
FIG. 27 depicts expansion of Gag-specific T cells by peptide stimulation, CD8/γδ/NK/B cell depletion and IL-7/IL-15 incubation. (A)-(B) depict flow cytometry data that shows that overgrowth of CD8+, γδ, or NK cells either inhibits CD4+ T cell growth or kills lentivirus-transduced antigen-specific CD4+ T cells. After depletion of CD8+, γδ, or NK cells, CD4+ T cells were expanded.
Figure 27:
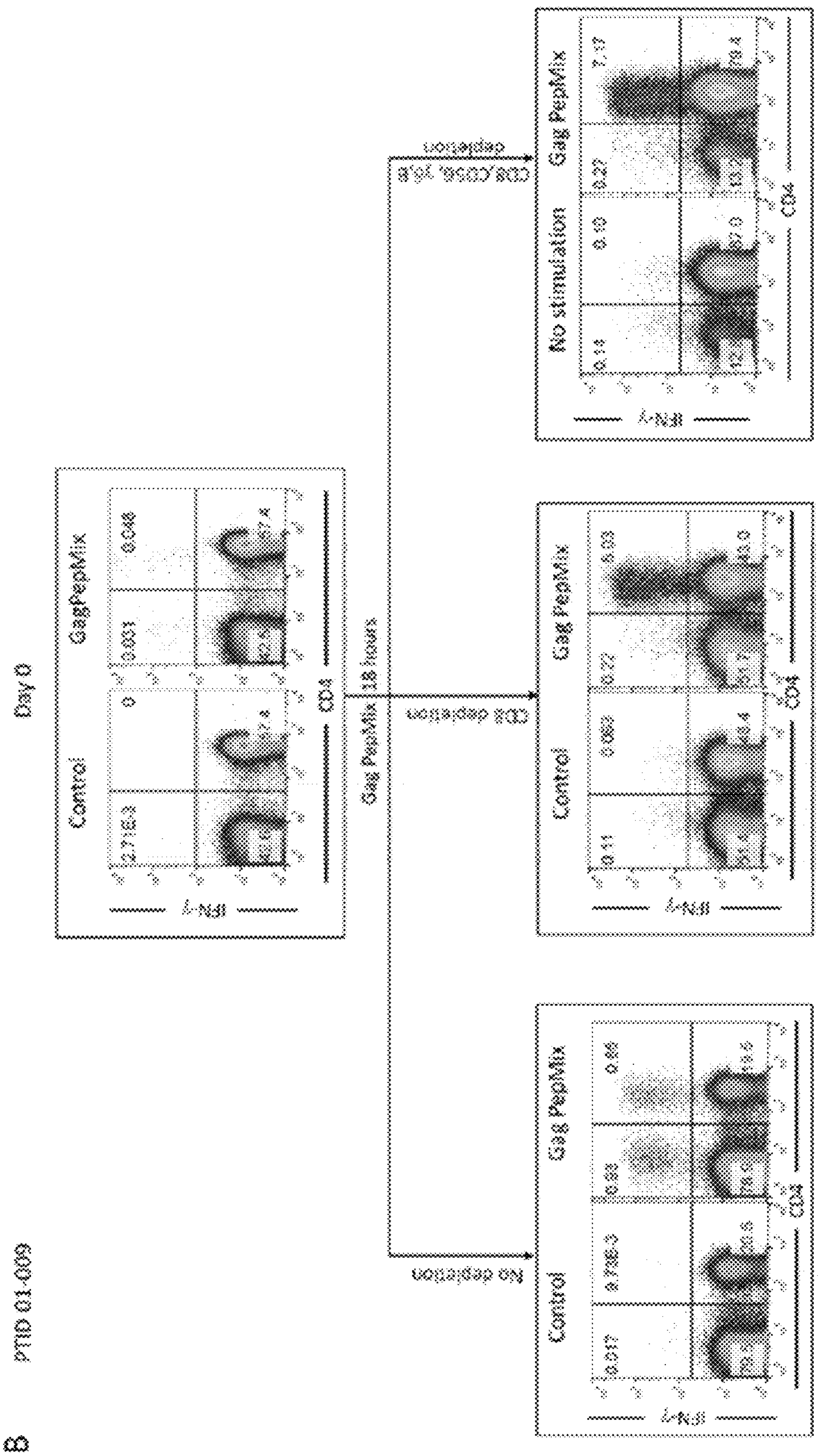

When additional cell subsets were depleted, HIV Gag-specific CD4 T cells were expanded to higher levels (FIG. 27A-B). The overgrowth of CD8, γδ, or NK cells appears to inhibit CD4 T cell growth or kill lentivirus-transduced antigen-specific CD4 T cells. This optimized protocol is suitable for scale-up and cell manufacturing.

Referring to FIG. 27A, on day 0, the lower left quadrant, the lower right quadrant, the upper left quadrant, and the upper right quadrant of the control, had a fluorescence intensity of 56.4%, 43.5%, 0.034%, and 7.44E-4%, respectively. On day 0, the lower left quadrant, the lower right quadrant, the upper left quadrant, and the upper right quadrant of the GagPepMix, had a fluorescence intensity of 54.8%, 44.8%, 0.30%, and 0.055%, respectively. After 18 hours with no depletion, the lower left quadrant, the lower right quadrant, the upper left quadrant, and the upper right quadrant of the control, had a fluorescence intensity of 83.9%, 16.0%, 0.061%, and 0.027%, respectively. After 18 hours with no depletion, the lower left quadrant, the lower right quadrant, the upper left quadrant, and the upper right quadrant of the GagPepMix, had a fluorescence intensity of 77.6%, 15.4%, 6.39%, and 0.54%, respectively. After 18 hours with CD8 depletion, the lower left quadrant, the lower right quadrant, the upper left quadrant, and the upper right quadrant of the control, had a fluorescence intensity of 41.9%, 57.9%, 0.094%, and 0.099%, respectively. After 18 hours with CD8 depletion, the lower left quadrant, the lower right quadrant, the upper left quadrant, and the upper right quadrant of the GagPepMix, had a fluorescence intensity of 43.3%, 50.7%, 3.00%, and 2.98%, respectively. After 18 hours with CD8 and 76 depletion, the lower left quadrant, the lower right quadrant, the upper left quadrant, and the upper right quadrant of the control, had a fluorescence intensity of 40.4%, 59.3%, 0.12%, and 0.13%, respectively. After 18 hours with CD8 and 76 depletion, the lower left quadrant, the lower right quadrant, the upper left quadrant, and the upper right quadrant of the GagPepMix, had a fluorescence intensity of 38.3%, 54.7%, 3.14%, and 3.86%, respectively. After 18 hours with CD8, 7S, and B depletion, the lower left quadrant, the lower right quadrant, the upper left quadrant, and the upper right quadrant of the control, had a fluorescence intensity of 46.2%, 53.6%, 0.13%, and 0.080%, respectively. After 18 hours with CD8, 7S, and B depletion, the lower left quadrant, the lower right quadrant, the upper left quadrant, and the upper right quadrant of the GagPepMix, had a fluorescence intensity of 42.1%, 48.5%, 4.28%, and 5.06%, respectively.

Referring to FIG. 27B, on day 0, the lower left quadrant, the lower right quadrant, the upper left quadrant, and the upper right quadrant of the control, had a fluorescence intensity of 42.6%, 57.4%, 2.71E-3%, and 0.0%, respectively. On day 0, the lower left quadrant, the lower right quadrant, the upper left quadrant, and the upper right quadrant of the GagPepMix, had a fluorescence intensity of 42.5%, 57.4%, 0.031%, and 0.048%, respectively. After 18 hours with no depletion, the lower left quadrant, the lower right quadrant, the upper left quadrant, and the upper right quadrant of the control, had a fluorescence intensity of 79.5%, 20.5%, 0.017%, and 9.73E-3%, respectively. After 18 hours with no depletion, the lower left quadrant, the lower right quadrant, the upper left quadrant, and the upper right quadrant of the GagPepMix, had a fluorescence intensity of 78.9%, 19.5%, 0.93%, and 0.65%, respectively. After 18 hours with CD8 depletion, the lower left quadrant, the lower right quadrant, the upper left quadrant, and the upper right quadrant of the control, had a fluorescence intensity of 51.4%, 48.4%, 0.11%, and 0.063%, respectively. After 18 hours with CD8 depletion, the lower left quadrant, the lower right quadrant, the upper left quadrant, and the upper right quadrant of the GagPepMix, had a fluorescence intensity of 51.7%, 43.0%, 0.22%, and 5.03%, respectively. After 18 hours with CD8, CD56, 7S, and B depletion, the lower left quadrant, the lower right quadrant, the upper left quadrant, and the upper right quadrant of the cells that had no stimulation, had a fluorescence intensity of 12.8%, 87.0%, 0.14%, and 0.10%, respectively. After 18 hours with CD8, CD56, 7S, and B depletion, the lower left quadrant, the lower right quadrant, the upper left quadrant, and the upper right quadrant of the GagPepMix, had a fluorescence intensity of 13.2%, 79.4%, 0.27%, and 7.17%, respectively.

Example 23: Method of Measuring Transduction Efficiency of the AGT103 Lentivirus To improve the expansion of CD4+ T cells, the target cell is lentivirus AGT103-transduced, antigen-specific CD4+ T cells. A lentivirus carrying GFP was used to measure transduction efficiency. Because intracellular staining causes significant GFP signal loss, CCS was used to identify antigen-specific CD4+ T cells and GFP positive cells were used to identify the transduced cell subsets.

$1\times10^7$ PBMCs from HIV positive patients were stimulated with PepMix™ HIV (GAG) Ultra (Cat: PM-HIV-GAG, JPT Peptide Technologies, Berlin, Germany) in 1 mL medium in a 24-well plate for 18 hours. CD8, γδ, NK or B cells were depleted with PE labeled specific antibodies and anti-PE microbeads. The negative selected cells were cultured at $2\times10^6$/mL in TexMACS GMP medium (Cat: 170-076-309, Miltenyi Biotech, Bergisch Gladbach, Germany) containing IL-7 (170-076-111, Miltenyi Biotech, Bergisch Gladbach, Germany), IL-15 (170-076-114, Miltenyi Biotech, Bergisch Gladbach, Germany) and Saquinavir (Cat: 4658, NIH AIDS Reagent Program, Germantown, MD). Lentivirus carrying GFP was added 24 hours later at MOI 5. Fresh medium containing IL-7, IL-15 and Saquinavir were added every 3 days during the expansion. The final concentration of IL-7/IL-15 was 10 ng/mL. At day 12-16, $2\text{-}3\times10^6$ cells were collected. Peptide restimulation and CCS assay was performed to evaluate IFN-γ-positive antigen-specific CD4+ T cells and transduction efficiency with GFP signaling. All experiments were performed following manufacturer's instructions.

Figure 28:
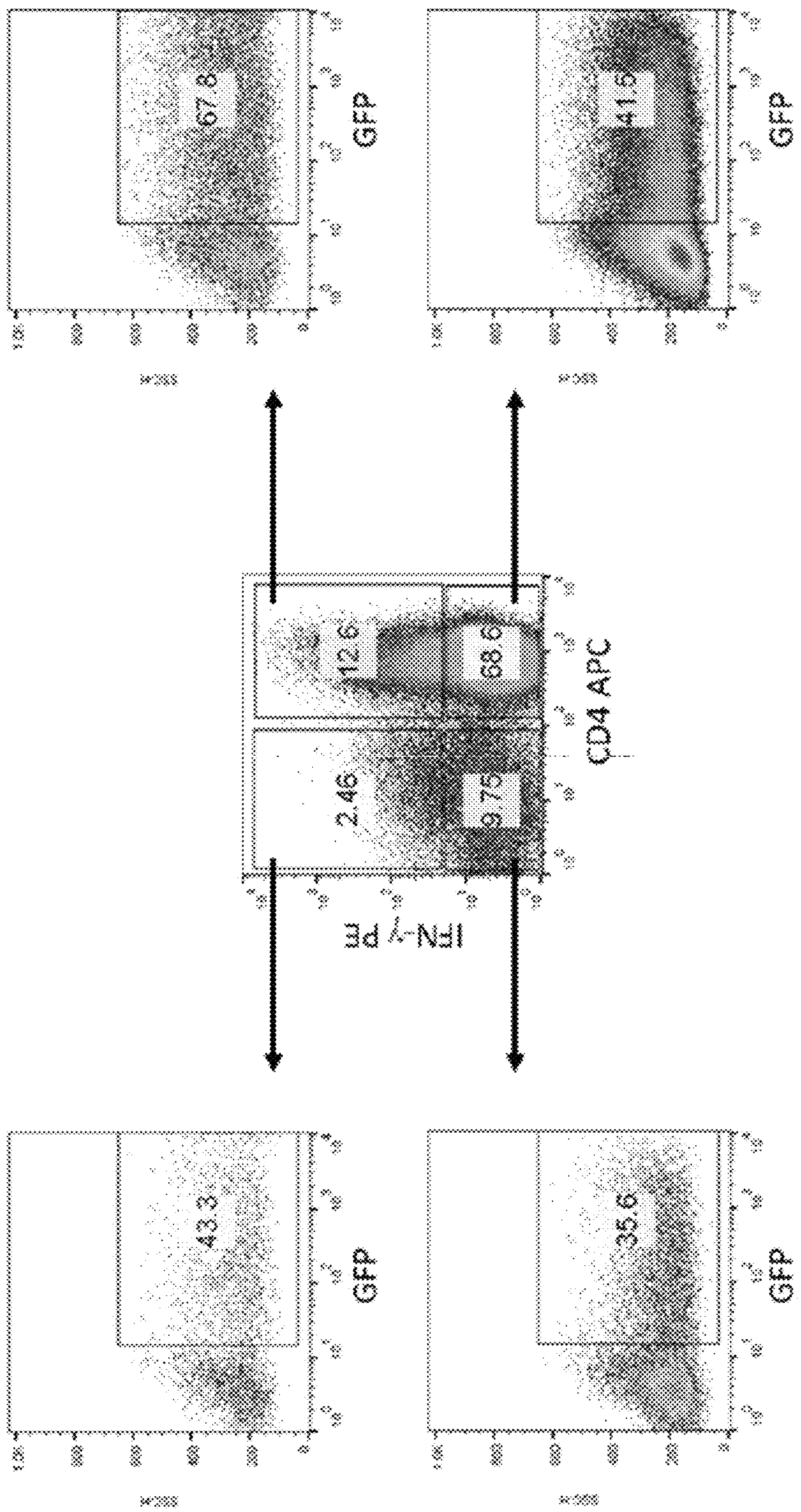
FIG. 28 depicts expansion and transduction of Gag-specific T cells by peptide stimulation, CD8/γδ/NK/B cell depletion and IL-7/IL-15 incubation. IFN-γ positive, antigen-specific CD4+ T cells resulted in better transduction efficiency compared to other subsets in culture.

IFN-γ positive, antigen-specific CD4+ T cells showed much better transduction efficiency compared to other cell subsets in the culture (FIG. 28). It is reasonable given that antigen-specific CD4+ T cells received TCR stimulation, proliferated faster, and were more easily infected by lentivirus. As shown in FIG. 28, the lower right quadrant (68.6% fluorescence) and upper right quadrant (12.6% fluorescence), had a GFP transduction efficiency of 41.5%, and 67.8%, respectively. Ibis is in contrast to the lower left quadrant (9.75% fluorescence) and the upper left quadrant (2.46% fluorescence), which had a GFP transduction efficiency of 35.6% and 43.3%, respectively.

Example 24: Method of Determining Relationship Between Percentage of Transduced Cells and Vector Copy Number Because the target cell is AGT103 lentivirus transduced, HIV-specific CD4 T cells, it is important to know how many target cells are included in the final cell product. However, there are no detectable markers included in the clinical grade AGT103 lentivirus. As a result, transduction efficiency was measured by detecting vector copy number (VCN) by qPCR. By establishing the relationship between percentage of transduced cells and VCN using a lentivirus carrying GFP, the percentage of transduced cells based on VCN in the final cell product can be estimated.

$1\times10^{7}$ PBMCs from HIV positive patients were stimulated with PepMix™ HIV (GAG) Ultra (Cat: PM-HIV-GAG, JPT Peptide Technologies, Berlin, Germany) in 1 mL medium in a 24-well plate for 18 hours. CD8, γδ, NK or B cells were depleted with PE labeled specific antibodies and anti-PE microbeads. The negative selected cells were cultured at $2\times10^{6}$/mL in TexMACS GMP medium (Cat: 170-076-309, Miltenyi Biotech, Bergisch Gladbach, Germany) containing IL-7 (170-076-111, Miltenyi Biotech, Bergisch Gladbach, Germany), IL-15 (170-076-114, Miltenyi Biotech, Bergisch Gladbach, Germany) and Saquinavir (Cat: 4658, NIH AIDS Reagent Program, Germantown, MD). Lentivirus carrying GFP was added 24 hours later at MOI 5. Fresh medium containing IL-7, IL-15 and Saquinavir were added every 3 days during the expansion. The final concentration of IL-7/IL-15 was 10 ng/mL. The final concentration of Saquinavir was 100 nM. At day 12-16, 2-$3\times10^{6}$ cells were collected. Peptide restimulation and CCS assay was performed to evaluate antigen-specific CD4+ T cells and transduction efficiency with GFP signaling. QPCR was performed to detect vector copy number. All experiments were performed following manufacturer's instructions.

After testing four samples, a positive correlation between percentage of transduced cells and vector copy number was observed (FIG. 29).

Sequences

The following sequences are referred to herein:

| SEQ ID NO: | Description | Sequence |
|---|---|---|
| 1 | miR30 CCR5 | AGGTATATTGCTGTTGACAGTGAGCGACTGTAAACT GAGCTTGCTCTACTGTGAAGCCACAGATGGGTAGA GCAAGCACAGTTTACCGCTGCCTACTGCCTCGGACT TCAAGGGGCTT |
| 2 | miR21 Vif | CATCTCCATGGCTGTACCACCTTGTCGGGGGATGTG TACTTCTGAACTTGTGTTGAATCTCATGGAGTTCAG AAGAACACATCCGCACTGACATTTTGGTATCTTTCA TCTGACCA |
| 3 | miR185 Tat | GGGCCTGGCTCGAGCAGGGGGCGAGGGATTCCGCT TCTTCCTGCCATAGCGTGG TCCCCTCCCCTATGGCAGGCAGAAGCGGCACCTTCC CTCCCAATGACCGCGTCTTCGTCG |
| 4, 64 | Elongation Factor-1 alpha (EF1-alpha) promoter | CCGGTGCCTAGAGAAGGTGGCGCGGGGTAAACTGG GAAAGTGATGTCGTGTACTGGCTCCGCCTTTTTCCC GAGGGTGGGGGAGAACCGTATATAAGTGCAGTAGT CGCCGTGAACGTTCTTTTTCGCAACGGGTTTGCCGC CAGAACACAGGTAAGTGCCGTGTGTGGTTCCCGCG GGCCTGGCCTCTTTACGGGTTATGGCCCTTGCGTGC CTTGAATTACTTCCACGCCCCTGGCTGCAGTACGTG ATTCTTGATCCCGAGCTTCGGGTTGGAAGTGGGTGG GAGAGTTCGAGGCCTTGCGCTTAAGGAGCCCCTTCG CCTCGTGCTTGAGTTGAGGCCTGGCCTGGGCGCTGG GGCCGCCGCGTGCGAATCTGGTGGCACCTTCGCGCC TGTCTCGCTGCTTTCGATAAGTCTCTAGCCATTTAAA ATTTTTGATGACCTGCTGCGACGCTTTTTTTCTGGCA AGATAGTCTTGTAAATGCGGGCCAAGATCTGCACAC TGGTATTTCGGTTTTTGGGGCCGCGGGCGGCGACGG GGCCCGTGCGTCCCAGCGCACATGTTCGGCGAGGC GGGGCCTGCGAGCGCGGCCACCGAGAATCGGACGG GGGTAGTCTCAAGCTGGCCGGCCTGCTCTGGTGCCT GGCCTCGCGCCGCCGTGTATCGCCCCGCCCTGGGCG GCAAGGCTGGCCCGGTCGGCACCAGTTGCGTGAGC GGAAAGATGGCCGCTTCCCGGCCCTGCTGCAGGGA GCTCAAAATGGAGGACGCGGCGCTCGGGAGAGCGG GCGGGTGAGTCACCCACACAAAGGAAAAGGGCCTT TCCGTCCTCAGCCGTCGCTTCATGTGACTCCACGGA GTACCGGGCGCCGTCCAGGCACCTCGATTAGTTCTC GAGCTTTTGGAGTACGTCGTCTTTAGGTTGGGGGGA |

-continued

| SEQ ID NO: | Description | Sequence |
|---|---|---|
| | | GGGGTTTTATGCGATGGAGTTTCCCCACACTGAGTG GGTGGAGACTGAAGTTAGGCCAGCTTGGCACTTGAT GTAATTCTCCTTGGAATTTGCCCTTTTTGAGTTTGGA TCTTGGTTCATTCTCAAGCCTCAGACAGTGGTTCAA AGTTTTTTTCTTCCATTTCAGGTGTCGTGA |
| 5 | CCR5 target sequence | GAGCAAGCTCAGTTTACA |
| 6 | Vif target sequence | GGGATGTGTACTTCTGAACTT |
| 7 | Tat target sequence | TCCGCTTCTTCCTGCCATAG |
| 8 | TAR decoy sequence | CTTGCAATGATGTCGTAATTTGCGTCTTACCTCGTTC TCGACAGCGACCAGATCTGAGCCTGGGAGCTCTCTG GCTGTCAGTAAGCTGGTACAGAAGGTTGACGAAAA TTCTTACTGAGCAAGAAA |
| 9 | Rev/Tat target sequence | GCGGAGACAGCGACGAAGAGC |
| 10 | Rev/Tat shRNA sequence | GCGGAGACAGCGACGAAGAGCTTCAAGAGAGCTCT TCGTCGCTGTCTCCGCTTTTT |
| 11 | Gag target sequence | GAAGAAATGATGACAGCAT |
| 12 | Gag shRNA sequence | GAAGAAATGATGACAGCATTTCAAGAGAATGCTGT CATCATTTCTTCTTTTT |
| 13 | Pol target sequence | CAGGAGCAGATGATACAG |
| 14 | Pol shRNA sequence | CAGGAGATGATACAGTTCAAGAGACTGTATCATCTG CTCCTGTTTTT |
| 15 | CCR5 target sequence #1 | GTGTCAAGTCCAATCTATG |
| 16 | CCR5 shRNA sequence #1 | GTGTCAAGTCCAATCTATGTTCAAGAGACATAGATT GGACTTGACACTTTTT |
| 17 | CCR5 target sequence #2 | GAGCATGACTGACATCTAC |
| 18 | CCR5 shRNA sequence #2 | GAGCATGACTGACATCTACTTCAAGAGAGTAGATGT CAGTCATGCTCTTTTT |
| 19 | CCR5 target sequence #3 | GTAGCTCTAACAGGTTGGA |
| 20 | CCR5 shRNA sequence #3 | GTAGCTCTAACAGGTTGGATTCAAGAGATCCAACCT GTTAGAGCTACTTTTT |
| 21 | CCR5 target sequence #4 | GTTCAGAAACTACCTCTTA |
| 22 | CCR5 shRNA sequence #4 | GTTCAGAAACTACCTCTTATTCAAGAGATAAGAGGT AGTTTCTGAACTTTTT |
| 23 | CCR5 target sequence #5 | GAGCAAGCTCAGTTTACACC |
| 24 | CCR5 shRNA sequence #5 | GAGCAAGCTCAGTTTACACCTTCAAGAGAGGTGTA AACTGAGCTTGCTCTTTTT |
| 25 | *Homo sapiens* CCR5 gene, sequence 1 | ATGGATTATCAAGTGTCAAGTCCAATCTATGACATC AATTATTATACATCGGAGCCCTGCCAAAAAATCAAT GTGAAGCAAATCGCAGCCCGCCTCCTGCCTCCGCTC TACTCACTGGTGTTCATCTTTGGTTTTGTGGGC |
| 26 | *Homo sapiens* CCR5 gene, sequence 2 | AACATGCTGGTCATCCTCATCCTGATAAACTGCAAA AGGCTGAAGAGCATGACTGACATCTACCTGCTCAAC CTGGCCATCTCTGACCTGTTTTTCCTTCTTACTGTCC |

-continued

| SEQ ID NO: | Description | Sequence |
|---|---|---|
| | | CCTTCTGGGCTCACTATGCTGCCGCCCAGTGGGACT TTGGAAATACAATGTGTCAACTCTTGACAGGGCTCT ATTTTATAGGCTTCTTCTCTGGAATCTTCTTCATCAT CCTCCTGACAATCGATAGGTACCTGGCTGTCGTCCA TGCTGTGTTTGCTTTAAAAGCCAGGACGGTCACCTT TGGGGTGGTGACAAGTGTGATCACTTGGGTGGTGGC TGTGTTTGCGTCTCTCCCAGGAATCATCTTTACCAG ATCTCAAAAAGAAGGTCTTCATTACACCTGCAGCTC TCATTTTCCATACAGTCAGTATCAATTCTGGAAGAA TTTCCAGACATTAAAGATAGTCATCTTGGGGCTGGT CCTGCCGCTGCTTGTCATGGTCATCTGCTACTCGGG AATCCTAAAAACTCTGCTTCGGTGTCGAAATGAGAA GAAGAGGCACAGGGCTGTGAGGCTTATCTTCACCAT CATGATTGTTTATTTTCTCTTCTGGGCTCCCTACAAC ATTGTCCTTCTCCTGAAC |
| 27 | *Homo sapiens* CCR5 gene, sequence 3 | ACCTTCCAGGAATTCTTTGGCCTGAATAATTGCAGT AGCTCTAACAGGTTGGACCAAGCTATGCAGGTGA |
| 28 | *Homo sapiens* CCR5 gene, sequence 4 | CAGAGACTCTTGGGATGACGCACTGCTGCATCAACC CCATCATCTATGCCTTTGTCGGGGAGAAGTTCAGAA ACTACCTCTTAGTCTTCTTCCAAAAGCACATTGCCA AACGCTTCTGCAAATGCTGTTCTATTTTCCAG |
| 29 | Homo sapiens CCR5 gene, sequence 5 | CAAGAGGCTCCCGAGCGAGCAAGCTCAGTTTACAC CCGATCCACTGGGGAGCAGGAAATATCTGTGGGCTT GTGA |
| 30 | CD4 promoter sequence | TGTTGGGGTTCAAATTTGAGCCCCAGCTGTTAGCCC TCTGCAAAGAAAAAAAAAAAAAAAAAAGAACAAA GGGCCTAGATTTCCCTTCTGAGCCCCACCCTAAGAT GAAGCCTCTTCTTTCAAGGGAGTGGGGTTGGGGTGG AGGCGGATCCTGTCAGCTTTGCTCTCTCTGTGGCTG GCAGTTTCTCCAAAGGGTAACAGGTGTCAGCTGGCT GAGCCTAGGCTGAACCCTGAGACATGCTACCTCTGT CTTCTCATGGCTGGAGGCAGCCTTTGTAAGTCACAG AAAGTAGCTGAGGGGCTCTGGAAAAAAGACAGCCA GGGTGGAGGTAGATTGGTCTTTGACTCCTGATTTAA GCCTGATTCTGCTTAACTTTTTCCCTTGACTTTGGCA TTTTCACTTTGACATGTTCCCTGAGAGCCTGGGGGG TGGGGAACCCAGCTCCAGCTGGTGACGTTTGGGGCC GGCCCAGGCCTAGGGTGTGGAGGAGCCTTGCCATC GGGCTTCCTGTCTCTCTTCATTTAAGCACGACTCTGC AGA |
| 31 | miR30-CCR5/miR21-Vif/miR185 Tat microRNA cluster sequence | AGGTATATTGCTGTTGACAGTGAGCGACTGTAAACT GAGCTTGCTCTACTGTGAAGCCACAGATGGGTAGA GCAAGCACAGTTTACCGCTGCCTACTGCCTCGGACT TCAAGGGGCTTCCCGGGCATCTCCATGGCTGTACCA CCTTGTCGGGGGATGTGTACTTCTGAACTTGTGTTG AATCTCATGGAGTTCAGAAGAACACATCCGCACTG ACATTTGGTATCTTTCATCTGACCAGCTAGCGGGC CTGGCTCGAGCAGGGGGCGAGGGATTCCGCTTCTTC CTGCCATAGCGTGGTCCCCTCCCCTATGGCAGGCAG AAGCGGCACCTTCCCTCCCAATGACCGCGTCTTCGT C |
| 32 | Long WPRE sequence | AATCAACCTCTGATTACAAAATTTGTGAAAGATTGA CTGGTATTCTTAACTATGTTGCTCCTTTTACGCTATG TGGATACGCTGCTTTAATGCCTTTGTATCATGCTATT GCTTCCCGTATGGCTTTCATTTTCTCCTCCTTGTATA AATCCTGGTTGCTGTCTCTTTATGAGGAGTTGTGGC CCGTTGTCAGGCAACGTGGCGTGGTGTGCACTGTGT TTGCTGACGCAACCCCCACTGGTTGGGGCATTGCCA CCACCTGTCAGCTCCTTTCCGGGACTTTCGCTTTCCC CCTCCCTATTGCCACGGCGGAACTCATCGCCGCCTG CCTTGCCCGCTGCTGGACAGGGGCTCGGCTGTTGGG CACTGACAATTCCGTGGTGTTGTCGGGGAAATCATC GTCCTTTCCTTGGCTGCTCGCCTGTGTTGCCACCTGG ATTCTGCGCGGGACGTCCTTCTGCTACGTCCCTTCG GCCCTCAATCCAGCGGACCTTCCTTCCCGCGGCCTG CTGCCGGCTCTGCGGCCTCTTCCGCGTCTTCGCCTTC GCCCTCAGACGAGTCGGATCTCCCTTTGGGCCGCCT CCCCGCCT |

-continued

| SEQ ID NO: | Description | Sequence |
|---|---|---|
| 33 | Elongation Factor-1 alpha (EF1-alpha) promoter; miR30CCR5; miR21Vif; miR185 Tat | CCGGTGCCTAGAGAAGGTGGCGCGGGGTAAACTGG GAAAGTGATGTCGTGTACTGGCTCCGCCTTTTTCCC GAGGGTGGGGGAGAACCGTATATAAGTGCAGTAGT CGCCGTGAACGTTCTTTTTCGCAACGGGTTTGCCGC CAGAACACAGGTAAGTGCCGTGTGTGGTTCCCGCG GGCCTGGCCTCTTTACGGGTTATGGCCCTTGCGTGC CTTGAATTACTTCCACGCCCCTGGCTGCAGTACGTG ATTCTTGATCCCGAGCTTCGGGTTGGAAGTGGGTGG GAGAGTTCGAGGCCTTGCGCTTAAGGAGCCCCTTCG CCTCGTGCTTGAGTTGAGGCCTGGCCTGGGCGCTGG GGCCGCCGCGTGCGAATCTGGTGGCACCTTCGCGCC TGTCTCGCTGCTTTCGATAAGTCTCTAGCCATTTAAA ATTTTTGATGACCTGCTGCGACGCTTTTTTTCTGGCA AGATAGTCTTGTAAATGCGGGCCAAGATCTGCACAC TGGTATTTCGGTTTTTGGGGCCGCGGGCGGCGACGG GGCCCGTGCGTCCCAGCGCACATGTTCGGCGAGGC GGGGCCTGCGAGCGCGGCCACCGAGAATCGGACGG GGGTAGTCTCAAGCTGGCCGGCCTGCTCTGGTGCCT GGCCTCGCGCCGCCGTGTATCGCCCCGCCCTGGGCG GCAAGGCTGGCCCGGTCGGCACCAGTTGCGTGAGC GGAAAGATGGCCGCTTCCCGGCCCTGCTGCAGGGA GCTCAAAATGGAGGACGCGGCGCTCGGGAGAGCGG GCGGGTGAGTCACCCACACAAAGGAAAAGGGCCTT TCCGTCCTCAGCCGTCGCTTCATGTGACTCCACGGA GTACCGGGCGCCGTCCAGGCACCTCGATTAGTTCTC GAGCTTTTGGAGTACGTCGTCTTTAGGTTGGGGGGA GGGGTTTTATGCGATGGAGTTTCCCCACACTGAGTG GGTGGAGACTGAAGTTAGGCCAGCTTGGCACTTGAT GTAATTCTCCTTGGAATTTGCCCTTTTTGAGTTTGGA TCTTGGTTCATTCTCAAGCCTCAGACAGTGGTTCAA AGTTTTTTTCTTCCATTTCAGGTGTCGTGATGTACA AGGTATATTGCTGTTGACAGTGAGCGACTGTAAACT GAGCTTGCTCTACTGTGAAGCCACAGATGGGTAGA GCAAGCACAGTTTACCGCTGCCTACTGCCTCGGACT TCAAGGGGCTTCCCGGGCATCTCCATGGCTGTACCA CCTTGTCGGGGGATGTGTACTTCTGAACTTGTGTTG AATCTCATGGAGTTCAGAAGAACACATCCGCACTG ACATTTTGGTATCTTTCATCTGACCAGCTAGCGGGC CTGGCTCGAGCAGGGGGCGAGGGATTCCGCTTCTTC CTGCCATAGCGTGGTCCCCTCCCCTATGGCAGGCAG AAGCGGCACCTTCCCTCCCAATGACCGCGTCTTCGT C |
| 34 | Rous Sarcoma virus (RSV) promoter | GTAGTCTTATGCAATACTCTTGTAGTCTTGCAACAT GGTAACGATGAGTTAGCAACATGCCTTACAAGGAG AGAAAAAGCACCGTGCATGCCGATTGGTGGAAGTA AGGTGGTACGATCGTGCCTTATTAGGAAGGCAACA GACGGGTCTGACATGGATTGGACGAACCACTGAAT TGCCGCATTGCAGAGATATTGTATTTAAGTGCCTAG CTCGATACAATAAACG |
| 35 | 5' Long terminal repeat (LTR) | GGTCTCTCTGGTTAGACCAGATCTGAGCCTGGGAGC TCTCTGGCTAACTAGGGAACCCACTGCTTAAGCCTC AATAAAGCTTGCCTTGAGTGCTTCAAGTAGTGTGTG CCCGTCTGTTGTGTGACTCTGGTAACTAGAGATCCC TCAGACCCTTTTAGTCAGTGTGGAAAATCTCTAGCA |
| 36 | Psi Packaging signal | TACGCCAAAAATTTTGACTAGCGGAGGCTAGAAGG AGAGAG |
| 37 | Rev response element (RRE) | AGGAGCTTTGTTCCTTGGGTTCTTGGGAGCAGCAGG AAGCACTATGGGCGCAGCCTCAATGACGCTGACGG TACAGGCCAGACAATTATTGTCTGGTATAGTGCAGC AGCAGAACAATTTGCTGAGGGCTATTGAGGCGCAA CAGCATCTGTTGCAACTCACAGTCTGGGGCATCAAG CAGCTCCAGGCAAGAATCCTGGCTGTGGAAAGATA CCTAAAGGATCAACAGCTCC |
| 38 | Central polypurine tract (cPPT) | TTTTAAAAGAAAAGGGGGGATTGGGGGGTACAGTG CAGGGGAAAGAATAGTAGACATAATAGCAACAGAC ATACAAACTAAAGAATTACAAAAACAAATTACAAA ATTCAAAATTTTA |
| 39, 102 | 3' delta LTR | TGGAAGGGCTAATTCACTCCCAACGAAGATAAGAT CTGCTTTTTGCTTGTACTGGGTCTCTCTGGTTAGACC AGATCTGAGCCTGGGAGCTCTCTGGCTAACTAGGGA |

-continued

| SEQ ID NO: | Description | Sequence |
|---|---|---|
| | | ACCCACTGCTTAAGCCTCAATAAAGCTTGCCTTGAG<br>TGCTTCAAGTAGTGTGTGCCCGTCTGTTGTGTGACT<br>CTGGTAACTAGAGATCCCTCAGACCCTTTTAGTCAG<br>TGTGGAAAATCTCTAGCAGTAGTAGTTCATGTCA |
| 40, 49 | Helper/Rev; CMV early (CAG) enhancer; Enhance Transcription | TAGTTATTAATAGTAATCAATTACGGGGTCATTAGT<br>TCATAGCCCATATATGGAGTTCCGCGTTACATAACT<br>TACGGTAAATGGCCCGCCTGGCTGACCGCCCAACG<br>ACCCCCGCCCATTGACGTCAATAATGACGTATGTTC<br>CCATAGTAACGCCAATAGGGACTTTCCATTGACGTC<br>AATGGGTGGACTATTTACGGTAAACTGCCCACTTGG<br>CAGTACATCAAGTGTATCATATGCCAAGTACGCCCC<br>CTATTGACGTCAATGACGGTAAATGGCCCGCCTGGC<br>ATTATGCCCAGTACATGACCTTATGGGACTTTCCTA<br>CTTGGCAGTACATCTACGTATTAGTCATC |
| 41, 50 | Helper/Rev; Chicken beta actin (CAG) promoter; Transcription | GCTATTACCATGGGTCGAGGTGAGCCCCACGTTCTG<br>CTTCACTCTCCCCATCTCCCCCCCCTCCCCACCCCCA<br>ATTTTGTATTTATTTATTTTTTAATTATTTTGTGCAGC<br>GATGGGGGCGGGGGGGGGGGGGGCGCGCGCCAGG<br>CGGGGCGGGGCGGGGCGAGGGGCGGGGCGGGGCG<br>AGGCGGAGAGGTGCGGCGGCAGCCAATCAGAGCGG<br>CGCGCTCCGAAAGTTTCCTTTTATGGCGAGGCGGCG<br>GCGGCGGCGGCCCTATAAAAAGCGAAGCGCGCGGC<br>GGGCG |
| 42, 51 | Helper/Rev; Chicken beta actin intron; Enhance gene expression | GGAGTCGCTGCGTTGCCTTCGCCCCGTGCCCCGCTC<br>CGCGCCGCCTCGCGCCGCCCGCCCCGGCTCTGACTG<br>ACCGCGTTACTCCCACAGGTGAGCGGGCGGGACGG<br>CCCTTCTCCTCCGGGCTGTAATTAGCGCTTGGTTTAA<br>TGACGGCTCGTTTCTTTTCTGTGGCTGCGTGAAAGC<br>CTTAAAGGGCTCCGGGAGGGCCCTTTGTGCGGGGG<br>GGAGCGGCTCGGGGGGTGCGTGCGTGTGTGTGTGC<br>GTGGGGAGCGCCGCGTGCGGCCCGCGCTGCCCGGC<br>GGCTGTGAGCGCTGCGGGCGCGGCGCGGGGCTTTG<br>TGCGCTCCGCGTGTGCGCGAGGGGAGCGCGGCCGG<br>GGGCGGTGCCCCGCGGTGCGGGGGGGCTGCGAGGG<br>GAACAAAGGCTGCGTGCGGGGTGTGTGCGTGGGGG<br>GGTGAGCAGGGGGTGTGGGCGCGGCGGTCGGGCTG<br>TAACCCCCCCCTGCACCCCCCTCCCCGAGTTGCTGA<br>GCACGGCCCGGCTTCGGGTGCGGGGCTCCGTGCGG<br>GGCGTGGCGCGGGGCTCGCCGTGCCGGGCGGGGGG<br>TGGCGGCAGGTGGGGGTGCCGGGCGGGGCGGGGCC<br>GCCTCGGGCCGGGGAGGGCTCGGGGGAGGGGCGCG<br>GCGGCCCCGGAGCGCCGGCGGCTGTCGAGGCGCGG<br>CGAGCCGCAGCCATTGCCTTTTATGGTAATCGTGCG<br>AGAGGGCGCAGGGACTTCCTTTGTCCCAAATCTGGC<br>GGAGCCGAAATCTGGGAGGCGCCGCCGCACCCCCT<br>CTAGCGGGCGCGGGCGAAGCGGTGCGGCGCCGGCA<br>GGAAGGAAATGGGCGGGGAGGGCCTTCGTGCGTCG<br>CCGCGCCGCCGTCCCCTTCTCCATCTCCAGCCTCGG<br>GGCTGCCGCAGGGGGACGGCTGCCTTCGGGGGGGA<br>CGGGGCAGGGCGGGGTTCGGCTTCTGGCGTGTGAC<br>CGGCGG |
| 43, 52 | Helper/Rev; HIV Gag; Viral capsid | ATGGGTGCGAGAGCGTCAGTATTAAGCGGGGGAGA<br>ATTAGATCGATGGGAAAAAATTCGGTTAAGGCCAG<br>GGGGAAAGAAAAAATATAAATTAAAACATATAGTA<br>TGGGCAAGCAGGGAGCTAGAACGATTCGCAGTTAA<br>TCCTGGCCTGTTAGAAACATCAGAAGGCTGTAGACA<br>AATACTGGGACAGCTACAACCATCCCTTCAGACAG<br>GATCAGAAGAACTTAGATCATTATATAATACAGTAG<br>CAACCCTCTATTGTGTGCATCAAAGGATAGAGATAA<br>AAGACACCAAGGAAGCTTTAGACAAGATAGAGGAA<br>GAGCAAAACAAAAGTAAGAAAAAAGCACAGCAAG<br>CAGCAGCTGACACAGGACACAGCAATCAGGTCAGC<br>CAAAATTACCCTATAGTGCAGAACATCCAGGGGCA<br>AATGGTACATCAGGCCATATCACCTAGAACTTTAAA<br>TGCATGGGTAAAAGTAGTAGAAGAGAAGGCTTTCA<br>GCCCAGAAGTGATACCCATGTTTTCAGCATTATCAG<br>AAGGAGCCACCCCACAAGATTTAAACACCATGCTA<br>AACACAGTGGGGGACATCAAGCAGCCATGCAAAT<br>GTTAAAAGAGACCATCAATGAGGAAGCTGCAGAAT<br>GGGATAGAGTGCATCCAGTGCATGCAGGGCCTATT<br>GCACCAGGCCAGATGAGAGAACCAAGGGGAAGTGA<br>CATAGCAGGAACTACTAGTACCCTTCAGGAACAAA |

-continued

| SEQ ID NO: | Description | Sequence |
|---|---|---|
| | | TAGGATGGATGACACATAATCCACCTATCCCAGTAG<br>GAGAAATCTATAAAAGATGGATAATCCTGGGATTA<br>AATAAAATAGTAAGAATGTATAGCCCTACCAGCATT<br>CTGGACATAAGACAAGGACCAAAGGAACCCTTTAG<br>AGACTATGTAGACCGATTCTATAAAACTCTAAGAGC<br>CGAGCAAGCTTCACAAGAGGTAAAAAATTGGATGA<br>CAGAAACCTTGTTGGTCCAAAATGCGAACCCAGATT<br>GTAAGACTATTTTAAAAGCATTGGGACCAGGAGCG<br>ACACTAGAAGAAATGATGACAGCATGTCAGGGAGT<br>GGGGGGACCCGGCCATAAAGCAAGAGTTTTGGCTG<br>AAGCAATGAGCCAAGTAACAAATCCAGCTACCATA<br>ATGATACAGAAAGGCAATTTTAGGAACCAAAGAAA<br>GACTGTTAAGTGTTTCAATTGTGGCAAAGAAGGGCA<br>CATAGCCAAAAATTGCAGGGCCCCTAGGAAAAAGG<br>GCTGTTGGAAATGTGGAAAGGAAGGACACCAAATG<br>AAAGATTGTACTGAGAGACAGGCTAATTTTTTAGGG<br>AAGATCTGGCCTTCCCACAAGGGAAGGCCAGGGAA<br>TTTTCTTCAGAGCAGACCAGAGCCAACAGCCCCACC<br>AGAAGAGAGCTTCAGGTTTGGGGAAGAGACAACAA<br>CTCCCTCTCAGAAGCAGGAGCCGATAGACAAGGAA<br>CTGTATCCTTTAGCTTCCCTCAGATCACTCTTTGGCA<br>GCGACCCCTCGTCACAATAA |
| 44, 53 | Helper/Rev; HIV Pol; Protease and reverse transcriptase | ATGAATTTGCCAGGAAGATGGAAACCAAAAATGAT<br>AGGGGGAATTGGAGGTTTTATCAAAGTAGGACAGT<br>ATGATCAGATACTCATAGAAATCTGCGGACATAAA<br>GCTATAGGTACAGTATTAGTAGGACCTACACCTGTC<br>AACATAATTGGAAGAAATCTGTTGACTCAGATTGGC<br>TGCACTTTAAATTTTCCCATTAGTCCTATTGAGACTG<br>TACCAGTAAAATTAAAGCCAGGAATGGATGGCCCA<br>AAAGTTAAACAATGGCCATTGACAGAAGAAAAAAT<br>AAAAGCATTAGTAGAAATTTGTACAGAAATGGAAA<br>AGGAAGGAAAAATTTCAAAAATTGGGCCTGAAAAT<br>CCATACAATACTCCAGTATTTGCCATAAAGAAAAAA<br>GACAGTACTAAATGGAGAAAATTAGTAGATTTCAG<br>AGAACTTAATAAGAGAACTCAAGATTTCTGGGAAG<br>TTCAATTAGGAATACCACATCCTGCAGGGTTAAAAC<br>AGAAAAAATCAGTAACAGTACTGGATGTGGGCGAT<br>GCATATTTTTCAGTTCCCTTAGATAAAGACTTCAGG<br>AAGTATACTGCATTTACCATACCTAGTATAAACAAT<br>GAGACACCAGGGATTAGATATCAGTACAATGTGCTT<br>CCACAGGGATGGAAAGGATCACCAGCAATATTCCA<br>GTGTAGCATGACAAAAATCTTAGAGCCTTTTAGAAA<br>ACAAAATCCAGACATAGTCATCTATCAATACATGGA<br>TGATTTGTATGTAGGATCTGACTTAGAAATAGGGCA<br>GCATAGAACAAAAATAGAGGAACTGAGACAACATC<br>TGTTGAGGTGGGGATTTACCACACCAGACAAAAAA<br>CATCAGAAAGAACCTCCATTCCTTTGGATGGGTTAT<br>GAACTCCATCCTGATAAATGGACAGTACAGCCTATA<br>GTGCTGCCAGAAAAGGACAGCTGGACTGTCAATGA<br>CATACAGAAATTAGTGGGAAAATTGAATTGGGCAA<br>GTCAGATTTATGCAGGGATTAAAGTAAGGCAATTAT<br>GTAAACTTCTTAGGGGAACCAAAGCACTAACAGAA<br>GTAGTACCACTAACAGAAGAAGCAGAGCTAGAACT<br>GGCAGAAAACAGGGAGATTCTAAAAGAACCGGTAC<br>ATGGAGTGTATTATGACCCATCAAAAGACTTAATAG<br>CAGAAATACAGAAGCAGGGGCAAGGCCAATGGACA<br>TATCAAATTTATCAAGAGCCATTTAAAAATCTGAAA<br>ACAGGAAAATATGCAAGAATGAAGGGTGCCCACAC<br>TAATGATGTGAAACAATTAACAGAGGCAGTACAAA<br>AAATAGCCACAGAAAGCATAGTAATATGGGGAAAG<br>ACTCCTAAATTTAAATTACCCATACAAAAGGAAACA<br>TGGGAAGCATGGTGGACAGAGTATTGGCAAGCCAC<br>CTGGATTCCTGAGTGGGAGTTTGTCAATACCCCTCC<br>CTTAGTGAAGTTATGGTACCAGTTAGAGAAAGAAC<br>CCATAATAGGAGCAGAAACTTTCTATGTAGATGGG<br>GCAGCCAATAGGGAAACTAAATTAGGAAAAGCAGG<br>ATATGTAACTGACAGAGGAAGACAAAAAGTTGTCC<br>CCCTAACGGACACAACAAATCAGAAGACTGAGTTA<br>CAAGCAATTCATCTAGCTTTGCAGGATTCGGGATTA<br>GAAGTAAACATAGTGACAGACTCACAATATGCATT<br>GGGAATCATTCAAGCACAACCAGATAAGAGTGAAT<br>CAGAGTTAGTCAGTCAAATAATAGAGCAGTTAATA<br>AAAAAGGAAAAAGTCTACCTGGCATGGGTACCAGC<br>ACACAAAGGAATTGGAGGAAATGAACAAGTAGATG<br>GGTTGGTCAGTGCTGGAATCAGGAAAGTACTA |

-continued

| SEQ ID NO: | Description | Sequence |
| --- | --- | --- |
| 45, 54 | Helper Rev; HIV Integrase; Integration of viral RNA | TTTTTAGATGGAATAGATAAGGCCCAAGAAGAACA TGAGAAATATCACAGTAATTGGAGAGCAATGGCTA GTGATTTTAACCTACCACCTGTAGTAGCAAAAGAAA TAGTAGCCAGCTGTGATAAATGTCAGCTAAAAGGG GAAGCCATGCATGGACAAGTAGACTGTAGCCCAGG AATATGGCAGCTAGATTGTACACATTTAGAAGGAA AAGTTATCTTGGTAGCAGTTCATGTAGCCAGTGGAT ATATAGAAGCAGAAGTAATTCCAGCAGAGACAGGG CAAGAAACAGCATACTTCCTCTTAAAATTAGCAGGA AGATGGCCAGTAAAAACAGTACATACAGACAATGG CAGCAATTTCACCAGTACTACAGTTAAGGCCGCCTG TTGGTGGGCGGGGATCAAGCAGGAATTTGGCATTCC CTACAATCCCCAAAGTCAAGGAGTAATAGAATCTAT GAATAAAGAATTAAAGAAAATTATAGGACAGGTAA GAGATCAGGCTGAACATCTTAAGACAGCAGTACAA ATGGCAGTATTCATCCACAATTTTAAAAGAAAAGG GGGGATTGGGGGGTACAGTGCAGGGGAAAGAATAG TAGACATAATAGCAACAGACATACAAACTAAAGAA TTACAAAAACAAATTACAAAAATTCAAAATTTTCGG GTTTATTACAGGGACAGCAGAGATCCAGTTTGGAA AGGACCAGCAAAGCTCCTCTGGAAAGGTGAAGGGG CAGTAGTAATACAAGATAATAGTGACATAAAAGTA TGCCAAGAAGAAAAGCAAAGATCATCAGGGATTA TGGAAAACAGATGGCAGGTGATGATTGTGTGGCAA GTAGACAGGATGAGGATTAA |
| 46, 55 | Helper/Rev; HIV RRE; Binds Rev element | AGGAGCTTTGTTCCTTGGGTTCTTGGGAGCAGCAGG AAGCACTATGGGCGCAGCGTCAATGACGCTGACGG TACAGGCCAGACAATTATTGTCTGGTATAGTGCAGC AGCAGAACAATTTGCTGAGGGCTATTGAGGCGCAA CAGCATCTGTTGCAACTCACAGTCTGGGGCATCAAG CAGCTCCAGGCAAGAATCCTGGCTGTGGAAAGATA CCTAAAGGATCAACAGCTCCT |
| 47, 57, 58 | Helper/Rev; HIV Rev; Nuclear export and stabilize viral mRNA | ATGGCAGGAAGAAGCGGAGACAGCGACGAAGAAC TCCTCAAGGCAGTCAGACTCATCAAGTTTCTCTATC AAAGCAACCCACCTCCCAATCCCGAGGGGACCCGA CAGGCCCGAAGGAATAGAAGAAGAAGGTGGAGAG AGAGACAGAGACAGATCCATTCGATTAGTGAACGG ATCCTTAGCACTTATCTGGGACGATCTGCGGAGCCT GTGCCTCTTCAGCTACCACCGCTTGAGAGACTTACT CTTGATTGTAACGAGGATTGTGGAACTTCTGGGACG CAGGGGGTGGGAAGCCCTCAAATATTGGTGGAATC TCCTACAATATTGGAGTCAGGAGCTAAAGAATAG |
| 48, 56 | Helper/Rev; Rabbit beta globin poly A; RNA stability | AGATCTTTTTCCCTCTGCCAAAAATTATGGGGACAT CATGAAGCCCCTTGAGCATCTGACTTCTGGCTAATA AAGGAAATTTATTTTCATTGCAATAGTGTGTTGGAA TTTTTTGTGTCTCTCACTCGGAAGGACATATGGGAG GGCAAATCATTTAAAACATCAGAATGAGTATTTGGT TTAGAGTTTGGCAACATATGCCATATGCTGGCTGCC ATGAACAAAGGTGGCTATAAAGAGGTCATCAGTAT ATGAAACAGCCCCCTGCTGTCCATTCCTTATTCCAT AGAAAAGCCTTGACTTGAGGTTAGATTTTTTTTATA TTTTGTTTTGTGTTATTTTTTTCTTTAACATCCCTAAA ATTTTCCTTACATGTTTTACTAGCCAGATTTTTCCTC CTCTCCTGACTACTCCCAGTCATAGCTGTCCCTCTTC TCTTATGAAGATC |
| 59, 63 | Rev; Rabbit beta globin poly A; RNA stability | AGATCTTTTTCCCTCTGCCAAAAATTATGGGGACAT CATGAAGCCCCTTGAGCATCTGACTTCTGGCTAATA AAGGAAATTTATTTTCATTGCAATAGTGTGTTGGAA TTTTTTGTGTCTCTCACTCGGAAGGACATATGGGAG GGCAAATCATTTAAAACATCAGAATGAGTATTTGGT TTAGAGTTTGGCAACATATGCCCATATGCTGGCTGC CATGAACAAAGGTTGGCTATAAAGAGGTCATCAGT ATATGAAACAGCCCCCTGCTGTCCATTCCTTATTCC ATAGAAAAGCCTTGACTTGAGGTTAGATTTTTTTTA TATTTTGTTTTGTGTTATTTTTTTCTTTAACATCCCTA AAATTTTCCTTACATGTTTTACTAGCCAGATTTTTCC TCCTCTCCTGACTACTCCCAGTCATAGCTGTCCCTCT TCTCTTATGGAGATC |
| 60 | Envelope; CMV promoter; | ACATTGATTATTGACTAGTTATTAATAGTAATCAAT TACGGGGTCATTAGTTCATAGCCCATATATGGAGTT |

-continued

| SEQ ID NO: | Description | Sequence |
|---|---|---|
| | Transcription | CCGCGTTACATAACTTACGGTAAATGGCCCGCCTGG CTGACCGCCCAACGACCCCCGCCCATTGACGTCAAT AATGACGTATGTTCCCATAGTAACGCCAATAGGGAC TTTCCATTGACGTCAATGGGTGGAGTATTTACGGTA AACTGCCCACTTGGCAGTACATCAAGTGTATCATAT GCCAAGTACGCCCCCTATTGACGTCAATGACGGTAA ATGGCCCGCCTGGCATTATGCCCAGTACATGACCTT ATGGGACTTTCCTACTTGGCAGTACATCTACGTATT AGTCATCGCTATTACCATGGTGATGCGGTTTTGGCA GTACATCAATGGGCGTGGATAGCGGTTTGACTCACG GGGATTTCCAAGTCTCCACCCCATTGACGTCAATGG GAGTTTGTTTTGGCACCAAAATCAACGGGACTTTCC AAAATGTCGTAACAACTCCGCCCCATTGACGCAAAT GGGCGGTAGGCGTGTACGGTGGGAGGTCTATATAA GC |
| 61 | Envelope; Beta globin intron; Enhance gene expression | GTGAGTTTGGGGACCCTTGATTGTTCTTTCTTTTTCG CTATTGTAAAATTCATGTTATATGGAGGGGGCAAAG TTTTCAGGGTGTTGTTTAGAATGGGAAGATGTCCCT TGTATCACCATGGACCCTCATGATAATTTTGTTTCTT TCACTTTCTACTCTGTTGACAACCATTGTCTCCTCTT ATTTTCTTTTCATTTTCTGTAACTTTTTCGTTAAACTT TAGCTTGCATTTGTAACGAATTTTTAAATTCACTTTT GTTTATTTGTCAGATTGTAAGTACTTTCTCTAATCAC TTTTTTTTCAAGGCAATCAGGGTATATTATATTGTAC TTCAGCACAGTTTTAGAGAACAATTGTTATAATTAA ATGATAAGGTAGAATATTTCTGCATATAAATTCTGG CTGGCGTGGAAATATTCTTATTGGTAGAAACAACTA CACCCTGGTCATCATCCTGCCTTTCTCTTTATGGTTA CAATGATATACACTGTTTGAGATGAGGATAAAATAC TCTGAGTCCAAACCGGGCCCCTCTGCTAACCATGTT CATGCCTTCTTCTCTTTCCTACAG |
| 62 | Envelope; VSV-G; Glycoprotein envelope-cell entry | ATGAAGTGCCTTTTGTACTTAGCCTTTTTATTCATTG GGGTGAATTGCAAGTTCACCATAGTTTTTCCACACA ACCAAAAAGGAAACTGGAAAAATGTTCCTTCTAATT ACCATTATTGCCCGTCAAGCTCAGATTTAAATTGGC ATAATGACTTAATAGGCACAGCCTTACAAGTCAAA ATGCCCAAGAGTCACAAGGCTATTCAAGCAGACGG TTGGATGTGTCATGCTTCCAAATGGGTCACTACTTG TGATTTCCGCTGGTATGGACCGAAGTATATAACACA TTCCATCCGATCCTTCACTCCATCTGTAGAACAATG CAAGGAAAGCATTGAACAAACGAAACAAGGAACTT GGCTGAATCCAGGCTTCCCTCCTCAAAGTTGTGGAT ATGCAACTGTGACGGATGCCGAAGCAGTGATTGTCC AGGTGACTCCTCACCATGTGCTGGTTGATGAATACA CAGGAGAATGGGTTGATTCACAGTTCATCAACGGA AAATGCAGCAATTACATATGCCCCACTGTCCATAAC TCTACAACCTGGCATTCTGACTATAAGGTCAAAGGG CTATGTGATTCTAACCTCATTTCCATGGACATCACCT TCTTCTCAGAGGACGGAGAGCTATCATCCCTGGGAA AGGAGGGCACAGGGTTCAGAAGTAACTACTTTGCTT ATGAAACTGGAGGCAAGGCCTGCAAAATGCAATAC TGCAAGCATTGGGGAGTCAGACTCCCATCAGGTGTC TGGTTCGAGATGGCTGATAAGGATCTCTTTGCTGCA GCCAGATTCCCTGAATGCCCAGAAGGGTCAAGTATC TCTGCTCCATCTCAGACCTCAGTGGATGTAAGTCTA ATTCAGGACGTTGAGAGGATCTTGGATTATTCCCTC TGCCAAGAAACCTGGAGCAAAATCAGAGCGGGTCT TCCAATCTCTCCAGTGGATCTCAGCTATCTTGCTCCT AAAAACCCAGGAACCGGTCCTGCTTTCACCATAATC AATGGTACCCTAAAATACTTTGAGACCAGATACATC AGAGTCGATATTGCTGCTCCAATCCTCTCAAGAATG GTCGGAATGATCAGTGGAACTACCACAGAAAGGGA ACTGTGGGATGACTGGGCACCATATGAAGACGTGG AAATTGGACCCAATGGAGTTCTGAGGACCAGTTCA GGATATAAGTTTCCTTTATACATGATTGGACATGGT ATGTTGGACTCCGATCTTCATCTTAGCTCAAAGGCT CAGGTGTTCGAACATCCTCACATTCAAGACGCTGCT TCGCAACTTCCTGATGATGAGAGTTTATTTTTTGGTG ATACTGGGCTATCCAAAAATCCAATCGAGCTTGTAG AAGGTTGGTTCAGTAGTTGGAAAAGCTCTATTGCCT CTTTTTTCTTTATCATAGGGTTAATCATTGGACTATT CTTGGTTCTCCGAGTTGGTATCCATCTTTGCATTAAA TTAAAGCACACCAAGAAAAGACAGATTTATACAGA CATAGAGATGA |

-continued

| SEQ ID NO: | Description | Sequence |
|---|---|---|
| 65 | Promoter; PGK | GGGGTTGGGGTTGCGCCTTTTCCAAGGCAGCCCTGG GTTTGCGCAGGGACGCGGCTGCTCTGGGCGTGGTTC CGGGAAACGCAGCGGCGCCGACCCTGGGTCTCGCA CATTCTTCACGTCCGTTCGCAGCGTCACCCGGATCT TCGCCGCTACCCTTGTGGGCCCCCCGGCGACGCTTC CTGCTCCGCCCCTAAGTCGGGAAGGTTCCTTGCGGT TCGCGGCGTGCCGGACGTGACAAACGGAAGCCGCA CGTCTCACTAGTACCCTCGCAGACGGACAGCGCCAG GGAGCAATGGCAGCGCGCCGACCGCGATGGGCTGT GGCCAATAGCGGCTGCTCAGCAGGGCGCGCCGAGA GCAGCGGCCGGGAAGGGGCGGTGCGGGAGGCGGG GTGTGGGGCGGTAGTGTGGGCCCTGTTCCTGCCCGC GCGGTGTTCCGCATTCTGCAAGCCTCCGGAGCGCAC GTCGGCAGTCGGCTCCCTCGTTGACCGAATCACCGA CCTCTCTCCCCAG |
| 66 | Promoter; UbC | GCGCCGGGTTTTGGCGCCTCCCGCGGGCGCCCCCCT CCTCACGGCGAGCGCTGCCACGTCAGACGAAGGGC GCAGGAGCGTTCCTGATCCTTCCGCCCGGACGCTCA GGACAGCGGCCCGCTGCTCATAAGACTCGGCCTTAG AACCCCAGTATCAGCAGAAGGACATTTTAGGACGG GACTTGGGTGACTCTAGGGCACTGGTTTTCTTTCCA GAGAGCGGAACAGGCGAGGAAAAGTAGTCCCTTCT CGGCGATTCTGCGGAGGGATCTCCGTGGGGCGGTG AACGCCGATGATTATATAAGGACGCGCCGGGTGTG GCACAGCTAGTTCCGTCGCAGCCGGGATTTGGGTCG CGGTTCTTGTTTGTGGATCGCTGTGATCGTCACTTGG TGAGTTGCGGGCTGCTGGGCTGGCCGGGGCTTTCGT GGCCGCCGGGCCGCTCGGTGGGACGGAAGCGTGTG GAGAGACCGCCAAGGGCTGTAGTCTGGGTCCGCGA GCAAGGTTGCCCTGAACTGGGGGTTGGGGGGAGCG CACAAAATGGCGGCTGTTCCCGAGTCTTGAATGGAA GACGCTTGTAAGGCGGGCTGTGAGGTCGTTGAAAC AAGGTGGGGGGCATGGTGGGCGGCAAGAACCCAAG GTCTTGAGGCCTTCGCTAATGCGGGAAAGCTCTTAT TCGGGTGAGATGGGCTGGGGCACCATCTGGGGACC CTGACGTGAAGTTTGTCACTGACTGGAGAACTCGGG TTTGTCGTCTGGTTGCGGGGGCGGCAGTTATGCGGT GCCGTTGGGCAGTGCACCCGTACCTTTGGGAGCGCG CGCCTCGTCGTGTCGTGACGTCACCCGTTCTGTTGG CTTATAATGCAGGGTGGGGCCACCTGCCGGTAGGTG TGCGGTAGGCTTTTCTCCGTCGCAGGACGCAGGGTT CGGGCCTAGGGTAGGCTCTCCTGAATCGACAGGCG CCGGACCTCTGGTGAGGGGAGGGATAAGTGAGGCG TCAGTTTCTTTGGTCGGTTTTATGTACCTATCTTCTT AAGTAGCTGAAGCTCCGGTTTTGAACTATGCGCTCG GGGTTGGCGAGTGTGTTTTGTGAAGTTTTTTAGGCA CCTTTTGAAATGTAATCATTTGGGTCAATATGTAAT TTTCAGTGTTAGACTAGTAAA |
| 67 | Poly A; SV40 | GTTTATTGCAGCTTATAATGGTTACAAATAAAGCAA TAGCATCACAAATTTCACAAATAAAGCATTTTTTTC ACTGCATTCTAGTTGTGGTTTGTCCAAACTCATCAA TGTATCTTATCA |
| 68 | Poly A; bGH | GACTGTGCCTTCTAGTTGCCAGCCATCTGTTGTTTGC CCCTCCCCCGTGCCTTCCTTGACCCTGGAAGGTGCC ACTCCCACTGTCCTTTCCTAATAAAATGAGGAAATT GCATCGCATTGTCTGAGTAGGTGTCATTCTATTCTG GGGGGTGGGGTGGGGCAGGACAGCAAGGGGGAGG ATTGGGAAGACAATAGCAGGCATGCTGGGGATGCG GTGGGCTCTATGG |
| 69 | HIV Gag; Bal | ATGGGTGCGAGAGCGTCAGTATTAAGCGGGGGAGA ATTAGATAGGTGGGAAAAAATTCGGTTAAGGCCAG GGGGAAAGAAAAAATATAGATTAAAACATATAGTA TGGGCAAGCAGGGAACTAGAAAGATTCGCAGTCAA TCCTGGCCTGTTAGAAACATCAGAAGGCTGCAGAC AAATACTGGGACAGCTACAACCATCCCTTCAGACA GGATCAGAAGAACTTAGATCATTATATAATACAGTA GCAACCCTCTATTGTGTACATCAAAAGATAGAGGTA AAAGACACCAAGGAAGCTTTAGACAAAATAGAGGA AGAGCAAAACAAATGTAAGAAAAAGGCACAGCAA GCAGCAGCTGACACAGGAAACAGCGGTCAGGTCAG CCAAAATTTCCCTATAGTGCAGAACCTCCAGGGGCA |

-continued

| SEQ ID NO: | Description | Sequence |
|---|---|---|
| | | AATGGTACATCAGGCCATATCACCTAGAACTTTAAA<br>TGCATGGGTAAAAGTAATAGAAGAGAAAGCTTTCA<br>GCCCAGAAGTAATACCCATGTTTTCAGCATTATCAG<br>AAGGAGCCACCCCACAAGATTTAAACACCATGCTA<br>AACACAGTGGGGGGACATCAAGCAGCCATGCAAAT<br>GTTAAAAGAACCCATCAATGAGGAAGCTGCAAGAT<br>GGGATAGATTGCATCCCGTGCAGGCAGGGCCTGTTG<br>CACCAGGCCAGATAAGAGATCCAAGGGGAAGTGAC<br>ATAGCAGGAACTACCAGTACCCTTCAGGAACAAAT<br>AGGATGGATGACAAGTAATCCACCTATCCCAGTAG<br>GAGAAATCTATAAAAGATGGATAATCCTGGGATTA<br>AATAAAATAGTAAGGATGTATAGCCCTACCAGCATT<br>TTGGACATAAGACAAGGACCAAAGGAACCCTTTAG<br>AGACTATGTAGACCGGTTCTATAAAACTCTAAGAGC<br>CGAGCAAGCTTCACAGGAGGTAAAAAATTGGATGA<br>CAGAAACCTTGTTGGTCCAAAATGCGAACCCAGATT<br>GTAAGACTATTTTAAAAGCATTGGGACCAGCAGCTA<br>CACTAGAAGAAATGATGACAGCATGTCAGGGAGTG<br>GGAGGACCCAGCCATAAAGCAAGAATTTTGGCAGA<br>AGCAATGAGCCAAGTAACAAATTCAGCTACCATAA<br>TGATGCAGAAAGGCAATTTTAGGAACCAAAGAAAG<br>ATTGTTAAATGTTTCAATTGTGGCAAAGAAGGGCAC<br>ATAGCCAGAAACTGCAGGGCCCCTAGGAAAAGGGG<br>CTGTTGGAAATGTGGAAAGGAAGGACACCAAATGA<br>AAGACTGTACTGAGAGACAGGCTAATTTTTTAGGGA<br>AAATCTGGCCTTCCCACAAAGGAAGGCCAGGGAAT<br>TTCCTTCAGAGCAGACCAGAGCCAACAGCCCCACC<br>AGCCCCACCAGAAGAGAGCTTCAGGTTTGGGGAAG<br>AGACAACAACTCCCTCTCAGAAGCAGGAGCTGATA<br>GACAAGGAACTGTATCCTTTAGCTTCCCTCAGATCA<br>CTCTTTGGCAACGACCCCTCGTCACAATAA<br>ATGAATTTGCCAGGAAGATGGAAACCAAAAATGAT |
| 70 | HIV Pol; Bal | AGGGGGAATTGGAGGTTTTATCAAAGTAAGACAGT<br>ATGATCAGATACTCATAGAAATCTGTGGACATAAA<br>GCTATAGGTACAGTATTAATAGGACCTACACCTGTC<br>AACATAATTGGAAGAAATCTGTTGACTCAGATTGGT<br>TGCACTTTAAATTTTCCCATTAGTCCTATTGAAACTG<br>TACCAGTAAAATTAAAACCAGGAATGGATGGCCCA<br>AAAGTTAAACAATGGCCACTGACAGAAGAAAAAAT<br>AAAAGCATTAATGGAAATCTGTACAGAAATGGAAA<br>AGGAAGGGAAAATTTCAAAAATTGGGCCTGAAAAT<br>CCATACAATACTCCAGTATTTGCCATAAAGAAAAAA<br>GACAGTACTAAATGGAGAAAATTAGTAGATTTCAG<br>AGAACTTAATAAGAAAACTCAAGACTTCTGGGAAG<br>TACAATTAGGAATACACATCCCGCAGGGGTTAAAA<br>AAGAAAAAATCAGTAACAGTACTGGATGTGGGTGA<br>TGCATATTTTTCAGTTCCCTTAGATAAAGAATTCAG<br>GAAGTATACTGCATTTACCATACCTAGTATAAACAA<br>TGAAACACCAGGGATCAGATATCAGTACAATGTAC<br>TTCCACAGGGATGGAAAGGATCACCAGCAATATTTC<br>AAAGTAGCATGACAAGAATCTTAGAGCCTTTTAGA<br>AAACAAAATCCAGAAATAGTGATCTATCAATACAT<br>GGATGATTTGTATGTAGGATCTGACTTAGAAATAGG<br>GCAGCATAGAACAAAAATAGAGGAACTGAGACAAC<br>ATCTGTTGAGGTGGGGATTTACCACACCAGACAAA<br>AAACATCAGAAAGAACCTCCATTCCTTTGGATGGGT<br>TATGAACTCCATCCTGATAAATGGACAGTACAGCCT<br>ATAGTGCTGCCAGAAAAAGACAGCTGGACTGTCAA<br>TGACATACAGAAGTTAGTGGGAAAATTGAATTGGG<br>CAAGTCAGATTTACCCAGGAATTAAAGTAAAGCAA<br>TTATGTAGGCTCCTTAGGGGAACCAAGGCATTAACA<br>GAAGTAATACCACTAACAAAAGAAACAGAGCTAGA<br>ACTGGCAGAGAACAGGGAAATTCTAAAAGAACCAG<br>TACATGGGGTGTATTATGACCCATCAAAAGACTTAA<br>TAGCAGAAATACAGAAGCAGGGGCAAGGCCAATGG<br>ACATATCAAATTTATCAAGAGCCATTTAAAAATCTG<br>AAAACAGGAAAATATGCAAGAATGAGGGGTGCCCA<br>CACTAATGATGTAAAACAATTAACAGAGGCAGTGC<br>AAAAAATAACCACAGAAAGCATAGTAATATGGGGA<br>AAGACTCCTAAATTTAAACTACCCATACAAAAAGA<br>AACATGGGAAACATGGTGGACAGAGTATTGGCAAG<br>CCACCTGGATTCCTGAGTGGGAGTTTGTCAATACCC<br>CTCCCTTAGTGAAATTATGGTACCAGTTAGAGAAAG<br>AACCCATAATAGGAGCAGAAACATTCTATGTAGAT<br>GGAGCAGCTAACCGGGAGACTAAATTAGGAAAAGC |

-continued

| SEQ ID NO: | Description | Sequence |
|---|---|---|
| | | AGGATATGTTACTAACAGAGGAAGACAAAAAGTTG<br>TCTCCCTAACTGACACAACAAATCAGAAGACTGAGT<br>TACAAGCAATTCATCTAGCTTTACAAGATTCAGGAT<br>TAGAAGTAAACATAGTAACAGACTCACAATATGCA<br>TTAGGAATCATTCAAGCACAACCAGATAAAAGTGA<br>ATCAGAGTTAGTCAGTCAAATAATAGAACAGTTAAT<br>AAAAAAGGAAAAGGTCTACCTGGCATGGGTACCAG<br>CGCACAAAGGAATTGGAGGAAATGAACAAGTAGAT<br>AAATTAGTCAGTACTGGAATCAGGAAAGTACTA |
| 71 | HIV Integrase;<br>Bal | TTTTTAGATGGAATAGATATAGCCCAAGAAGAACAT<br>GAGAAATATCACAGTAATTGGAGAGCAATGGCTAG<br>TGATTTTAACCTGCCACCTGTGGTAGCAAAAGAAAT<br>AGTAGCCAGCTGTGATAAATGTCAGCTAAAAGGAG<br>AAGCCATGCATGGACAAGTAGACTGTAGTCCAGGA<br>ATATGGCAACTAGATTGTACACATTTAGAAGGAAA<br>AATTATCCTGGTAGCAGTTCATGTAGCCAGTGGATA<br>TATAGAAGCAGAAGTTATTCCAGCAGAGACAGGGC<br>AGGAAACAGCATACTTTCTCTTAAAATTAGCAGGAA<br>GATGGCCAGTAAAAACAATACATACAGACAATGGC<br>AGCAATTTCACTAGTACTACAGTCAAGGCCGCCTGT<br>TGGTGGGCGGGGATCAAGCAGGAATTTGGCATTCC<br>CTACAATCCCCAAAGTCAGGGAGTAGTAGAATCTAT<br>AAATAAAGAATTAAAGAAAATTATAGGACAGGTAA<br>GAGATCAGGCTGAACATCTTAAAACAGCAGTACAA<br>ATGGCAGTATTCATCCACAATTTTAAAAGAAAAGG<br>GGGGATTGGGGGGTATAGTGCAGGGGAAAGAATAG<br>TAGACATAATAGCAACAGACATACAAACTAAAGAA<br>TTACAAAAACAAATTACAAAAATTCAAAATTTTCGG<br>GTTTATTACAGGGACAGCAGAGATCCACTTTGGAAA<br>GGACCAGCAAAGCTTCTCTGGAAAGGTGAAGGGGC<br>AGTAGTAATACAAGATAATAGTGACATAAAAGTAG<br>TACCAAGAAGAAAAGCAAAGATCATTAGGGATTAT<br>GGAAAACAGATGGCAGGTGATGATTGTGTGGCAAG<br>TAGACAGGATGAGGATTAG |
| 72 | Envelope;<br>RD114 | ATGAAACTCCCAACAGGAATGGTCATTTTATGTAGC<br>CTAATAATAGTTCGGGCAGGGTTTGACGACCCCCGC<br>AAGGCTATCGCATTAGTACAAAAACAACATGGTAA<br>ACCATGCGAATGCAGCGGAGGGCAGGTATCCGAGG<br>CCCCACCGAACTCCATCCAACAGGTAACTTGCCCAG<br>GCAAGACGGCCTACTTAATGACCAACCAAAAATGG<br>AAATGCAGAGTCACTCCAAAAAATCTCACCCCTAGC<br>GGGGGAGAACTCCAGAACTGCCCCTGTAACACTTTC<br>CAGGACTCGATGCACAGTTCTTGTTATACTGAATAC<br>CGGCAATGCAGGGCGAATAATAAGACATACTACAC<br>GGCCACCTTGCTTAAAATACGGTCTGGGAGCCTCAA<br>CGAGGTACAGATATTACAAAACCCCAATCAGCTCCT<br>ACAGTCCCCTTGTAGGGGCTCTATAAATCAGCCCGT<br>TTGCTGGAGTGCCACAGCCCCCATCCATATCTCCGA<br>TGGTGGAGGACCCCTCGATACTAAGAGAGTGTGGA<br>CAGTCCAAAAAAGGCTAGAACAAATTCATAAGGCT<br>ATGCATCCTGAACTTCAATACCACCCCTTAGCCCTG<br>CCCAAAGTCAGAGATGACCTTAGCCTTGATGCACGG<br>ACTTTTGATATCCTGAATACCACTTTTAGGTTACTCC<br>AGATGTCCAATTTTAGCCTTGCCCAAGATTGTTGGC<br>TCTGTTTAAAACTAGGTACCCCTACCCCTCTTGCGA<br>TACCCACTCCCTCTTTAACCTACTCCCTAGCAGACTC<br>CCTAGCGAATGCCTCCTGTCAGATTATACCTCCCCT<br>CTTGGTTCAACCGATGCAGTTCTCCAACTCGTCCTG<br>TTTATCTTCCCCTTTCATTAACGATACGGAACAAAT<br>AGACTTAGGTGCAGTCACCTTTACTAACTGCACCTC<br>TGTAGCCAATGTCAGTAGTCCTTTATGTGCCCTAAA<br>CGGGTCAGTCTTCCTCTGTGGAAATAACATGGCATA<br>CACCTATTTACCCCAAAACTGGACAGGACTTTGCGT<br>CCAAGCCTCCCTCCTCCCCGACATTGACATCATCCC<br>GGGGGATGAGCCAGTCCCCATTCCTGCCATTGATCA<br>TTATATACATAGACCTAAACGAGCTGTACAGTTCAT<br>CCCTTTACTAGCTGGACTGGGAATCACCGCAGCATT<br>CACCACCGGAGCTACAGGCCTAGGTGTCTCCGTCAC<br>CCAGTATACAAAATTATCCCATCAGTTAATATCTGA<br>TGTCCAAGTCTTATCCGGTACCATACAAGATTTACA<br>AGACCAGGTAGACTCGTTAGCTGAAGTAGTTCTCCA<br>AAATAGGAGGGGACTGGACCTACTAACGGCAGAAC<br>AAGGAGGAATTTGTTTAGCCTTACAAGAAAAATGCT<br>GTTTTTATGCTAACAAGTCAGGAATTGTGAGAAACA |

-continued

| SEQ ID NO: | Description | Sequence |
|---|---|---|
| | | AAATAAGAACCCTACAAGAAGAATTACAAAAACGC<br>AGGGAAAGCCTGGCATCCAACCCTCTCTGGACCGG<br>GCTGCAGGGCTTTCTTCCGTACCTCCTACCTCTCCTG<br>GGACCCCTACTCACCCTCCTACTCATACTAACCATT<br>GGGCCATGCGTTTTCAATCGATTGGTCCAATTTGTT<br>AAAGACAGGATCTCAGTGGTCCAGGCTCTGGTTTTG<br>ACTCAGCAATATCACCAGCTAAAACCCATAGAGTA<br>CGAGCCATGA |
| 73 | Envelope; GALV | ATGCTTCTCACCTCAAGCCCGCACCACCTTCGGCAC<br>CAGATGAGTCCTGGGAGCTGGAAAAGACTGATCAT<br>CCTCTTAAGCTGCGTATTCGGAGACGGCAAAACGA<br>GTCTGCAGAATAAGAACCCCCACCAGCCTGTGACCC<br>TCACCTGGCAGGTACTGTCCCAAACTGGGGACGTTG<br>TCTGGGACAAAAAGGCAGTCCAGCCCCTTTGGACTT<br>GGTGGCCCTCTCTTACACCTGATGTATGTGCCCTGG<br>CGGCCGGTCTTGAGTCCTGGGATATCCCGGGATCCG<br>ATGTATCGTCCTCTAAAAGAGTTAGACCTCCTGATT<br>CAGACTATACTGCCGCTTATAAGCAAATCACCTGGG<br>GAGCCATAGGGTGCAGCTACCCTCGGGCTAGGACC<br>AGGATGGCAAATTCCCCCTTCTACGTGTGTCCCCGA<br>GCTGGCCGAACCCATTCAGAAGCTAGGAGGTGTGG<br>GGGGCTAGAATCCCTATACTGTAAAGAATGGAGTT<br>GTGAGACCACGGGTACCGTTTATTGGCAACCCAAGT<br>CCTCATGGGACCTCATAACTGTAAAATGGGACCAA<br>AATGTGAAATGGGAGCAAAAATTTCAAAAGTGTGA<br>ACAAACCGGCTGGTGTAACCCCCTCAAGATAGACTT<br>CACAGAAAAAGGAAAACTCTCCAGAGATTGGATAA<br>CGGAAAAAACCTGGGAATTAAGGTTCTATGTATATG<br>GACACCCAGGCATACAGTTGACTATCCGCTTAGAGG<br>TCACTAACATGCCGGTTGTGGCAGTGGGCCCAGACC<br>CTGTCCTTGCGGAACAGGGACCTCCTAGCAAGCCCC<br>TCACTCTCCCTCTCTCCCCACGGAAAGCGCCGCCCA<br>CCCCTCTACCCCCGGCGGCTAGTGAGCAAACCCCTG<br>CGGTGCATGGAGAAACTGTTACCCTAAACTCTCCGC<br>CTCCCACCAGTGGCGACCGACTCTTTGGCCTTGTGC<br>AGGGGGCCTTCCTAACCTTGAATGCTACCAACCCAG<br>GGGCCACTAAGTCTTGCTGGCTCTGTTTGGGCATGA<br>GCCCCCCTTATTATGAAGGGATAGCCTCTTCAGGAG<br>AGGTCGCTTATACCTCCAACCATACCCGATGCCACT<br>GGGGGGCCCAAGGAAAGCTTACCCTCACTGAGGTC<br>TCCGGACTCGGGTCATGCATAGGGAAGGTGCCTCTT<br>ACCCATCAACATCTTTGCAACCAGACCTTACCCATC<br>AATTCCTCTAAAAACCATCAGTATCTGCTCCCCTCA<br>AACCATAGCTGGTGGGCCTGCAGCACTGGCCTCACC<br>CCCTGCCTCTCCACCTCAGTTTTTAATCAGTCTAAAG<br>ACTTCTGTGTCCAGGTCCAGCTGATCCCCCGCATCT<br>ATTACCATTCTGAAGAAACCTTGTTACAAGCCTATG<br>ACAAATCACCCCCCAGGTTTAAAAGAGAGCCTGCCT<br>CACTTACCCTAGCTGTCTTCCTGGGGTTAGGGATTG<br>CGGCAGGTATAGGTACTGGCTCAACCGCCCTAATTA<br>AAGGGCCCATAGACCTCCAGCAAGGCCTAACCAGC<br>CTCCAAATCGCCATTGACGCTGACCTCCGGGCCCTT<br>CAGGACTCAATCAGCAAGCTAGAGGACTCACTGAC<br>TTCCCTATCTGAGGTAGTACTCCAAAATAGGAGAGG<br>CCTTGACTTACTATTCCTTAAAGAAGGAGGCCTCTG<br>CGCGGCCCTAAAAGAAGAGTGCTGTTTTTATGTAGA<br>CCACTCAGGTGCAGTACGAGACTCCATGAAAAAAC<br>TTAAAGAAAGACTAGATAAAAGACAGTTAGAGCGC<br>CAGAAAAACCAAAACTGGTATGAAGGGTGGTTCAA<br>TAACTCCCCTTGGTTTACTACCCTACTATCAACCATC<br>GCTGGGCCCCTATTGCTCCTCCTTTTGTTACTCACTC<br>TTGGGCCCTGCATCATCAATAAATTAATCCAATTCA<br>TCAATGATAGGATAAGTGCAGTCAAAATTTTAGTCC<br>TTAGACAGAAATATCAGACCCTAGATAACGAGGAA<br>AACCTTTAA |
| 74 | Envelope; FUG | ATGGTTCCGCAGGTTCTTTTGTTTGTACTCCTTCTGG<br>GTTTTTCGTTGTGTTTCGGGAAGTTCCCCATTTACAC<br>GATACCAGACGAACTTGGTCCCTGGAGCCCTATTGA<br>CATACACCATCTCAGCTGTCCAAATAACCTGGTTGT<br>GGAGGATGAAGGATGTACCAACCTGTCCGAGTTCTC<br>CTACATGGAACTCAAAGTGGGATACATCTCAGCCAT<br>CAAAGTGAACGGGTTCACTTGCACAGGTGTTGTGAC<br>AGAGGCAGAGACCTACACCAACTTTGTTGGTTATGT<br>CACAACCACATTCAAGAGAAAGCATTTCCGCCCCAC |

-continued

| SEQ ID NO: | Description | Sequence |
|---|---|---|
| | | CCCAGACGCATGTAGAGCCGCGTATAACTGGAAGA<br>TGGCCGGTGACCCCAGATATGAAGAGTCCCTACAC<br>AATCCATACCCCGACTACCACTGGCTTCGAACTGTA<br>AGAACCACCAAAGAGTCCCTCATTATCATATCCCCA<br>AGTGTGACAGATTTGGACCCATATGACAAATCCCTT<br>CACTCAAGGGTCTTCCCTGGCGGAAAGTGCTCAGGA<br>ATAACGGTGTCCTCTACCTACTGCTCAACTAACCAT<br>GATTACACCATTTGGATGCCCGAGAATCCGAGACCA<br>AGGACACCTTGTGACATTTTTACCAATAGCAGAGGG<br>AAGAGAGCATCCAACGGGAACAAGACTTGCGGCTT<br>TGTGGATGAAAGAGGCCTGTATAAGTCTCTAAAAG<br>GAGCATGCAGGCTCAAGTTATGTGGAGTTCTTGGAC<br>TTAGACTTATGGATGGAACATGGGTCGCGATGCAA<br>ACATCAGATGAGACCAAATGGTGCCCTCCAGATCA<br>GTTGGTGAATTTGCACGACTTTCGCTCAGACGAGAT<br>CGAGCATCTCGTTGTGGAGGAGTTAGTTAAGAAAA<br>GAGAGGAATGTCTGGATGCATTAGAGTCCATCATG<br>ACCACCAAGTCAGTAAGTTTCAGACGTCTCAGTCAC<br>CTGAGAAAACTTGTCCCAGGGTTTGGAAAAGCATAT<br>ACCATATTCAACAAAACCTTGATGGAGGCTGATGCT<br>CACTACAAGTCAGTCCGGACCTGGAATGAGATCATC<br>CCCTCAAAAGGGTGTTTGAAAGTTGGAGGAAGGTG<br>CCATCCTCATGTGAACGGGGTGTTTTTCAATGGTAT<br>AATATTAGGGCCTGACGACCATGTCCTAATCCCAGA<br>GATGCAATCATCCCTCCTCCAGCAACATATGGAGTT<br>GTTGGAATCTTCAGTTATCCCCCTGATGCACCCCCT<br>GGCAGACCCTTCTACAGTTTTCAAAGAAGGTGATGA<br>GGCTGAGGATTTTGTTGAAGTTCACCTCCCCGATGT<br>GTACAAACAGATCTCAGGGGTTGACCTGGGTCTCCC<br>GAACTGGGGAAAGTATGTATTGATGACTGCAGGGG<br>CCATGATTGGCCTGGTGTTGATATTTTCCCTAATGA<br>CATGGTGCAGAGTTGGTATCCATCTTTGCATTAAAT<br>TAAAGCACACCAAGAAAAGACAGATTTATACAGAC<br>ATAGAGATGAACCGACTTGGAAAGTAA |
| 75 | Envelope;<br>LCMV | ATGGGTCAGATTGTGACAATGTTTGAGGCTCTGCCT<br>CACATCATCGATGAGGTGATCAACATTGTCATTATT<br>GTGCTTATCGTGATCACGGGTATCAAGGCTGTCTAC<br>AATTTTGCCACCTGTGGGATATTCGCATTGATCAGT<br>TTCCTACTTCTGGCTGGCAGGTCCTGTGGCATGTAC<br>GGTCTTAAGGGACCCGACATTTACAAAGGAGTTTAC<br>CAATTTAAGTCAGTGGAGTTTGATATGTCACATCTG<br>AACCTGACCATGCCCAACGCATGTTCAGCCAACAAC<br>TCCCACCATTACATCAGTATGGGGACTTCTGGACTA<br>GAATTGACCTTCACCAATGATTCCATCATCAGTCAC<br>AACTTTTGCAATCTGACCTCTGCCTTCAACAAAAAG<br>ACCTTTGACCACACACTCATGAGTATAGTTTCGAGC<br>CTACACCTCAGTATCAGAGGGAACTCCAACTATAAG<br>GCAGTATCCTGCGACTTCAACAATGGCATAACCATC<br>CAATACAACTTGACATTCTCAGATCGACAAAGTGCT<br>CAGAGCCAGTGTAGAACCTTCAGAGGTAGAGTCCT<br>AGATATGTTTAGAACTGCCTTCGGGGGGAAATACAT<br>GAGGAGTGGCTGGGGCTGGACAGGCTCAGATGGCA<br>AGACCACCTGGTGTAGCCAGACGAGTTACCAATAC<br>CTGATTATACAAAATAGAACCTGGGAAAACCACTG<br>CACATATGCAGGTCCTTTTGGGATGTCCAGGATTCT<br>CCTTTCCCAAGAGAAGACTAAGTTCTTCACTAGGAG<br>ACTAGCGGGCACATTCACCTGGACTTTGTCAGACTC<br>TTCAGGGGTGGAGAATCCAGGTGGTTATTGCCTGAC<br>CAAATGGATGATTCTTGCTGCAGAGCTTAAGTGTTT<br>CGGGAACACAGCAGTTGCGAAATGCAATGTAAATC<br>ATGATGCCGAATTCTGTGACATGCTGCGACTAATTG<br>ACTACAACAAGGCTGCTTTGAGTAAGTTCAAAGAG<br>GACGTAGAATCTGCCTTGCACTTATTCAAAACAACA<br>GTGAATTCTTTGATTTCAGATCAACTACTGATGAGG<br>AACCACTTGAGAGATCTGATGGGGGTGCCATATTGC<br>AATTACTCAAAGTTTTGGTACCTAGAACATGCAAAG<br>ACCGGCGAAACTAGTGTCCCCAAGTGCTGGCTTGTC<br>ACCAATGGTTCTTACTTAAATGAGACCCACTTCAGT<br>GATCAAATCGAACAGGAAGCCGATAACATGATTAC<br>AGAGATGTTGAGGAAGGATTACATAAAGAGGCAGG<br>GGAGTACCCCCCTAGCATTGATGGACCTTCTGATGT<br>TTTCCACATCTGCATATCTAGTCAGCATCTTCCTGCA<br>CCTTGTCAAAATACCAACACACAGGCACATAAAAG<br>GTGGCTCATGTCCAAAGCCACACCGATTAACCAACA |

-continued

| SEQ ID NO: | Description | Sequence |
|---|---|---|
| | | AAGGAATTTGTAGTTGTGGTGCATTTAAGGTGCCTG<br>GTGTAAAAACCGTCTGGAAAAGACGCTGA |
| 76 | Envelope; FPV | ATGAACACTCAAATCCTGGTTTTCGCCCTTGTGGCA<br>GTCATCCCCACAAATGCAGACAAAATTTGTCTTGGA<br>CATCATGCTGTATCAAATGGCACCAAAGTAAACAC<br>ACTCACTGAGAGAGGAGTAGAAGTTGTCAATGCAA<br>CGGAAACAGTGGAGCGGACAAACATCCCCAAAATT<br>TGCTCAAAAGGGAAAAGAACCACTGATCTTGGCCA<br>ATGCGGACTGTTAGGGACCATTACCGGACCACCTCA<br>ATGCGACCAATTTCTAGAATTTTCAGCTGATCTAAT<br>AATCGAGAGACGAGAAGGAAATGATGTTTGTTACC<br>CGGGGAAGTTTGTTAATGAAGAGGCATTGCGACAA<br>ATCCTCAGAGGATCAGGTGGGATTGACAAAGAAAC<br>AATGGGATTCACATATAGTGGAATAAGGACCAACG<br>GAACAACTAGTGCATGTAGAAGATCAGGGTCTTCAT<br>TCTATGCAGAAATGGAGTGGCTCCTGTCAAATACAG<br>ACAATGCTGCTTTCCCACAAATGACAAAATCATACA<br>AAAACACAAGGAGAGAATCAGCTCTGATAGTCTGG<br>GGAATCCACCATTCAGGATCAACCACCGAACAGAC<br>CAAACTATATGGGAGTGGAAATAAACTGATAACAG<br>TCGGGAGTTCCAAATATCATCAATCTTTTGTGCCGA<br>GTCCAGGAACACGACCGCAGATAAATGGCCAGTCC<br>GGACGGATTGATTTTCATTGGTTGATCTTGGATCCC<br>AATGATACAGTTACTTTTAGTTTCAATGGGGCTTTC<br>ATAGCTCCAAATCGTGCCAGCTTCTTGAGGGGAAAG<br>TCCATGGGGATCCAGAGCGATGTGCAGGTTGATGCC<br>AATTGCGAAGGGGAATGCTACCACAGTGGAGGGAC<br>TATAACAAGCAGATTGCCTTTTCAAAACATCAATAG<br>CAGAGCAGTTGGCAAATGCCCAAGATATGTAAAAC<br>AGGAAAGTTTATTATTGGCAACTGGGATGAAGAAC<br>GTTCCCGAACCTTCCAAAAAAAGGAAAAAAAGAGG<br>CCTGTTTGGCGCTATAGCAGGGTTTATTGAAAATGG<br>TTGGGAAGGTCTGGTCGACGGGTGGTACGGTTTCAG<br>GCATCAGAATGCACAAGGAGAAGGAACTGCAGCAG<br>ACTACAAAAGCACCCAATCGGCAATTGATCAGATA<br>ACCGGAAAGTTAAATAGACTCATTGAGAAAACCAA<br>CCAGCAATTTGAGCTAATAGATAATGAATTCACTGA<br>GGTGGAAAAGCAGATTGGCAATTTAATTAACTGGA<br>CCAAAGACTCCATCACAGAAGTATGGTCTTACAATG<br>CTGAACTTCTTGTGGCAATGGAAAACCAGCACACTA<br>TTGATTTGGCTGATTCAGAGATGAACAAGCTGTATG<br>AGCGAGTGAGGAAACAATTAAGGGAAAATGCTGAA<br>GAGGATGGCACTGGTTGCTTTGAAATTTTTCATAAA<br>TGTGACGATGATTGTATGGCTAGTATAAGGAACAAT<br>ACTTATGATCACAGCAAATACAGAGAAGAAGCGAT<br>GCAAAATAGAATACAAATTGACCCAGTCAAATTGA<br>GTAGTGGCTACAAAGATGTGATACTTTGGTTTAGCT<br>TCGGGGCATCATGCTTTTTGCTTCTTGCCATTGCAAT<br>GGGCCTTGTTTTCATATGTGTGAAGAACGGAAACAT<br>GCGGTGCACTATTTGTATATAA |
| 77, 78 | Envelope; RRV | AGTGTAACAGAGCACTTTAATGTGTATAAGGCTACT<br>AGACCATACCTAGCACATTGCGCCGATTGCGGGGA<br>CGGGTACTTCTGCTATAGCCCAGTTGCTATCGAGGA<br>GATCCGAGATGAGGCGTCTGATGGCATGCTTAAGAT<br>CCAAGTCTCCGCCCAAATAGGTCTGGACAAGGCAG<br>GCACCCACGCCCACACGAAGCTCCGATATATGGCTG<br>GTCATGATGTTCAGGAATCTAAGAGAGATTCCTTGA<br>GGGTGTACACGTCCGCAGCGTGCTCCATACATGGGA<br>CGATGGGACACTTCATCGTCGCACACTGTCCACCAG<br>GCGACTACCTCAAGGTTTCGTTCGAGGACGCAGATT<br>CGCACGTGAAGGCATGTAAGGTCCAATACAAGCAC<br>AATCCATTGCCGGTGGGTAGAGAGAAGTTCGTGGTT<br>AGACCACACTTTGGCGTAGAGCTGCCATGCACCTCA<br>TACCAGCTGACAACGGCTCCCACCGACGAGGAGAT<br>TGACATGCATACACCGCCAGATATACCGGATCGCAC<br>CCTGCTATCACAGACGGCGGGCAACGTCAAAATAA<br>CAGCAGGCGGCAGGACTATCAGGTACAACTGTACC<br>TGCGGCCGTGACAACGTAGGCACTACCAGTACTGA<br>CAAGACCATCAACACATGCAAGATTGACCAATGCC<br>ATGCTGCCGTCACCAGCCATGACAAATGGCAATTTA<br>CCTCTCCATTTGTTCCCAGGGCTGATCAGACAGCTA<br>GGAAAGGCAAGGTACACGTTCCGTTCCCTCTGACTA<br>ACGTCACCTGCCGAGTGCCGTTGGCTCGAGCGCCGG<br>ATGCCACCTATGGTAAGAAGGAGGTGACCCTGAGA |

-continued

| SEQ ID NO: | Description | Sequence |
|---|---|---|
| | | TTACACCCAGATCATCCGACGCTCTTCTCCTATAGG AGTTTAGGAGCCGAACCGCACCCGTACGAGGAATG GGTTGACAAGTTCTCTGAGCGCATCATCCCAGTGAC GGAAGAAGGGATTGAGTACCAGTGGGGCAACAACC CGCCGGTCTGCCTGTGGGCGCAACTGACGACCGAG GGCAAACCCCATGGCTGGCCACATGAAATCATTCA GTACTATTATGGACTATACCCCGCCGCCACTATTGC CGCAGTATCCGGGGCGAGTCTGATGGCCCTCCTAAC TCTGGCGGCCACATGCTGCATGCTGGCCACCGCGAG GAGAAAGTGCCTAACACCGTACGCCCTGACGCCAG GAGCGGTGGTACCGTTGACACTGGGGCTGCTTTGCT GCGCACCGAGGGCGAATGCA |
| 79 | Envelope; Ebola | ATGGGTGTTACAGGAATATTGCAGTTACCTCGTGAT CGATTCAAGAGGACATCATTCTTTCTTTGGGTAATT ATCCTTTTCCAAAGAACATTTTCCATCCCACTTGGA GTCATCCACAATAGCACATTACAGGTTAGTGATGTC GACAAACTGGTTTGCCGTGACAAACTGTCATCCACA AATCAATTGAGATCAGTTGGACTGAATCTCGAAGG GAATGGAGTGGCAACTGACGTGCCATCTGCAACTA AAAGATGGGGCTTCAGGTCCGGTGTCCCACCAAAG GTGGTCAATTATGAAGCTGGTGAATGGGCTGAAAA CTGCTACAATCTTGAAATCAAAAAACCTGACGGGA GTGAGTGTCTACCAGCAGCGCCAGACGGGATTCGG GGCTTCCCCCGGTGCCGGTATGTGCACAAAGTATCA GGAACGGGACCGTGTGCCGGAGACTTTGCCTTCCAC AAAGAGGGTGCTTTCTTCCTGTATGACCGACTTGCT TCCACAGTTATCTACCGAGGAACGACTTTCGCTGAA GGTGTCGTTGCATTTCTGATACTGCCCCAAGCTAAG AAGGACTTCTTCAGCTCACACCCCTTGAGAGAGCCG GTCAATGCAACGGAGGACCCGTCTAGTGGCTACTAT TCTACCACAATTAGATATCAAGCTACCGGTTTTGGA ACCAATGAGACAGAGTATTTGTTCGAGGTTGACAAT TTGACCTACGTCCAACTTGAATCAAGATTCACACCA CAGTTTCTGCTCCAGCTGAATGAGACAATATATACA AGTGGGAAAAGGAGCAATACCACGGGAAAACTAAT TTGGAAGGTCAACCCCGAAATTGATACAACAATCG GGGAGTGGGCCTTCTGGGAAACTAAAAAAACCTCA CTAGAAAAATTCGCAGTGAAGAGTTGTCTTTCACAG CTGTATCAAACAGAGCCAAAAACATCAGTGGTCAG AGTCCGGCGCGAACTTCTTCCGACCCAGGGACCAAC ACAACAACTGAAGACCACAAAATCATGGCTTCAGA AAATTCCTCTGCAATGGTTCAAGTGCACAGTCAAGG AAGGGAAGCTGCAGTGTCGCATCTGACAACCCTTGC CACAATCTCCACGAGTCCTCAACCCCCCACAACCAA ACCAGGTCCGGACAACAGCACCCACAATACACCCG TGTATAAACTTGACATCTCTGAGGCAACTCAAGTTG AACAACATCACCGCAGAACAGACAACGACAGCACA GCCTCCGACACTCCCCCCGCCACGACCGCAGCCGGA CCCCTAAAAGCAGAGAACACCAACACGAGCAAGGG TACCGACCTCCTGGACCCCGCCACCACAACAAGTCC CCAAAACCACAGCGAGACCGCTGGCAACAACAACA CTCATCACCAAGATACCGGAGAAGAGAGTGCCAGC AGCGGGAAGCTAGGCTTAATTACCAATACTATTGCT GGAGTCGCAGGACTGATCACAGGCGGGAGGAGAGC TCGAAGAGAAGCAATTGTCAATGCTCAACCCAAAT GCAACCCTAATTTACATTACTGGACTACTCAGGATG AAGGTGCTGCAATCGGACTGGCCTGGATACCATATT TCGGGCCAGCAGCCGAGGGAATTTACATAGAGGGG CTGATGCACAATCAAGATGGTTTAATCTGTGGGTTG AGACAGCTGGCCAACGAGACGACTCAAGCTCTTCA ACTGTTCCTGAGAGCCACAACCGAGCTACGCACCTT TTCAATCCTCAACCGTAAGGCAATTGATTTCTTGCT GCAGCGATGGGGCGGCACATGCCACATTTTGGGAC CGGACTGCTGTATCGAACCACATGATTGGACCAAG AACATAACAGACAAAATTGATCAGATTATTCATGAT TTTGTTGATAAAACCCTTCCGGACCAGGGGGACAAT GACAATTGGTGGACAGGATGGAGACAATGGATACC GGCAGGTATTGGAGTTACAGGCGTTATAATTGCAGT TATCGCTTTATTCTGTATATGCAAATTTGTCTTTTAG |
| 80 | Short WPRE sequence | AATCAACCTCTGGATTACAAAATTTGTGAAAGATTG ACTGATATTCTTAACTATGTTGCTCCTTTTACGCTGT GTGGATATGCTGCTTTAATGCCTCTGTATCATGCTAT TGCTTCCCGTACGGCTTTCGTTTTCTCCTCCTTGTAT AAATCCTGGTTGCTGTCTCTTTATGAGGAGTTGTGG |

-continued

| SEQ ID NO: | Description | Sequence |
|---|---|---|
| | | CCCGTTGTCCGTCAACGTGGCGTGGTGTGCTCTGTG<br>TTTGCTGACGCAACCCCCACTGGCTGGGGCATTGCC<br>ACCACCTGTCAACTCCTTTCTGGGACTTTCGCTTTCC<br>CCCTCCCGATCGCCACGGCAGAACTCATCGCCGCCT<br>GCCTTGCCCGCTGCTGGACAGGGGCTAGGTTGCTGG<br>GCACTGATAATTCCGTGGTGTTGTC |
| 81 | Primer | TAAGCAGAATTCATGAATTTGCCAGGAAGAT |
| 82 | Primer | CCATACAATGAATGGACACTAGGCGGCCGCACGAA<br>T |
| 83 | Gag, Pol, Integrase fragment | GAATTCATGAATTTGCCAGGAAGATGGAAACCAAA<br>AATGATAGGGGGAATTGGAGGTTTTATCAAAGTAA<br>GACAGTATGATCAGATACTCATAGAAATCTGCGGA<br>CATAAAGCTATAGGTACAGTATTAGTAGGACCTACA<br>CCTGTCAACATAATTGGAAGAAATCTGTTGACTCAG<br>ATTGGCTGCACTTTAAATTTTCCCATTAGTCCTATTG<br>AGACTGTACCAGTAAAATTAAAGCCAGGAATGGAT<br>GGCCCAAAAGTTAAACAATGGCCATTGACAGAAGA<br>AAAAATAAAAGCATTAGTAGAAATTTGTACAGAAA<br>TGGAAAAGGAAGGAAAAATTTCAAAAATTGGGCCT<br>GAAAATCCATACAATACTCCAGTATTTGCCATAAAG<br>AAAAAAGACAGTACTAAATGGAGAAAATTAGTAGA<br>TTTCAGAGAACTTAATAAGAGAACTCAAGATTTCTG<br>GGAAGTTCAATTAGGAATACCACATCCTGCAGGGTT<br>AAAACAGAAAAAATCAGTAACAGTACTGGATGTGG<br>GCGATGCATATTTTTCAGTTCCCTTAGATAAAGACT<br>TCAGGAAGTATACTGCATTTACCATACCTAGTATAA<br>ACAATGAGACACCAGGGATTAGATATCAGTACAAT<br>GTGCTTCCACAGGGATGGAAAGGATCACCAGCAAT<br>ATTCCAGTGTAGCATGACAAAAATCTTAGAGCCTTT<br>TAGAAAACAAAATCCAGACATAGTCATCTATCAAT<br>ACATGGATGATTTGTATGTAGGATCTGACTTAGAAA<br>TAGGGCAGCATAGAACAAAAATAGAGGAACTGAGA<br>CAACATCTGTTGAGGTGGGGATTTACCACACCAGAC<br>AAAAAACATCAGAAAGAACCTCCATTCCTTTGGATG<br>GGTTATGAACTCCATCCTGATAAATGGACAGTACAG<br>CCTATAGTGCTGCCAGAAAAGGACAGCTGGACTGT<br>CAATGACATACAGAAATTAGTGGGAAAATTGAATT<br>GGGCAAGTCAGATTTATGCAGGGATTAAAGTAAGG<br>CAATTATGTAAACTTCTTAGGGGAACCAAAGCACTA<br>ACAGAAGTAGTACCACTAACAGAAGAAGCAGAGCT<br>AGAACTGGCAGAAAACAGGGAGATTCTAAAAGAAC<br>CGGTACATGGAGTGTATTATGACCCATCAAAAGACT<br>TAATAGCAGAAATACAGAAGCAGGGGCAAGGCCAA<br>TGGACATATCAAATTTATCAAGAGCCATTTAAAAAT<br>CTGAAAACAGGAAAGTATGCAAGAATGAAGGGTGC<br>CCACACTAATGATGTGAAACAATTAACAGAGGCAG<br>TACAAAAAATAGCCACAGAAAGCATAGTAATATGG<br>GGAAAGACTCCTAAATTTAAATTACCCATACAAAA<br>GGAAACATGGGAAGCATGGTGGACAGAGTATTGGC<br>AAGCCACCTGGATTCCTGAGTGGGAGTTTGTCAATA<br>CCCCTCCCTTAGTGAAGTTATGGTACCAGTTAGAGA<br>AAGAACCCATAATAGGAGCAGAAACTTTCTATGTA<br>GATGGGGCAGCCAATAGGGAAACTAAATTAGGAAA<br>AGCAGGATATGTAACTGACAGAGGAAGACAAAAAG<br>TTGTCCCCCTAACGGACACAACAAATCAGAAGACT<br>GAGTTACAAGCAATTCATCTAGCTTTGCAGGATTCG<br>GGATTAGAAGTAAACATAGTGACAGACTCACAATA<br>TGCATTGGGAATCATTCAAGCACAACCAGATAAGA<br>GTGAATCAGAGTTAGTCAGTCAAATAATAGAGCAG<br>TTAATAAAAAAGGAAAAAGTCTACCTGGCATGGGT<br>ACCAGCACACAAAGGAATTGGAGGAAATGAACAAG<br>TAGATAAATTGGTCAGTGCTGGAATCAGGAAAGTA<br>CTATTTTTAGATGGAATAGATAAGGCCCAAGAAGA<br>ACATGAGAAATATCACAGTAATTGGAGAGCAATGG<br>CTAGTGATTTTAACCTACCACCTGTAGTAGCAAAAG<br>AAATAGTAGCCAGCTGTGATAAATGTCAGCTAAAA<br>GGGGAAGCCATGCATGGACAAGTAGACTGTAGCCC<br>AGGAATATGGCAGCTAGATTGTACACATTTAGAAG<br>GAAAAGTTATCTTGGTAGCAGTTCATGTAGCCAGTG<br>GATATATAGAAGCAGAAGTAATTCCAGCAGAGACA<br>GGGCAAGAAACAGCATACTTCCTCTTAAAATTAGCA<br>GGAAGATGGCCAGTAAAAACAGTACATACAGACAA<br>TGGCAGCAATTTCACCAGTACTACAGTTAAGGCCGC |

-continued

| SEQ ID NO: | Description | Sequence |
|---|---|---|
| | | CTGTTGGTGGGCGGGGATCAAGCAGGAATTTGGCA TTCCCTACAATCCCCAAAGTCAAGGAGTAATAGAAT CTATGAATAAAGAATTAAAGAAAATTATAGGACAG GTAAGAGATCAGGCTGAACATCTTAAGACAGCAGT ACAAATGGCAGTATTCATCCACAATTTTAAAAGAAA AGGGGGGATTGGGGGGTACAGTGCAGGGGAAAGA ATAGTAGACATAATAGCAACAGACATACAAACTAA AGAATTACAAAAACAAATTACAAAAATTCAAAATT TTCGGGTTTATTACAGGGACAGCAGAGATCCAGTTT GGAAAGGACCAGCAAAGCTCCTCTGGAAAGGTGAA GGGGCAGTAGTAATACAAGATAATAGTGACATAAA AGTAGTGCCAAGAAGAAAAGCAAAGATCATCAGGG ATTATGGAAAACAGATGGCAGGTGATGATTGTGTG GCAAGTAGACAGGATGAGGATTAA |
| 84 | DNA Fragment containing Rev, RRE and rabbit beta globin poly A | TCTAGAATGGCAGGAAGAAGCGGAGACAGCGACGA AGAGCTCATCAGAACAGTCAGACTCATCAAGCTTCT CTATCAAAGCAACCCACCTCCCAATCCCGAGGGGA CCCGACAGGCCCGAAGGAATAGAAGAAGAAGGTGG AGAGAGAGACAGAGACAGATCCATTCGATTAGTGA ACGGATCCTTGGCACTTATCTGGGACGATCTGCGGA GCCTGTGCCTCTTCAGCTACCACCGCTTGAGAGACT TACTCTTGATTGTAACGAGGATTGTGGAACTTCTGG GACGCAGGGGGTGGGAAGCCCTCAAATATTGGTGG AATCTCCTACAATATTGGAGTCAGGAGCTAAAGAAT AGAGGAGCTTTGTTCCTTGGGTTCTTGGGAGCAGCA GGAAGCACTATGGGCGCAGCGTCAATGACGCTGAC GGTACAGGCCAGACAATTATTGTCTGGTATAGTGCA GCAGCAGAACAATTTGCTGAGGGCTATTGAGGCGC AACAGCATCTGTTGCAACTCACAGTCTGGGGCATCA AGCAGCTCCAGGCAAGAATCCTGGCTGTGGAAAGA TACCTAAAGGATCAACAGCTCCTAGATCTTTTTCCC TCTGCCAAAAATTATGGGGACATCATGAAGCCCCTT GAGCATCTGACTTCTGGCTAATAAAGGAAATTTATT TTCATTGCAATAGTGTGTTGGAATTTTTTGTGTCTCT CACTCGGAAGGACATATGGGAGGGCAAATCATTTA AAACATCAGAATGAGTATTTGGTTTAGAGTTTGGCA ACATATGCCATATGCTGGCTGCCATGAACAAAGGTG GCTATAAAGAGGTCATCAGTATATGAAACAGCCCC CTGCTGTCCATTCCTTATTCCATAGAAAAGCCTTGA CTTGAGGTTAGATTTTTTTTATATTTTGTTTTGTGTT ATTTTTTTCTTTAACATCCCTAAAATTTTCCTTACAT GTTTTACTAGCCAGATTTTTCCTCCTCTCCTGACTAC TCCCAGTCATAGCTGTCCCTCTTCTCTTATGAAGATC CCTCGACCTGCAGCCCAAGCTTGGCGTAATCATGGT CATAGCTGTTTCCTGTGTGAAATTGTTATCCGCTCAC AATTCCACACAACATACGAGCCGGAAGCATAAAGT GTAAAGCCTGGGGTGCCTAATGAGTGAGCTAACTC ACATTAATTGCGTTGCGCTCACTGCCCGCTTTCCAG TCGGGAAACCTGTCGTGCCAGCGGATCCGCATCTCA ATTAGTCAGCAACCATAGTCCCGCCCCTAACTCCGC CCATCCCGCCCCTAACTCCGCCCAGTTCCGCCCATT CTCCGCCCCATGGCTGACTAATTTTTTTTATTTATGC AGAGGCCGAGGCCGCCTCGGCCTCTGAGCTATTCCA GAAGTAGTGAGGAGGCTTTTTTGGAGGCCTAGGCTT TTGCAAAAAGCTAACTTGTTTATTGCAGCTTATAAT GGTTACAAATAAAGCAATAGCATCACAAATTTCAC AAATAAAGCATTTTTTTCACTGCATTCTAGTTGTGGT TTGTCCAAACTCATCAATGTATCTTATCAGCGGCCG CCCCGGG |
| 85 | DNA fragment containing the CAG enhancer/promoter/ intron sequence | ACGCGTTAGTTATTAATAGTAATCAATTACGGGGTC ATTAGTTCATAGCCCATATATGGAGTTCCGCGTTAC ATAACTTACGGTAAATGGCCCGCCTGGCTGACCGCC CAACGACCCCCGCCCATTGACGTCAATAATGACGTA TGTTCCCATAGTAACGCCAATAGGGACTTTCCATTG ACGTCAATGGGTGGACTATTTACGGTAAACTGCCCA CTTGGCAGTACATCAAGTGTATCATATGCCAAGTAC GCCCCCTATTGACGTCAATGACGGTAAATGGCCCGC CTGGCATTATGCCCAGTACATGACCTTATGGGACTT TCCTACTTGGCAGTACATCTACGTATTAGTCATCGC TATTACCATGGGTCGAGGTGAGCCCCACGTTCTGCT TCACTCTCCCCATCTCCCCCCCCTCCCCACCCCCAAT TTTGTATTTATTTATTTTTTAATTATTTTGTGCAGCG ATGGGGGCGGGGGGGGGGGGGGCGCGCGCCAGGC GGGGCGGGGCGGGGCGAGGGGCGGGGCGGGGCGA |

-continued

| SEQ ID NO: | Description | Sequence |
|---|---|---|
| | | GGCGGAGAGGTGCGGCGGCAGCCAATCAGAGCGGC<br>GCGCTCCGAAAGTTTCCTTTTATGGCGAGGCGGCGG<br>CGGCGGCGGCCCTATAAAAAGCGAAGCGCGCGGCG<br>GGCGGGAGTCGCTGCGTTGCCTTCGCCCCGTGCCCC<br>GCTCCGCGCCGCCTCGCGCCGCCCGCCCCGGCTCTG<br>ACTGACCGCGTTACTCCCACAGGTGAGCGGGCGGG<br>ACGGCCCTTCTCCTCCGGGCTGTAATTAGCGCTTGG<br>TTTAATGACGGCTCGTTTCTTTTCTGTGGCTGCGTGA<br>AAGCCTTAAAGGGCTCCGGGAGGGCCCTTTGTGCG<br>GGGGGGAGCGGCTCGGGGGGTGCGTGCGTGTGTGT<br>GTGCGTGGGGAGCGCCGCGTGCGGCCCGCGCTGCC<br>CGGCGGCTGTGAGCGCTGCGGGCGCGGCGCGGGGC<br>TTTGTGCGCTCCGCGTGTGCGCGAGGGGAGCGCGGC<br>CGGGGGCGGTGCCCCGCGGTGCGGGGGGGCTGCGA<br>GGGGAACAAAGGCTGCGTGCGGGGTGTGTGCGTGG<br>GGGGGTGAGCAGGGGGTGTGGGCGCGGCGGTCGGG<br>CTGTAACCCCCCCCTGCACCCCCCTCCCCGAGTTGC<br>TGAGCACGGCCCGGCTTCGGGTGCGGGGCTCCGTGC<br>GGGGCGTGGCGCGGGGCTCGCCGTGCCGGGCGGGG<br>GGTGGCGGCAGGTGGGGGTGCCGGGCGGGGCGGGG<br>CCGCCTCGGGCCGGGGAGGGCTCGGGGGAGGGGCG<br>CGGCGGCCCCGGAGCGCCGGCGGCTGTCGAGGCGC<br>GGCGAGCCGCAGCCATTGCCTTTTATGGTAATCGTG<br>CGAGAGGGCGCAGGGACTTCCTTTGTCCCAAATCTG<br>GCGGAGCCGAAATCTGGGAGGCGCCGCCGCACCCC<br>CTCTAGCGGGCGCGGGCGAAGCGGTGCGGCGCCGG<br>CAGGAAGGAAATGGGCGGGGAGGGCCTTCGTGCGT<br>CGCCGCGCCGCCGTCCCCTTCTCCATCTCCAGCCTC<br>GGGGCTGCCGCAGGGGGACGGCTGCCTTCGGGGGG<br>GACGGGGCAGGGCGGGGTTCGGCTTCTGGCGTGTG<br>ACCGGCGGGAATTC |
| 86 | DNA fragment containing VSV-G | GAATTCATGAAGTGCCTTTTGTACTTAGCCTTTTTAT<br>TCATTGGGGTGAATTGCAAGTTCACCATAGTTTTTC<br>CACACAACCAAAAAGGAAACTGGAAAAATGTTCCT<br>TCTAATTACCATTATTGCCCGTCAAGCTCAGATTTA<br>AATTGGCATAATGACTTAATAGGCACAGCCTTACAA<br>GTCAAAATGCCCAAGAGTCACAAGGCTATTCAAGC<br>AGACGGTTGGATGTGTCATGCTTCCAAATGGGTCAC<br>TACTTGTGATTTCCGCTGGTATGGACCGAAGTATAT<br>AACACATTCCATCCGATCCTTCACTCCATCTGTAGA<br>ACAATGCAAGGAAAGCATTGAACAAACGAAACAAG<br>GAACTTGGCTGAATCCAGGCTTCCCTCCTCAAAGTT<br>GTGGATATGCAACTGTGACGGATGCCGAAGCAGTG<br>ATTGTCCAGGTGACTCCTCACCATGTGCTGGTTGAT<br>GAATACACAGGAGAATGGGTTGATTCACAGTTCATC<br>AACGGAAAATGCAGCAATTACATATGCCCCACTGTC<br>CATAACTCTACAACCTGGCATTCTGACTATAAGGTC<br>AAAGGGCTATGTGATTCTAACCTCATTTCCATGGAC<br>ATCACCTTCTTCTCAGAGGACGGAGAGCTATCATCC<br>CTGGGAAAGGAGGGCACAGGGTTCAGAAGTAACTA<br>CTTTGCTTATGAAACTGGAGGCAAGGCCTGCAAAAT<br>GCAATACTGCAAGCATTGGGGAGTCAGACTCCCATC<br>AGGTGTCTGGTTCGAGATGGCTGATAAGGATCTCTT<br>TGCTGCAGCCAGATTCCCTGAATGCCCAGAAGGGTC<br>AAGTATCTCTGCTCCATCTCAGACCTCAGTGGATGT<br>AAGTCTAATTCAGGACGTTGAGAGGATCTTGGATTA<br>TTCCCTCTGCCAAGAAACCTGGAGCAAAATCAGAG<br>CGGGTCTTCCAATCTCTCCAGTGGATCTCAGCTATC<br>TTGCTCCTAAAAACCCAGGAACCGGTCCTGCTTTCA<br>CCATAATCAATGGTACCCTAAAATACTTTGAGACCA<br>GATACATCAGAGTCGATATTGCTGCTCCAATCCTCT<br>CAAGAATGGTCGGAATGATCAGTGGAACTACCACA<br>GAAAGGGAACTGTGGGATGACTGGGCACCATATGA<br>AGACGTGGAAATTGGACCCAATGGAGTTCTGAGGA<br>CCAGTTCAGGATATAAGTTTCCTTTATACATGATTG<br>GACATGGTATGTTGGACTCCGATCTTCATCTTAGCT<br>CAAAGGCTCAGGTGTTCGAACATCCTCACATTCAAG<br>ACGCTGCTTCGCAACTTCCTGATGATGAGAGTTTAT<br>TTTTTGGTGATACTGGGCTATCCAAAAATCCAATCG<br>AGCTTGTAGAAGGTTGGTTCAGTAGTTGGAAAAGCT<br>CTATTGCCTCTTTTTTCTTTATCATAGGGTTAATCAT<br>TGGACTATTCTTGGTTCTCCGAGTTGGTATCCATCTT<br>TGCATTAAATTAAAGCACACCAAGAAAAGACAGAT<br>TTATACAGACATAGAGATGAGAATTC |

-continued

| SEQ ID NO: | Description | Sequence |
|---|---|---|
| 87 | Helper plasmid containing RRE and rabbit beta globin poly A | TCTAGAAGGAGCTTTGTTCCTTGGGTTCTTGGGAGC AGCAGGAAGCACTATGGGCGCAGCGTCAATGACGC TGACGGTACAGGCCAGACAATTATTGTCTGGTATAG TGCAGCAGCAGAACAATTTGCTGAGGGCTATTGAG GCGCAACAGCATCTGTTGCAACTCACAGTCTGGGGC ATCAAGCAGCTCCAGGCAAGAATCCTGGCTGTGGA AAGATACCTAAAGGATCAACAGCTCCTAGATCTTTT TCCCTCTGCCAAAAATTATGGGGACATCATGAAGCC CCTTGAGCATCTGACTTCTGGCTAATAAAGGAAATT TATTTTCATTGCAATAGTGTGTTGGAATTTTTTGTGT CTCTCACTCGGAAGGACATATGGGAGGGCAAATCA TTTAAAACATCAGAATGAGTATTTGGTTTAGAGTTT GGCAACATATGCCATATGCTGGCTGCCATGAACAA AGGTGGCTATAAAGAGGTCATCAGTATATGAAACA GCCCCCTGCTGTCCATTCCTTATTCCATAGAAAAGC CTTGACTTGAGGTTAGATTTTTTTTATATTTTGTTTT GTGTTATTTTTTTCTTTAACATCCCTAAAATTTTCCT TACATGTTTTACTAGCCAGATTTTTCCTCCTCTCCTG ACTACTCCCAGTCATAGCTGTCCCTCTTCTCTTATGA AGATCCCTCGACCTGCAGCCCAAGCTTGGCGTAATC ATGGTCATAGCTGTTTCCTGTGTGAAATTGTTATCC GCTCACAATTCCACACAACATACGAGCCGGAAGCA TAAAGTGTAAAGCCTGGGGTGCCTAATGAGTGAGC TAACTCACATTAATTGCGTTGCGCTCACTGCCCGCT TTCCAGTCGGGAAACCTGTCGTGCCAGCGGATCCGC ATCTCAATTAGTCAGCAACCATAGTCCCGCCCCTAA CTCCGCCCATCCCGCCCCTAACTCCGCCCAGTTCCG CCCATTCTCCGCCCCATGGCTGACTAATTTTTTTTAT TTATGCAGAGGCCGAGGCCGCCTCGGCCTCTGAGCT ATTCCAGAAGTAGTGAGGAGGCTTTTTTGGAGGCCT AGGCTTTTGCAAAAAGCTAACTTGTTTATTGCAGCT TATAATGGTTACAAATAAAGCAATAGCATCACAAA TTTCACAAATAAAGCATTTTTTTCACTGCATTCTAGT TGTGGTTTGTCCAAACTCATCAATGTATCTTATCACC CGGG |
| 88 | RSV promoter and HIV Rev | CAATTGCGATGTACGGGCCAGATATACGCGTATCTG AGGGGACTAGGGTGTGTTTAGGCGAAAAGCGGGGC TTCGGTTGTACGCGGTTAGGAGTCCCCTCAGGATAT AGTAGTTTCGCTTTTGCATAGGGAGGGGGAAATGTA GTCTTATGCAATACACTTGTAGTCTTGCAACATGGT AACGATGAGTTAGCAACATGCCTTACAAGGAGAGA AAAAGCACCGTGCATGCCGATTGGTGGAAGTAAGG TGGTACGATCGTGCCTTATTAGGAAGGCAACAGAC AGGTCTGACATGGATTGGACGAACCACTGAATTCCG CATTGCAGAGATAATTGTATTTAAGTGCCTAGCTCG ATACAATAAACGCCATTTGACCATTCACCACATTGG TGTGCACCTCCAAGCTCGAGCTCGTTTAGTGAACCG TCAGATCGCCTGGAGACGCCATCCACGCTGTTTTGA CCTCCATAGAAGACACCGGGACCGATCCAGCCTCCC CTCGAAGCTAGCGATTAGGCATCTCCTATGGCAGGA AGAAGCGGAGACAGCGACGAAGAACTCCTCAAGGC AGTCAGACTCATCAAGTTTCTCTATCAAAGCAACCC ACCTCCCAATCCCGAGGGGACCCGACAGGCCCGAA GGAATAGAAGAAGAAGGTGGAGAGAGAGACAGAG ACAGATCCATTCGATTAGTGAACGGATCCTTAGCAC TTATCTGGGACGATCTGCGGAGCCTGTGCCTCTTCA GCTACCACCGCTTGAGAGACTTACTCTTGATTGTAA CGAGGATTGTGGAACTTCTGGGACGCAGGGGGTGG GAAGCCCTCAAATATTGGTGGAATCTCCTACAATAT TGGAGTCAGGAGCTAAAGAATAGTCTAGA |
| 89 | Target sequence | ATGGCAGGAAGAAGCGGAG |
| 90 | shRNA sequence | ATGGCAGGAAGAAGCGGAGTTCAAGAGACTCCGCT TCTTCCTGCCATTTTTT |
| 91 | H1 promoter and shRT sequence | GAACGCTGACGTCATCAACCCGCTCCAAGGAATCG CGGGCCCAGTGTCACTAGGCGGGAACACCCAGCGC GCGTGCGCCCTGGCAGGAAGATGGCTGTGAGGGAC AGGGGAGTGGCGCCCTGCAATATTTGCATGTCGCTA TGTGTTCTGGGAAATCACCATAAACGTGAAATGTCT TTGGATTTGGGAATCTTATAAGTTCTGTATGAGACC ACTTGGATCCGCGGAGACAGCGACGAAGAGCTTCA AGAGAGCTCTTCGTCGCTGTCTCCGCTTTTT |

-continued

| SEQ ID NO: | Description | Sequence |
|---|---|---|
| 92 | H1 CCR5 sequence | GAACGCTGACGTCATCAACCCGCTCCAAGGAATCG CGGGCCCAGTGTCACTAGGCGGGAACACCCAGCGC GCGTGCGCCCTGGCAGGAAGATGGCTGTGAGGGAC AGGGGAGTGGCGCCCTGCAATATTTGCATGTCGCTA TGTGTTCTGGGAAATCACCATAAACGTGAAATGTCT TTGGATTTGGGAATCTTATAAGTTCTGTATGAGACC ACTTGGATCCGTGTCAAGTCCAATCTATGTTCAAGA GACATAGATTGGACTTGACACTTTTT |
| 93 | CCR5 Forward Primer | AGGAATTGATGGCGAGAAGG |
| 94 | CCR5 Reverse Primer | CCCCAAAGAAGGTCAAGGTAATCA |
| 95 | Actin Forward Primer | AGCGCGGCTACAGCTTCA |
| 96 | Actin Reverse Primer | GGCGACGTAGCACAGCTTCT |
| 97 | AGT103 CCR5 miR30 | TGTAAACTGAGCTTGCTCTA |
| 98 | AGT103-R5-1 | TGTAAACTGAGCTTGCTCGC |
| 99 | AGT103-R5-2 | CATAGATTGGACTTGACAC |
| 100 | CAG promoter | TAGTTATTAATAGTAATCAATTACGGGGTCATTAGT TCATAGCCCATATATGGAGTTCCGCGTTACATAACT TACGGTAAATGGCCCGCCTGGCTGACCGCCCAACG ACCCCCGCCCATTGACGTCAATAATGACGTATGTTC CCATAGTAACGCCAATAGGGACTTTCCATTGACGTC AATGGGTGGACTATTTACGGTAAACTGCCCACTTGG CAGTACATCAAGTGTATCATATGCCAAGTACGCCCC CTATTGACGTCAATGACGGTAAATGGCCCGCCTGGC ATTATGCCCAGTACATGACCTTATGGGACTTTCCTA CTTGGCAGTACATCTACGTATTAGTCATCGCTATTA CCATGGGTCGAGGTGAGCCCCACGTTCTGCTTCACT CTCCCCATCTCCCCCCCCTCCCCACCCCCAATTTTGT ATTTATTTATTTTTTAATTATTTTGTGCAGCGATGGG GGCGGGGGGGGGGGGGGCGCGCGCCAGGCGGGGC GGGGCGGGGCGAGGGGCGGGGCGGGGCGAGGCGG AGAGGTGCGGCGGCAGCCAATCAGAGCGGCGCGCT CCGAAAGTTTCCTTTTATGGCGAGGCGGCGGCGGCG GCGGCCCTATAAAAAGCGAAGCGCGCGGCGGGCG |
| 101 | H1 element | GAACGCTGACGTCATCAACCCGCTCCAAGGAATCG CGGGCCCAGTGTCACTAGGCGGGAACACCCAGCGC GCGTGCGCCCTGGCAGGAAGATGGCTGTGAGGGAC AGGGGAGTGGCGCCCTGCAATATTTGCATGTCGCTA TGTGTTCTGGGAAATCACCATAAACGTGAAATGTCT TTGGATTTGGGAATCTTATAAGTTCTGTATGAGACC ACTT |
| 103 | 7SK promoter | CTGCAGTATTTAGCATGCCCCACCCATCTGCAAGGC ATTCTGGATAGTGTCAAAACAGCCGGAAATCAAGT CCGTTTATCTCAAACTTTAGCATTTTGGGAATAAAT GATATTTGCTATGCTGGTTAAATTAGATTTTAGTTA AATTTCCTGCTGAAGCTCTAGTACGATAAGCAACTT GACCTAAGTGTAAAGTTGAGATTTCCTTCAGGTTTA TATAGCTTGTGCGCCGCCTGGCTACCTC |
| 104 | miR155 Tat | CTGGAGGCTTGCTGAAGGCTGTATGCTGTCCGCTTC TTCCTGCCATAGGGTTTTGGCCACTGACTGACCCTA TGGGGAAGAAGCGGACAGGACACAAGGCCTGTTAC TAGCACTCACATGGAACAAATGGCC |
| 105 | Elongation Factor-1 alpha (EF1-alpha) promoter with 3' restriction recognition site | CCGGTGCCTAGAGAAGGTGGCGCGGGGTAAACTGG GAAAGTGATGTCGTGTACTGGCTCCGCCTTTTTCCC GAGGGTGGGGGAGAACCGTATATAAGTGCAGTAGT CGCCGTGAACGTTCTTTTTCGCAACGGGTTTGCCGC CAGAACACAGGTAAGTGCCGTGTGTGGTTCCCGCG GGCCTGGCCTCTTTACGGGTTATGGCCCTTGCGTGC CTTGAATTACTTCCACGCCCCTGGCTGCAGTACGTG ATTCTTGATCCCGAGCTTCGGGTTGGAAGTGGGTGG |

-continued

| SEQ ID NO: | Description | Sequence |
|---|---|---|
| | | GAGAGTTCGAGGCCTTGCGCTTAAGGAGCCCCTTCG CCTCGTGCTTGAGTTGAGGCCTGGCCTGGGCGCTGG GGCCGCCGCGTGCGAATCTGGTGGCACCTTCGCGCC TGTCTCGCTGCTTTTCGATAAGTCTCTAGCCATTTAAA ATTTTTGATGACCTGCTGCGACGCTTTTTTTCTGGCA AGATAGTCTTGTAAATGCGGGCCAAGATCTGCACAC TGGTATTTCGGTTTTTGGGGCCGCGGGCGGCGACGG GGCCCGTGCGTCCCAGCGCACATGTTCGGCGAGGC GGGGCCTGCGAGCGCGGCCACCGAGAATCGGACGG GGGTAGTCTCAAGCTGGCCGGCCTGCTCTGGTGCCT GGCCTCGCGCCGCCGTGTATCGCCCCGCCCTGGGCG GCAAGGCTGGCCCGGTCGGCACCAGTTGCGTGAGC GGAAAGATGGCCGCTTCCCGGCCCTGCTGCAGGGA GCTCAAAAATGGAGGACGCGGCGCTCGGGAGAGCGG GCGGGTGAGTCACCCACACAAAGGAAAAGGGCCTT TCCGTCCTCAGCCGTCGCTTCATGTGACTCCACGGA GTACCGGGCGCCGTCCAGGCACCTCGATTAGTTCTC GAGCTTTTGGAGTACGTCGTCTTTAGGTTGGGGGGA GGGGTTTTATGCGATGGAGTTTCCCCACACTGAGTG GGTGAGACTGAAGTTAGGCCAGCTTGGCACTTGAT GTAATTCTCCTTGGAATTTGCCCTTTTTGAGTTTGGA TCTTGGTTCATTCTCAAGCCTCAGACAGTGGTTCAA AGTTTTTTTCTTCCATTTCAGGTGTCGTGATGTACA |
| 106 | miR21 Vif coding sequence with 5' restriction recognition site | CCCGGGCATCTCCATGGCTGTACCACCTTGTCGGGG GATGTGTACTTCTGAACTTGTGTTGAATCTCATGGA GTTCAGAAGAACACATCCGCACTGACATTTTGGTAT CTTTCATCTGACCA |
| 107 | miR185 Tat coding sequence with 5' restriction recognition site | GCTAGCGGGCCTGGCTCGAGCAGGGGGCGAGGGAT TCCGCTTCTTCCTGCCATAGCGTGGTCCCCTCCCCTA TGGCAGGCAGAAGCGGCACCTTCCCTCCCAATGACC GCGTCTTCGTC |
| 108 | miR185 Tat coding sequence | GGGCCTGGCTCGAGCAGGGGGCGAGGGATTCCGCT TCTTCCTGCCATAGCGTGGTCCCCTCCCCTATGGCA GGCAGAAGCGGCACCTTCCCTCCCAATGACCGCGTC TTCGTC |

While certain of the preferred embodiments of the present invention have been described and specifically exemplified above, it is not intended that the invention be limited to such embodiments. Various modifications may be made thereto without departing from the scope and spirit of the present invention.

What is claimed is:

1. A method of treating cells, wherein the cells were isolated from a subject not previously immunized with an HIV-1 vaccine, the method comprising:

(a) contacting peripheral blood mononuclear cells (PBMC) isolated from a subject infected with HIV-1 and not previously immunized with an HIV vaccine, with a therapeutically effective amount of a stimulatory agent, wherein the contacting is carried out ex vivo;

(b) transducing, the PBMC ex vivo with a viral delivery system encoding at least one genetic element, wherein at least one genetic element comprises:

a sequence having at least 95% sequence identity with SEQ ID NO: 31; or at least two of: (i) a sequence comprising at least 95% sequence identity with SEQ ID NO: 1, (ii) a sequence comprising at least 95% sequence identity with SEQ ID NO: 2, and (iii) a sequence comprising at least 95% sequence identity with SEQ ID NO: 3; or each of: (iv) a sequence comprising at least 95% sequence identity with SEQ ID NO: 97, (v) a sequence comprising at least 95% sequence identity with SEQ ID NO: 6, and (vi) a sequence comprising at least 95% sequence identity with SEQ ID NO: 7 and (c) culturing, or having cultured, the transduced PBMC for at least 1 day.

2. The method of claim 1, wherein the transduced PBMC are cultured from about 1 to about 35 days.

3. The method of claim 1, further comprising infusing, or having infused, the transduced PBMC into a subject.

4. The method of claim 3, wherein the subject is a human.

5. The method of claim 1, wherein the stimulatory agent comprises a peptide.

6. The method of claim 5, wherein the peptide comprises a GAG peptide.

7. The method of claim 1, wherein the stimulatory agent comprises a vaccine.

8. The method of claim 7, wherein the vaccine comprises an HIV-1 vaccine.

9. The method of claim 8, wherein the HIV-1 vaccine comprises a MVA/HIV62B vaccine or a variant thereof.

10. The method of claim 1, wherein the viral delivery system comprises a lentiviral particle.

11. The method of claim 1, wherein the at least one genetic element, when expressed, is capable of targeting an HIV-1 RNA sequence.

12. The method of claim 11, wherein the at least one genetic element comprises a sequence having at least 95% identity with any one of SEQ ID NO: 31, SEQ ID NO: 1, or SEQ ID NO: 97, and wherein the at least one genetic element, when expressed, is capable of inhibiting production of chemokine receptor CCR5.

13. The method of claim 1, wherein the at least one genetic element comprises:

SEQ ID NO: 31; or at least two of: SEQ ID NO: 1, SEQ ID NO: 2, and SEQ ID NO: 3; or each of: SEQ ID NO: 97, SEQ ID NO: 6, and SEQ ID NO: 7.

14. A method of treating HIV-1 infection in a subject not previously immunized with an HIV-1 vaccine, the method comprising:

(a) removing leukocytes from the subject, wherein the subject was not previously immunized with an HIV-1 vaccine;

(b) purifying peripheral blood mononuclear cells (PBMC) ex vivo from the leukocytes;

(c) contacting the PBMC ex vivo with a therapeutically effective amount of a stimulatory agent;

(d) transducing the PBMC ex vivo with a viral delivery system encoding at least one genetic element, wherein the at least one genetic element comprises:

a sequence having at least 95% sequence identity with-SEQ ID NO; or at least two of: (i) a sequence comprising at least 95% sequence identity with SEQ ID NO: 1, (ii) a sequence comprising at least 95% sequence identity with SEQ ID NO: 2, and (iii) a sequence comprising at least 95% sequence identity with SEQ ID NO: 3; or each of: (iv) a sequence comprising at least 95% sequence identity with SEQ ID NO: 97, (v) a sequence comprising at least 95% sequence identity with SEQ ID NO: 6, and (vi) a sequence comprising at least 95% sequence identity with SEQ ID NO: 7; and (e) culturing, or having cultured, the transduced PBMC for at least 1 day.

15. The method of claim 14, wherein the transduced PBMC are cultured from about 1 to about 35 days.

16. The method of claim 14, further comprising infusing, or having infused, the transduced PBMC into the subject.

17. The method of any one of claim 14, wherein the subject is a human.

18. The method of claim 14, wherein the stimulatory agent comprises a peptide.

19. The method of claim 18, wherein the peptide comprises a GAG peptide.

20. The method of claim 14, wherein the stimulatory agent comprises a vaccine.

21. The method of claim 20, wherein the vaccine comprises an HIV-1 vaccine.

22. The method of claim 21, wherein the HIV-1 vaccine comprises a MVA/HIV62B vaccine or a variant thereof.

23. The method of claim 1, wherein the viral delivery system comprises a lentiviral particle.

24. The method of claim 1, wherein the at least one genetic element comprises at least one small RNA capable of targeting an HIV-1 RNA sequence.

25. The method of claim 24, wherein the at least one genetic element comprises a sequence having at least 95% identity with any one of SEQ ID NO: 31, SEQ ID NO: 1, SEQ ID NO: 97, and wherein the at least one genetic element, when expressed, is capable of inhibiting production of chemokine receptor CCR5.

26. The method of claim 24, wherein the at least one genetic element comprises:

SEQ ID NO: 31; or at least two of: SEQ ID NO: 1, SEQ ID NO: 2, and SEQ ID NO: 3; or each of: SEQ ID NO: 97, SEQ ID NO: 6, and SEQ ID NO: 7.

* * * * *